US009862927B2

(12) United States Patent
Banchereau et al.

(10) Patent No.: US 9,862,927 B2
(45) Date of Patent: Jan. 9, 2018

(54) DENDRITIC CELL VACCINES

(75) Inventors: Jacques F. Banchereau, Dallas, TX (US); Monica Montes, Dallas, TX (US); Anna Karolina Palucka, Dallas, TX (US); Louis M. Sloan, Dallas, TX (US); Yves Levy, Paris (FR)

(73) Assignees: Baylor Research Institute, Dallas, TX (US); Agence Nationale de Recherches Sur le Sida Et Les Hepatitis Virales, Paris (FR)

( * ) Notice: Subject to any disclaimer, the term of this patent is extended or adjusted under 35 U.S.C. 154(b) by 782 days.

(21) Appl. No.: 13/011,798

(22) Filed: Jan. 21, 2011

(65) Prior Publication Data

US 2011/0182937 A1 Jul. 28, 2011

Related U.S. Application Data

(60) Provisional application No. 61/297,555, filed on Jan. 22, 2010, provisional application No. 61/375,829, filed on Aug. 21, 2010.

(51) Int. Cl.
*A61K 39/21* (2006.01)
*C12N 5/0784* (2010.01)
(Continued)

(52) U.S. Cl.
CPC ............ *C12N 5/0639* (2013.01); *A61K 39/12* (2013.01); *A61K 39/21* (2013.01); *C07K 14/005* (2013.01);
(Continued)

(58) Field of Classification Search
CPC ........ A61K 39/00; A61K 39/12; C12N 15/86; C12N 2760/16043; C12N 2760/16122; C12N 2760/16134; C12N 2760/16143; C12N 2760/16161; C12N 7/00; C12N 5/0639
See application file for complete search history.

(56) References Cited

U.S. PATENT DOCUMENTS

| | | | |
|---|---|---|---|
| 7,083,787 B2 | 8/2006 | Duke et al. | |
| 7,348,015 B2 | 3/2008 | Lawman et al. | |
| 2009/0010948 A1 | 1/2009 | Huang et al. | |

FOREIGN PATENT DOCUMENTS

EP    1795589 A1    6/2007

OTHER PUBLICATIONS

Guermonprez, et al. Antigen Presentation and T Cell Stimulation by Dendritic Cells. Annu. Rev. Immunol. 2002; 20:621-67.*
(Continued)

*Primary Examiner* — Janet L Andres
*Assistant Examiner* — Stuart W Snyder
(74) *Attorney, Agent, or Firm* — Norton Rose Fulbright US LLP

(57) ABSTRACT

Compositions and methods for the prophylaxis and treatment of human immunodeficiency virus (HIV) infections are disclosed herein. More specifically the present invention discloses describes an autologous dendritic cell (DC) vaccine product derived by culturing a patient's monocytes with granulocyte macrophage colony stimulating factor (GM-CSF) and interferon alpha 2b (IFN-α), loading the DC with a mixture of five lipopeptides of Gag, Nef and Pol HIV antigens, and, optionally activating the DC with lipopolysaccharide (LPS).

13 Claims, 100 Drawing Sheets

(51) Int. Cl.
  C07K 14/005  (2006.01)
  A61K 39/12   (2006.01)
  A61K 39/00   (2006.01)
(52) U.S. Cl.
  CPC ........... A61K 2039/5154 (2013.01); A61K
          2039/545 (2013.01); A61K 2039/6018
      (2013.01); C12N 2501/052 (2013.01); C12N
      2501/22 (2013.01); C12N 2501/24 (2013.01);
          C12N 2740/16222 (2013.01); C12N
          2740/16234 (2013.01); C12N 2740/16322
              (2013.01); C12N 2740/16334 (2013.01)

(56) References Cited

OTHER PUBLICATIONS

Lu, et al. Therapeutic dendritic-cell vaccine for chronic HIV-1 infection. Nature Medicine. 2004; 10(12): 1359-1365.*
Durier, et al. Clinical safety of HIV lipopeptides used as vaccines in healthy volunteers and HIV-infected adults. AIDS 2006, 20:1039-1049.*
Fischer, et al. The human immunodeficiency virus preventive vaccine research at the French National Agency for acquired immunodeficiency syndrome research. Mem. Inst. Oswaldo Cruz, Rio de Janeiro, 2005; 100(1): 79-84.*
Excler, et al. AIDS vaccine development: Perspectives, challenges & hopes. Indian J. Med. Res. 2005; 121: 568-581.*
Hoeffel et al. Antigen Cross-presentation by Human Plasmacytoid Dendritic Cells. Immunity, 2007; 9: 481-492.*
Banchereau et al. Vaccination of HIV-1 Infected Patients With Dendritic Cells in Addition to Antiretroviral Treatment; 2008: Clinical Trial NCT00796770.*
Kiepiela et al. CD8+ T-cell responses to different HIV proteins have discordant associations with viral load. Nature Med. 2007; 13(1): 46-53 and supplemental information.*
Banchereau et al. P18-11. DALIA: dendritic cell and lipopeptide-induced immunity against AIDS: a phase I trial. Retrovirology 2009, 6(Suppl 3):p. 320.*
Launay et al. Cellular Immune Responses Induced with Dose-Sparing Intradermal Administration of HIV Vaccine to HIV-Uninfected Volunteers in the ANRS VAC16 Trial. PLoSone. 2(8): e725: 1-9.*
Banchereau et al. P 18-1 I. DALIA: dendritic cell and lipopeptide-induced immunity against AIDS: a phase I trial. Retrovirology 2009, 6(Suppl 3):p. 320.*
Hoeffel et al. Antigen Cross-presentation by Human Plasmacytoid Dendritic Cells. Immunity. 2007; 17:481-492.*
Gahéry-Sêgard et al. (Multiepitopic B- and T-Cell Responses Induced in Humans by a Human Immunodeficiency Virus Type 1 Lipopeptide Vaccine. J. Virol. 2000; 74(4):1694-1703.*
Castelli et al. "P17-18. ANRS lipo5 sequences induce in vitro cross-reactive CD4+ T cell response against clade B and C", Retrovirol. 2009, 6(Suppl 3):p. 300.*
Sojka et al. IL-2 Secretion by CD4+ T Cells In Vivo Is Rapid, Transient, and Influenced by TCR-Specific Competition. J. Immunol. 2004; 172: 6136-6143.*
Cobb et al., "PI 9-45. Development of a therapeutic HIV vaccine comprised of autologous dendritic cells loaded with a mixture of lipopeptide HIV antigens", Oct. 22, 2009, Retrovirology 2009, 6 (Suppl 3): p. 365. (Abstract).
Banchereau et al., "PI 8-11. DALIA: dendritic cell and lipopeptide-induced immunity against AIDS: a phase I trial", Oct. 22, 2009, Retrovirology 2009, 6 (Suppl 3): p. 320. (Abstract).
Loof et al., "S04-04 OA. HIV-specific responses induced by anti-CD40 targeting antibodies", Oct. 22, 2009, Retrovirology 2009, 6 (Suppl 3): O46 (Abstract).
Montes et al., "PI 6-29. HIV Nef-specific T cells: Th1/CTL, Th2 and Th17 responses", Oct. 22, 2009, Retrovirology 2009, 6 (Suppl 3): p. 258. (Abstract).
Banchereau et al., "PL01-02: Harnessing human dendritic cell subsets for HIV vaccines", AIDS Vaccine 2009, p. 21.
Andrieu, Muriel, et al., "Two Human Immunodeficiency Virus Vaccinal Lipopeptides Follow Different Cross-Presentation Pathways in Human Dendritic Cells," Journal of Virology, Jan. 2003, vol. 77, No. 2, pp. 1564-1570.
International Search Report and Written Opinion for PCT/US2011/022147 prepared by the Australian Patent Office, dated Sep. 20, 2011, 14 pages.

* cited by examiner

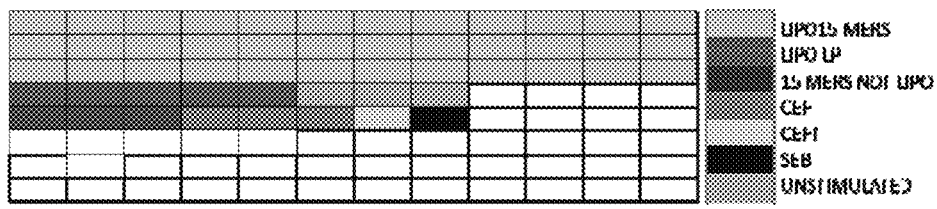

Fig.3a. DALIA-Plate1

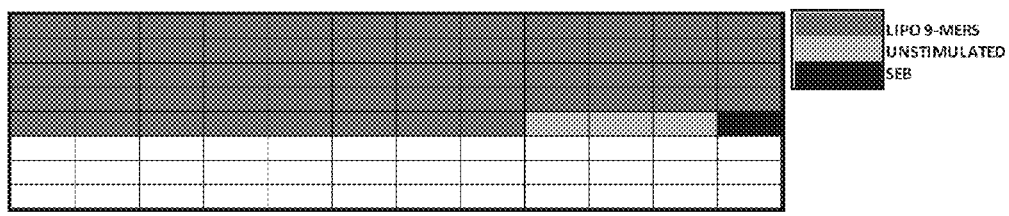

Fig.3b

| B Cell | DC 1 | DC 2 | Monocyte | TFh 1 | TFh 2 | TFh 3 | T Reg | T Cytotoxic | NK 1 | NK 2 | NK 3 |
|---|---|---|---|---|---|---|---|---|---|---|---|
| IgD | Lin-1 | Lin-1 | CD86 | CXCR5 | CXCR5 | CXCR5 | FoxP3 | Perforin | TCR gd | TCR gd | CD69 |
| CD24 | BDCA-2 | CD123 | CD40 | CCR6 | CCR6 | CCR6 | CTLA-4 | Granzyme A | NKp30 | NKp44 | CD158 |
| CD19 | CD45RA | HLA-DR | CD62L | CD45RA | CD45RA | CD45RA | CD25 | CD45RA | CD16 | CD16 | CD16 |
| CD20 | HLA-DR | CD11c | CD11b | CXCR3 | CXCR3 | CXCR3 | CD3 | CD3 | CD56 | CD56 | CD56 |
| CD38 | CD2 | | CD16 | CCR4 | CCR4 | CCR7 | CD8 | CCR7 | NKp46 | NKg2D | NKG2A |
| CD138 | BDCA-1 | | HLA-DR | CRTH2 | ICOS | HLADR | CD4 | CD28 | CD3 | CD3 | CD3 |
| CD27 | CD4 | | CD14 | CD3 | CD3 | CD3 | CD45 | Granzyme B | HLA-DR | HLA-DR | HLA-DR |
| CD45 | | | CD45 | CD8 | CD8 | CD8 | | CD27 | CD25 | CD25 | CD25 |
| | | | | CD4 | CD4 | CD4 | | CD4 | CD45 | CD45 | CD45 |
| | | | | CD45 | CD45 | CD45 | | CD8 | | | |

Fig. 4

DENDRITIC CELL VACCINES

CROSS-REFERENCE TO RELATED APPLICATIONS

This application claims priority to U.S. Provisional Application Ser. Nos. 61/297,555 and 61/375,829 filed Jan. 22, 2010, and Aug. 21, 2010, respectively, the entire contents of which are incorporated herein by reference.

TECHNICAL FIELD OF THE INVENTION

The present invention relates in general to the field of Dendritic Cell (DC) vaccines, and more particularly, to composition and methods for the development of immunity against retroviruses, e.g., HIV.

STATEMENT OF FEDERALLY FUNDED RESEARCH

None.

REFERENCE TO A SEQUENCE LISTING

THE present application includes a Sequence Listing filed separately as required by 37 CFR 1.821-1.825.

BACKGROUND OF THE INVENTION

Without limiting the scope of the invention, its background is described in connection with DC vaccines.

U.S. Pat. No. 7,083,787 issued to Duke et al. (2006) discloses a vaccine that includes a dendritic cell loaded with a yeast vehicle and antigen. The Duke patent further describes methods of making the vaccine and using the vaccine to elicit cellular and humoral immune responses in a mammal. Additionally, a method to elicit an immune response by administration of a yeast vehicle and an antigen that is not complexed to the yeast vehicle is disclosed.

U.S. Pat. No. 7,348,015 issued to Lawman and Lawman (2008) describes methods for treating cancers, particularly tumorigenic types. Cancer cells are modified to express highly immunogenic antigens so that the cells will generate a defensive response in a mammal that exhibits the cancer or is predisposed to cancer and prevent or ameliorate proliferation of cancer cells. The novel cancer cell vaccines are expected to be effective against a wide range of tumors and leukemias.

Finally, U.S. Patent Application No. 20090010948 (Huang et al. 2009) discloses that reducing, inhibiting or preventing the expression of immunosuppressive cytokines or tolergenic agents in antigen presenting cells improves the ability of the antigen presenting cell to promote an immune response. In one embodiment the Huang invention provides a genetically engineered antigen presenting cell that has reduced or no expression of IL-10. Preferred antigen presenting cells are dendritic cells. Expression of IL-10 can be inhibited or blocked by genetically engineering the antigen presenting cell to express inhibitory nucleic acids that inhibit or prevent the expression mRNA encoding immunosuppressive cytokines. Inhibitory nucleic acids include siRNA, antisense RNA, antisense DNA, microRNA, and enzymatic nucleic acids that target mRNA encoding immunosuppressive cytokines. Immunosuppressive cytokines include, but are not limited to IL-10, TGF-β, IL-27, IL-35, or combinations thereof. Tolerogenic agents include but are not limited to indoleamine 2,3-dioxygenase.

SUMMARY OF THE INVENTION

The present invention describes an autologous dendritic cell (DC) vaccine product derived by culturing a patient's monocytes with granulocyte macrophage colony stimulating factor (GM-CSF) and interferon alpha 2b (IFN-α), loading the DC with a mixture of five lipopeptides of Gag, Nef and Pol HIV antigens, and then activating the DC with lipopolysaccharide (LPS).

In one embodiment, the present invention includes compositions and methods for generating an immune response, and for therapy, in a human or animal subject comprising: granulocyte macrophage colony stimulating factor (GM-CSF) and interferon alpha 2b (IFN-α) stimulated Dendritic cells (DCs); a lipopeptide mixture comprising five antigenic peptides loaded onto the DCs, wherein the antigenic peptides are representative of one or more epitopes of the five antigen implicated or involved in a disease or a condition against which the immune response, and the therapy is desired; and lipopolysaccharides for activating the lipopeptide loaded DCs. In one aspect, the lipopeptide mixture comprises five Human Immunodeficiency Virus (HIV) antigenic peptides. In another aspect, the HIV antigenic peptides are selected from the group consisting of Gag p17(17-35) (SEQ. ID NO: 1), Gag p24(253-284) (SEQ. ID NO: 2), Nef(66-97) (SEQ. ID NO: 3), Nef(166-145) (SEQ. ID NO: 4), and Pol(325-355) (SEQ. ID NO: 5).

In another embodiment, the present invention includes an immunogenic composition comprising: one or more dendritic cells (DCs) obtained by culturing monocytes obtained from a blood sample of a human or animal subject in a culture medium comprising granulocyte macrophage colony stimulating factor (GM-CSF) and interferon alpha 2b (IFN-α); a lipopeptide mixture comprising one or more antigenic peptides loaded onto the one or more DCs, wherein the antigenic peptides are Human Immunodeficiency Virus (HIV) antigenic peptides selected from the group consisting of Gag p17(17-35) (SEQ. ID NO: 1), Gag p24(253-284) (SEQ. ID NO: 2), Nef(66-97) (SEQ. ID NO: 3), Nef(166-145) (SEQ. ID NO: 4), and Pol(325-355) (SEQ. ID NO: 5); and lipopolysaccharides for activating the lipopeptide loaded DCs. In one aspect, the HIV antigenic peptides are linked to a lipid by a covalent bond between the C-terminal group of the peptide and a palmitolyl-lysylamide group of the lipid. In another aspect, the composition is used in the treatment of an HIV infection. In yet another aspect the composition is used alone or in combination with one or more anti-viral therapies selected from Highly Active Anti-Retroviral Therapy (HAART), protease inhibitors, reverse transcriptase inhibitors, or nucleotide analogs for the treatment of a HIV infection.

Yet another embodiment of the present invention is a method of making a dendritic cell (DC) vaccine for generating an immune response and for therapy, in a human or animal subject comprising the steps of: obtaining blood from the one or more human or animal subjects, wherein the human or the animal subjects suffer from a disease or a condition against which the immune response and the therapy is desired; isolating monocytes comprising one or more DCs from the blood by an apheresis/elutriation procedure; loading a lipopeptide mixture comprising one or more antigenic peptides onto the DCs, wherein the one or more antigenic peptides are representative of one or more epitopes of the one or more antigenic peptides are implicated or involved in the disease or the condition against which the immune response and the therapy is desired; activating the lipopeptide loaded DCs with a lipopolysaccharide; and harvesting the DC vaccine after activation. In one aspect, the method further comprises the steps of: washing the harvested DC vaccine by centrifugation; resuspending the DCs in a freezing solution in a glass vial or any other suitable container; and freezing the solution contained in the glass vial or in the suitable container. In one aspect, the cytokines comprise granulocyte macrophage colony stimulating factor (GM-CSF) and interferon alpha 2b (IFN-α). In another aspect, the lipopeptide mixture comprises five Human Immunodeficiency Virus (HIV) antigenic peptides. In one aspect, the HIV antigenic peptides are selected from the group consisting of Gag p17(17-35) (SEQ. ID NO: 1), Gag p24(253-284) (SEQ. ID NO: 2), Nef(66-97) (SEQ. ID NO: 3), Nef(166-145) (SEQ. ID NO: 4), and Pol(325-355) (SEQ. ID NO: 5). In another aspect, the HIV antigenic peptides are linked to a lipid by a covalent bond between the C-terminal group of the peptide and a palmitolyl-lysylamide group of a lipid. In another aspect, the DC vaccine is used in the treatment of a HIV infection. In yet another aspect the DC vaccine is used alone or in combination with one or more anti-viral therapies selected from Highly Active AntiRetroviral Therapy (HAART), protease inhibitors, reverse transcriptase inhibitors, or nucleotide analogs for the treatment of a HIV infection. In a related aspect, the human or animal subject is vaccinated once a month for one, two, three, four, five months or as required by the human or animal subject to elicit a therapeutic immune response.

In yet another embodiment, the present invention includes a method of treating a human immunodeficiency virus (HIV) infection in a patient comprising the steps of: identifying a patient in need of treatment of HIV infection; and injecting an immunogenic composition or a vaccine, wherein the immunogenic composition or the vaccine comprises dendritic cells (DCs) loaded with a lipopeptide mixture comprising one, two, three, four, five or more HIV antigenic peptides, wherein the lipopeptide loaded DCs are further activated by lipopolysaccharides. In one aspect, the immunogenic composition or the vaccine is administered once a month for one, two, three, four, five months or as required in the human or animal subject to treat the HIV infection.

In another aspect, the lipopeptide comprises at least five antigenic HIV peptides selected from the group consisting of Gag p17(17-35) (SEQ. ID NO: 1), Gag p24(253-284) (SEQ. ID NO: 2), Nef(66-97) (SEQ. ID NO: 3), Nef(166-145) (SEQ. ID NO: 4), and Pol(325-355) (SEQ. ID NO: 5). In another aspect, the HIV antigenic peptides are linked to a lipid by a covalent bond between the C-terminal group of the peptide and a palmitolyl-lysylamide group of a lipid. In yet another aspect the treatment further optionally comprises one or more anti-viral therapies selected from Highly Active AntiRetroviral Therapy (HAART), protease inhibitors, reverse transcriptase inhibitors, or nucleotide analogs Yet another embodiment of the present invention is a composition made by a method comprising: isolating monocytes comprising one or more DCs from a subject (e.g., from the blood by an apheresis/elutriation procedure); loading a lipopeptide mixture comprising one or more antigenic peptides onto the DCs, wherein the antigenic peptides are representative of one or more epitopes of one or more antigenic peptides are implicated or involved in the disease or the condition against which the immune response, and the therapy is desired; activating the lipopeptide loaded DCs with a lipopolysaccharide; and harvesting the DC vaccine after activation. In one aspect, the lipopeptide comprises at least five antigenic HIV peptides selected from the group consisting of Gag p17(17-35) (SEQ. ID NO: 1), Gag p24 (253-284) (SEQ. ID NO: 2), Nef(66-97) (SEQ. ID NO: 3), Nef(166-145) (SEQ. ID NO: 4), and Pol(325-355) (SEQ. ID NO: 5). In another aspect, the HIV antigenic peptides are linked to a lipid by a covalent bond between the C-terminal group of the peptide and a palmitolyl-lysylamide group of a lipid.

In another embodiment of the present invention, the vaccine described herein is a component of a preventive (prophylactic) vaccine against HIV.

BRIEF DESCRIPTION OF THE DRAWINGS

For a more complete understanding of the features and advantages of the present invention, reference is now made to the detailed description of the invention along with the accompanying figures and in which:

FIG. 3a. DALIA-Plate1. Description Plate1: LIPO5, 15-mers (36 peptides): Gag17 (4 peptides), Gag253 (8 peptides), Nef66 (8 peptides), Nef116 (8 peptides), Pol325 (8 peptides); LIPO5: long peptides or LP (5 peptides): Gag17, Gag253, Nef66, Nef116, Pol325; Unstimulated (3); No LIPO5, 15-mers (34 peptides): Gag p2/p7/p1/p6 Pool1 (11), Pool2 (11), Pool3 (12); CEF (58 peptides): CMV, EBV, FLU peptides Pool1-FLU (21), Pool2-EBV (25), Pool3-CMV (12); CEFT (23 peptides): CMV, EBV, FLU and Tetanus toxoid peptides; SEB (1 mg/ml).

FIG. 3b. DALIA-Plate2. Description Plate 2: LIPO5, 9-mers (56 peptides): Gag17 (6 peptides), Gag253 (13 peptides), Nef66 (13 peptides), Nef116 (12 peptides), Pol325 (12 peptides); Unstimulated (3); SEB (1 mg/ml).

FIG. 4. Multicolor flow panels used to stain Whole Blood samples.

DETAILED DESCRIPTION OF THE INVENTION

Figures 1, 2:
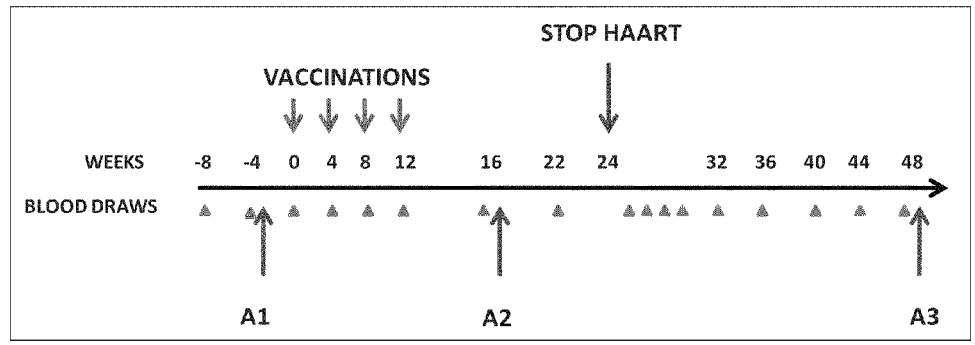
FIG. 1. DALIA vaccination schedule.
FIG. 2. DALIA status.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2d ed. 1994); The Cambridge Dictionary of Science and Technology (Walker ed., 1988); The Glossary of Genetics, 5TH ED., R. Rieger et al. (eds.), Springer Verlag (1991); and Hale & Marham, The Harper Collins Dictionary of Biology (1991).

Various biochemical and molecular biology methods are well known in the art. For example, methods of isolation and purification of nucleic acids are described in detail in WO 97/10365; WO 97/27317; Chapter 3 of Laboratory Techniques in Biochemistry and Molecular Biology: Hybridization with Nucleic Acid Probes, Part I. Theory and Nucleic Acid Preparation, (P. Tijssen, ed.) Elsevier, N.Y. (1993); Sambrook, et al., Molecular Cloning: A Laboratory Manual, Cold Spring Harbor Press, N.Y., (1989); and Current Protocols in Molecular Biology, (Ausubel, F. M. et al., eds.) John Wiley & Sons, Inc., New York (1987-1999), including supplements.

Bioinformatics Definitions

The term "transcriptional profile" refers to the expression levels of a set of genes in a cell in a particular state, particularly by comparison with the expression levels of that same or equivalent set of genes in a cell of the same type in a reference state. The transcriptional profile can be presented as a list of those genes whose expression level is significantly different between the two treatments, and the difference ratios. Differences and similarities between expression levels may also be evaluated and calculated using statistical and clustering methods.

The term "microarray" in the broadest sense refers to a substrate in which specific molecules are densely immobilized in a predetermined region. Examples of the microarray include, for example, a polynucleotide microarray and a protein microarray. The term "polynucleotide microarray" refers to a substrate on which polynucleotides are densely immobilized in each predetermined region. The microarray is well known in the art, for example, U.S. Pat. Nos. 5,445,934 and 5,744,305. The term also includes all the devices so called in Schena (ed.), DNA Microarrays: A Practical Approach (Practical Approach Series), Oxford University Press (1999) (ISBN: 0199637768); Nature Genet. 21 (1) (suppl): 1-60 (1999); and Schena (ed.), Microarray Biochip: Tools and Technology, Eaton Publishing Company/BioTechniques Books Division (2000) (ISBN: 1881299376), the disclosures of which are incorporated herein by reference in their entireties.

As used herein, an "object" refers to any item or information of interest (generally textual, including noun, verb, adjective, adverb, phrase, sentence, symbol, numeric characters, etc.). Therefore, an object is anything that can form a relationship and anything that can be obtained, identified, and/or searched from a source. "Objects" include, but are not limited to, an entity of interest such as gene, protein, disease, phenotype, mechanism, drug, etc. In some aspects, an object may be data, as further described below.

As used herein, a "relationship" refers to the co-occurrence of objects within the same unit (e.g., a phrase, sentence, two or more lines of text, a paragraph, a section of a webpage, a page, a magazine, paper, book, etc.). It may be text, symbols, numbers and combinations, thereof.

As used herein, "meta data content" refers to information as to the organization of text in a data source. Meta data can comprise standard metadata such as Dublin Core metadata or can be collection-specific. Examples of metadata formats include, but are not limited to, Machine Readable Catalog (MARC) records used for library catalogs, Resource Description Format (RDF) and the Extensible Markup Language (XML). Meta objects may be generated manually or through automated information extraction algorithms.

As used herein, an "engine" refers to a program that performs a core or essential function for other programs. For example, an engine may be a central program in an operating system or application program that coordinates the overall operation of other programs. The term "engine" may also refer to a program containing an algorithm that can be changed. For example, a knowledge discovery engine may be designed so that its approach to identifying relationships can be changed to reflect new rules of identifying and ranking relationships.

As used herein, "semantic analysis" refers to the identification of relationships between words that represent similar concepts, e.g., though suffix removal or stemming or by employing a thesaurus. "Statistical analysis" refers to a technique based on counting the number of occurrences of each term (word, word root, word stem, n-gram, phrase, etc.). In collections unrestricted as to subject, the same phrase used in different contexts may represent different concepts. Statistical analysis of phrase co-occurrence can help to resolve word sense ambiguity. "Syntactic analysis" can be used to further decrease ambiguity by part-of-speech analysis. As used herein, one or more of such analyses are referred to more generally as "lexical analysis." "Artificial intelligence (AI)" refers to methods by which a non-human device, such as a computer, performs tasks that humans would deem noteworthy or "intelligent." Examples include identifying pictures, understanding spoken words or written text, and solving problems.

Terms such "data", "dataset" and "information" are often used interchangeably, as are "information" and "knowledge." As used herein, "data" is the most fundamental unit that is an empirical measurement or set of measurements. Data is compiled to contribute to information, but it is fundamentally independent of it and may be combined into a dataset, that is, a set of data. Information, by contrast, is derived from interests, e.g., data (the unit) may be gathered on ethnicity, gender, height, weight and diet for the purpose of finding variables correlated with risk of cardiovascular disease. However, the same data could be used to develop a formula or to create "information" about dietary preferences, i.e., likelihood that certain products in a supermarket have a higher likelihood of selling.

As used herein, the term "database" refers to repositories for raw or compiled data, even if various informational facets can be found within the data fields. A database may include one or more datasets. A database is typically organized so its contents can be accessed, managed, and updated (e.g., the database is dynamic). The term "database" and "source" are also used interchangeably in the present invention, because primary sources of data and information are databases. However, a "source database" or "source data" refers in general to data, e.g., unstructured text and/or structured data that are input into the system for identifying objects and determining relationships. A source database may or may not be a relational database. However, a system database usually includes a relational database or some equivalent type of database which stores values relating to relationships between objects.

As used herein, a "system database" and "relational database" are used interchangeably and refer to one or more collections of data organized as a set of tables containing data fitted into predefined categories. For example, a database table may comprise one or more categories defined by columns (e.g. attributes), while rows of the database may contain a unique object for the categories defined by the columns. Thus, an object such as the identity of a gene might have columns for its presence, absence and/or level of expression of the gene. A row of a relational database may also be referred to as a "set" and is generally defined by the values of its columns. A "domain" in the context of a relational database is a range of valid values a field such as a column may include.

As used herein, a "domain of knowledge" refers to an area of study over which the system is operative, for example, all biomedical data. It should be pointed out that there is advantage to combining data from several domains, for example, biomedical data and engineering data, for this diverse data can sometimes link things that cannot be put together for a normal person that is only familiar with one area or research/study (one domain). A "distributed database" refers to a database that may be dispersed or replicated among different points in a network.

As used herein, "information" refers to a data set that may include numbers, letters, sets of numbers, sets of letters, or conclusions resulting or derived from a set of data. "Data" is then a measurement or statistic and the fundamental unit of information. "Information" may also include other types of data such as words, symbols, text, such as unstructured free text, code, etc. "Knowledge" is loosely defined as a set of information that gives sufficient understanding of a system to model cause and effect. To extend the previous example, information on demographics, gender and prior purchases may be used to develop a regional marketing strategy for food sales while information on nationality could be used by buyers as a guideline for importation of products. It is important to note that there are no strict boundaries between data, information, and knowledge; the three terms are, at times, considered to be equivalent. In general, data comes from examining, information comes from correlating, and knowledge comes from modeling.

As used herein, "a program" or "computer program" refers generally to a syntactic unit that conforms to the rules of a particular programming language and that is composed of declarations and statements or instructions, divisible into, "code segments" needed to solve or execute a certain function, task, or problem. A programming language is generally an artificial language for expressing programs.

As used herein, a "system" or a "computer system" generally refers to one or more computers, peripheral equipment, and software that perform data processing. A "user" or "system operator" in general includes a person, that uses a computer network accessed through a "user device" (e.g., a computer, a wireless device, etc) for the purpose of data processing and information exchange. A "computer" is generally a functional unit that can perform substantial computations, including numerous arithmetic operations and logic operations without human intervention.

As used herein, "application software" or an "application program" refers generally to software or a program that is specific to the solution of an application problem. An "application problem" is generally a problem submitted by an end user and requiring information processing for its solution.

As used herein, a "natural language" refers to a language whose rules are based on current usage without being specifically prescribed, e.g., English, Spanish or Chinese. As used herein, an "artificial language" refers to a language whose rules are explicitly established prior to its use, e.g., computer-programming languages such as C, C++, Java, BASIC, FORTRAN, or COBOL.

As used herein, "statistical relevance" refers to using one or more of the ranking schemes (O/E ratio, strength, etc.), where a relationship is determined to be statistically relevant if it occurs significantly more frequently than would be expected by random chance.

As used herein, the terms "coordinately regulated genes" or "transcriptional modules" are used interchangeably to refer to grouped, gene expression profiles (e.g., signal values associated with a specific gene sequence) of specific genes. Each transcriptional module correlates two key pieces of data: (2) a literature search portion and (2) the actual empirical gene expression value data obtained from a gene microarray. The set of genes that is selected into a transcriptional module that is based on the analysis of gene expression data (module extraction algorithm described above). Additional steps are taught by Chaussabel, D. & Sher, A. Mining microarray expression data by literature profiling. Genome Biol 3, RESEARCH 0055 (2002), (see, e.g., the following website genomebiology.com/2002/3/10/research/0055) relevant portions incorporated herein by reference and expression data obtained from a disease or condition of interest, e.g., infectious diseases, systemic Lupus erythematosus, arthritis, lymphoma, carcinoma, melanoma, acute infection, autoimmune disorders, autoinflammatory disorders, etc.).

The Table below lists examples of keywords that were used to develop the literature search portion or contribution to the transcription modules and the genes that are part of the modules. The skilled artisan will recognize that other terms may easily be selected for other conditions, e.g., specific cancers, specific infectious disease, transplantation, etc. For example, genes and signals for those genes associated with T cell activation are described hereinbelow as Module ID "M 2.8" in which certain keywords (e.g., Lymphoma, T-cell, CD4, CD8, TCR, Thymus, Lymphoid, IL2) were used to identify key T-cell associated genes, e.g., T-cell surface markers (CD5, CD6, CD7, CD26, CD28, CD96); molecules expressed by lymphoid lineage cells (lymphotoxin beta, IL2-inducible T-cell kinase, TCF7; and T-cell differentiation protein mal, GATA3, STAT5B). Next, the complete module is developed by correlating data from a patient population for these genes (regardless of platform, presence/absence and/or up or down-regulation) to generate the transcriptional module. In some cases, the gene profile does not match (at this time) any particular clustering of genes for these disease conditions and data, however, certain physiological pathways (e.g., cAMP signaling, zinc-finger proteins, cell surface markers, etc.) are found within the "Underdetermined" modules. In fact, the gene expression data set may be used to extract genes that have coordinated expression prior to matching to the keyword search, i.e., either data set may be correlated prior to cross-referencing with the second data set. The skilled artisan will recognize that each module will include genes that are upregulated or down-regulated, however, the overall score for each module will be the sum of overexpression and under-expression of the various genes, which leads to a composite final over-expression or under-expression of all the genes in the module. The module summaries provided herein show the final overall expression (over, under or neither) for each patient in each of the categories.

TABLE 1

Transcriptional Modules

| Module I.D. | Example Keyword selection | Gene Profile Assessment |
| --- | --- | --- |
| M 1.1 | Ig, Immunoglobulin, Bone, Marrow, PreB, IgM, Mu. | Plasma cells: Includes genes encoding for Immunoglobulin chains (e.g. IGHM, IGJ, IGLL1, IGKC, IGHD) and the plasma cell marker CD38. |

TABLE 1-continued

Transcriptional Modules

| Module I.D. | Example Keyword selection | Gene Profile Assessment |
|---|---|---|
| M 1.2 | Platelet, Adhesion, Aggregation, Endothelial, Vascular | Platelets: Includes genes encoding for platelet glycoproteins (ITGA2B, ITGB3, GP6, GP1A/B), and platelet-derived immune mediators such as PPPB (pro-platelet basic protein) and PF4 (platelet factor 4). |
| M 1.3 | Immunoreceptor, BCR, B-cell, IgG | B-cells: Includes genes encoding for B-cell surface markers (CD72, CD79A/B, CD19, CD22) and other B-cell associated molecules: Early B-cell factor (EBF), B-cell linker (BLNK) and B lymphoid tyrosine kinase (BLK). |
| M 1.4 | Replication, Repression, Repair, CREB, Lymphoid, TNF-alpha | Undetermined. This set includes regulators and targets of cAMP signaling pathway (JUND, ATF4, CREM, PDE4, NR4A2, VIL2), as well as repressers of TNF-alpha mediated NF-KB activation (CYLD, ASK, TNFAIP3). |
| M 1.5 | Monocytes, Dendritic, MHC, Costimulatory, TLR4, MYD88 | Myeloid lineage: Includes molecules expressed by cells of the myeloid lineage (CD86, CD163, FCGR2A), some of which being involved in pathogen recognition (CD14, TLR2, MYD88). This set also includes TNF family members (TNFR2, BAFF). |
| M 1.6 | Zinc, Finger, P53, RAS | Undetermined. This set includes genes encoding for signaling molecules, e.g., the zinc finger containing inhibitor of activated STAT (PIAS1 and PIAS2), or the nuclear factor of activated T-cells NFATC3. |
| M 1.7 | Ribosome, Translational, 40S, 60S, HLA | MHC/Ribosomal proteins: Almost exclusively formed by genes encoding MHC class I molecules (HLA-A, B, C, G, E) + Beta 2-microglobulin (B2M) or Ribosomal proteins (RPLs, RPSs). |
| M 1.8 | Metabolism, Biosynthesis, Replication, Helicase | Undetermined. Includes genes encoding metabolic enzymes (GLS, NSF1, NAT1) and factors involved in DNA replication (PURA, TERF2, EIF2S1). |
| M 2.1 | NK, Killer, Cytolytic, CD8, Cell-mediated, T-cell, CTL, IFN-g | Cytotoxic cells: Includes cytotoxic T-cells and NK-cells surface markers (CD8A, CD2, CD160, NKG7, KLRs), cytolytic molecules (granzyme, perforin, granulysin), chemokines (CCL5, XCL1) and CTL/NK-cell associated molecules (CTSW). |
| M 2.2 | Granulocytes, Neutrophils, Defense, Myeloid, Marrow | Neutrophils: This set includes innate molecules that are found in neutrophil granules (Lactotransferrin: LTF, defensin: DEAF1, Bacterial Permeability Increasing protein: BPI, Cathelicidin antimicrobial protein: CAMP). |
| M 2.3 | Erythrocytes, Red, Anemia, Globin, Hemoglobin | Erythrocytes: Includes hemoglobin genes (HGBs) and other erythrocyte-associated genes (erythrocytic alkirin: ANK1, Glycophorin C: GYPC, hydroxymethylbilane synthase: HMBS, erythroid associated factor: ERAF). |
| M 2.4 | Ribonucleoprotein, 60S, nucleolus, Assembly, Elongation | Ribosomal proteins: Including genes encoding ribosomal proteins (RPLs, RPSs), Eukaryotic Translation Elongation factor family members (EEFs) and Nucleolar proteins (NPM1, NOAL2, NAP1L1). |
| M 2.5 | Adenoma, Interstitial, Mesenchyme, Dendrite, Motor | Undetermined. This module includes genes encoding immune-related (CD40, CD80, CXCL12, IFNA5, IL4R) as well as cytoskeleton-related molecules (Myosin, Dedicator of Cytokenesis, Syndecan 2, Plexin C1, Distrobrevin). |
| M 2.6 | Granulocytes, Monocytes, Myeloid, ERK, Necrosis | Myeloid lineage: Related to M 1.5. Includes genes expressed in myeloid lineage cells (IGTB2/CD18, Lymphotoxin beta receptor, Myeloid related proteins 8/14 Formyl peptide receptor 1), such as Monocytes and Neutrophils: |
| M 2.7 | No keywords extracted. | Undetermined. This module is largely composed of transcripts with no known function. Only 20 genes associated with literature, including a member of the chemokine-like factor superfamily (CKLFSF8). |
| M 2.8 | Lymphoma, T-cell, CD4, CD8, TCR, Thymus, Lymphoid, IL2 | T-cells: Includes T-cell surface markers (CD5, CD6, CD7, CD26, CD28, CD96) and molecules expressed by lymphoid lineage cells (lymphotoxin beta, IL2-inducible T-cell kinase, TCF7, T-cell differentiation protein mal, GATA3, STAT5B). |
| M 2.9 | ERK, Transactivation, Cytoskeletal, MAPK, JNK | Undetermined. Includes genes encoding molecules that associate to the cytoskeleton (Actin related protein 2/3, MAPK1, MAP3K1, RAB5A). Also present are T-cell expressed genes (FAS, ITGA4/CD49D, ZNF1A1). |
| M 2.10 | Myeloid, Macrophage, Dendritic, Inflammatory, Interleukin | Undetermined. Includes genes encoding for Immune -related cell surface molecules (CD36, CD86, LILRB), cytokines (IL15) and molecules involved in signaling pathways (FYB, TICAM2-Toll-like receptor pathway). |
| M 2.11 | Replication, Repress, RAS, Autophosphorylation, Oncogenic | Undetermined. Includes kinases (UHMK1, CSNK1G1, CDK6, WNK1, TAOK1, CALM2, PRKCI, ITPKB, SRPK2, STK17B, DYRK2, PIK3R1, STK4, CLK4, PKN2) and RAS family members (G3BP, RAB14, RASA2, RAP2A, KRAS). |
| M 3.1 | ISRE, Influenza, Antiviral, IFN-gamma, IFN-alpha, Interferon | Interferon-inducible: This set includes interferon-inducible genes: antiviral molecules (OAS1/2/3/L, GBP1, G1P2, EIF2AK2/PKR, MX1, PML), chemokines (CXCL10/IP-10), signaling molecules (STAT1, STAt2, IRF7, ISGF3G). |

TABLE 1-continued

Transcriptional Modules

| Module I.D. | Example Keyword selection | Gene Profile Assessment |
|---|---|---|
| M 3.2 | TGF-beta, TNF, Inflammatory, Apoptotic, Lipopolysaccharide | Inflammation I: Includes genes encoding molecules involved in inflammatory processes (e.g., IL8, ICAM1, C5R1, CD44, PLAUR, IL1A, CXCL16), and regulators of apoptosis (MCL1, FOXO3A, RARA, BCL3/6/2A1, GADD45B). |
| M 3.3 | Granulocyte, Inflammatory, Defense, Oxidize, Lysosomal | Inflammation II: Includes molecules inducing or inducible by Granulocyte-Macrophage CSF (SPI1, IL18, ALOX5, ANPEP), as well as lysosomal enzymes (PPT1, CTSB/S, CES1, NEU1, ASAH1, LAMP2, CAST). |
| M 3.4 | No keyword extracted | Undetermined. Includes protein phosphates (PPP1R12A, PTPRC, PPP1CB, PPM1B) and phosphoinositide 3-kinase (PI3K) family members (PIK3CA, PIK32A, PIP5K3). |
| M 3.5 | No keyword extracted | Undetermined. Composed of only a small number of transcripts. Includes hemoglobin genes (HBA1, HBA2, HBB). |
| M 3.6 | Complement, Host, Oxidative, Cytoskeletal, T-cell | Undetermined. Large set that includes T-cell surface markers (CD101, CD102, CD103) as well as molecules ubiquitously expressed among blood leukocytes (CXRCR1: fraktalkine receptor, CD47, P-selectin ligand). |
| M 3.7 | Spliceosome, Methylation, Ubiquitin, Beta-catenin | Undetermined. Includes genes encoding proteasome subunits (PSMA2/5, PSMB5/8); ubiquitin protein ligases HIP2, STUB1, as well as components of ubiqutin ligase complexes (SUGT1). |
| M 3.8 | CDC, TCR, CREB, Glycosylase | Undetermined. Includes genes encoding for several enzymes: aminomethyltransferase, arginyltransferase, asparagines synthetase, diacylglycerol kinase, inositol phosphatases, methyltransferases, helicases . . . |
| M 3.9 | Chromatin, Checkpoint, Replication, Transactivation | Undetermined. Includes genes encoding for protein kinases (PRKPIR, PRKDC, PRKCI) and phosphatases (e.g., PTPLB, PPP1R8/2CB). Also includes RAS oncogene family members and the NK cell receptor 2B4 (CD244). |

As used herein, the term "array" refers to a solid support or substrate with one or more peptides or nucleic acid probes attached to the support. Arrays typically have one or more different nucleic acid or peptide probes that are coupled to a surface of a substrate in different, known locations. These arrays, also described as "microarrays" or "gene-chips" that may have 10,000; 20,000, 30,000; or 40,000 different identifiable genes based on the known genome, e.g., the human genome. These pan-arrays are used to detect the entire "transcriptome" or transcriptional pool of genes that are expressed or found in a sample, e.g., nucleic acids that are expressed as RNA, mRNA and the like that may be subjected to RT and/or RT-PCR to made a complementary set of DNA replicons. Arrays may be produced using mechanical synthesis methods, light directed synthesis methods and the like that incorporate a combination of non-lithographic and/or photolithographic methods and solid phase synthesis methods.

Various techniques for the synthesis of these nucleic acid arrays have been described, e.g., fabricated on a surface of virtually any shape or even a multiplicity of surfaces. Arrays may be peptides or nucleic acids on beads, gels, polymeric surfaces, fibers such as fiber optics, glass or any other appropriate substrate. Arrays may be packaged in such a manner as to allow for diagnostics or other manipulation of an all inclusive device, see for example, U.S. Pat. No. 6,955,788, relevant portions incorporated herein by reference.

As used herein, the term "disease" refers to a physiological state of an organism with any abnormal biological state of a cell. Disease includes, but is not limited to, an interruption, cessation or disorder of cells, tissues, body functions, systems or organs that may be inherent, inherited, caused by an infection, caused by abnormal cell function, abnormal cell division and the like. A disease that leads to a "disease state" is generally detrimental to the biological system, that is, the host of the disease. With respect to the present invention, any biological state, such as an infection (e.g., viral, bacterial, fungal, helminthic, etc.), inflammation, autoinflammation, autoimmunity, anaphylaxis, allergies, premalignancy, malignancy, surgical, transplantation, physiological, and the like that is associated with a disease or disorder is considered to be a disease state. A pathological state is generally the equivalent of a disease state.

Disease states may also be categorized into different levels of disease state. As used herein, the level of a disease or disease state is an arbitrary measure reflecting the progression of a disease or disease state as well as the physiological response upon, during and after treatment. Generally, a disease or disease state will progress through levels or stages, wherein the affects of the disease become increasingly severe. The level of a disease state may be impacted by the physiological state of cells in the sample.

As used herein, the terms "therapy" or "therapeutic regimen" refer to those medical steps taken to alleviate or alter a disease state, e.g., a course of treatment intended to reduce or eliminate the affects or symptoms of a disease using pharmacological, surgical, dietary and/or other techniques. A therapeutic regimen may include a prescribed dosage of one or more drugs or surgery. Therapies will most often be beneficial and reduce the disease state but in many instances the effect of a therapy will have non-desirable or side-effects. The effect of therapy will also be impacted by the physiological state of the host, e.g., age, gender, genetics, weight, other disease conditions, etc.

As used herein, the term "pharmacological state" or "pharmacological status" refers to those samples that will be, are and/or were treated with one or more drugs, surgery and the like that may affect the pharmacological state of one or more nucleic acids in a sample, e.g., newly transcribed, stabilized and/or destabilized as a result of the pharmacological intervention. The pharmacological state of a sample relates to changes in the biological status before, during and/or after drug treatment and may serve a diagnostic or prognostic function, as taught herein. Some changes following drug treatment or surgery may be relevant to the disease state and/or may be unrelated side-effects of the therapy. Changes in the pharmacological state are the likely results of the duration of therapy, types and doses of drugs prescribed, degree of compliance with a given course of therapy, and/or un-prescribed drugs ingested.

As used herein, the term "biological state" refers to the state of the transcriptome (that is the entire collection of RNA transcripts) of the cellular sample isolated and purified for the analysis of changes in expression. The biological state reflects the physiological state of the cells in the sample by measuring the abundance and/or activity of cellular constituents, characterizing according to morphological phenotype or a combination of the methods for the detection of transcripts.

As used herein, the term "expression profile" refers to the relative abundance of RNA, DNA or protein abundances or activity levels. The expression profile can be a measurement for example of the transcriptional state or the translational state by any number of methods and using any of a number of gene-chips, gene arrays, beads, multiplex PCR, quantitative PCR, run-on assays, Northern blot analysis, Western blot analysis, protein expression, fluorescence activated cell sorting (FACS), enzyme linked immunosorbent assays (ELISA), chemiluminescence studies, enzymatic assays, proliferation studies or any other method, apparatus and system for the determination and/or analysis of gene expression that are readily commercially available.

As used herein, the term "transcriptional state" of a sample includes the identities and relative abundances of the RNA species, especially mRNAs present in the sample. The entire transcriptional state of a sample, that is the combination of identity and abundance of RNA, is also referred to herein as the transcriptome. Generally, a substantial fraction of all the relative constituents of the entire set of RNA species in the sample are measured.

As used herein, the term "modular transcriptional vectors" refers to transcriptional expression data that reflects the "proportion of differentially expressed genes." For example, for each module the proportion of transcripts differentially expressed between at least two groups (e.g. healthy subjects vs patients). This vector is derived from the comparison of two groups of samples. The first analytical step is used for the selection of disease-specific sets of transcripts within each module. Next, there is the "expression level." The group comparison for a given disease provides the list of differentially expressed transcripts for each module. It was found that different diseases yield different subsets of modular transcripts. With this expression level it is then possible to calculate vectors for each module(s) for a single sample by averaging expression values of disease-specific subsets of genes identified as being differentially expressed. This approach permits the generation of maps of modular expression vectors for a single sample, e.g., those described in the module maps disclosed herein. These vector module maps represent an averaged expression level for each module (instead of a proportion of differentially expressed genes) that can be derived for each sample.

Using the present invention it is possible to identify and distinguish diseases not only at the module-level, but also at the gene-level; i.e., two diseases can have the same vector (identical proportion of differentially expressed transcripts, identical "polarity"), but the gene composition of the vector can still be disease-specific. Gene-level expression provides the distinct advantage of greatly increasing the resolution of the analysis. Furthermore, the present invention takes advantage of composite transcriptional markers. As used herein, the term "composite transcriptional markers" refers to the average expression values of multiple genes (subsets of modules) as compared to using individual genes as markers (and the composition of these markers can be disease-specific). The composite transcriptional markers approach is unique because the user can develop multivariate microarray scores to assess disease severity in patients with, e.g., SLE, or to derive expression vectors disclosed herein. Most importantly, it has been found that using the composite modular transcriptional markers of the present invention the results found herein are reproducible across microarray platform, thereby providing greater reliability for regulatory approval.

Gene expression monitoring systems for use with the present invention may include customized gene arrays with a limited and/or basic number of genes that are specific and/or customized for the one or more target diseases. Unlike the general, pan-genome arrays that are in customary use, the present invention provides for not only the use of these general pan-arrays for retrospective gene and genome analysis without the need to use a specific platform, but more importantly, it provides for the development of customized arrays that provide an optimal gene set for analysis without the need for the thousands of other, non-relevant genes. One distinct advantage of the optimized arrays and modules of the present invention over the existing art is a reduction in the financial costs (e.g., cost per assay, materials, equipment, time, personnel, training, etc.), and more importantly, the environmental cost of manufacturing pan-arrays where the vast majority of the data is irrelevant. The modules of the present invention allow for the first time the design of simple, custom arrays that provide optimal data with the least number of probes while maximizing the signal to noise ratio. By eliminating the total number of genes for analysis, it is possible to, e.g., eliminate the need to manufacture thousands of expensive platinum masks for photolithography during the manufacture of pan-genetic chips that provide vast amounts of irrelevant data. Using the present invention it is possible to completely avoid the need for microarrays if the limited probe set(s) of the present invention are used with, e.g., digital optical chemistry arrays, ball bead arrays, beads (e.g., Luminex), multiplex PCR, quantitative PCR, run-on assays, Northern blot analysis, or even, for protein analysis, e.g., Western blot analysis, 2-D and 3-D gel protein expression, MALDI, MALDI-TOF, fluorescence activated cell sorting (FACS) (cell surface or intracellular), enzyme linked immunosorbent assays (ELISA), chemiluminescence studies, enzymatic assays, proliferation studies or any other method, apparatus and system for the determination and/or analysis of gene expression that are readily commercially available.

The "molecular fingerprinting system" of the present invention may be used to facilitate and conduct a comparative analysis of expression in different cells or tissues, different subpopulations of the same cells or tissues, different physiological states of the same cells or tissue, different developmental stages of the same cells or tissue, or different cell populations of the same tissue against other diseases and/or normal cell controls. In some cases, the normal or wild-type expression data may be from samples analyzed at or about the same time or it may be expression data obtained or culled from existing gene array expression databases, e.g., public databases such as the NCBI Gene Expression Omnibus database.

As used herein, the term "differentially expressed" refers to the measurement of a cellular constituent (e.g., nucleic acid, protein, enzymatic activity and the like) that varies in two or more samples, e.g., between a disease sample and a normal sample. The cellular constituent may be on or off (present or absent), upregulated relative to a reference or down-regulated relative to the reference. For use with gene-chips or gene-arrays, differential gene expression of nucleic acids, e.g., mRNA or other RNAs (miRNA, siRNA, hnRNA, rRNA, tRNA, etc.) may be used to distinguish between cell types or nucleic acids. Most commonly, the measurement of the transcriptional state of a cell is accomplished by quantitative reverse transcriptase (RT) and/or quantitative reverse transcriptase-polymerase chain reaction (RT-PCR), genomic expression analysis, post-translational analysis, modifications to genomic DNA, translocations, in situ hybridization and the like.

For some disease states it is possible to identify cellular or morphological differences, especially at early levels of the disease state. The present invention avoids the need to identify those specific mutations or one or more genes by looking at modules of genes of the cells themselves or, more importantly, of the cellular RNA expression of genes from immune effector cells that are acting within their regular physiologic context, that is, during immune activation, immune tolerance or even immune energy. While a genetic mutation may result in a dramatic change in the expression levels of a group of genes, biological systems often compensate for changes by altering the expression of other genes. As a result of these internal compensation responses, many perturbations may have minimal effects on observable phenotypes of the system but profound effects to the composition of cellular constituents. Likewise, the actual copies of a gene transcript may not increase or decrease, however, the longevity or half-life of the transcript may be affected leading to greatly increases protein production. The present invention eliminates the need of detecting the actual message by, in one embodiment, looking at effector cells (e.g., leukocytes, lymphocytes and/or sub-populations thereof) rather than single messages and/or mutations.

The skilled artisan will appreciate readily that samples may be obtained from a variety of sources including, e.g., single cells, a collection of cells, tissue, cell culture and the like. In certain cases, it may even be possible to isolate sufficient RNA from cells found in, e.g., urine, blood, saliva, tissue or biopsy samples and the like. In certain circumstances, enough cells and/or RNA may be obtained from: mucosal secretion, feces, tears, blood plasma, peritoneal fluid, interstitial fluid, intradural, cerebrospinal fluid, sweat or other bodily fluids. The nucleic acid source, e.g., from tissue or cell sources, may include a tissue biopsy sample, one or more sorted cell populations, cell culture, cell clones, transformed cells, biopies or a single cell. The tissue source may include, e.g., brain, liver, heart, kidney, lung, spleen, retina, bone, neural, lymph node, endocrine gland, reproductive organ, blood, nerve, vascular tissue, and olfactory epithelium.

The present invention includes the following basic components, which may be used alone or in combination, namely, one or more data mining algorithms; one or more module-level analytical processes; the characterization of blood leukocyte transcriptional modules; the use of aggregated modular data in multivariate analyses for the molecular diagnostic/prognostic of human diseases; and/or visualization of module-level data and results. Using the present invention it is also possible to develop and analyze composite transcriptional markers, which may be further aggregated into a single multivariate score.

An explosion in data acquisition rates has spurred the development of mining tools and algorithms for the exploitation of microarray data and biomedical knowledge. Approaches aimed at uncovering the modular organization and function of transcriptional systems constitute promising methods for the identification of robust molecular signatures of disease. Indeed, such analyses can transform the perception of large scale transcriptional studies by taking the conceptualization of microarray data past the level of individual genes or lists of genes.

The present inventors have recognized that current microarray-based research is facing significant challenges with the analysis of data that are notoriously "noisy," that is, data that is difficult to interpret and does not compare well across laboratories and platforms. A widely accepted approach for the analysis of microarray data begins with the identification of subsets of genes differentially expressed between study groups. Next, the users try subsequently to "make sense" out of resulting gene lists using pattern discovery algorithms and existing scientific knowledge.

Rather than deal with the great variability across platforms, the present inventors have developed a strategy that emphasized the selection of biologically relevant genes at an early stage of the analysis. Briefly, the method includes the identification of the transcriptional components characterizing a given biological system for which an improved data mining algorithm was developed to analyze and extract groups of coordinately expressed genes, or transcriptional modules, from large collections of data.

The present invention describes an autologous dendritic cell (DC) vaccine product derived by culturing the patient's monocytes with granulocyte macrophage colony stimulating factor (GM-CSF) and interferon alpha 2b (IFN-α), loading the DC with a mixture of five lipopeptides of Gag, Nef and Pol HIV antigens, and then activating the DC with lipopolysaccharide (LPS). These dendritic cells are commonly referred to as IFNα DCs loaded with the five HIV peptides or 5-HIV lipopeptides. The present invention may be used alone or in conjunction with other anti-viral therapies, e.g., Highly Active AntiRetroviral Therapy (HAART), protease inhibitors, reverse transcriptase inhibitors, nucleotide analogs.

As used herein, the terms "Ag" or "antigen" refer to a substance capable of either binding to an antigen binding region of an immunoglobulin molecule or of eliciting an immune response, e.g., a T cell-mediated immune response by the presentation of the antigen on Major Histocompatibility Antigen (MHC) cellular proteins. As used herein, "antigen" includes, but is not limited to, antigenic determinants, haptens, and immunogens, which may be peptides, small molecules, carbohydrates, lipids, nucleic acids or combinations thereof. The skilled immunologist will recognize that when discussing antigens that are processed for presentation to T cells, the term "antigen" refers to those portions of the antigen (e.g., a peptide fragment) that is a T cell epitope presented by MHC to the T cell receptor. When used in the context of a B cell mediated immune response in the form of an antibody that is specific for an "antigen", the portion of the antigen that binds to the complementarity determining regions of the variable domains of the antibody (light and heavy) the bound portion may be a linear or three-dimensional epitope.

As used herein, the term "antigenic peptide" refers to that portion of a polypeptide antigen that is specifically recognized by either B-cells or T-cells. B-cells respond to foreign antigenic determinants via antibody production, whereas T-lymphocytes mediate cellular immunity. Thus, antigenic peptides are those parts of an antigen that are recognized by antibodies, or in the context of an MHC, by T-cell receptors.

As used herein, the term "pulsing" refers to dendritic cells (DCs) are activated by antigens that enter into the MHC class II and/or MHC class I processing pathway. DCs may be loaded with antigen by a variety of methods, e.g., those described by Fong L. and Engleman E G. Dendritic Cells in Cancer Immunotherapy. Annu Rev. Immunol. 2000, relevant portions incorporated herein by reference.

As used herein, the term "antigen loading" refers to a method of delivering to dendritic cells antigens by incubating dendritic cells or progenitor cells with the peptide, polypeptide, lipopeptide, DNA (naked or within a plasmid vector) or RNA; or with antigen-expressing recombinant bacterium or viruses (e.g., vaccinia, adenovirus or lentivirus) such that the antigenic epitopes thereof are loaded and expressed on the cell surface by MHC.

As used herein, the term "epitope" refers to any protein determinant capable of specific binding to an immunoglobulin or of being presented by a Major Histocompatibility Complex (MHC) protein (e.g., Class I or Class II) to a T-cell receptor. Epitopic determinants are generally short peptides 5-30 amino acids long that fit within the groove of the MHC molecule that presents certain amino acid side groups toward the T cell receptor and has certain other residues in the groove, e.g., due to specific charge characteristics of the groove, the peptide side groups and the T cell receptor. Generally, an antibody specifically binds to an antigen when the dissociation constant is 1 mM, 100 nM or even 10 nM.

As used herein, the term "vector" is used in two different contexts. When using the term "vector" with reference to a vaccine, a vector is used to describe a non-antigenic portion that is used to direct or deliver the antigenic portion of the vaccine. For example, an antibody or fragments thereof may be bound to or form a fusion protein with the antigen that elicits the immune response. For cellular vaccines, the vector for delivery and/or presentation of the antigen is the antigen presenting cell, which is delivered by the cell that is loaded with antigen. In certain cases, the cellular vector itself may also process and present the antigen(s) to T cells and activate an antigen-specific immune response. When used in the context of nucleic acids, a "vector" refers a construct that is capable of delivering, and preferably expressing, one or more genes or polynucleotide sequences of interest in a host cell. Examples of vectors include, but are not limited to, viral vectors, naked DNA or RNA expression vectors, DNA or RNA expression vectors associated with cationic condensing agents, DNA or RNA expression vectors encapsulated in liposomes, and certain eukaryotic cells, such as producer cells.

As used herein, "polynucleotide" or "nucleic acid" refers to a strand of deoxyribonucleotides or ribonucleotides in either a single- or a double-stranded form (including known analogs of natural nucleotides). A double-stranded nucleic acid sequence will include the complementary sequence.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "domain," or "polypeptide domain" refers to that sequence of a polypeptide that folds into a single globular region in its native conformation, and that may exhibit discrete binding or functional properties.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3-5 amino acids, preferably at least 4-7 amino acids, more preferably at least 8-10 amino acids, and even more preferably at least 11-15 amino acids, or which is immunologically identifiable with a polypeptide encoded in the sequence. This terminology also includes a polypeptide expressed from a designated nucleic acid sequence.

As used herein, "pharmaceutically acceptable carrier" refers to any material that when combined with the vaccine of the present invention allows the vaccine to retain biological activity and is generally non-reactive with the subject's immune system. Examples include, but are not limited to, standard pharmaceutical carriers such as a phosphate buffered saline solution, water, emulsions such as an oil/water emulsion, and various types of wetting agents. Certain diluents may be used with the present invention, e.g., for aerosol or parenteral administration, that may be phosphate buffered saline or normal (0.85%) saline.

As used herein, the term "epitope" refers to a molecule or substance capable of stimulating an immune response. In one example, epitopes include but are not limited to a polypeptide and a nucleic acid encoding a polypeptide, wherein expression of the nucleic acid into a polypeptide is capable of stimulating an immune response when the polypeptide is processed and presented on a Major Histocompatibility Complex (MHC) molecule. Generally, epitopes include peptides presented on the surface of cells non-covalently bound to the binding groove of Class I or Class II MHC, such that they can interact with T cell receptors and the respective T cell accessory molecules.

Proteolytic Processing of Antigens. Epitopes that are displayed by MHC on antigen presenting cells are cleavage peptides or products of larger peptide or protein antigen precursors. For MHC I epitopes, protein antigens are often digested by proteasomes resident in the cell. Intracellular proteasomal digestion produces peptide fragments of about 3 to 23 amino acids in length that are then loaded onto the MHC protein. Additional proteolytic activities within the cell, or in the extracellular milieu, can trim and process these fragments further. Processing of MHC Class II epitopes generally occurs via intracellular proteases from the lysosomal/endosomal compartment. The present invention includes, in one embodiment, pre-processed peptides that are attached to the anti-CD40 antibody (or fragment thereof) that directs the peptides against which an enhanced immune response is sought directly to antigen presenting cells.

Antigenic targets that may be delivered using the vaccines of the present invention include antigens such as viral antigens, bacterial antigens, fungal antigens or parasitic antigens. Pathogens include trypanosomes, tapeworms, roundworms, helminthes, malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long-term expression of the transgene, for which a strong immune response would be desired. In some cases, vaccination of an individual may only be required infrequently, such as yearly or biennially, and provide long-term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Bacterial antigens for use with the vaccines disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, Mycobacterium tuberculosis bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *haemophilus influenza* bacterial antigens such as capsular polysaccharides and other *haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: haemophilus influenza; Plasmodium falciparum; neisseria meningitidis; streptococcus pneumoniae; neisseria gonorrhoeae; salmonella serotype typhi; shigella; vibrio cholerae; Dengue Fever; Encephalitides; Japanese Encephalitis; lyme disease; Yersinia pestis; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, e.g., plasmodium falciparum antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components.

As used herein, the term "Lipopolysaccharide" refers to large molecules that comprise a lipid and a polysaccharide joined by a covalent bond and are generally found in the outer membrane of Gram-negative bacteria. Lipopolysaccharides for use with the present invention include those that act as endotoxins and/or elicit strong immune responses in an animal.

The vaccines are administered in a manner compatible with the dosage formulation, and in such amount as will be therapeutically effective and immunogenic. The quantity to be administered depends on the subject to be treated, including, e.g., the capacity of the individual's immune system to generate an immune response. Precise amounts of cells or active ingredient required to be administered depend on the judgment of the practitioner. However, suitable dosage ranges are of the order of a few thousand cells (to millions of cells) for cellular vaccines. For standard epitope or epitope delivery vaccines then the vaccine may be several hundred micrograms active ingredient per vaccination. Suitable regimes for initial administration and booster shots are also variable, but are typified by an initial administration followed by subsequent inoculations or other administrations.

The manner of application may vary widely, however, certain embodiments herein will most likely be delivered intravenously, subcutaneously, peritoneally, intramuscularly and vaginally or at the site of a tumor or infection directly. Regardless, any of the conventional methods for administration of a vaccine are applicable. The dosage of the vaccine will depend on the route of administration and will vary according to the size of the host.

In many instances, it will be desirable to have multiple administrations of the vaccine, e.g., four to six vaccinations provided weekly or every other week. A normal vaccination regimen will often occur in two to twelve week intervals or from three to six week intervals. Periodic boosters at intervals of 1-5 years, usually three years, may be desirable to maintain protective levels of the immune response or upon a likelihood of a remission or re-infection. The course of the immunization may be followed by assays for, e.g., T cell activation, cytokine secretion or even antibody production, most commonly conducted in vitro. These immune response assays are well known and may be found in a wide variety of patents and as taught herein.

The vaccine of the present invention may be provided in one or more "unit doses". Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The three key components of the vaccine of the present invention are:

I. DC vaccine generated from monocytes by culturing in the presence of GM-CSF and IFN-α (IFN-DCs), which demonstrate powerful priming functions in vitro. The in vivo activity of primed dendritic cells may be used to treat patients with HIV to induce immune and clinical responses and have a good tolerability.

II. The Lipo5 which is a mixture of five HIV antigen peptides, Gag p17(17-35), Gag p24(253-284), Nef(66-97), Nef(166-145), and Pol(325-355) covalently-linked at the C-terminal end to a palmitolyl-lysylamide group. These lipopeptides which cover HIV epitopes binding to >90% of HLA molecules, permit presentation to CD4+ and CD8+ T cell epitopes as well as generation of humoral immunity. These have already been used as vaccine antigens in prophylactic and therapeutic studies. A meta-analysis of lipopeptide vaccine studies in non-HIV infected volunteers and in HIV-patients by the present inventors showed that administration of this vaccine was well tolerated.

III. LPS activation of DC vaccine by the present inventors demonstrated that LPS (TLR4 ligand) is superior to poly I:C (TLR3) and/or a mixture of inflammatory cytokines in priming IFN-DCs to secrete IL12p70 in response to CD40 ligation, a T cell signal.

Generation of GM-CSF/IFN-α Dendritic Cell Vaccine From The Monocytes of HIV-Infected Subjects: The present inventors produced six pilot separate full-scale batches of the vaccine. The DC vaccines were prepared from fresh apheresis blood product obtained from HIV infected subjects. Four of them were consecutive subjects some of which did not meet the inclusion criteria, i.e., had low CD4+ T cell counts and high HIV plasma levels.

Vaccine generation: Monocytes isolated from the patients' apheresis blood by elutriation and collected in Fraction 5 were cultured in CellGenix DC culture media supplemented with 100 ng/mL of GM-CSF and 500 IU/mL of IFN-α. The cultures were made in 100 mL cell culture bags. After 24 hours of culture, fresh media with cytokines was added to each cell culture bag. After antigen loading at 48 hours and activation, the DC vaccines were harvested at approximately 72 hours, washed by centrifugation, and resuspended to a concentration of 30×106 cells/mL with freezing solution consisting of 80% PlasmaLyte, 10% human serum albumin (HSA), and 10% DMSO. One mL of the cell suspension was filled into glass vaccine vials and frozen Antigen loading: Lipo5 was reconstituted to a stock concentration of approximately 134 µM per peptide (5×500 µg lyophilized mixture) using a supplied diluent. After 48 hours of culture, Lipo5 was added to the cells at a concentration of approximately 0.25 µM per peptide.

Vaccine activation: Approximately 20 hours after addition of Lipo5 to the culture, some of the DC vaccines were activated for six hours with 5 EU/mL LPS, and some of the DC vaccines were activated for six hours with 5 EU/mL LPS followed by stimulation for two hours with 100 ng/mL of CD40L.

DC vaccines were assessed by the analysis of: i) vaccine recovery and viability, ii) vaccine phenotype, iii) DC function as determined in a mixed lymphocyte reaction (MLR), and iv) the capacity of DC to present vaccine antigens to autologous T cells Vaccine recovery and viability: Recovery after thawing was 100% in all batches. This may be due to cell aggregation that impacts vaccines counts. Vaccine viability was >80% by Trypan Blue exclusion across the batches.

Phenotype: In all three batches GM-CSF/IFN-α DC vaccine contained cells expressing CD 1b/c and CD14 consistent with the differentiation of two DC subsets in these cultures, i.e., CD1b/c+ Langerhans-like cells (LCs) and CD14+ interstitial DCs (intDCs). Generation of LCs was further confirmed by the expression of surface CD207 (Langerin) in a fraction of cells. Both DC subsets expressed high levels of HLA-DR, as well as co-stimulatory molecules CD80, and CD86 consistent with their activation.

Function in mixed lymphocyte reaction (MLR): The capacity to trigger the proliferation of allogeneic T cells in an MLR remains a hallmark for the in vitro studies assessing DC function. To this end, DCs were placed in cultures with allogeneic T cells and T cell proliferation was assessed at day 5 using standard assays based on either thymidine incorporation or CFSE dye dilution. All batches were consistent in their ability to elicit proliferative response of allogeneic lymphocytes in both assays. T cell proliferation in response to DCs. Proliferating T cells lose carboxyfluorescein succinimidyl ester (CFSE) staining (shift to the left) indicating T cell division and proliferation.

Presentation of HIV antigens to autologous T cells: The ultimate assessment of DC vaccine performance is the capacity of DCs to present loaded antigens to autologous T cells. DC vaccine induced HIV antigen-specific autologous T-cell IFN-γ responses as measured by flow cytometry. Batch #1 (GM-CSF/IFN-α activated with LPS DC vaccine of a donor) stimulated CD8+ T cells that responded to Nef (66-97), Nef (116-145), and the peptide mixture (0.88-1.22%, 0.94-0.95%, and 1.71-1.72%, respectively). In batch #2, CD4+ T cells responded to peptides Nef (66-97) and Pol (325-355). In batch #3, CD4+ T cells responded to Gag p24 (253-284). The variability in T-cell responses elicited by the DC vaccines among these HIV infected donors is most likely due to differences between individuals (for example, their overall health, disease status, T-cell repertoire/immunological competency, their HLA type, and variability in the DC vaccine production process).

Analysis of the DC vaccines can be manufactured from monocytes obtained from HIV-infected donors as described in the present invention suggests stimulation of CD8+ or CD4+ T cells from HIV patients to mount an antigen-specific response as measured by production of IFN-α. Thus, demonstrating the capacity of DCs to present antigens that were loaded during the manufacturing process.

Determination of the Optimal Antigen Dose: To determine the optimal concentration of antigen that needs to be loaded onto DC vaccines the present inventors conducted three separate studies on a small-scale vaccine batch production process.

Vaccine generation: DC vaccines were prepared using protocol described above with monocytes from frozen apheresis blood product obtained from three different HIV infected subjects.

Antigen loading: Vaccines were pulsed with various concentrations of Lipo5 (3.0 µM, 1.0 µM, 0.3 µM, 0.1 µM, 0.03 µM, 0.01 µM, and 0.003 µM). A control culture did not receive any HIV peptides.

Vaccine activation: Approximately 20 hours after loading, the DC vaccines were activated for four hours with 5 EU/mL of LPS. The DCs were then harvested, washed by centrifugation, and analyzed.

The DC vaccines were assessed by the analysis of recovery, phenotype and functional parameters as described above:

Vaccine recovery and viability: There was no impact on vaccine viability by Trypan Blue exclusion across analyzed batches at Lipo5 concentrations <1.0 μM. However, in two out of three tested subjects the inventors observed a progressive decrease in cell viability at the Lipo5 concentrations >1.0 μM (Table 2).

TABLE 2

The percent of viable DCs by Trypan Blue exclusion.

| Lipo5 Concentration | Aph002 Viability (%) | Aph003 Viability (%) | Aph005 Viability (%) |
| --- | --- | --- | --- |
| No Lipo5 | 81 | N/A | 80 |
| 0.003 μM | 94 | 99 | 92 |
| 0.01 μM | 89 | 99 | 78 |
| 0.03 μM | 92 | 96 | 73 |
| 0.1 μM | 86 | 99 | 80 |
| 0.3 μM | N/A | 94 | 79 |
| 1.0 μM | 93 | N/A | 72 |
| 3.0 μM | N/A | 56 | N/A |

Phenotype: There was no impact on vaccine phenotype across analyzed batches at Lipo5 concentrations <3.0 μM. However, a decrease in cell surface marker expression and an increased population of dead cells in the forward scatter/side scatter analysis by flow cytometry at the Lipo5 concentrations >3.0 μM was observed. These results were consistent with the cell recovery and viability by Trypan Blue exclusion.

Function in MLR: Regardless of cell recovery, at all Lipo5 concentrations the DCs were able to elicit an allogeneic MLR in both thymidine incorporation and in CFSE dilution assays.

Presentation of HIV antigens to autologous T cells: The capacity to present antigens to autologous T cells represents an important parameter in assessing the dose of antigen that needs to be loaded on the DC vaccine. This was measured again by flow cytometry and by determination of the percentage of IFN-γ producing T cells in response to DC vaccines. The frequency of IFN-γ producing T cells peaked when DC were loaded with Lipo5 at 0.1 μM and then decreased as the Lipo5 loading concentration increased. It was found that the peak of autologous T cell response occurred when DC were loaded with Lipo5 at 0.1 μM, while in another study the optimal DC Lipo5 loading concentration was 0.3 μM. Each donor responded to a different set of HIV peptide antigens and the magnitude of response varied, as measured by T cell production of IFN-γ. The differences in HIV peptide responses are expected and are likely due to differences between donors, such as differences between their T cell repertoires, their HLA types, or the status of their disease/HIV infection. The difference in the magnitude of IFN-γ produced by the responding T cells could also be due to the difference in HLA types.

A general discussion on the manufacture and the testing of the DC vaccines including determination of the DC viability, DC dose, the phenotype and the allogenic MLR was presented hereinabove. From the studies above, the specific details of the steps undertaken by the present inventors to manufacture and test the HIV therapeutic DC vaccines, described in the present invention is presented below. Based on the DC viability, phenotype, and the allogeneic MLR, a concentration of <3.0 μM Lipo5 should be used when loading the DCs during manufacture of the HIV therapeutic DC vaccines. The tritium incorporation and the CFSE dilution assay indicate that the Lipo5-loaded DCs in each vaccine are capable of eliciting a proliferation response when cultured with allogeneic lymphocytes. However, the considerable increase in the number of dead cells present in the DC vaccine, as well as decrease in DC marker expression by DC loaded with Lipo5 at 3.0 μM suggests that at high concentrations the Lipo5 might be toxic to the DC.

Based on the capacity of loaded DCs to elicit autologous T cells responses, it can be seen that the Lipo5 loading concentration for the DC vaccine lies between 0.1 μM and 0.3 μM. Due to the differences between donors in regard to their T cell repertoires, their HLA type, the status of their disease and general health, and the manifestation of the HIV virus, there might not be a clear concentration of Lipo5 for loading the DC vaccine that will be optimal for every patient.

Determination of the Optimal DC Vaccine Activation Time: The inventors determined the length of time for LPS activation of the DC vaccine to avoid potential exhaustion of cells which will diminish their immunogenicity after injection into subjects.

The inventors prepared the vaccine batches in two ways: (1) full-scale manufacturing process (using large 100 mL GMP grade cell culture bags); and (2) pilot-scale laboratory process (using smaller 25 mL cell culture bags). The DC vaccines made by the full-scale process were prepared according to the cGMP procedures to determine Lipo5 loading and how effective the LPS activation would be for DC vaccines intended for actual use in HIV patients. The DC vaccines made by the pilot-scale were intended to provide further data on the effectiveness of the vaccines. Both the full-scale and the pilot-scale studies included 3 vaccine batches each for a total of 6 separate vaccine batches that were evaluated.

Vaccine generation: Each of the DC vaccine batches were prepared from either fresh or frozen apheresis blood product obtained from different HIV infected donors selected accordingly to the inclusion criteria for the proposed clinical trial. Vaccines were made and stored frozen as for the clinical trial. Frozen DC vaccines were thawed, washed by centrifugation, counted, and then resuspended at a concentration of $1 \times 10^6$ cells per mL of cRPMI media with 10% human serum for analysis.

Antigen loading: Vaccines were pulsed with various concentrations of 0.1 μM, 0.2 μM, and 0.3 μM.

Vaccine activation: LPS was added for 6 or 16 hours.

DC vaccines were assessed by the analysis of recovery, phenotype and functional parameters as described above.

Vaccine recovery and viability: Neither the Lipo5 concentration, nor the duration of LPS activation had a consistent nor remarkable effect on the percentage of DCs recovered from cell cultures and analyzed prior to freezing. However, upon thawing and analysis of frozen vaccines it was observed that both the number of cells recovered and the percentage of viable cells were lower for those DC vaccines that were activated with LPS for 16 hours compared to those activated with LPS for 6 hours (Table 3). Thus, the duration of LPS activation had a marked effect on DC recovery and viability. No impact of Lipo5 in the range of tested concentrations was observed consistent with an earlier analysis described above.

TABLE 3

Percentage of Viable and Recovered Cells in the Full-Scale DC Vaccine Batches at Release.

|  |  | All Lipo5 Concentrations | Lipo5 0.1 μM | Lipo5 0.2 μM | Lipo5 0.3 μM |
|---|---|---|---|---|---|
| Percent Recovered Cells |  |  |  |  |  |
| 6 hr LPS | Average | 95% | 97% | 97% | 92% |
|  | Std Dev | 7% | 3% | 4% | 12% |
| 16 hr LPS | Average | 77% | 68% | 74% | 90% |
|  | Std Dev | 15% | 11% | 17% | 8% |
| Percent Viable Cells |  |  |  |  |  |
| 6 hr LPS | Average | 91% | 92% | 91% | 91% |
|  | Std Dev | 2% | 3% | 3% | 2% |
| 16 hr LPS | Average | 76% | 80% | 72% | 75% |
|  | Std Dev | 9% | 5% | 11% | 12% |

Phenotype: The length of LPS activation had an impact on the percentages of DC subsets in analyzed cultures. Thus, at 6 hours DC vaccines contained higher percentages of CD14+, CD1b/c+/CD11c+, and CD207+ cells compared to those activated with LPS for 16 hours (Table 4). Similarly, the percentages of CD83+ cells were lower at 16 hours. No substantial differences were observed in the percentages of cells expressing co-stimulatory molecules CD80 and CD86, or chemokine receptor CCR7 (Table 3). Lipo5 dose in tested range had no impact on DC phenotype.

TABLE 4

Phenotypes of Full-Scale Batches Comparing the Length of LPS Activation.

|  |  | CD14+ | CD1b/c+ CD11c+ | HLA-DR+ | CD83+ | CD80+ | CD86+ | CCR7+ | CD207+ |
|---|---|---|---|---|---|---|---|---|---|
| 6 hr LPS | Average | 41.76 | 49.73 | 94.92 | 49.76 | 95.75 | 89.16 | 0.06 | 17.71 |
|  | Std Dev | 20.94 | 9.99 | 3.81 | 20.74 | 1.23 | 9.45 | 0.04 | 8.63 |
| 16 hr LPS | Average | 13.95* | 41.23 | 98.43 | 25.66 | 96.59 | 97.52 | 0.15 | 8.18 |
|  | Std Dev | 8.35 | 6.00 | 0.83 | 19.97 | 0.75 | 0.46 | 0.11 | 7.10 |

*Data are expressed as the percentage of cells expressing the specified cell surface marker.

Function in Mixed Lymphocyte Reaction (MLR): In the full-scale studies to evaluate the antigen-presenting capability of the DC vaccines, the CFSE dilution and 3H-TdR incorporation methods used to measure T-cell proliferation indicated that all of the DC vaccines were capable of eliciting a proliferation response when cultured with allogeneic lymphocytes. Although some of the DC vaccines activated with LPS for 16 hours stimulated stronger allogeneic MLR proliferation responses, this trend was neither consistent across studies nor between different dilutions of DCs assessed in the assays. The allogeneic MLR proliferation response in the pilot-scale studies demonstrated that the fresh DCs activated for 16 hours with LPS elicited a stronger response compared to those activated for 6 hours; especially for those vaccines in which the DCs were loaded with 0.2 μM or 0.3 μM Lipo5. This trend appeared to be consistent across studies and between the different DC concentrations assessed in the MLR assays.

Presentation of HIV antigens to autologous T cells: The pilot-scale DC vaccines activated with LPS for 16 hours generally elicited higher IFN-γ production by the T cells compared to DC activated with LPS for 6 hours. In contrast, in the full-scale study, there was less of a difference between the antigen-presenting potency as measured by autologous HIV antigen specific T-cell response assays of DC vaccines activated for 6 or 16 hours with LPS. Furthermore, despite some modest differences, there was no significant effect of Lipo5 loading concentration on the potency of the various DC vaccines.

Thus, equivalent and more consistent responses were generally observed with those vaccine batches produced with a lower period of LPS activation and lower concentration of Lipo5 loading.

Analysis Of Residual Lipo5 (Identity): The inventors determined if the dendritic cell (DC) vaccines, referred to herein as BIIR/ANRS-HIVax-001 or Dendritic cells And Lipopeptides induced Immunity against AIDS (DALIA), contained any residual Lipo5. Lipo5 is a mixture of five HIV antigen peptides (when they include a lipid tail they are referred to as lipopeptides), that is, Gag p17 (17-35) (EKIRLRPGGKKKYKLKHIV) (SEQ. ID NO: 1), Gag p24 (253-284) (NPPIPVGEIYKRWIIL-GLNKIVRMYSPTSILD) (SEQ. ID NO: 2), Nef (66-97) (VGFPVTPQVPLRPMTYKAAVDLSHFLKEKGGL) (SEQ. ID NO: 3), Nef (116-145) (HTQGYFPDWQNYT-PGPGVRYPLTFGWLYKL) (SEQ. ID NO: 4), and Pol (325-355) (AIFQSSMTKILEPFRKQNPDIVIYQYMD-DLY) (SEQ. ID NO: 5).

DALIA Vaccine generation: Each of the DC vaccine batches were prepared from fresh apheresis blood product obtained from different HIV infected donors selected accordingly to the inclusion criteria for the proposed clinical trial. On day 0 of the process, the elutriated monocytes were removed from the HBSS by centrifugation and resuspended in serum-free Cellgro® DC media (CellGenix Technologie Transfer GmbH, Germany) at a concentration of $1 \times 10^6$ cells/mL for culture in disposable plastic culture bags (AFC, Gaithersburg, Md., USA). The media was supplemented with 100 ng/mL GM-CSF (Berlex, Wayne, N.J., USA) and 500 IU/mL IFN-α (Schering-Plough, Kenilworth, N.J., USA). After 24 hours in culture, day 1, fresh cytokines were added to the cell culture. Antigen loading: Vaccines were pulsed with 0.1 μM of Lipo5 after 48 hours of culture initiation. Vaccine activation: LPS was added at a concentration of 5 EU/mL for 6 hours prior to harvesting.

Vaccine harvesting and freezing: The cells were then harvested from the culture bags, washed with normal saline (NaCl; Hospira, Lake Forest, Ill., USA), suspended in freezing-solution consisting of 90% autologous serum/plasmalyte (Hospira)/dextrose (Baxter) mixture and 10% DMSO (Bioniche, Lake Forest, Ill.), and filled into single-dose glass vaccine vials with flip-off cap at a concentration of $30 \times 10^6$ cells/mL/vial. The cells in the vaccine vials were frozen using a rate-controlled freezer and the vials were kept in the vapor-phase of a liquid nitrogen tank for long-term storage, the loaded dendritic cells activated by this method are referred to as the DALIA vaccine.

The samples obtained for analysis of residual Lipo5 were supernatants retained at various points during manufacture of the DC vaccine using freshly isolated monocytes. These samples were from DC vaccine batches #007-014-01-005 and #007-014-01-006, in which a portion of the cells in each batch were cultured with GM-CSF/IFN-α, and then pulsed with Lipo5 at a concentration of 0.25 µM of each peptide. A separate vaccine batch #007-014-01-008 was manufactured from frozen monocytes. This batch was manufactured with GM-CSF and IFN-α and the DC were pulsed with Lipo5 at a concentration of 0.1 µM per peptide.

Assay sensitivity: To establish the sensitivity of the assay, the sample of Lipo5 antigen was analyzed over a dilution range of: stock concentration, 1:50, 1:100, 1:150, 1:200, 1:250, 1:300, 1:350, 1:1000, 1:1500, 1:3000, and 1:4500. The molecular weights (MW) in Daltons of the individual peptides in the Lipo5 mixture are listed in Table 5. The peaks that were identified as Lipo5 peptides are Gag p17 (17-35) at ~2656, Nef (66-97) at ~3965, Nef (116-145) at ~4059, Gag p24 (254-355) at ~4131, and Pol (325-355) at ~4175. The 1:1000 dilution at an intensity of $1.1 \times 10^4$ delineated all the recognizable peaks of the peptides thus establishing the sensitivity of the assay. Another DC vaccine sample contained Lipo5 peptides at a 0.25 µM concentration, which is equivalent to a 1:600 dilution and is within the concentration range used for establishing the sensitivity of the assay.

TABLE 5

Molecular Weight, in Daltons, of Lipo5 Peptides With or Without the Lipid Tail.

| Peptide | MW | Lipid Tail | Total MW |
|---|---|---|---|
| Gag p17 (17-35) | 2291 | 368 | 2659 |
| Nef (66-97) | 3496 | 368 | 3864 |
| Nef (116-145) | 3602 | 368 | 3970 |
| Gag p24 (253-284) | 3696 | 368 | 4064 |
| Pol (325-355) | 3767 | 368 | 4135 |

The following are the sequences for the various peptides: Nef (66-97): VGFPVTPQVPLRPMTYKAAVDLSH-FLKEKGGL (SEQ. ID NO: 1); Nef (116-145): HTQGYF-PDWQNYTPGPGVRYPLTFGWLYKL (SEQ. ID NO: 2); Gag p17 (17-35): EKIRLRPGGKKKYKLKHIV (SEQ. ID NO: 3); Gag p17-p24 (253-284): NPPIPVGEIYKRWIIL-GLNKIVRMYSPTSILD (SEQ. ID NO: 4); or Pol 325-355 (RT 158-188) is: AIFQSSMTKILEPFRKQNPDIVIY-QYMDDLY (SEQ. ID NO: 5).

Peptide detection: The cell culture media without adding Lipo5 showed numerous peaks that were not specific for Lipo5. Diluting the Lipo5 mix with H₂O and media at a 1:200 generated visible peptide peaks. Following 20 hours of pulsing with Lipo5 and activation with LPS, the GM-CSF/IFN-α DC vaccines were negative for the Lipo5 peaks. Thus, the BIIR/ANRS-HIVax-001 DC vaccines of the present invention analyzed in this study, that is, samples taken after 20 hours of peptide loading do not contain any residual levels of Lipo5 peptide at concentrations at the limit of detection of the mass spectrometry assay.

Determination of the Viral Replication Status in DC Vaccine: The inventors determined if the dendritic cell (DC) or DALIA vaccines of the present invention enhanced HIV productive infection. The DC vaccine described herein is made from HIV-infected subjects. Therefore, it is important to determine if in vitro culture would enhance the replication of the virus and production of the viral antigen.

The inventors used HIV p24 antigen ELISA kit (Perkin Elmer, Waltham, Mass.) to detect the viral load. To assure the Gag p24 (253-284) would not interfere with the study, an ELISA Test was performed using culture media spiked with a known concentration of a Gag p24 peptide (253-284). The HIV p24 Antigen ELISA was performed using a 96 well flat bottom plate coated with a monoclonal antibody to HIV p24. For quantitative analysis, the positive control was diluted with media (or cell culture) in 2 fold dilutions starting at 100 pg/mL. For each positive control dilution, 200 µL were plated including media (or cell culture) and blank for negative controls. The samples were plated at a volume of 200 µL. All conditions were tested in duplicates. To each of the samples, 20 µL of Triton-X100 was added to lyse the cells. The plate was incubated for 2 hours at 37° then washed 6 times with wash buffer. Detector antibody was added at 100 µL to each well and the plate was incubated for 1 hour at 37° then washed. Streptavidin-HRP was diluted 1:100 and 100 µL was added to each well. The plate was incubated for 30 minutes at room temperature then washed. OPD substrate solution was made and 100 µL was added to each well. The plate was incubated for 30 minutes at room temperature in the dark. Stop solution was added at 100 µL to each of the wells and read on a spectrophotometer using 490 nm wavelength.

If the sample contained HIV p24 from the virus, the antibody coated on the plate will capture the protein and will be detected by the antibody and seen as a color change by streptavidin-HRP and OPD Substrate. The stop solution allowed the reaction to be stopped and read.

Vaccine samples: Samples for analysis were $1 \times 10^6$/mL cells suspended in culture supernatant harvested at various points during manufacture of the DC vaccine after 4 hours, 20 hours, and 72 hours. Two DC vaccine batches were manufactured from frozen monocytes. One batch was of a healthy uninfected subject and one batch using an HIV-infected subject. The batches were manufactured using process established for the trial as described above.

In order to measure the total viral load, supernatant and cells were used in one sample. To obtain lysates, some samples were snap-frozen with liquid nitrogen and thawed three times followed by centrifugation to remove debris. Other samples were used untouched in the ELISA in which the cells are lysed by Triton-X100. The total viral load and CD4 T cell phenotypes of patients D1-1 to D1-6 are shown in FIGS. 79, 81, 83, 85, 87, and 89.

Assessment of the non-Lipo5 peptide gag p24 (253-284) interference in the ELISA, concluded to be negative. DC vaccine harvested at 4 hours and 20 hours were negative for HIV p24 antigen. To test for the possible presence of inhibitory factors in the culture, a sample of the 72 hour cell cultures were spiked with HIV p24 positive control and titrated as done for the positive control with media. The samples at 72 hours were also negative for HIV p24 antigen.

The DALIA vaccines of the present invention analyzed in this study, that is, samples taken during 4, 20, and 72 hours of cell culturing, does not contain any HIV p24 as detected by HIV p24 antigen ELISA.

Patient Results.

Fifteen HIV infected patients (D1-1 to D1-15) under HAART were vaccinated four times at monthly intervals with IFNa-DCs loaded with the five lipopeptides (LIPO5: Gag17, Gag253, Nef66, Nef116, Pol325; FIG. 1). Patients have undergone two aphereses: the first at one month before vaccination (Aph1) and the second at one month following the last vaccine (Aph 2) and 19 blood draws during the trial.

All the 19 patients that were planned for this trial have been enrolled as of August 2010 (FIG. 2). Fifteen patients have received the four vaccinations planned for the trial. Fifteen patients already gave their second apheresis (week 16), 15 started the ATI protocol. Finally, eight patients have already finished the protocol. Patient D1-12 has been excluded from the Immunomonitoring for reason that was unrelated to the clinical trial. Patient D1-13 hasn't been included in the analysis as no apheresis 2 (week 16) could be collected.

ANALYTICAL STRATEGY. Five different tests have been performed on pre and post vaccination apheresis and small blood draws. All of the analyses were performed in a blinded fashion.

Enumeration of LIPO5-Specific T Cells using Cytoplasmic Cytokine Staining: Frozen PBMC were thawed and rested at 37° C. overnight in RPMI 1640 media with 10% HS. The next day, $5 \times 10^6$ cells were stimulated with a mix of peptides based on the LIPO5 sequences without the lipid tail (long peptides and pools of 15-mers and 9-mers) at a final concentration of 2 µM each in the presence of 1 mg/ml anti-CD28/anti-CD49d. One hour later, 10 µ/ml BFA was added and the culture was continued for additional 5 hours.

Cells were then washed and stained for CD3-PerCP, CD4-PECy7, CD8-Pacific Blue and live/dead marker (Aqua) for 20 minutes. Following fixation and permeabilization, cells were stained with IFNγ-PE, TNFα-APC and IL-2-FITC.

Samples were analyzed in a FacSCanto II and data was acquired with DIVA software. FlowJo software was used for data analysis.

Analysis of LIPO5-Induced Cytokine Secretion at 48 Hours: Frozen PBMC from Aph1 and Aph2 were thawed and rested at 37° C. for 1 h. Samples were filtered and resuspended in RPMI 1640 media supplemented with 10% HS. DALIA1 Peptide-Plate1 and Plate2 (FIG. 3a-3b) were thawed at room temperature and $1 \times 10^6$ cells were added in each well.

After 48 h of culture, the plates were centrifuged and 200 l of each supernatant was collected and frozen at −80° C. for cytokine detection.

Luminex analysis for IL-2, IL-5, IL-10, IL-13, IL-17, IL-21, IFNγ, TNFα and IP10 was performed, as described previously.

Assessment of Anti-HIV Antibodies in Plasma: CBP-doc was conjugated to seroMAP luminex carboxylated beads (multi regions 33, 21, 45 used for each cohesin antigen that would be coupled to CBP-doc) at 25 µg per $5 \times 10^6$ beads using the Luminex 2-step carboxylation protocol. Following this initial conjugation, the antigens were coupled via the high affinity association of cohesin and dockerin. Independently, each CBP-doc bead-set was incubated with antigen at a ratio of 10 µg/ml to $6.4 \times 10^4$/ml of beads in 1×PBS (Ca/Mg), 1% BSA and 0.05% T20 (wash buffer) for a minimum of 2 hours. Following this incubation, during which the high affinity complex was established, the complexed beads were thoroughly washed 3× to remove any excess, unbound antigen. Serum was prepared for incubation with this bead complex by completing a serial titration in 2.5% Chemiblock (to reduce non-specific binding of the serum to the seroMAP beads and reduce background). The serial titration was initiated at 1:10, carried over 2-3 logs, and incubated on a shaking platform for a minimum of 1 hour. Following the pretreatment of serum with the Chemiblock reagent, 50 ml of the titrated serum was added to 50 ml of the prepared complexed seroMAP beads in 1.2-mm filter membrane 96-well microtiter plates (MABVN1250, Millipore Corp., Billerica, Mass.), in a multiplex format. Incubation with beads and serum continued on a shaking platform for 2 hours at RT or overnight at 4 C. After 3× washing, 2 mg/ml of Phycolink goat anti-human IgG (Fc Specific) R-Phycoerythrin was added for an additional 1 hour. Beads were washed 2×, resuspended in 125 ml wash buffer with 2% PFA, and read on the BioPlex200 (BioRad). Mean fluorescent intensities are plotted vs. titration dilution.

Polychromatic Flow Cytometry Analysis of Blood Cells: Whole blood samples were obtained from the clinical site. The samples were stained for flow cytometry analysis using the lyse/wash protocol. Two hundred microliters of whole blood was incubated with the antibody cocktails described in the figures for 15 minutes. After incubation, samples were lysed with 1× FacsLysing solution. After lysing, the samples were washed and re-suspended in 250 µl of PBS. For tubes 11 and 12 (CD8 cytotoxic panel) the cells were further permeabilized with BD Cytofix/Cytoperm Buffer for 30 minutes and incubated with antibodies against intracellular antigens Perforin, Granzyme A and Granzyme B. For Tubes 9 and 10 (Regulatory panel) the cells were permeabilized with BD FoxP3 Buffer and incubated with antibodies FoxP3 and CTLA4. After incubation with antibodies against intracellular antigens, the samples were washed and re-suspended in 250 ul PBS. All the samples were analyzed on a Becton Dickinson LSRII cytometer.

Transcriptome Analysis of Whole Blood: Whole blood was collected into Tempus vaccutainer tubes with additional sampling for PCR-based viral load determination and CD4 counts. Total RNA was isolated from the whole blood lysate followed by depletion of Globin mRNA. All samples passing quality control were then amplified and labeled using the Illumina TotalPrep-96 RNA amplification kit. Amplified RNA was then hybridized to Illumina HT-12 V3 beadchips (48,803 probes) and scanned on an Illumina Beadstation 500.

Module-Level Analysis: A set of 260 transcriptional modules were used as a pre-existing framework for the analysis of this dataset. The approach used for the construction of such a framework was previously reported. Molecular Distance to Health (MDTH) was calculated for pre-seroconversion enrollment samples to quantify the extent of global transcriptional perturbation measured for each sample from the healthy baseline.

This analysis strategy has been previously described. Previously, peripheral blood leukocyte gene expression profiles were generated using Affymetrix GeneChips, however in the present invention the inventors have created a new set of transcriptional modules using whole blood samples and Illumina Hu6 V2 BeadChips, matching both the RNA source and platform used in this study. For the analysis of the acute HIV infection (AHI) signature, the inventors used a set of 260 transcriptional modules generated through the analysis of 410 whole blood profiles. Briefly, nine datasets were used as input, including blood profiles generated from patients with HIV, tuberculosis, sepsis, systemic lupus erythematosus, systemic arthritis, and liver transplant. Each dataset was then clustered independently and the analysis of cluster membership of each gene across all the datasets was used to define transcriptional modules with varying degrees of stringency. Those modules with conserved expression across diseases (i.e. formed by transcripts that cluster together for all nine datasets) were selected in early rounds whereas modules with greater disease specificity (i.e. formed by transcripts that cluster together only in a subset of the nine datasets) were selected in later rounds. This modular framework for gene expression was then applied a priori to the datasets described in this manuscript.

The modular activity of each sample was determined by the following steps: (1) Each sample was placed into its own dataset containing healthy controls (n=7). (2) Genes that were significantly expressed for the single experimental sample and healthy controls were selected (a=0.01). (3) A one-sample t-test (a=0.05) was conducted between each experimental sample and healthy controls to identify transcripts with significant differences in expression between the sample and control groups. In the case of healthy controls, a leave-one-out approach was followed by the recalculation of the non-infected mean. (4) The gene list was then split into those genes with greater expression in the experimental sample than the healthy control group (UP, Red) and those with lower expression (Down, Blue). (5) Each gene was then filtered into the a priori generated transcriptional module framework and the percent up and down expression of genes for each module was calculated for each sample. (6) The modular expression percentages and the polarity (Up, Down) were then entered into Genespring GX 7.3 for heatmap visualization. In order to do this a transformation by adding 1 to each value was necessary.

Module Annotation: An Ingenuity Pathway Analysis (IPA) was used to annotate the modules (Ingenuity Systems, Redwood City, Calif.). In some cases the coverage of IPA was incomplete and therefore the inventors resorted to individual searches for each gene to make connections between genes and biological function. Both Pubmed and iHOP databases were used for annotations and functional analysis Annotated modules contained multiple genes with similar function, cellular localization, or membership in known biological pathways. Furthermore, the Novartis Gene Atlas2 was queried for modules containing genes with expression limited to particular cell types. Those modules without shared characteristics between member genes were not annotated.

Molecular Distance to Health (MDTH): This quantitative approach to module-level analyses results in the computation of a score representing the "molecular distance" of a given sample relative to a baseline (healthy controls). This analysis was performed by merging the transcripts from the first 6 rounds of module selection (M1.1-M6.20; n=62). The distance of each sample from the uninfected control baseline was calculated as follows: (1) Establishing the baseline: For each gene, the average expression level and standard deviation of the uninfected control group is calculated. (2) Calculating the "distance" of an individual gene from the baseline: The difference in raw expression level from the baseline average of a gene is determined for a given sample. Next, the number of standard deviations from baseline levels is calculated. (3) Applying filters: Qualifying genes must differ from the average baseline expression by at least 100 and 2 standard deviations. (4) Calculating a global distance from baseline: The number of standard deviations for all qualifying genes is added to yield a single value, the global distance of the sample from the baseline.

Measuring patient-specific responses using a transcriptional module framework. Module activity for each patient sample collected from pre-vaccination (week—8) to post-ATI (Week 32) was assessed for significant changes in module activity compared to seven age and sex matched healthy controls. Modules with greater than 15% of constituent genes with significantly increased abundance over healthy controls are indicated with red spots. As the number of significantly different genes within a module increases the intensity of the associated spot becomes more intense. Modules containing genes with decreased abundance are presented on a similar blue gradated scale. Using Ingenuity Pathway Analysis, Novartis Gene Atlas, and literature searches, those modules with representing distinct pathways or cell types were annotated. Modules 1.1-6.20 (n=62) are shown for each sample. (See FIGS. 102-107).

Results: T Cell LIPO5-Specific Responses to LIPO5 Long Peptides.

Patient D1-1:

ICS analysis: The intracellular staining showed an increase of peptide-specific CD4+ T cell response after vaccination: from 0.04% to 0.07% TNFα+, from 0.02% to 0.05% IL-2+ cells and from 0.02% to 0.05% IFNγ+ cells. 0.02% of CD4+ T cell express both IL-2 and TNFα and 0.02% express both TNFα and IFNγ.

Figure 19:
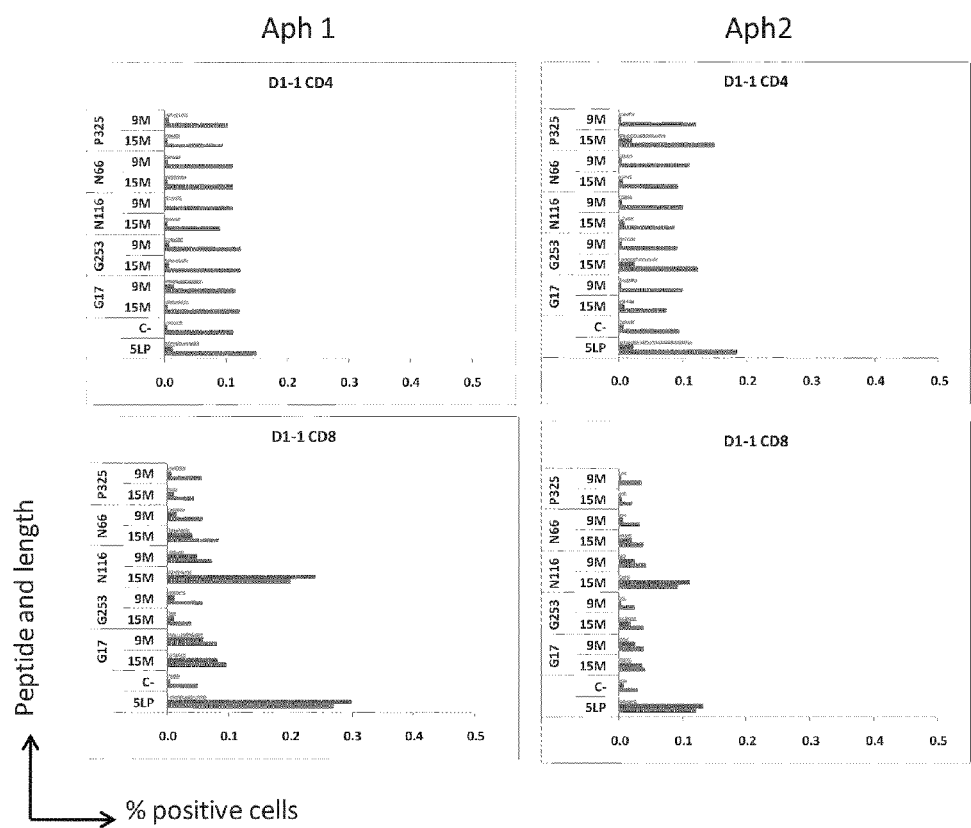
FIG. 19. D1-1: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

The peptide-specific CD8+ T cell response decreased from 0.52% IFN secreting cells to 0.16% and cells expressing both TNFα and IFNγ decreased from 0.22% to 0.07% after vaccination (FIG. 4). The stimulation with pools of 15-mer and 9-mers derived from LIPO5 sequences showed small CD4 responses to Gag253 and Pol325 after vaccination. CD8 responses to Gag17 and Nef116 were observed before and after vaccination (FIG. 19).

Cytokine secretion analysis: 48 h culture supernatants showed a slight increase in secretion of IL-2, IFNγ and IP10 in response to Gag253 and Pol325 post-vaccination.

Gag253 long peptide (LP) induces 50 µg/ml IL-2, 50 µg/ml IFNγ and 1.3 g/ml IP10. Pol325 LP induces 50 pg/ml IL-2, 80 pg/ml IFNγ and 7.2 µg/ml IP10 (FIG. 30-41).

Figure 74:
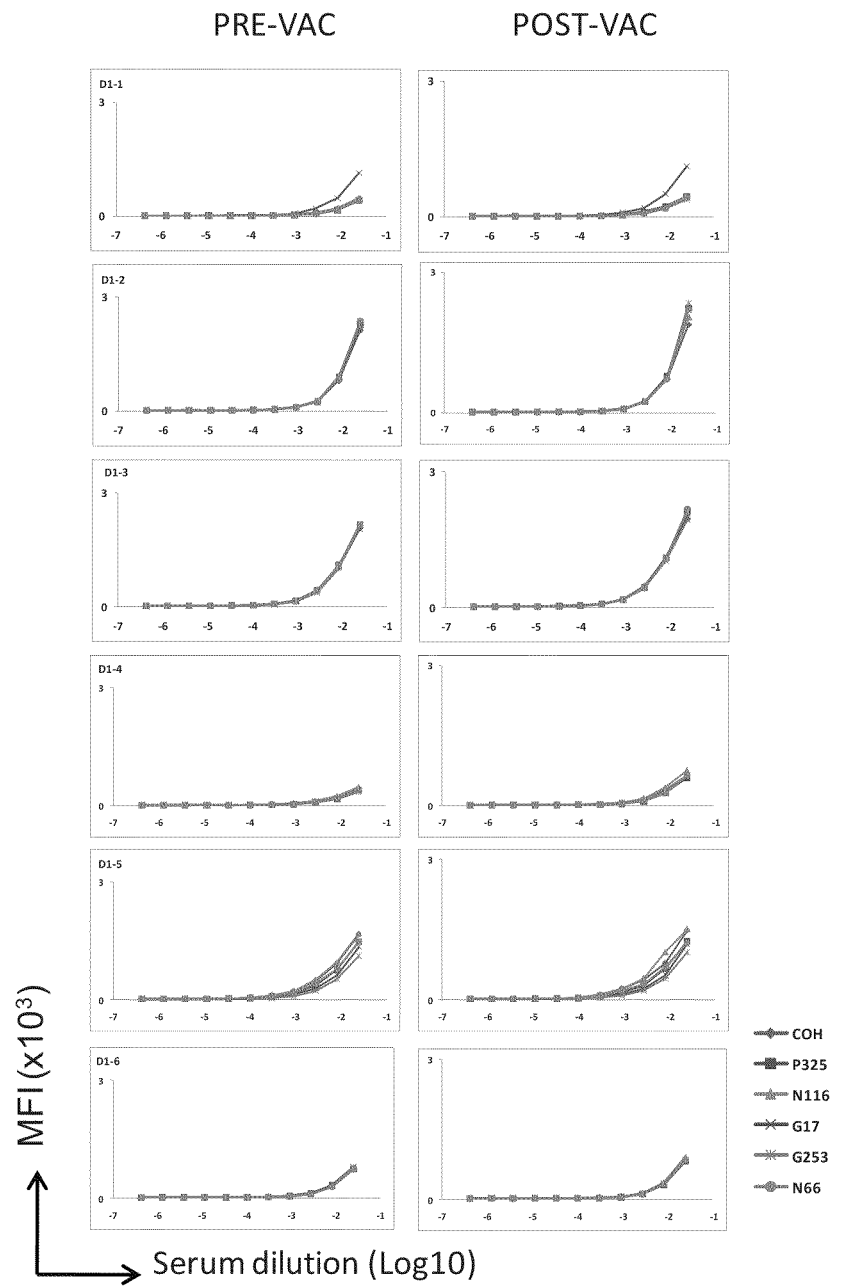
FIG. 74. Serum samples from patients D1-1 to D1-6 taken before and after vaccination were tested for antibody responses against LIPO5 long peptides.
Figure 75:
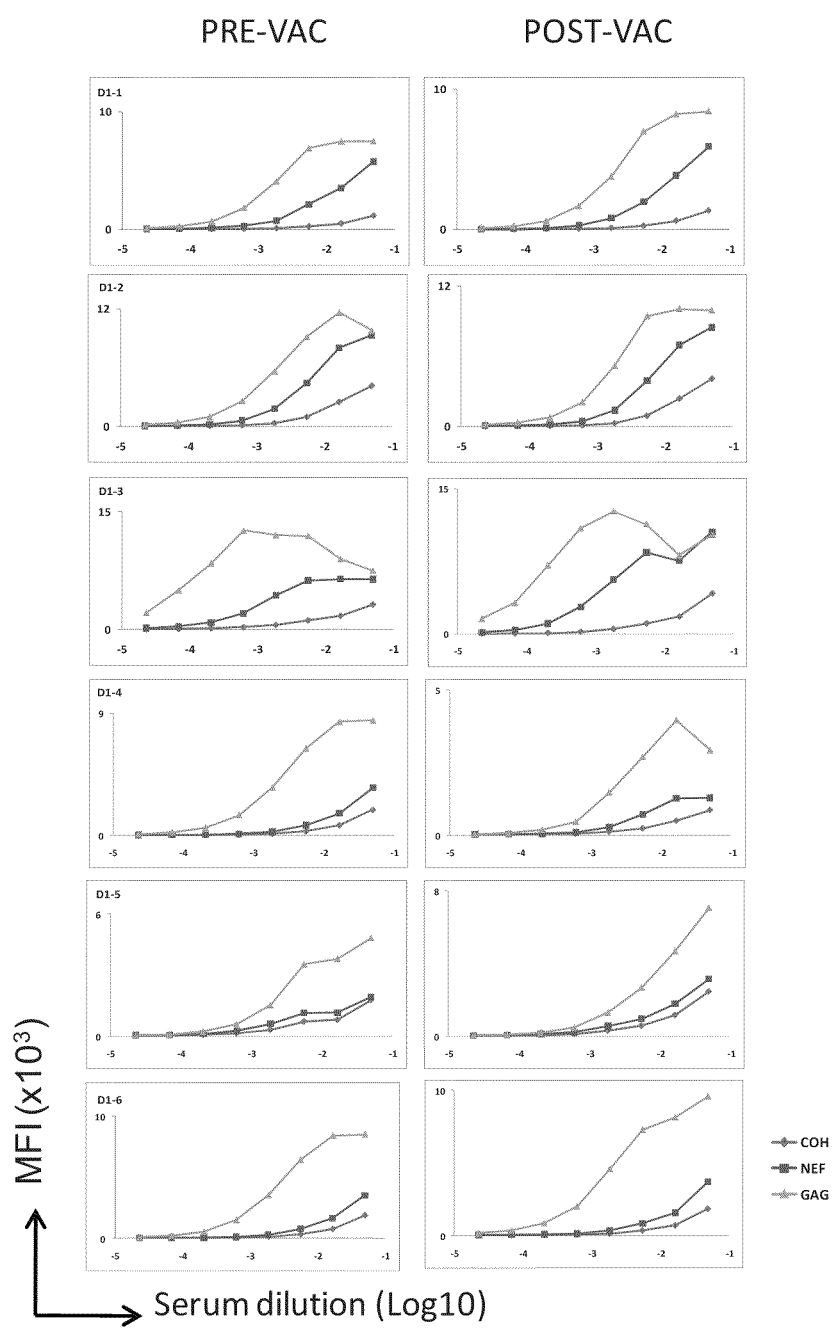
FIG. 75. Serum samples from patients D1-1 to D1-6 taken before and after vaccination were tested for antibody responses against Nef and Gag p24 proteins.
Figure 76:
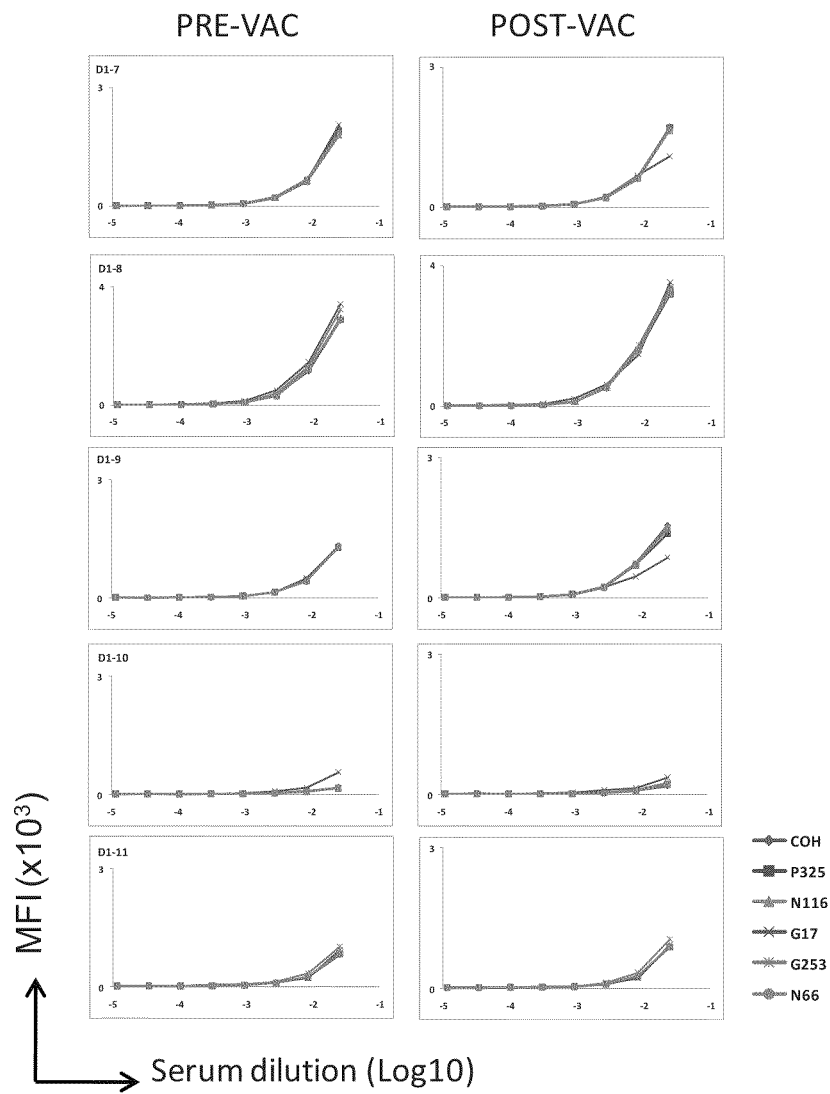
FIG. 76. Serum samples from patients D1-7 to D1-11 taken before and after vaccination were tested for antibody responses against LIPO5 peptides.
Figure 77:
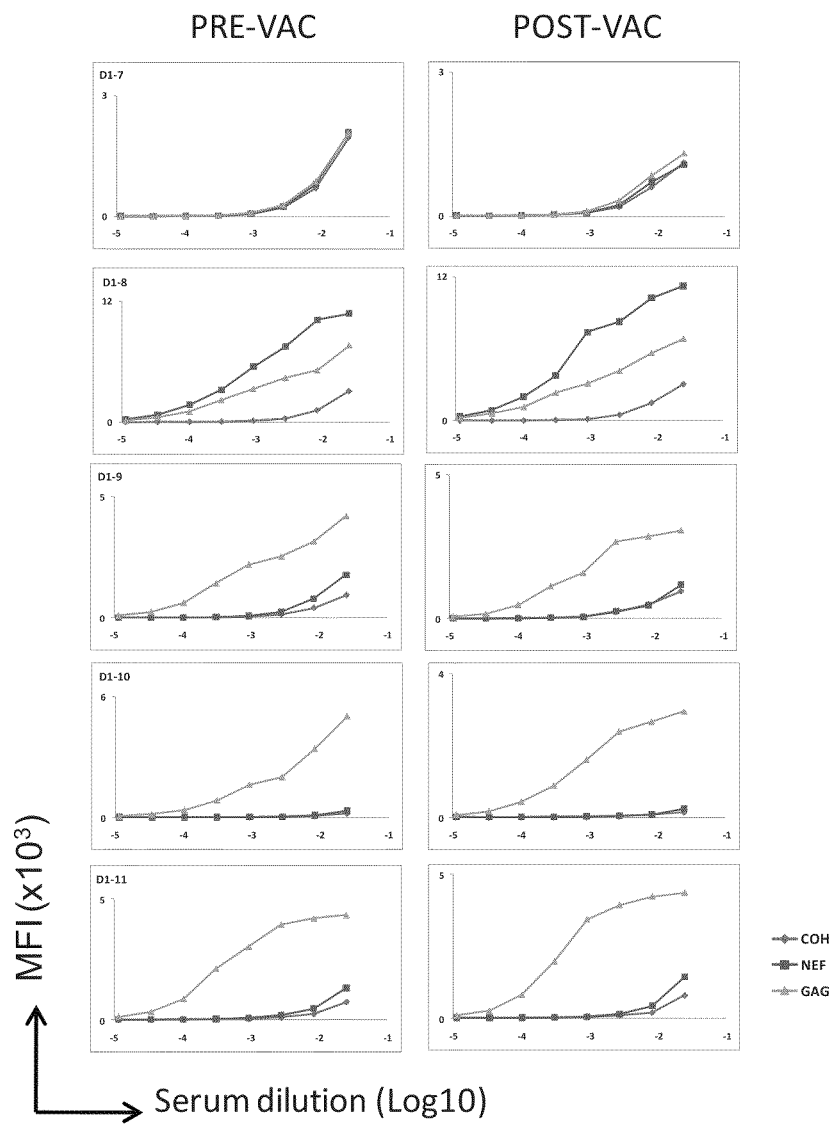
FIG. 77. Serum samples from patients D1-7 to D1-11 taken before and after vaccination were tested for antibody responses against Nef and Gag p24 proteins.

Anti HIV-antibodies: The inventors observed no detectable antibodies against any of the LIPO5 peptides (Gag17, Gag253, Nef116, Nef66 and Pol325) in the serum from patient D1-1. However, antibodies recognizing Nef and Gag p24 proteins were detectable at the same level before and after vaccination (FIG. 74-76). The Serum samples from patients D1-7 to D1-11 taken before and after vaccination were tested for antibody responses against Nef and Gag p24 proteins (FIG. 77).

Polychromatic flow cytometry analysis: The longitudinal study showed equal numbers of CD4+ and CD8+ T cells before and after vaccination. The vaccination does not seem to alter the CD4+/CD8+ ratio. However, after ATI, the CD8+ T cell population became the larger fraction though the total number of CD3+ T cells does not seem to be considerably altered.

Figure 78:
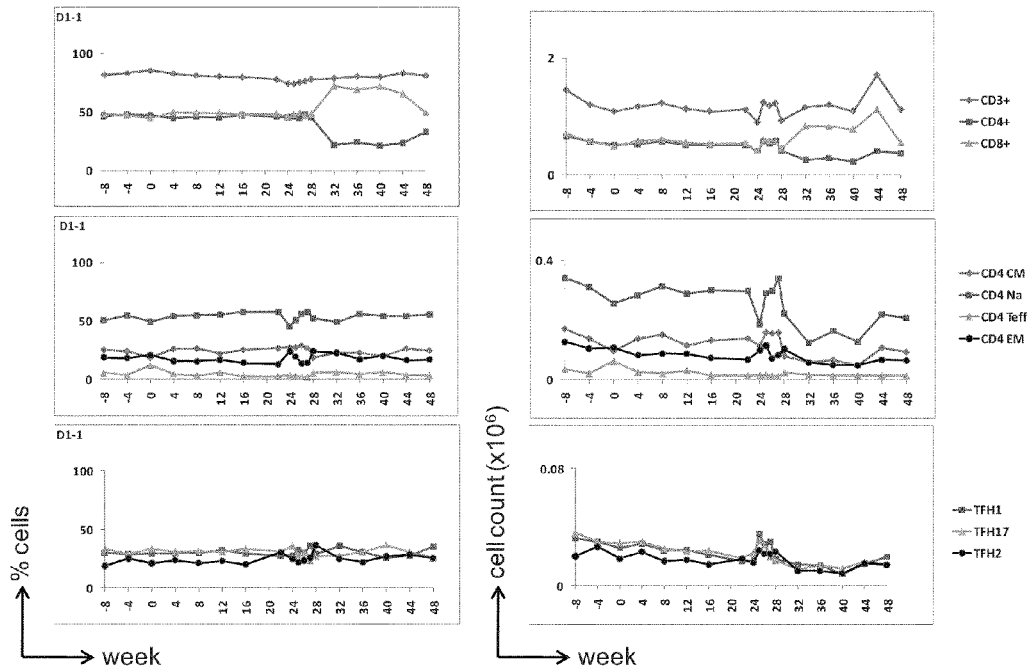
FIG. 78. Longitudinal study of CD4 T cell phenotype patient D1-1.
Figure 79:
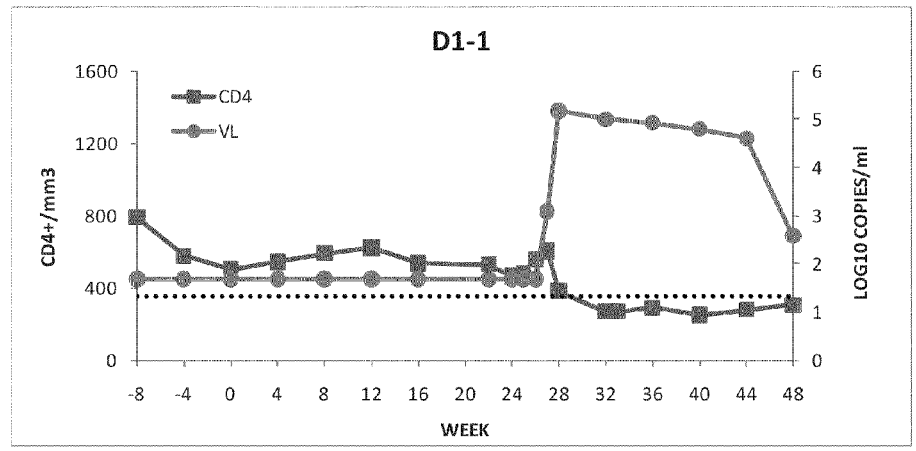
FIG. 79. Longitudinal study of CD4+ T cell count and viral load for patient D1-1.

CD4+ T cells: At study entry, the CD4+ T cells are about 50% naïve (CCR7+ CD45RA+), 25% central memory (CCR7+ CD45RA−) and 25% effector memory (CCR7− CD45RA−). The vaccination does not appear to considerably alter the balance between the subsets. ATI results in a decrease of CD4+ T cells, which affects the naïve and central memory populations. There is no significant change in the percentage of each subset of follicular helper cells, although their numbers decrease equally after ATI—consistent with them belonging to the central memory compartment (FIG. 78).

Figure 90:
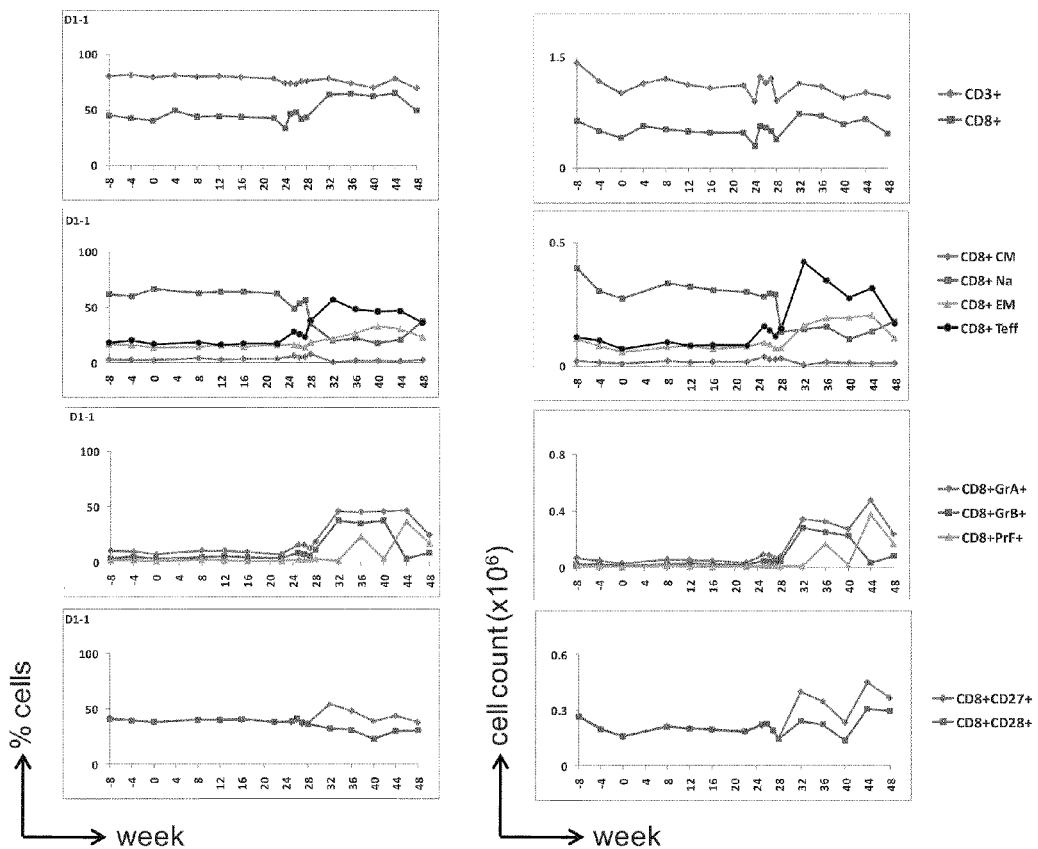
FIG. 90. Longitudinal study of CD8 T cell phenotype patient D1-1.

CD8+ T cells: At study entry, more of 60% of this patient's CD8+ T cells are naïve (CCR7+ CD45RA+), while effector memory (CCR7−CD45RA−) and effector (CCR7−CD45RA+) cells each represent about 20% of the CD8+ T cells. The vaccination procedure does not seem to affect significantly the number of each subset. ATI, on the other hand, has a significant impact on CD8+ T cell composition. First, the overall number of CD8+ T cells slightly increases. Second, the number with a naïve phenotype decreases while effector and effector memory cell numbers increase sharply. The increase of effector CD8+ T cells correspond to an increase of intracellular cytotoxic molecules (Granzyme A and Granzyme B) at week 28 and a more transitory increase of perforin at week 32. ATI has an effect on CD27 and CD28 expression markers of effector memory populations (FIG. 90).

Figure 96:
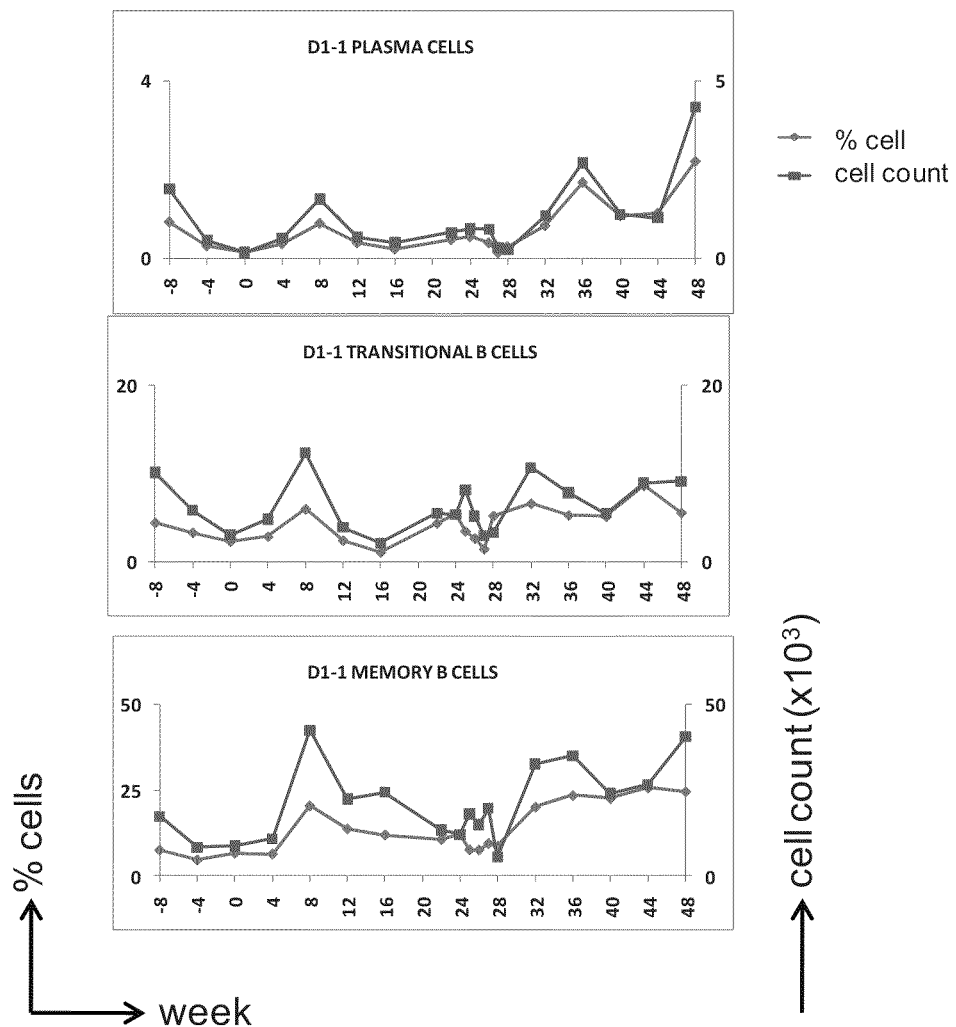
FIG. 96. Longitudinal study of B cell phenotype patient D1-1.

The study of the B cell subsets shows an increase of plasma cells after the third vaccination (week 8) and after ATI (starting on week 32). The inventors also observed an increase of transitional (CD24+CD38+) and memory cells (CD19+CD20+CD27+IgD−) at w8 and w32 (FIG. 96).

Figure 102:
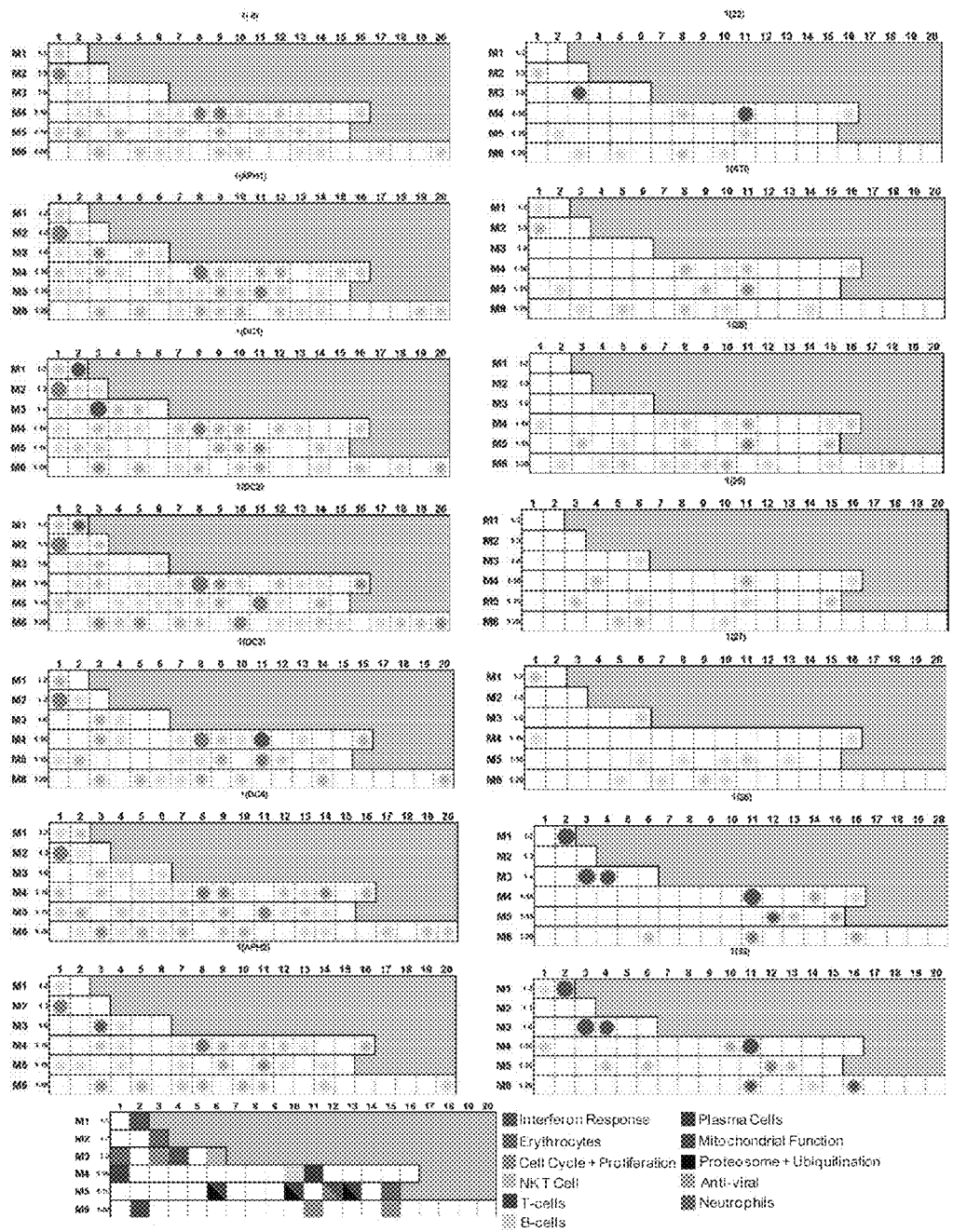
FIG. 102. D1-1 transcriptional module framework.
Figure 108:
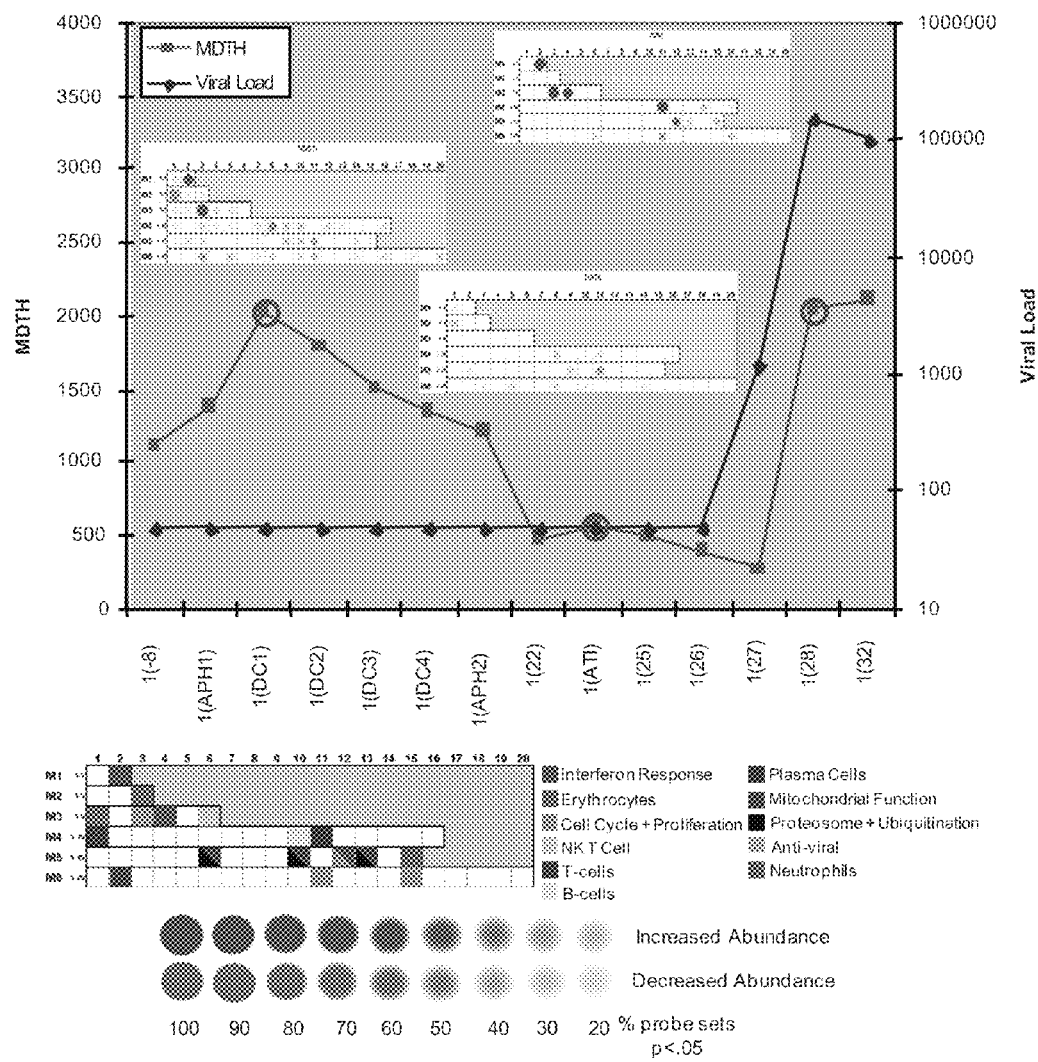
FIG. 108. D1-1 module activity summary.
Figure 114:
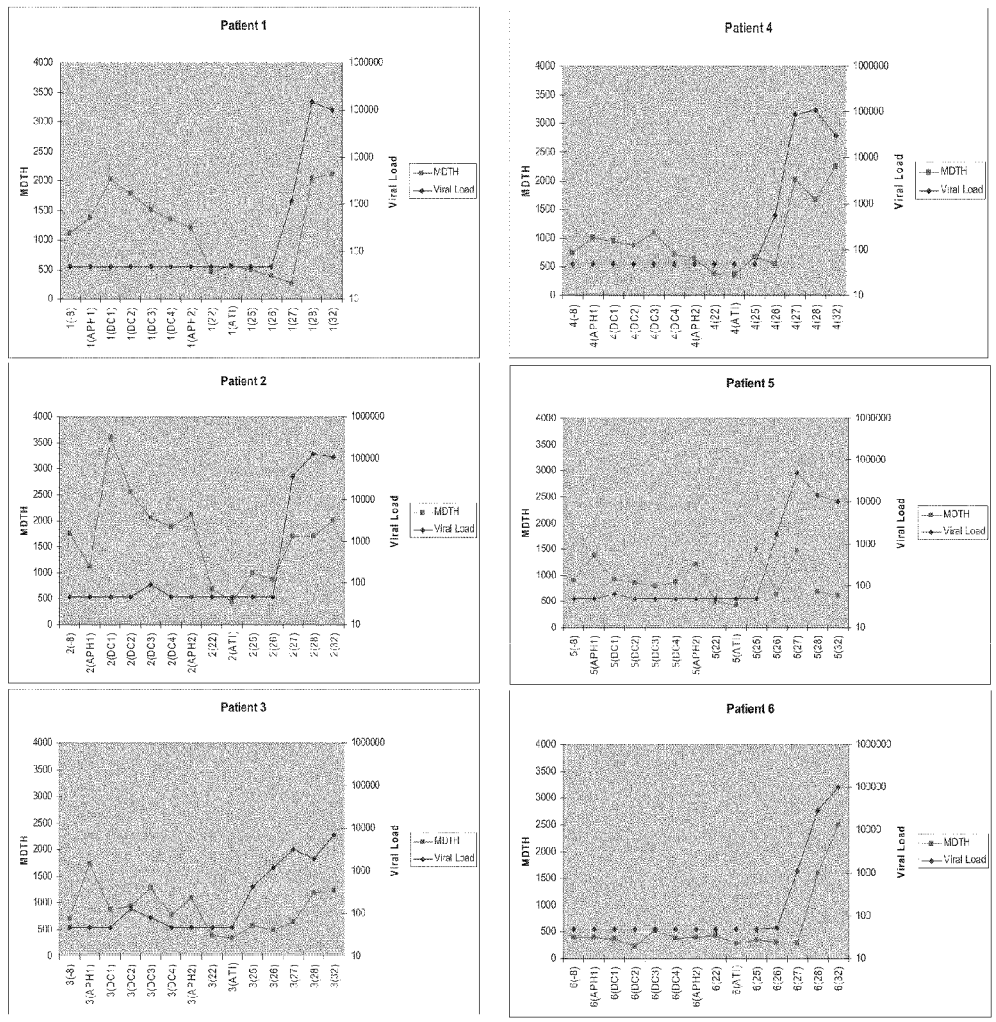
FIG. 114. Molecular Distance to Health (MDTH) and viral load for Dalia-1 patients 1-6. A quantitative metric of global module activity, MDTH, was used to quantify the trancriptional variance of each sample relative to a healthy baseline composed of seven age and sex matched controls (left y-axis) The MDTH was calculated for M1.1-M6.20. Viral load measured in copies/ml is plotted on the right y-axis for each time point.

Blood Transcriptome: D1-1 exhibited an increase in MDTH following apheresis 1 (APH1) that was associated with increased interferon (M1.2) and cell cycle (M3.3) activity at the time of vaccination (DC1). This signature resolved by DC3, at which time a plasma cell signature was noted. Following the second apheresis (APH2), the M3.3 cell cycle signature returned as did the M4.11 plasma cell activity. By two weeks later, this signature was extinguished. Minimal transcriptional perturbations were noted post-ATI until week 28 when strong increases in interferon (M1.2, M3.4, M5.12), plasma cell (M4.11), and cell cycle (M3.3) modules were noted. The activity of cell cycle modules expanded by week 32 to include M6.11. Notably, the transcriptional activity initiated at week 28 lagged behind the resurgence of circulating virus first noted at week 27 (FIG. 102 and FIG. 108). MDTH and viral load for patients D1-1 to D1-6 is presented in FIG. 114.

Figure 5:
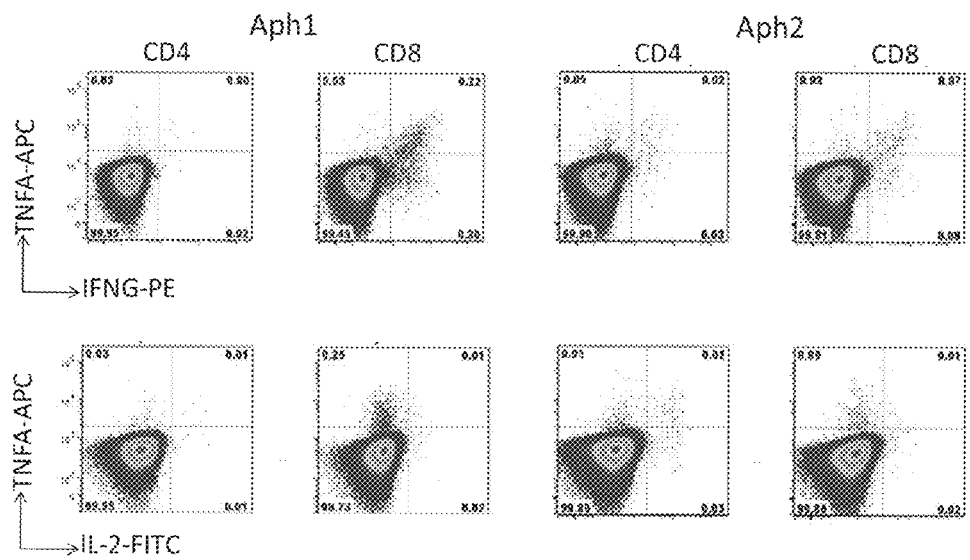
FIG. 5. D1-1: ICS after 6 hours LIPO5 long peptides mix stimulation of Aph1 and Aph2.
Figure 20:
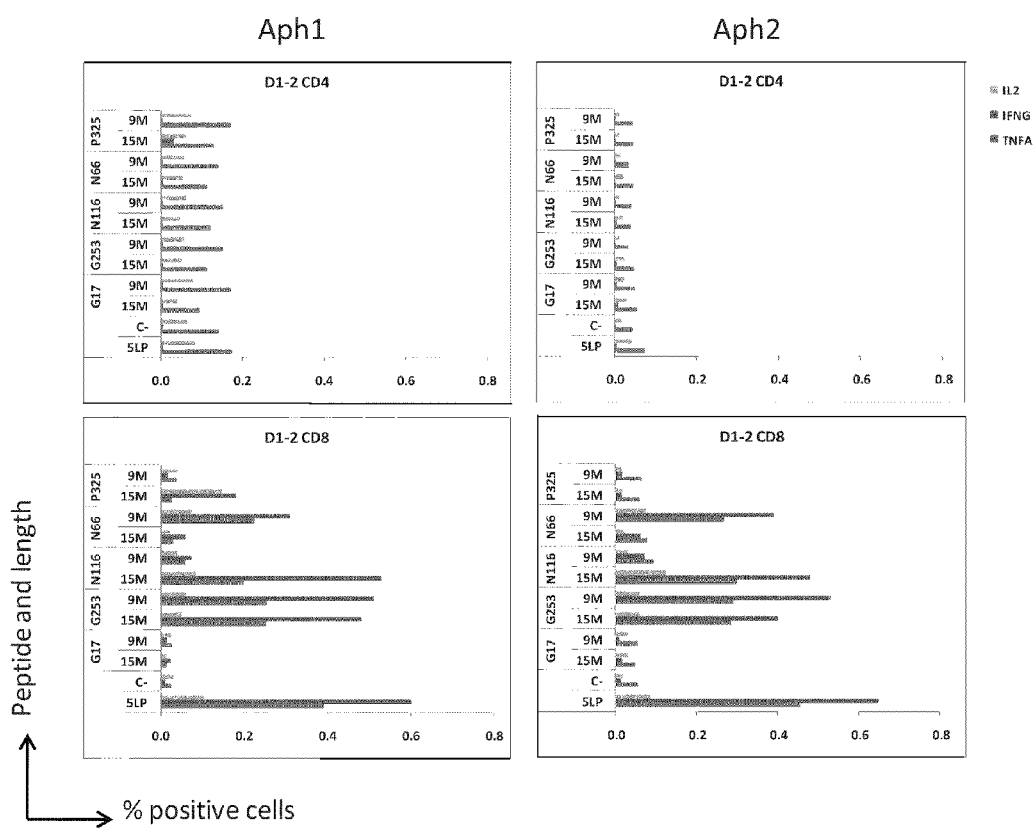
FIG. 20. D1-2: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

Patient D1-2:

ICS analysis: There was no change in the peptide-specific CD4+ T cell response after vaccination. The inventors observed a slight decrease in peptide-specific CD8+ T cells (double positive cells expressing TNFα and IFNγ from 0.5% to 0.45% (FIG. 5). The stimulation with pools of 15-mers and 9-mers derived from LIPO5 sequences showed strong CD8 responses to Gag253, Nef66, Nef116 and Pol325 before and after vaccination (FIG. 20).

Cytokine secretion analysis: Small responses to Gag253 and Nef66 were observed by IL-2 production: 40 pg/ml for Gag253 and 10 pg/ml for Nef66. These responses were not confirmed by the secretion of any other cytokine (FIG. 30-41).

Anti HIV-antibodies: The inventors observed no detectable antibodies against any of the LIPO5 peptides in serum from patient D1-2. However, antibodies recognizing Nef and Gag p24 proteins were detectable at the same level before and after vaccination (FIG. 74-76).

Polychromatic flow cytometry analysis: The longitudinal study showed no changes in the numbers of CD4+ and CD8+ T cells. Vaccination does not seem to alter the CD4+/CD8+ ratio. However, after ATI, the CD8+ population became the larger fraction, though the total number of CD3+ T cells did not seem to be considerably altered.

Figure 80:
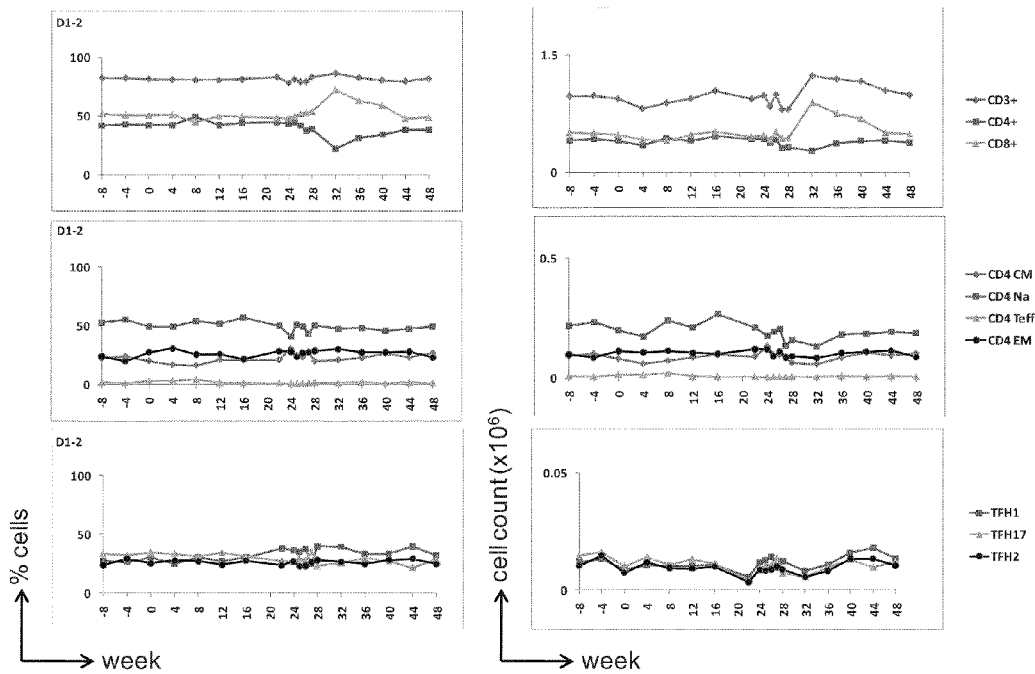
FIG. 80. Longitudinal study of CD4 T cell phenotype patient D1-2.
Figure 81:
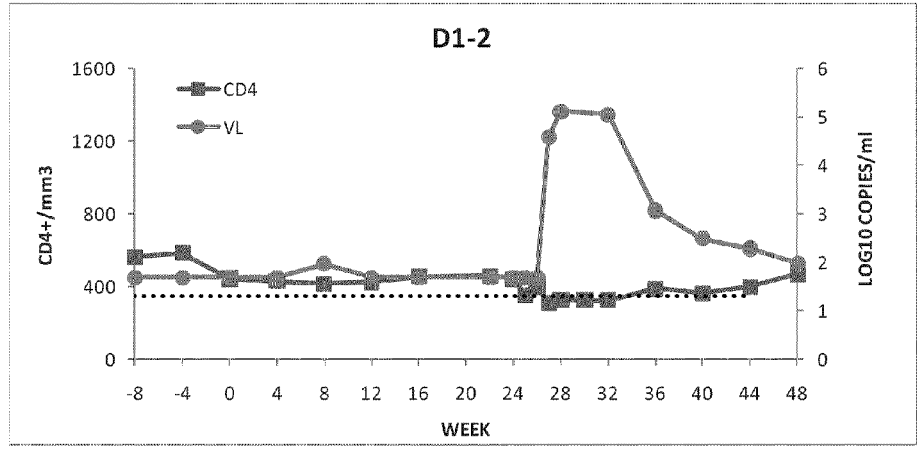
FIG. 81. Longitudinal study of CD4+ T cell count and viral load for patient D1-2.

CD4+ T cells: At study entry, CD4+ T cells are about 50% naïve (CCR7+ CD45RA+), 25% central memory (CCR7+ CD45RA−) and 25% effector memory (CCR7− CD45RA−). The vaccination does not appear to considerably alter the balance between the subsets. ATI results in a decrease of CD4+ T cells, which affects the naïve and central memory populations. There is no significant change in the percentage or number of each subset of follicular helper cells (FIG. 80).

Figure 91:
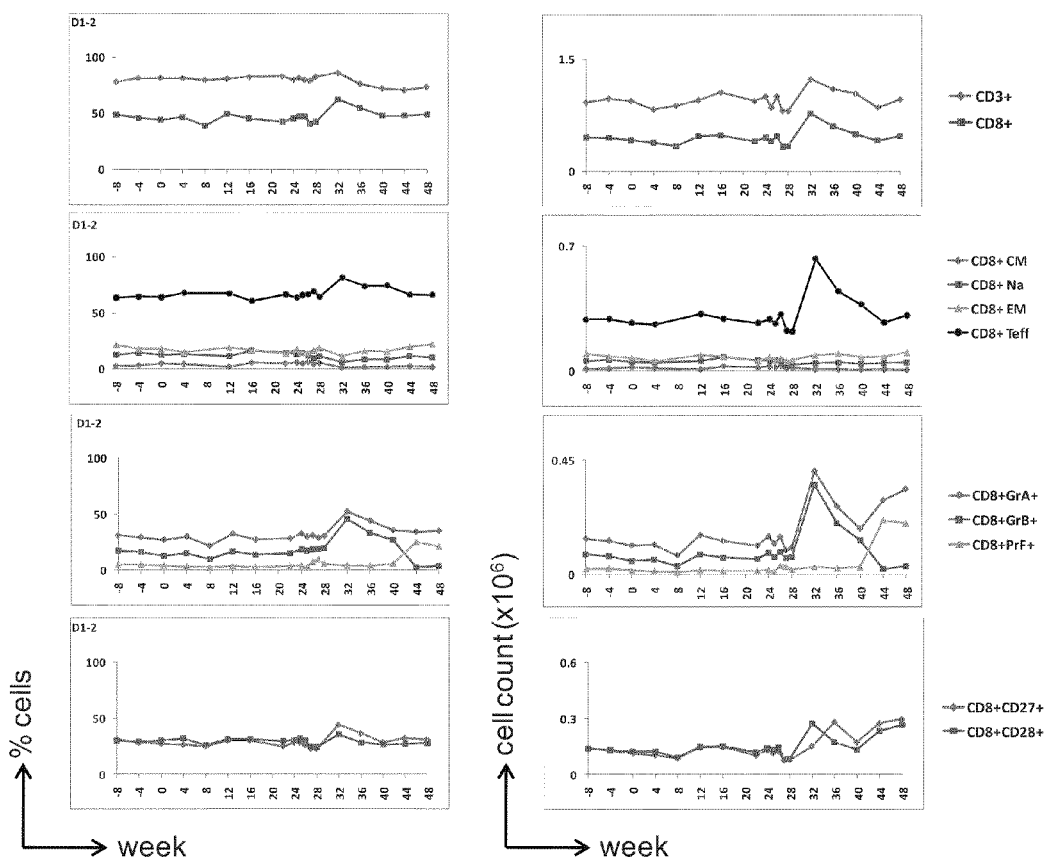
FIG. 91. Longitudinal study of CD8 T cell phenotype patient D1-2.

CD8+ T cells: At study entry, more of 60% of this patient's CD8+ T cells are effector cells (CCR7− CD45RA+), while effector memory (CCR7− CD45RA−) and naïve (CCR7+ CD45RA+) cells each represent about 20% of the CD8+ T cells. The vaccination procedure does not seem to affect significantly the number of each subset. After ATI, the overall number of CD8+ T cells slightly increases. The population affected is the effector cells with not evident change in the other subsets. The increase of effector CD8+ T cells correspond to an increase of intracellular cytotoxic molecules (Granzyme A and Granzyme B) at week 28 (FIG. 91)

Figure 97:
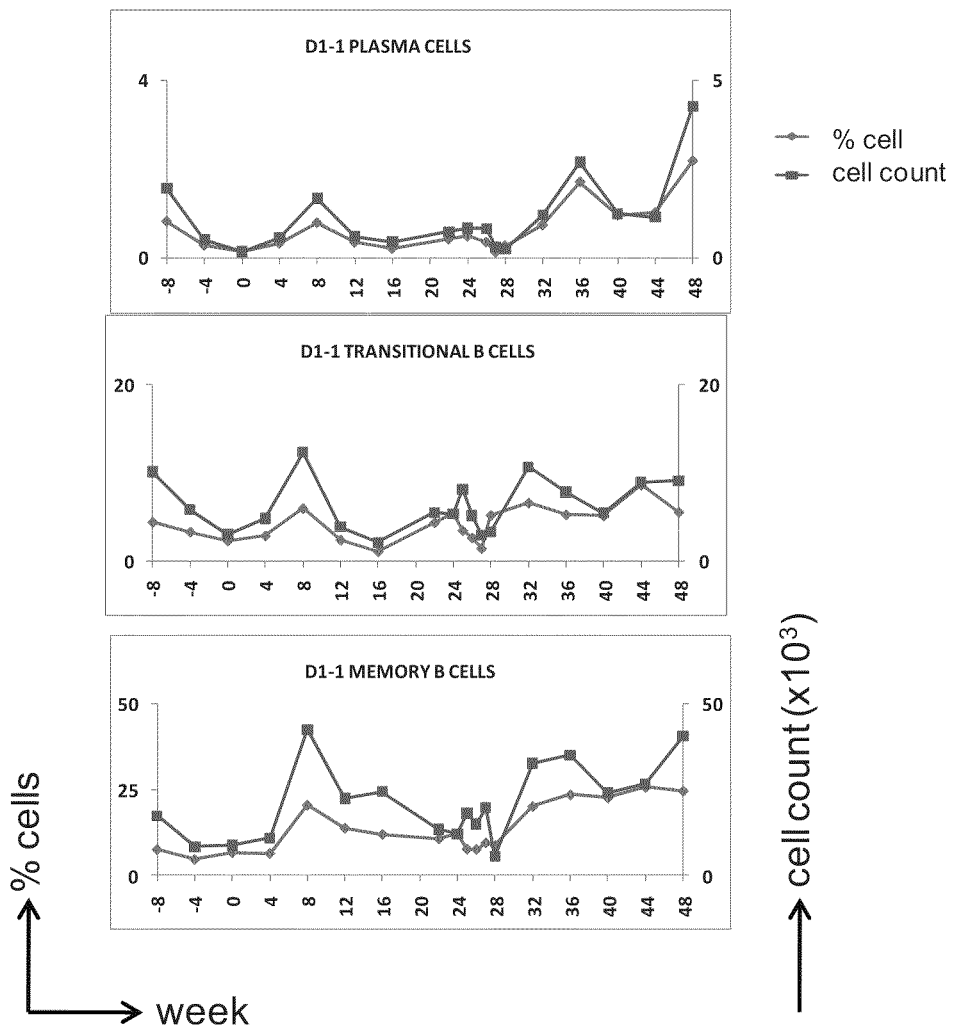
FIG. 97. Longitudinal study of B cell phenotype patient D1-2.

The study of the B cell subsets shows an increase of plasma cells after ATI (starting on week 32). The inventors also observed an increase of transitional cells (CD24+ CD38+) (FIG. 97).

Figure 103:
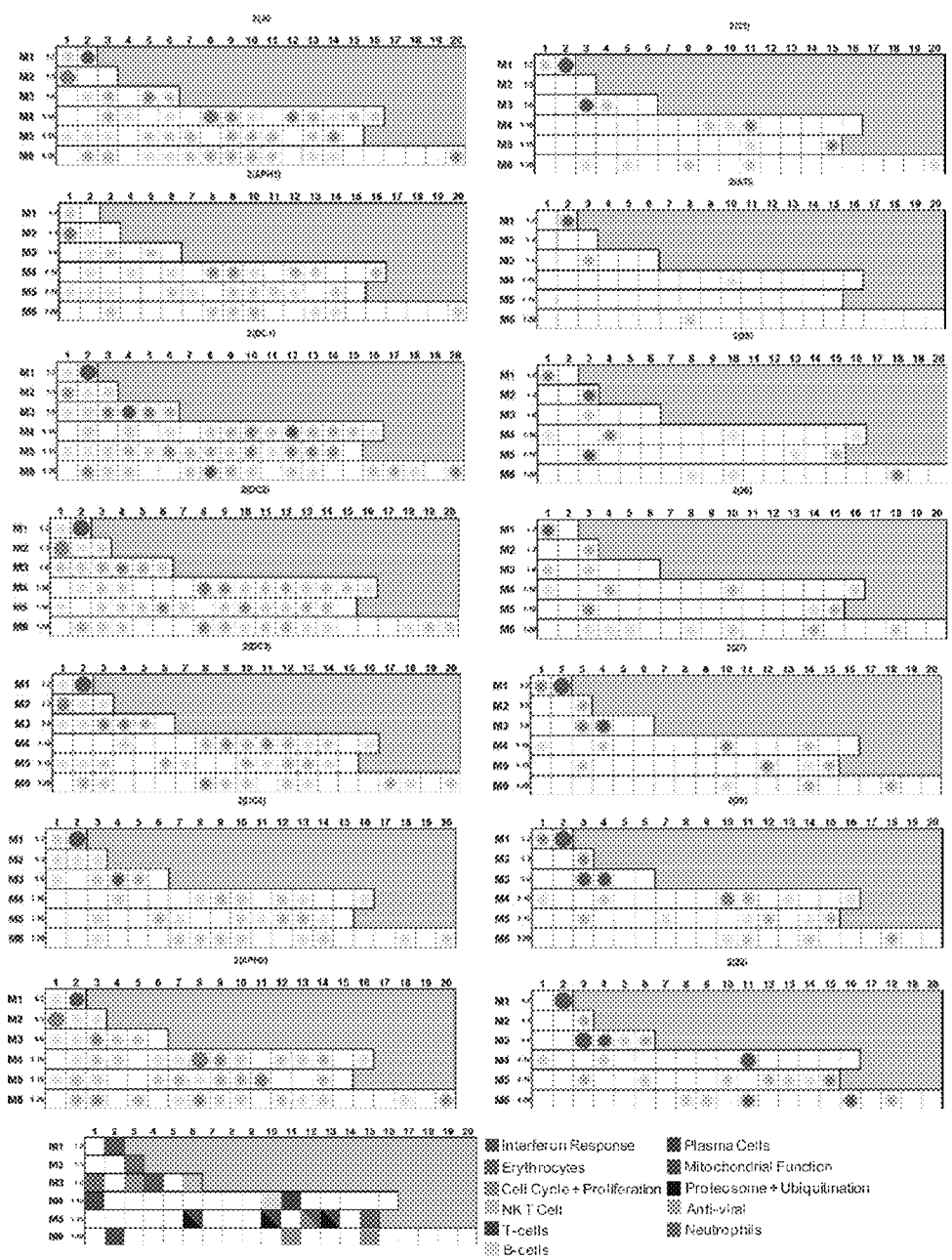
FIG. 103. D1-2 transcriptional module framework.
Figure 109:
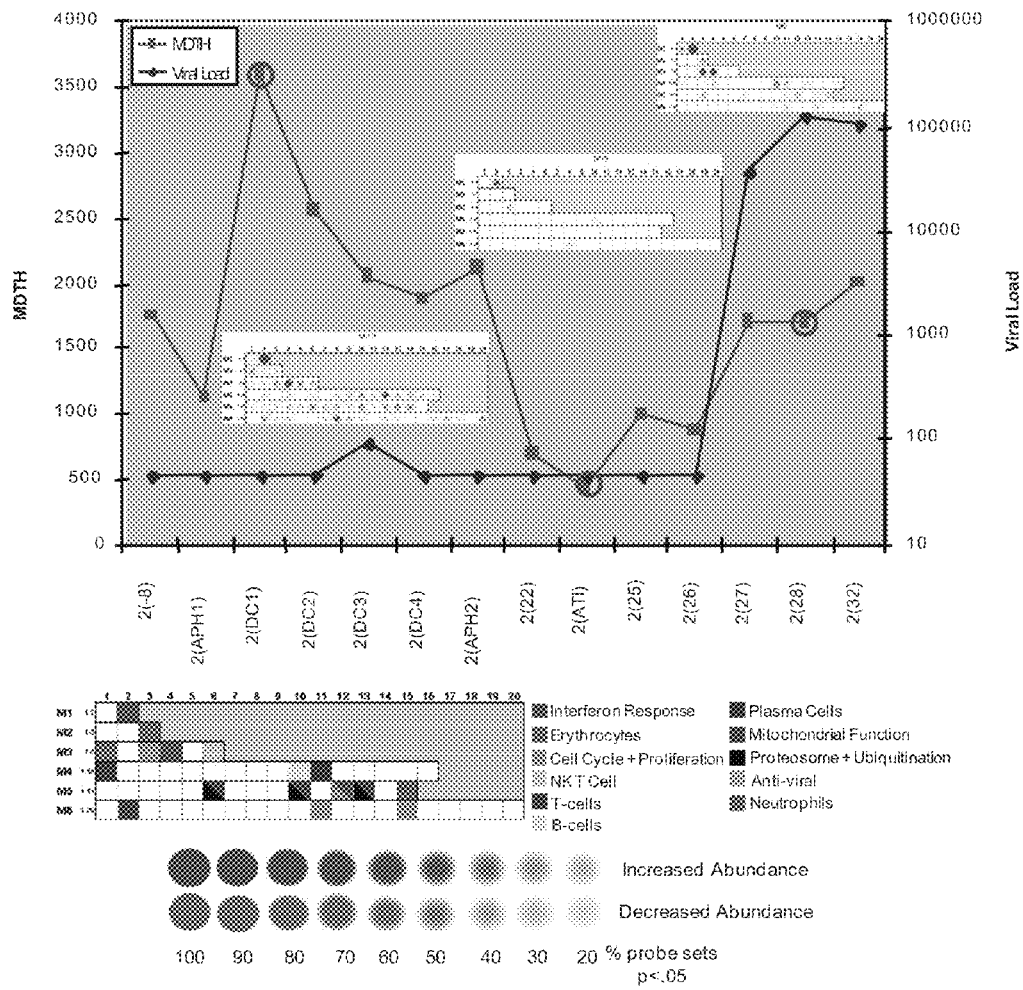
FIG. 109. D1-2 module activity summary.

Blood Transcriptome: D1-2 exhibited an increase in MDTH following apheresis 1 that was associated with increased interferon (M1.2, M3.4). This interferon signature is maintained through the vaccination sequence until ATI. The complete interferon signature (M1.2, M3.4, M5.12) emerges 3 weeks post-ATI (week 27) and is accompanied by reduced abundance of B-cell transcripts (M4.10). By weeks 28 and 32 cell cycle activity emerges (M3.3, M6.11) along with increased plasma cell activity (M4.11). Notably, the transcriptional activity initiated at week 27 corresponds to the first increase in circulating virus (FIG. 103 and FIG. 109).

Patient D1-3:

ICS analysis: Increase of peptide-specific CD4+ T cell response after vaccination: From 0.05% to 0.41% TNFα+ cells, from 0% to 0.32% IL-2+ cells and from 0.01% to 0.12% IFN+ cells. Among HIV-specific CD4+ T cells, 0.20% expresses both IL-2 and TNFα and 0.07% are double positive for TNFα and IFNγ.

Figure 6:
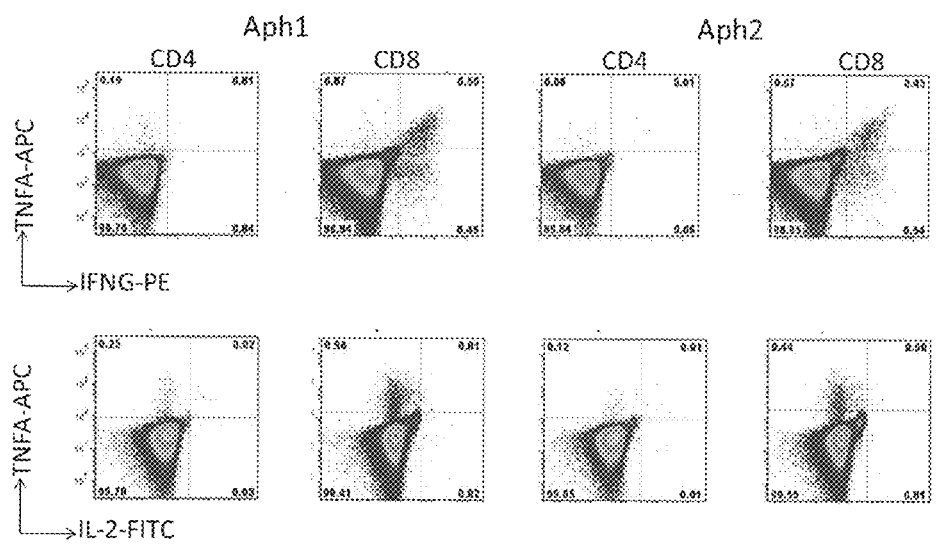
FIG. 6. D1-2: ICS after 6 hours LIPO5 long peptides mix stimulation of Aph1 and Aph2.
Figure 21:
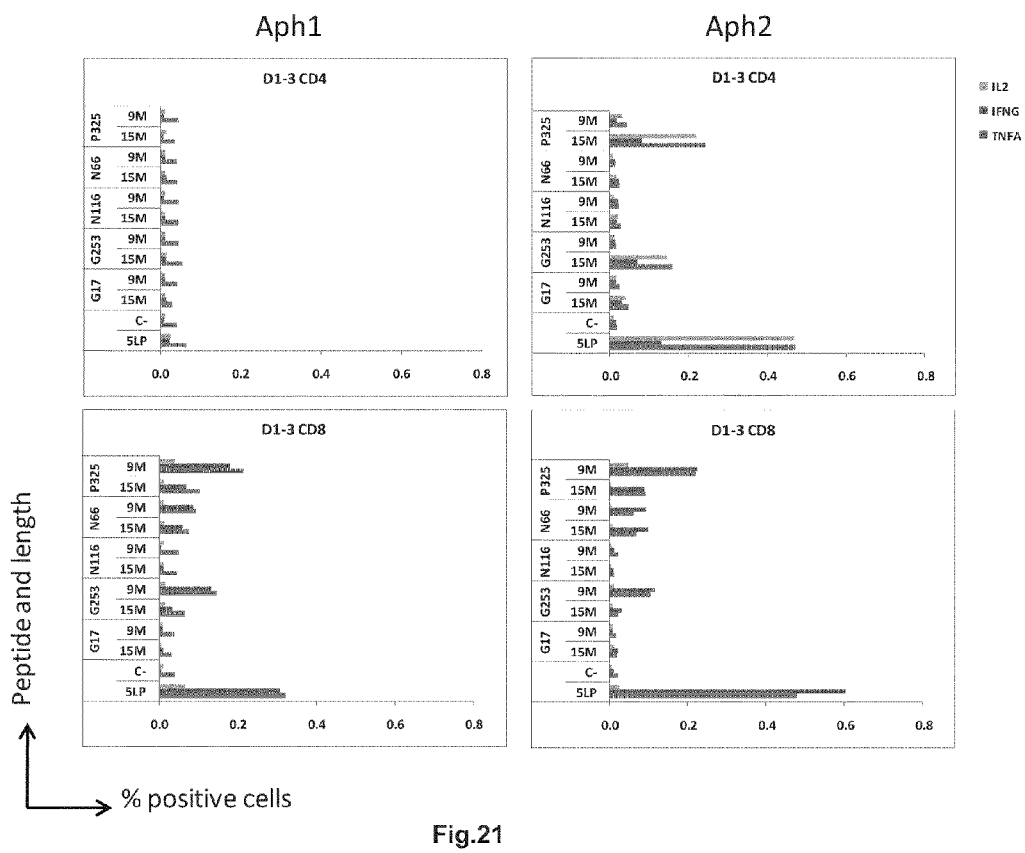
FIG. 21. D1-3: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

The inventors observed an increase in peptide-specific CD8+ T cells from 0.77% IFN secreting cells to 1%. An increase of double positive cells expressing TNFα and IFNγ from 0.63% to 0.74% after vaccination was observed (FIG. 6). The stimulation with pools of 15-mers and 9-mers derived from LIPO5 sequences showed small CD4 responses to Gag17, Gag253 and Pol325 after vaccination and CD8 responses to Gag253, Nef66 and Pol325 observed before and after vaccination (FIG. 21).

Cytokine secretion analysis: Luminex showed a significant increase in responses against Gag253, Nef116 and Pol325 post-vaccination with strong secretion of IL-2, IL-5, IL-13, IL-21 and IFNγ against the three peptides (FIG. 30-41).

Gag253 induces 300 pg/ml IL-2, 140 pg/ml IL-5, 460 pg/ml IL-13, 230 pg/ml IL-21 and 2.2 μg/ml IFNγ

Nef116 induces 190 pg/ml IL-2, 50 pg/ml IL-5, 220 pg/ml IL-13, 50 pg/ml IL-21 and 1 μg/ml IFNγ.

Pol325 induces 270 pg/ml IL-2, 250 pg/ml IL-5, 430 pg/ml IL-13, 640 pg/ml IL-21 and 2.4 μg/ml IFNγ

Nef66 stimulated a small secretion of IL-2 (40 pg/ml) and IFNγ (460 pg/ml). Gag17 stimulation induces 300 pg/ml of IL-2 secretion.

Figure 44:
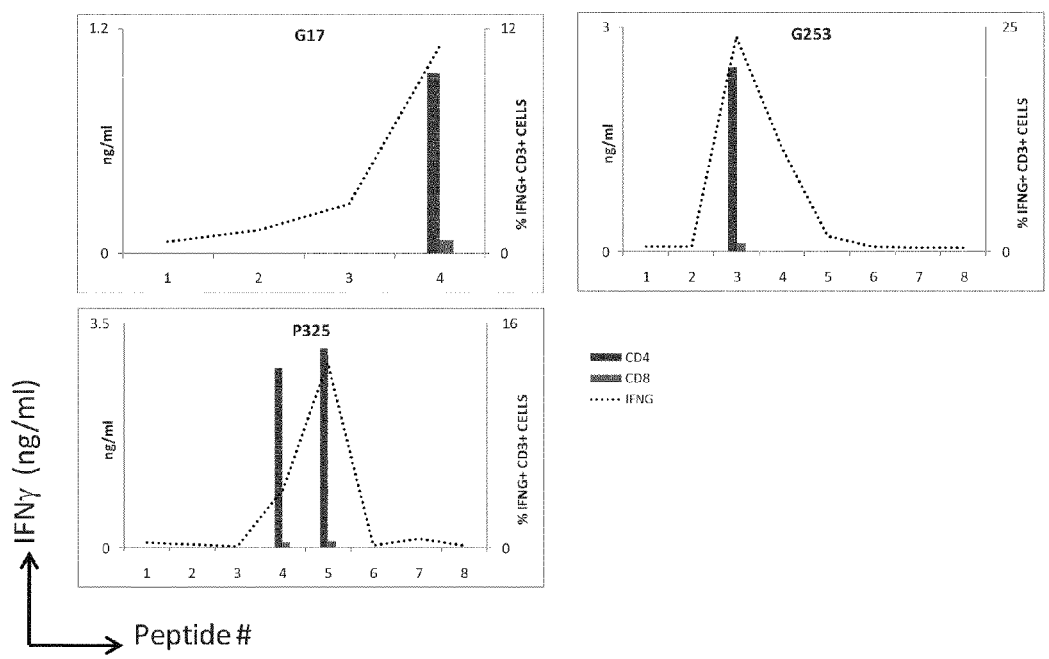
FIG. 44. D1-3: 7 days peptide stimulated cultures from Aph 2 were used for ICS after 6 hours 15-mer peptide stimulation.
Figure 45:
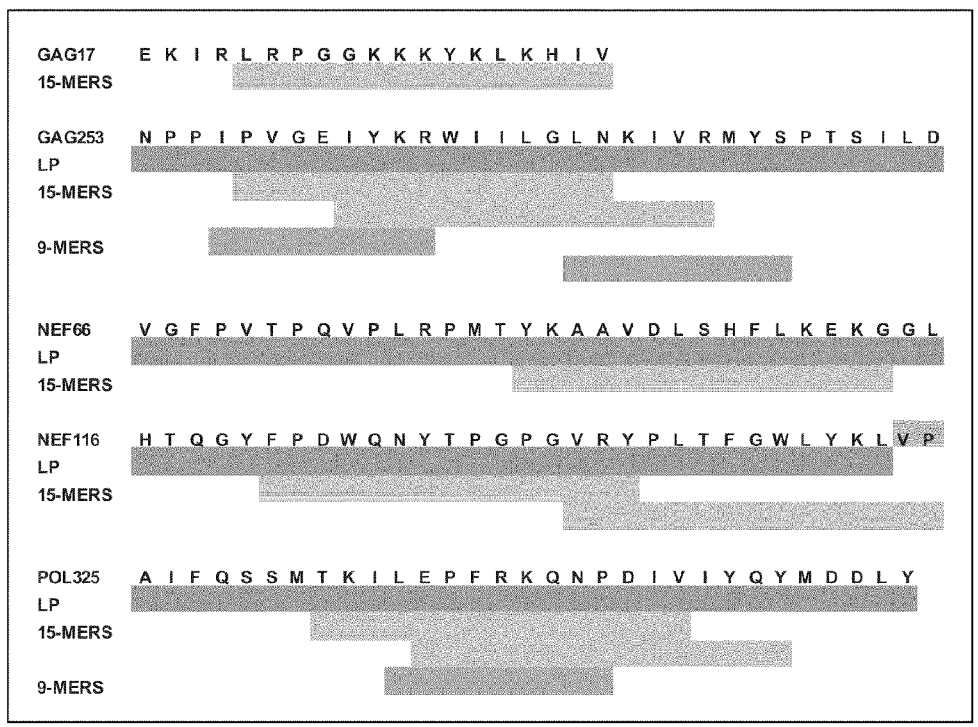
FIG. 45. Summary of the results obtained by Luminex analysis of patient D1-3 T cells stimulated with LIPO5 long peptides (19-32 aa), 15-mers and 9-mers (SEQ ID NOs. 1, 2, 3, 6, 5).
Figure 46:
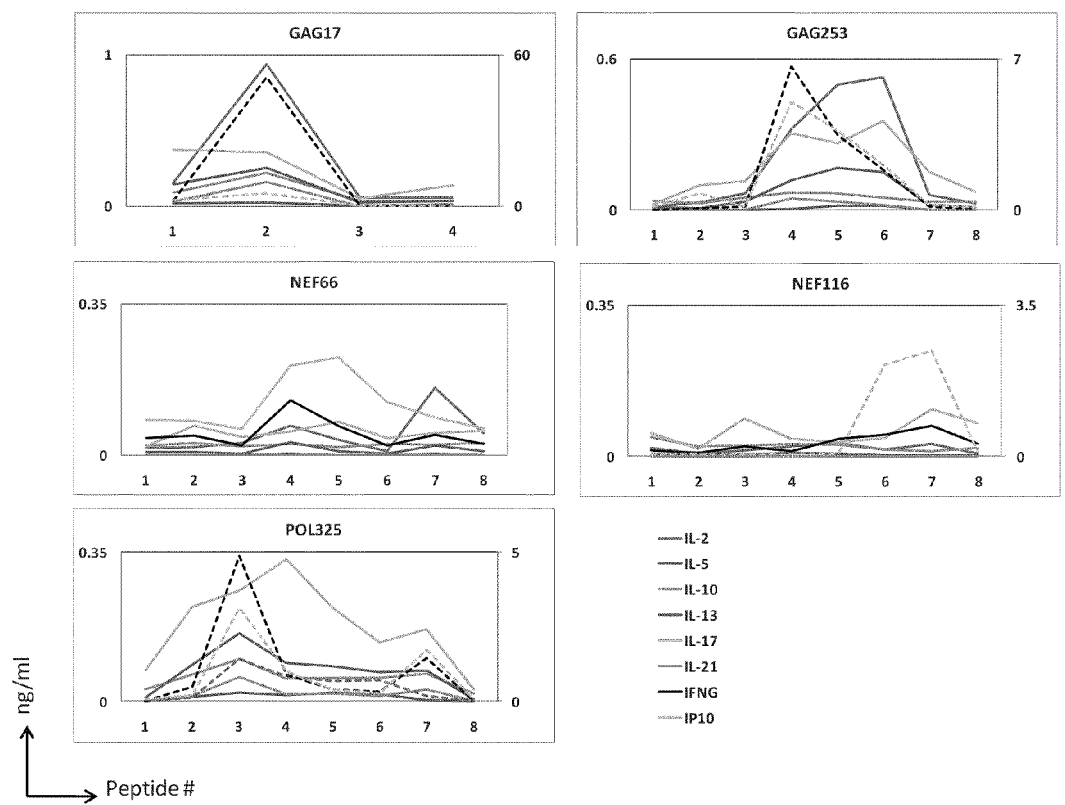
FIG. 46. DALIA vaccinated patient D1-4 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 47:
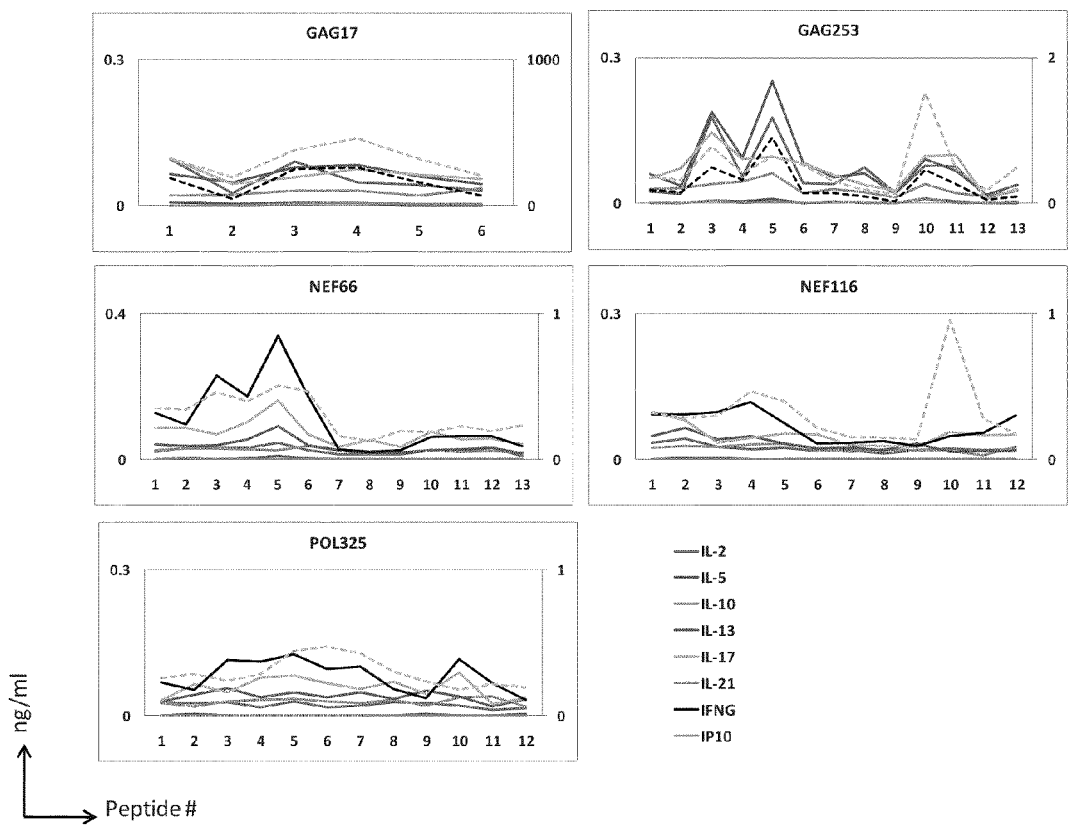
FIG. 47. DALIA vaccinated patient D1-4 PBMCs were stimulated with 9-mers of LIPO5 peptides for 48 hours. Luminex analysis of cytokine secretion post-vaccination samples. Dotted lines represent cytokines with high concentration in the supernatants (right side axes).

The epitopes recognized from the 15-mer peptides were p3 in Gag 17, peptides p3 and p4 in Gag 253, peptide p6 in Nef 66, peptides p4 and p7 in Nef 116, and peptides p4 and p5 in Pol 325. The epitopes from the 9-mers were peptides p3 and p10 in Gag 253 and p1 and p6 in Pol 325 (FIG. 42-45). Detailed ICS showed that Gag17, G253, Nef66 and Pol325 15-mer epitopes are mostly CD4+ T cell epitopes (FIG. 44).

Anti HIV-antibodies: The inventors observed no detectable antibodies against any of the LIPO5 peptides in serum from patient D1-3; however, antibodies recognizing Nef and Gag p24 proteins were detectable at the same level before and after vaccination (FIG. 74-76).

Polychromatic flow cytometry analysis: The longitudinal study showed no change in the numbers of CD4+ and CD8+ T cells. Vaccination does not seem to alter the CD4+/CD8+ ratio. However, after ATI, the CD8+ population becomes the larger fraction, though the total number of CD3+ T cells does not seem to be considerably altered.

Figure 82:
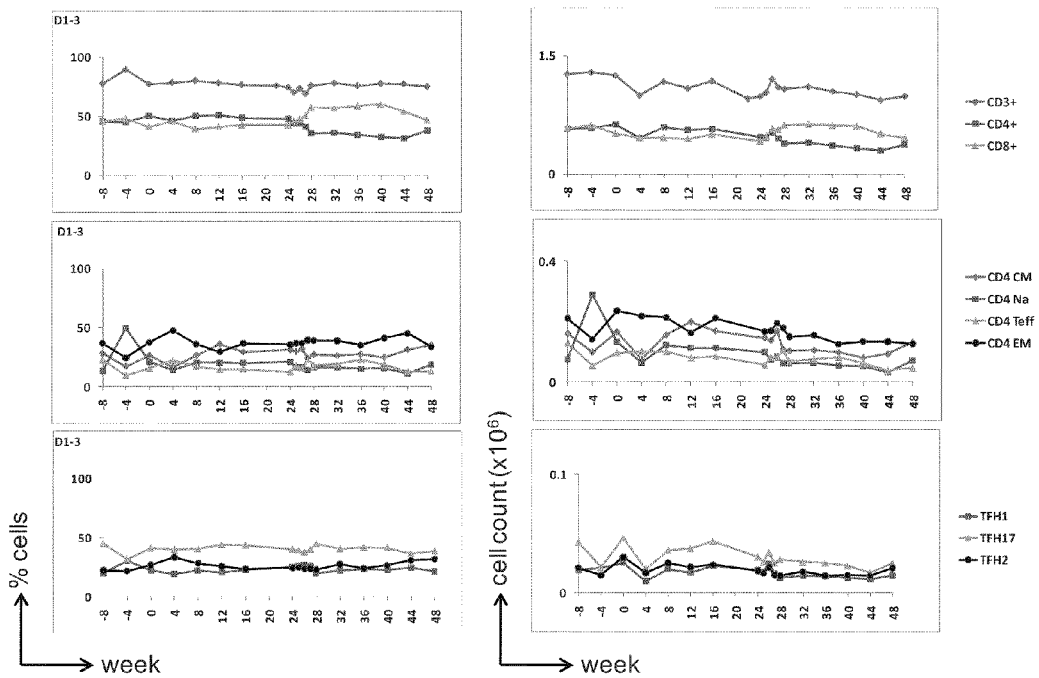
FIG. 82. Longitudinal study of CD4 T cell phenotype patient D1-3.
Figure 83:
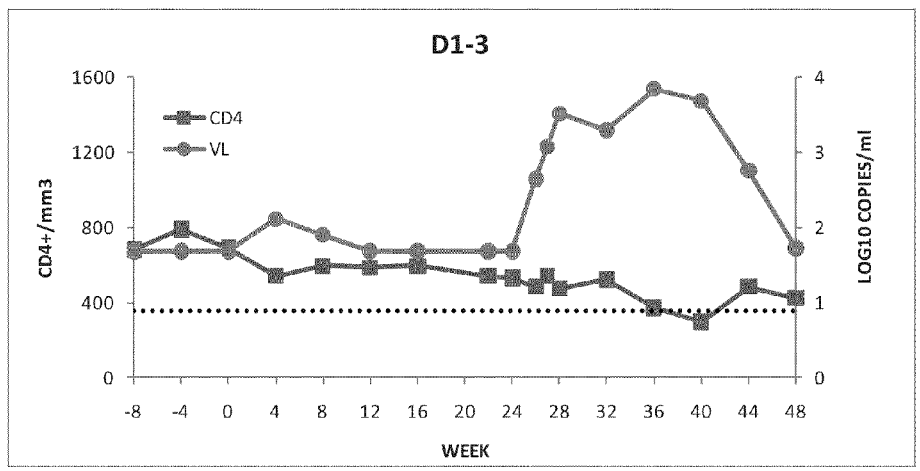
FIG. 83. Longitudinal study of CD4+ T cell count and viral load for patient D1-3.

CD4+ T cells: At study entry, CD4+ T cells are about 50% effector memory (CCR7−CD45RA−), 15% central memory (CCR7+ CD45RA−), 15% effector memory (CCR7− CD45RA−) and 15% naïve cells (CCR7+ CD45RA+). The first apheresis (week—4) transiently increased the naïve subset. The vaccination does not appear to considerably alter the balance between the subsets. ATI results in a small decrease of CD4+ T cells, which affects all populations. There is no significant change in the percentage of each subset of follicular helper cells. However, their numbers decrease equally after ATI, consistent with them belonging to the central memory compartment (FIG. 82).

Figure 92:
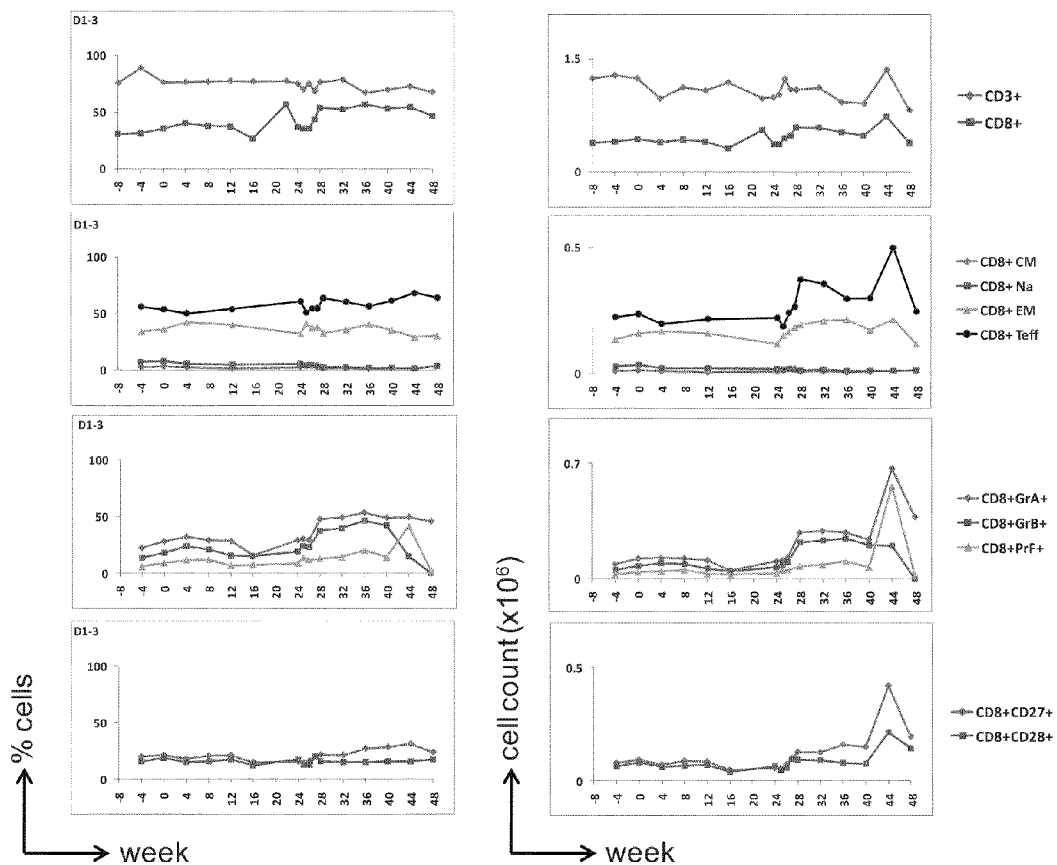
FIG. 92. Longitudinal study of CD8 T cell phenotype patient D1-3.

CD8+ T cells: At study entry, more of 60% of this patient's CD8+ T cells are naïve (CCR7+ CD45RA+), while effector memory (CCR7− CD45RA−) cells represent about 40% of the CD8+ T cells. The vaccination procedure does not seem to affect significantly the number of each subset. ATI, on the other hand, has a significant impact on CD8+ T cell composition. First, the overall number of CD8+ T cells slightly increases. Second, the numbers of effector and effector memory cells increase sharply. The increase of effector CD8+ T cells corresponds to an increase of intracellular cytotoxic molecules (Granzyme A, Granzyme B and perforin) (FIG. 92).

Figure 98:
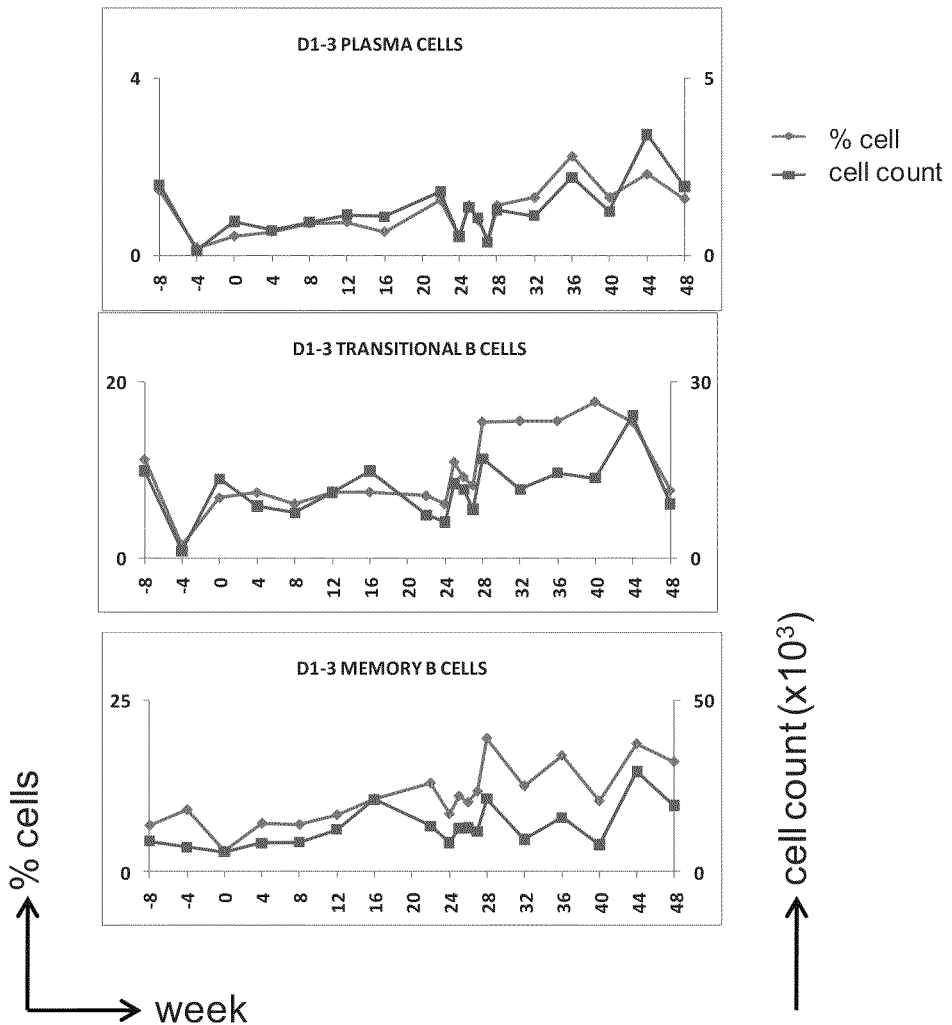
FIG. 98. Longitudinal study of B cell phenotype patient D1-3.

The study of the B cell subsets shows an increase of plasma cells, an increase of transitional cells (CD24+ CD38+) and CD38Bright cells in the CD19+CD20+ population after ATI (starting at week 32). There is a slight decrease of naïve B cells (CD19+CD20+CD27−IgD+) after ATI (FIG. 98).

Figure 104:
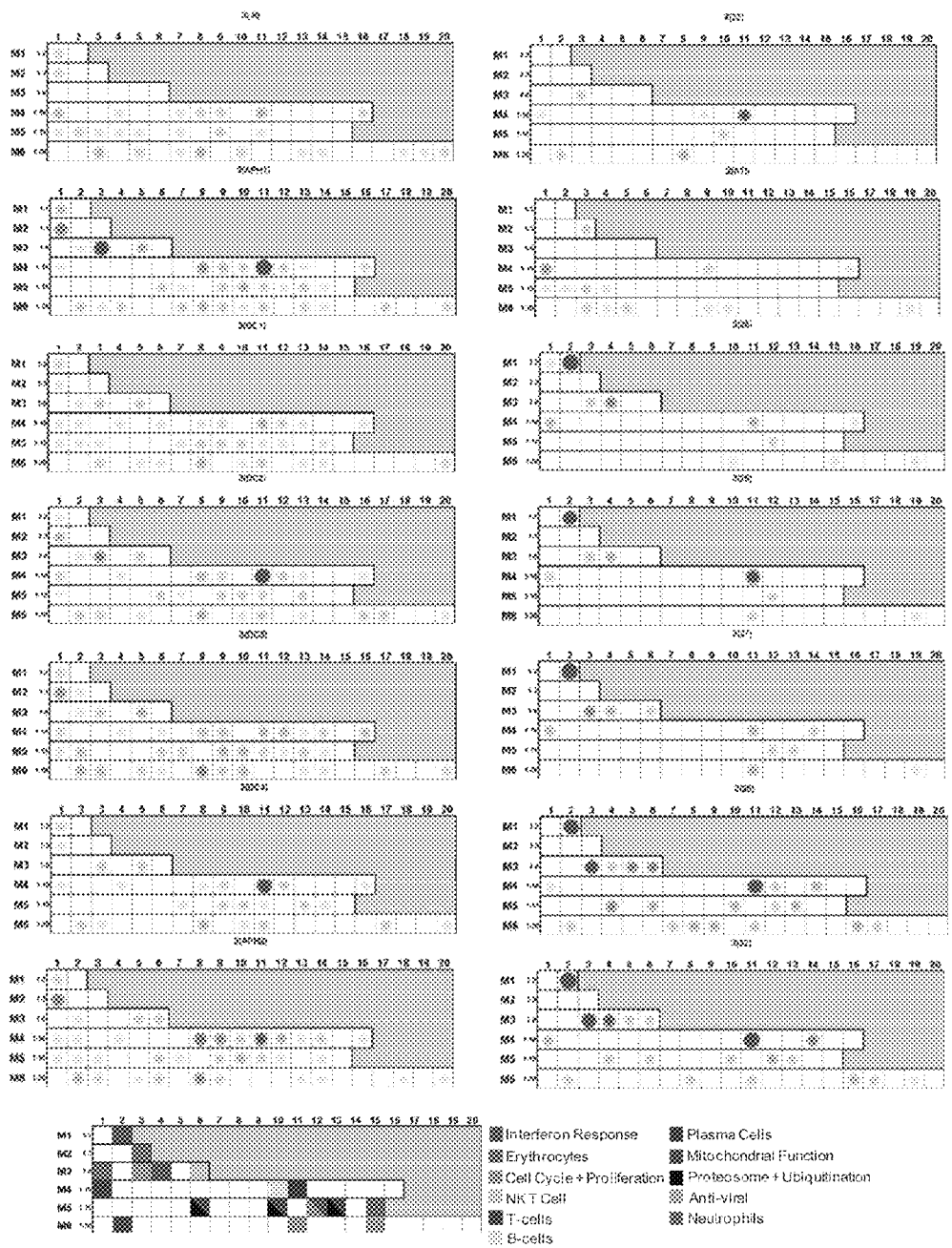
FIG. 104. D1-3 transcriptional module framework.
Figure 110:
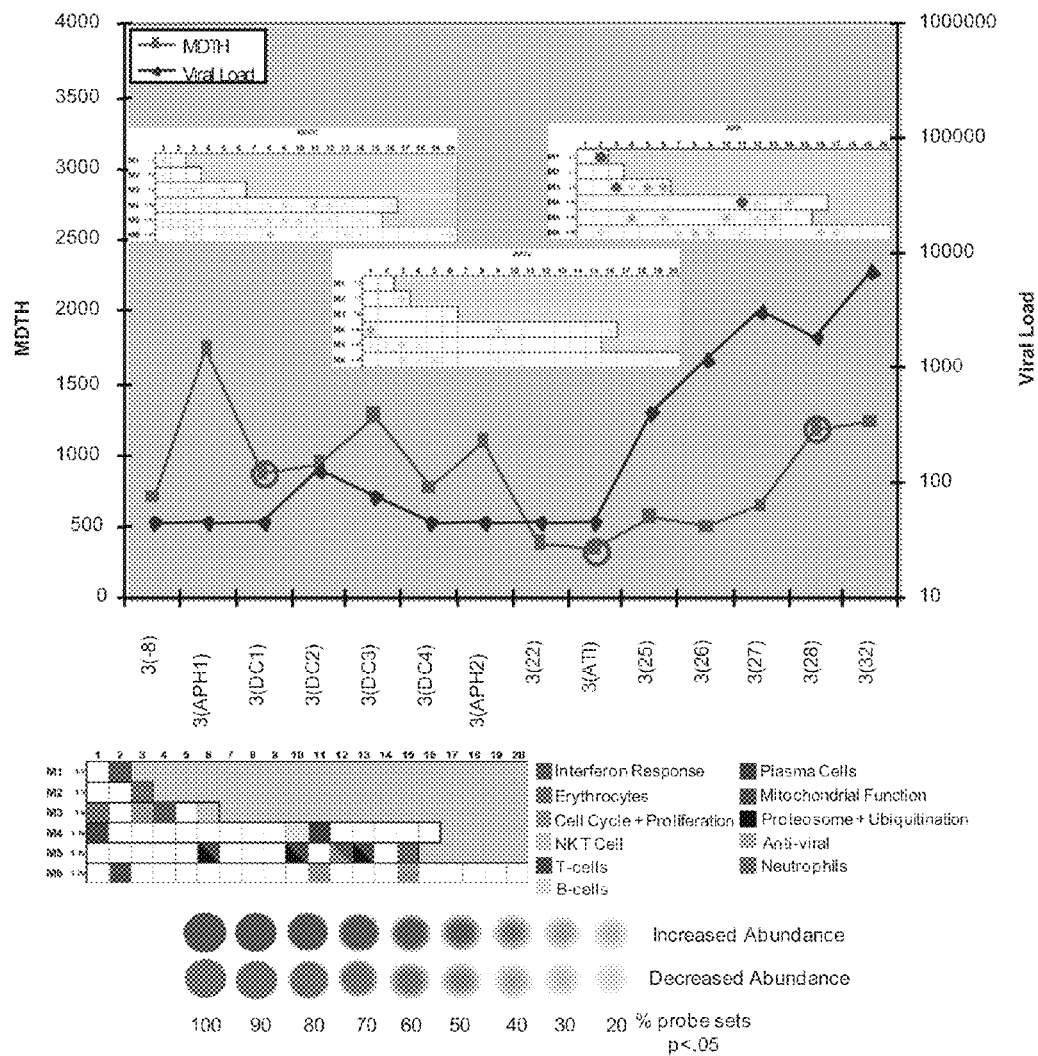
FIG. 110. D1-3 module activity summary.

Blood Transcriptome: D1-3 exhibited a decrease in module activity measured by MDTH following apheresis 1 but still exhibited increased cell cycle (M3.3) and plasma cell (M4.11) module activity at DC1. During the vaccination course, strong but transient plasma cell activity (M4.11) was noted. Interferon activity (M1.2 only) was noted one week following ATI and corresponded with the first measured increase in circulating viral load. A week later (week 26), this activity was augmented by short-lived plasma cell activity (M4.11). By week 28, cell cycle module 3.3 exhibited an increased activity along with a return of the plasma cell module. At week 32, interferon module 3.4 exhibited moderately increased activity, joining M1.2 (FIG. 104 and FIG. 110).

Patient D1-4:

ICS analysis: There is a increase in the peptide-specific CD4+ T cell response after vaccination: From 0.04% to 0.28% TNF+ cells, from 0.01% to 0.27% IL-2+ cells and from 0% to 0.09% IFNγ+ cells. Among HIV-specific CD4+ T cells 0.15% express both IL-2 and TNF and 0.07% are double positive for TNFα and IFNγ.

Figure 7:
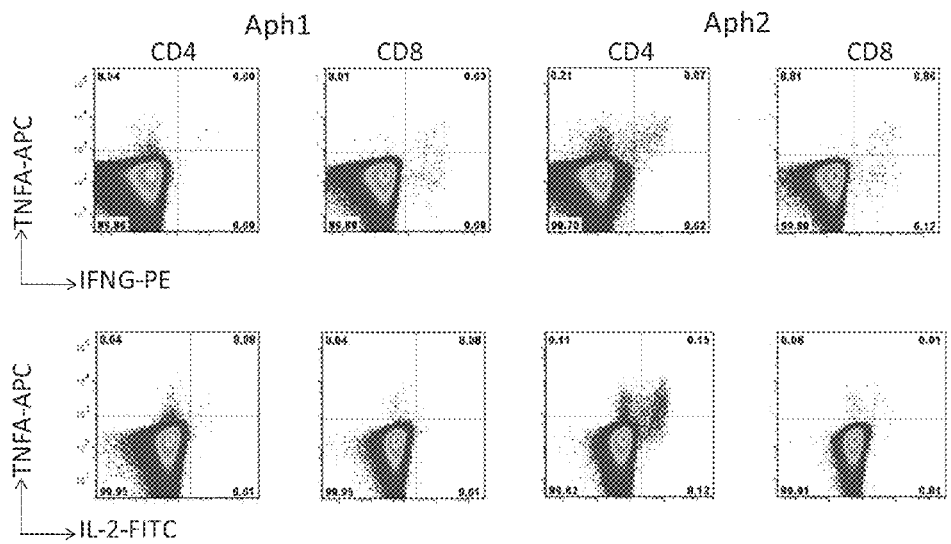
FIG. 7. D1-4: ICS after 6 hours LIPO5 long peptides mix stimulation of Aph1 and Aph2.
Figure 22:
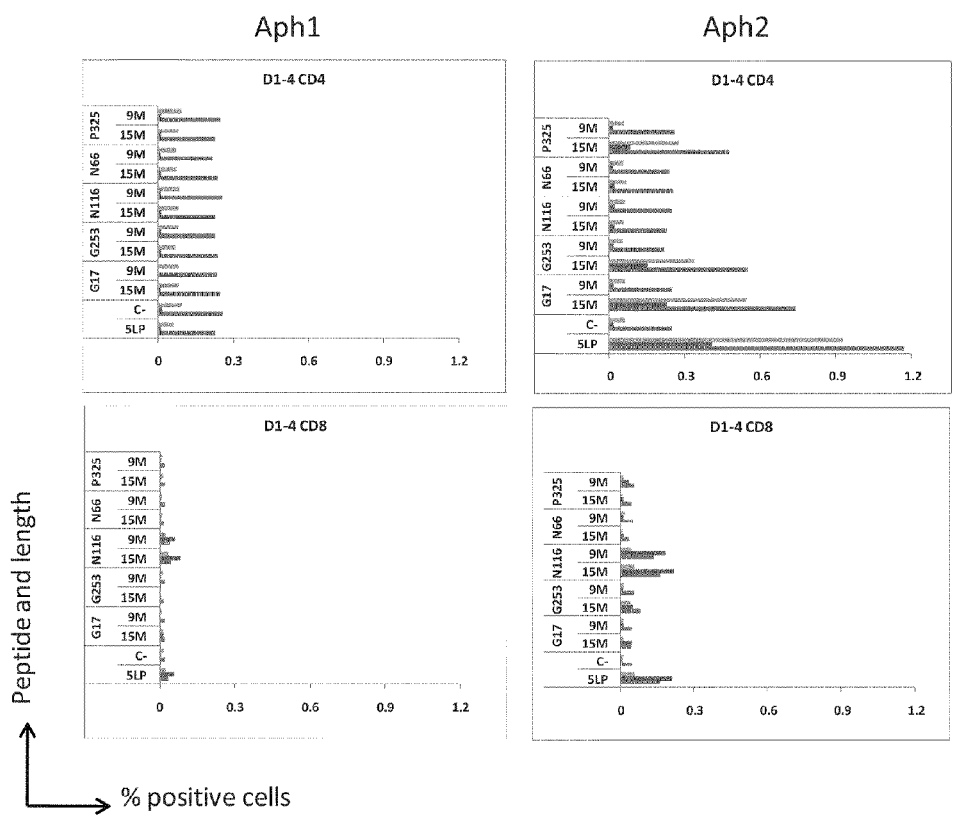
FIG. 22. D1-4: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

The inventors observed an increase in peptide-specific CD8+ T cells from 0.11% IFN secreting cells to 0.18%. The inventorse observed an increase of double positive cells expressing TNFα and IFNγ from 0.03% to 0.06% after vaccination (FIG. 7). The stimulation with pools of 15-mers and 9-mers derived from LIPO5 sequences showed small CD4 responses to Gag17, Gag253 and Pol325 after vaccination and CD8 responses to Nef116 observed before and after vaccination (FIG. 22).

Cytokine secretion analysis: Important responses against Gag17, Gag253 and Pol325 are detected after vaccination by secretion of IL-2, IL-5, IL-10, IL-13, IL-17, IL-21, IFNγ and IP-10 (FIG. 30-41).

Gag17 stimulated secretion of 2.2 µg/ml IL-2, 30 pg/ml IL-5, 200 pg/ml IL-10, 350 pg/ml IL-13, 680 pg/ml IL-17, 100 pg/ml IL-21, 40 µg/ml IFNγ and >20 µg/ml of IP10.

Gag253 stimulated secretion of 2.2 µg/ml IL-2, 20 pg/ml IL-5, 100 pg/ml IL-10, 300 pg/ml IL-13, 1.1 µg/ml IL-17, 140 pg/ml IL-21, >20 µg/ml IFNγ and >20 µg/ml of IP10.

Pol325 stimulated secretion of 1.4 µg/ml IL-2, 30 pg/ml IL-5, 120 pg/ml IL-10, 330 pg/ml IL-13, 630 pg/ml IL-17, 80 pg/ml IL-21, >20 µg/ml IFNγ and >20 µg/ml of IP10.

Responses against Nef 66 were observed by IL-5 (10 pg/ml), IL-13 (115 pg/ml), IL-17 (510 pg/ml) secretion.

Nef 116 stimulation increases IP-10 secretion (1 µg/ml).

Figure 48:
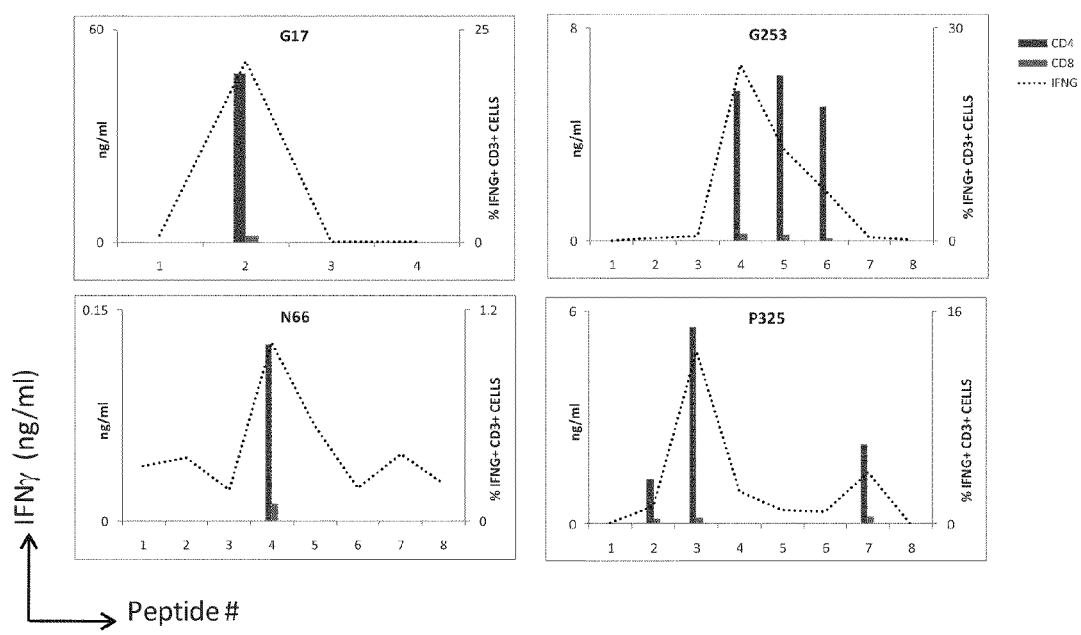
FIG. 48. D1-4: 7 days peptide stimulated cultures from Aph 2 were used for ICS after 6 hours 15-mer peptide stimulation.
Figure 49:
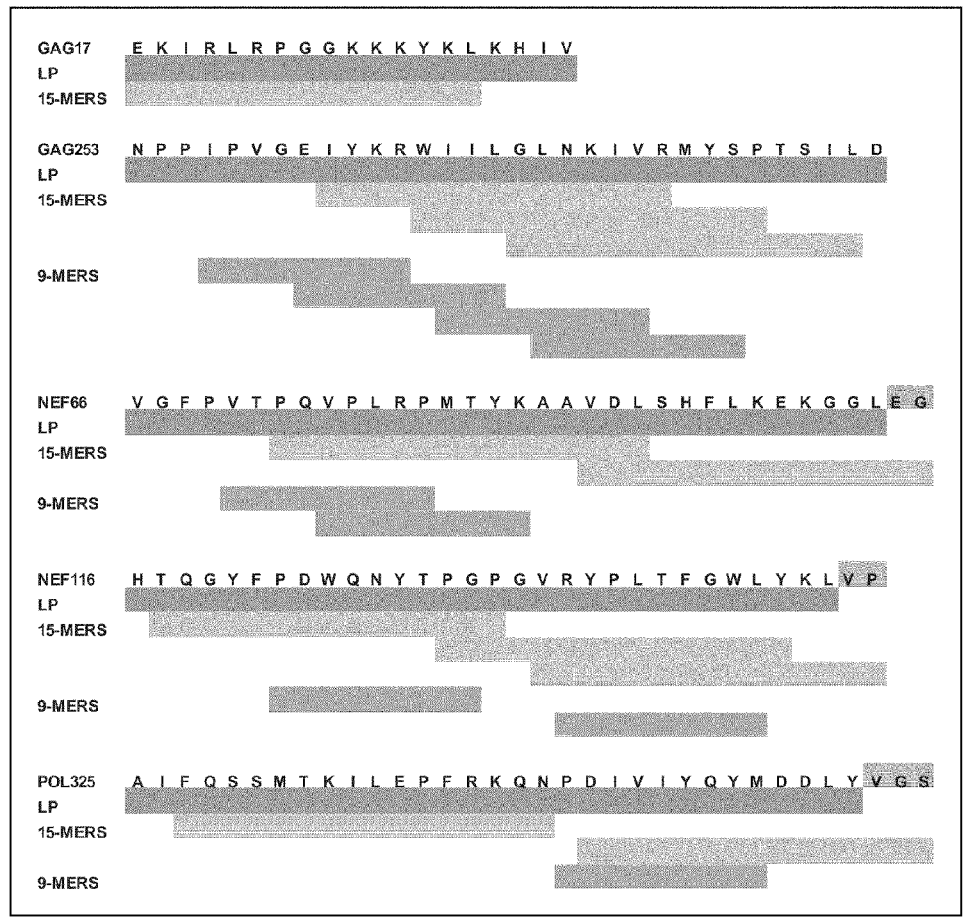
FIG. 49. Summary of the results obtained by Luminex analysis of patient DI-4 T cells stimulated with LIP05 long peptides (I9-32 aa), 15-mers and 9-mers (SEQ ID NOs. 1, 2, 7, 6, 8).
Figure 50:
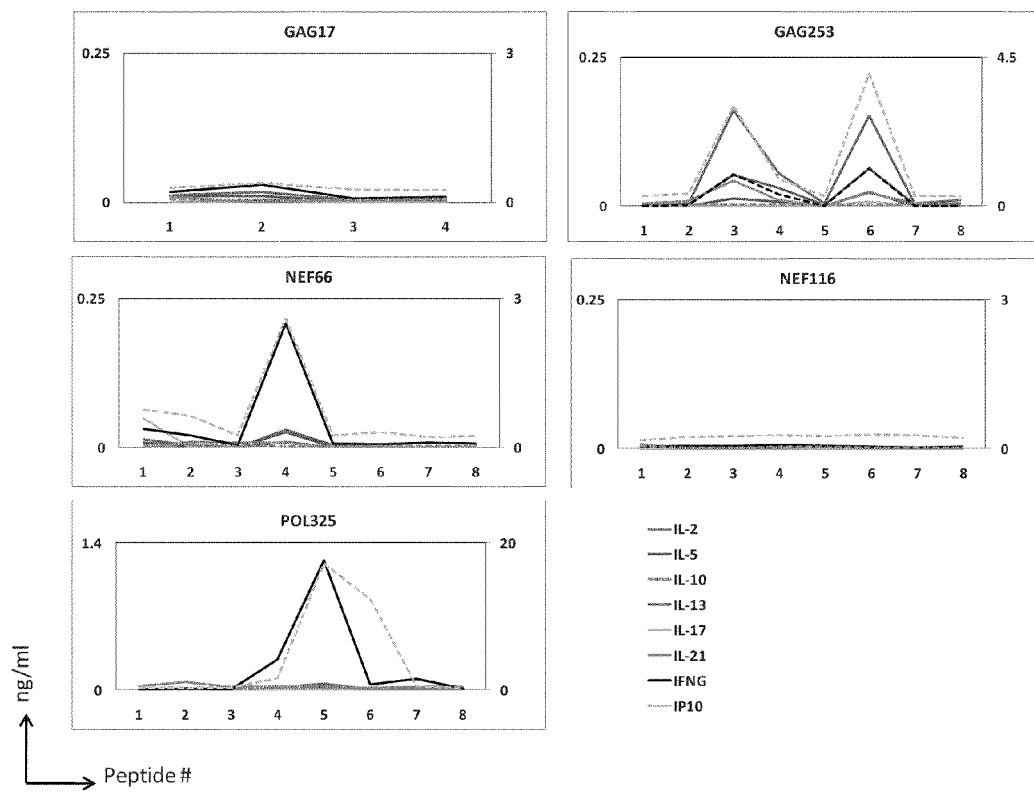
FIG. 50. DALIA vaccinated patient D1-5 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 51:
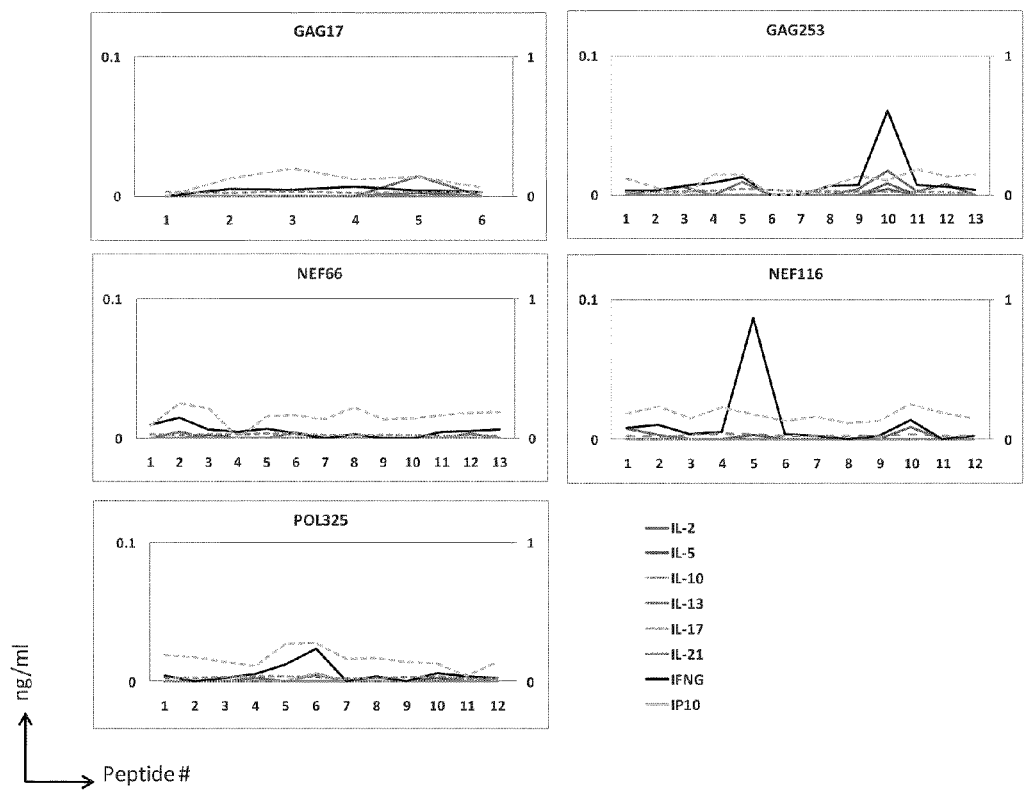
FIG. 51. DALIA vaccinated patient D1-5 PBMCs were stimulated with 9-mers of LIPO5 peptides for 48 hours. Luminex analysis of cytokine secretion post-vaccination samples. Dotted lines represent cytokines with high concentration in the supernatants (right side axes).

The epitopes recognized are 15mer peptides p2 in Gag 17; peptides p4, p5 and p6 in Gag 253; peptides p4 and p7 in Nef 66; peptides p3, p6 and p7 in Nef 116; and peptides p3 and p7 in Pol 325. Recognition of 9mer peptides p3, p5, p8 and p10 in Gag 253; peptides p3, and p5 in Nef 66; peptides p4 and p10 in Nef 116; and peptides p10 in Pol 325 (FIG. 46-49). Detailed ICS showed that Gag17, G253, Nef66 and Pol325 15-mer epitopes are mostly CD4+ T cell epitopes (FIG. 48).

Anti HIV-antibodies: The inventors observed no detectable antibodies against any of the LIPO5 peptides in serum from patient D1-4. However, antibodies recognizing Nef protein were detectable at the same level before and after vaccination (FIG. 74-76).

Polychromatic Flow Cytometry Analysis:

The longitudinal study showed no change in the numbers of CD4+ and CD8+ T cells. Vaccination does not seem to alter the CD4+/CD8+ ratio. However, after ATI, the CD8+ population became the larger fraction, and the total number of CD3+ T cells decreased as the CD4+ T cell population did.

Figure 84:
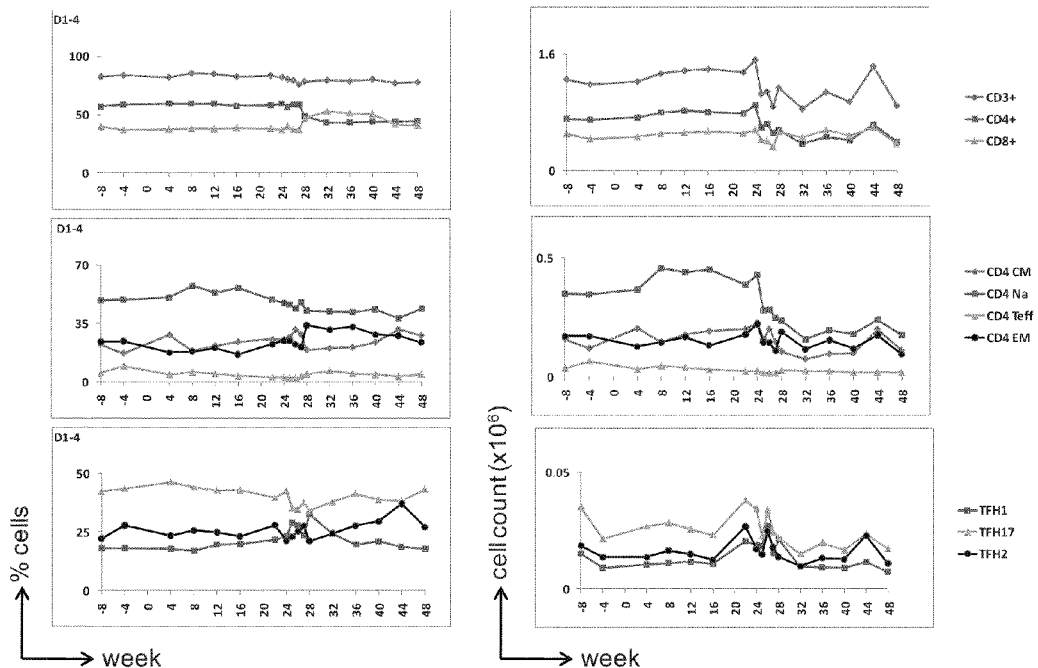
FIG. 84. Longitudinal study of CD4 T cell phenotype patient D1-4.
Figure 85:
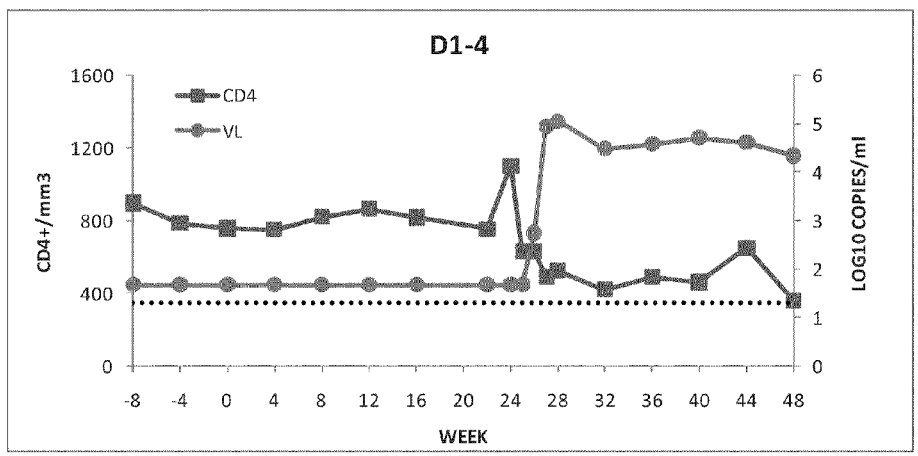
FIG. 85. Longitudinal study of CD4+ T cell count and viral load for patient D1-4.

CD4+ T cells: At study entry, CD4+ T cells are about 50% naïve (CCR7+ CD45RA−), 25% central memory (CCR7+ CD45RA−) and 25% effector memory (CCR7− CD45RA−). The vaccination does not appear to considerably alter the balance between the subsets. ATI results in a decrease of CD4+ T cells, which affects the naïve and central memory populations. There is no significant change in the percentage of each subset of follicular helper cells, however the number of TH17 cells decreased after ATI (FIG. 84).

Figure 93:
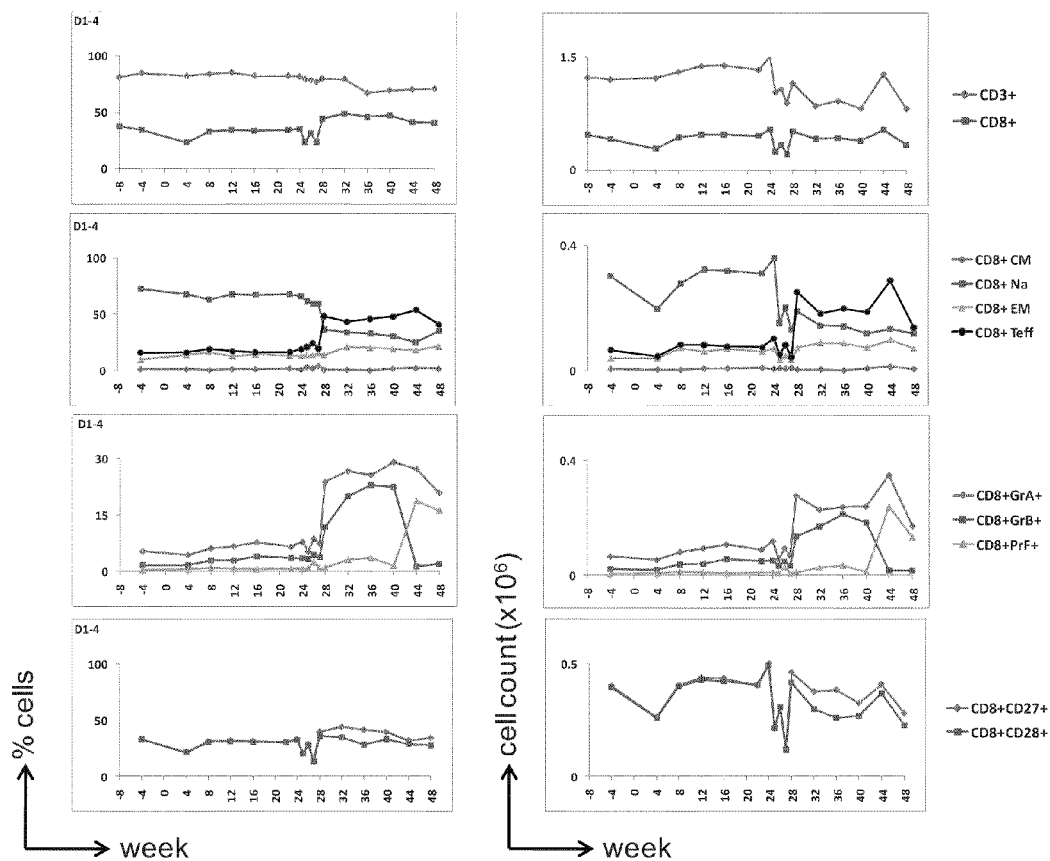
FIG. 93. Longitudinal study of CD8 T cell phenotype patient D1-4.

CD8+ T cells: At study entry, more of 70% of this patient's CD8+ T cells are naïve (CCR7+ CD45RA+), while effector memory (CCR7− CD45RA−) and effector (CCR7− CD45RA+) cells each represent about 15% of the CD8+ T cells. The vaccination procedure does not seem to affect significantly the number of each subset. ATI, on the other hand, has a significant impact on CD8+ T cell composition. The number of cells with a naïve phenotype decreases while effector cell numbers increase sharply. The increase of effector CD8+ T cells corresponded to an increase of intracellular cytotoxic molecules (Granzyme A and Granzyme B) at week 28 (FIG. 93).

Figure 99:
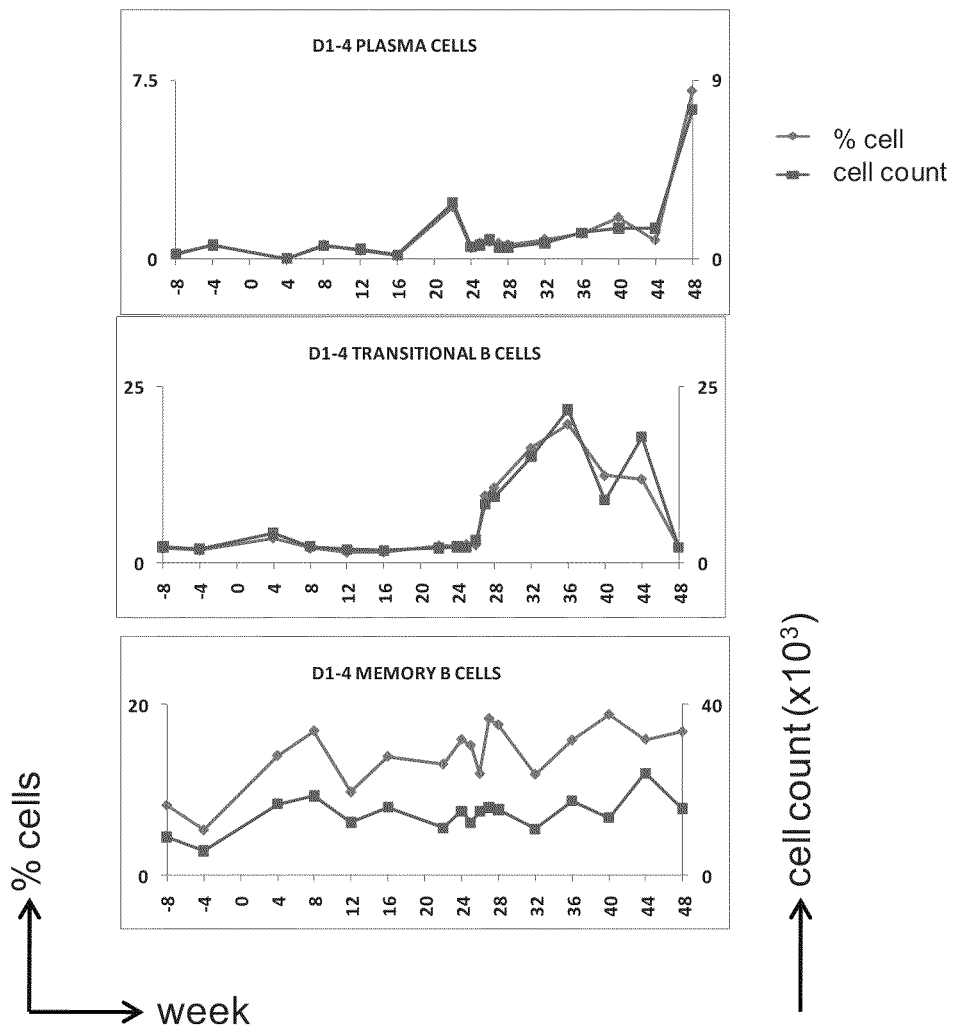
FIG. 99. Longitudinal study of B cell phenotype patient D1-4.

The study of the B cell subsets shows an increase of plasma cells with ATI (starting at week 32). The inventors also observed an increase of transitional cells (CD24+ CD38+) (FIG. 99).

Figure 105:
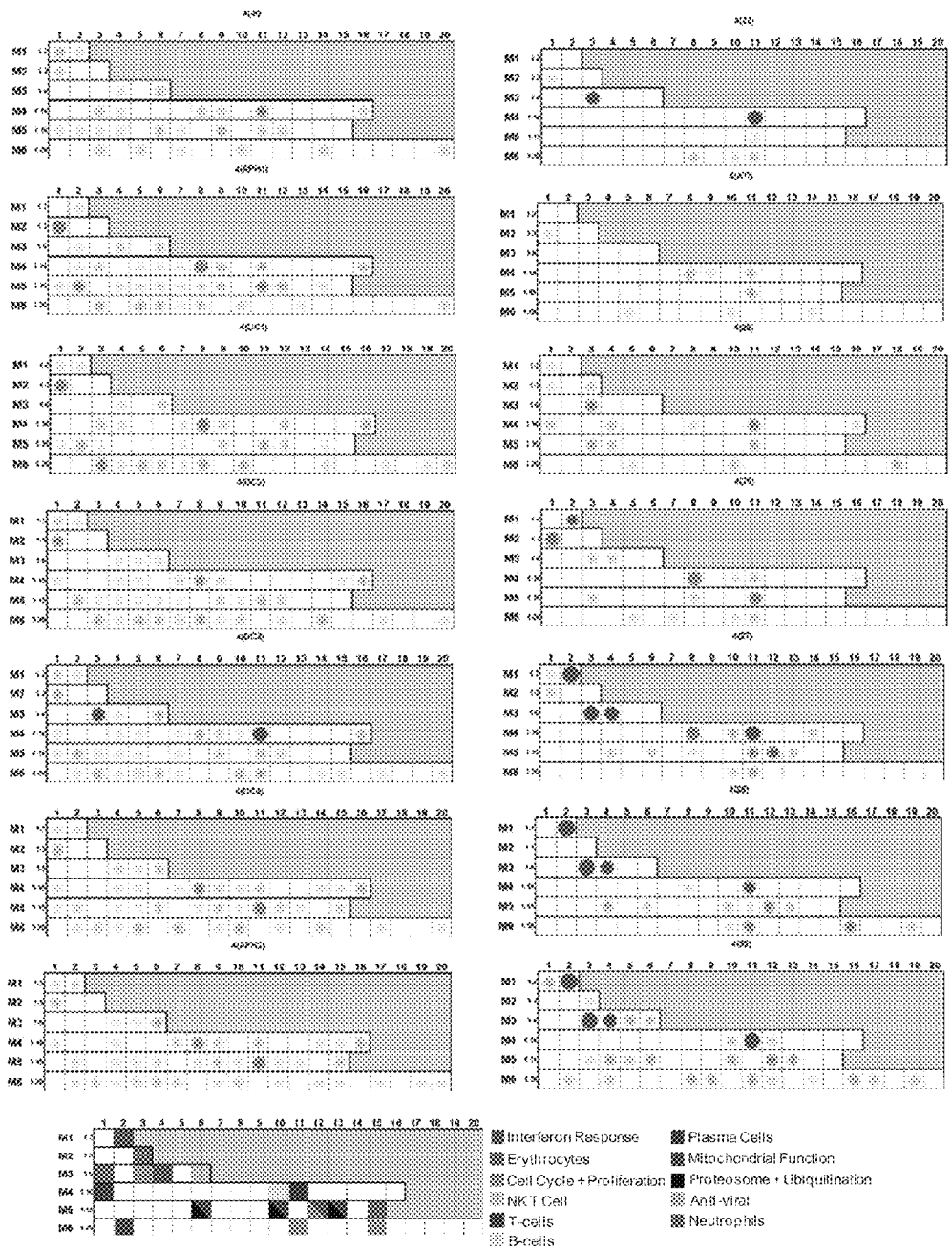
FIG. 105. D1-4 transcriptional module framework.
Figure 111:
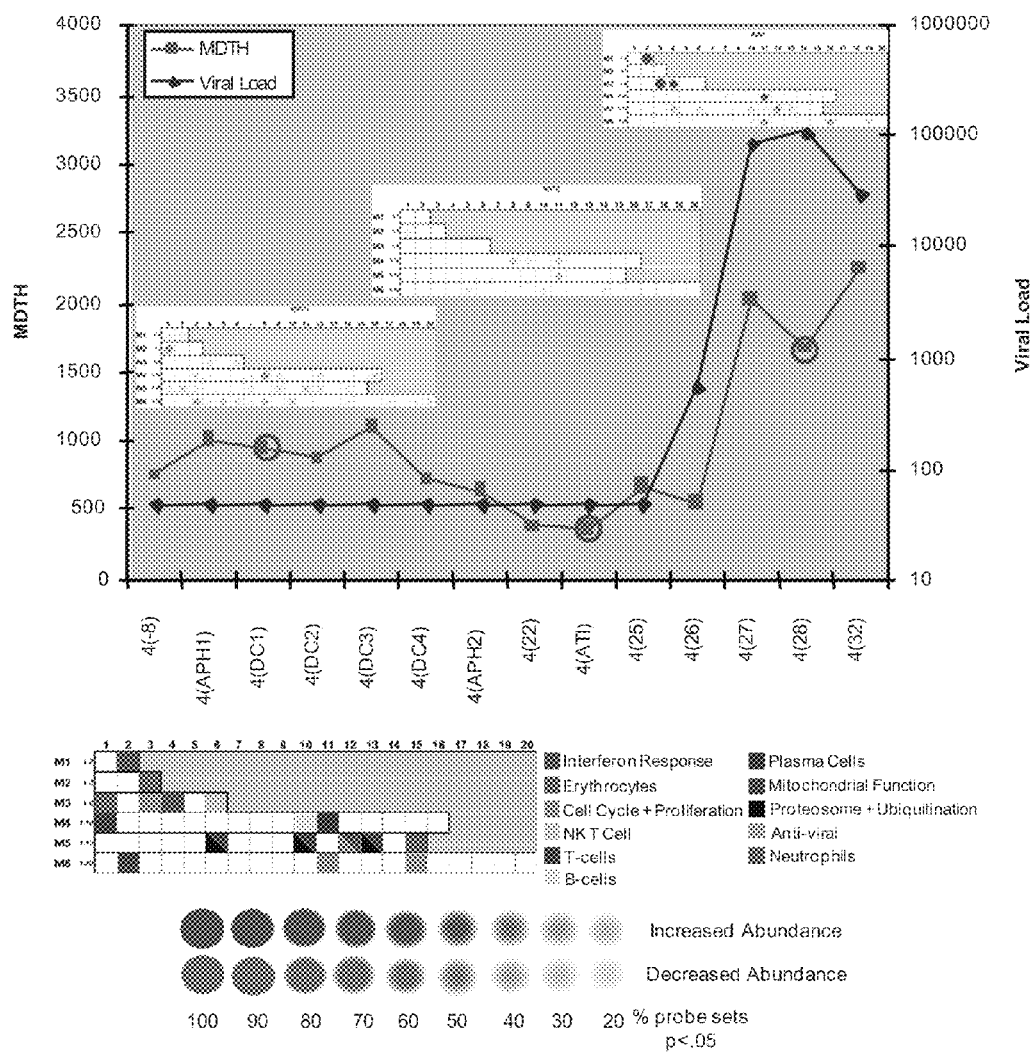
FIG. 111. D1-4 module activity summary.

Blood Transcriptome: D1-4 exhibited no change in module activity resulting from apheresis 1. At DC3 and Week 22, cell cycle (M3.3) and plasma cell (M4.11) modules exhibited increased activity. Interferon M1.2 exhibited increased activity concurrent with the first measured increase in circulating viral load two weeks post-ATI (week 27). The following week, the complete interferon signature was active (M1.2, M3.4, M5.12) in addition to cell cycle (M3.3)

and plasma cell (M4.11) modules. This activity remained until week 32 (FIG. 105 and FIG. 111).

Patient D1-5:

ICS analysis: There is an increased peptide-specific CD4+ T cell response after vaccination: From 0.05% to 0.19% TNFα+ cells, from 0.02% to 0.12% IL-2+ cells and from 0% to 0.07% IFNγ+ cells. Among HIV-specific CD4+ T cells 0.08% expresses both IL-2 and TNF and 0.05% are double positive for TNFα and IFNγ.

Figure 8:
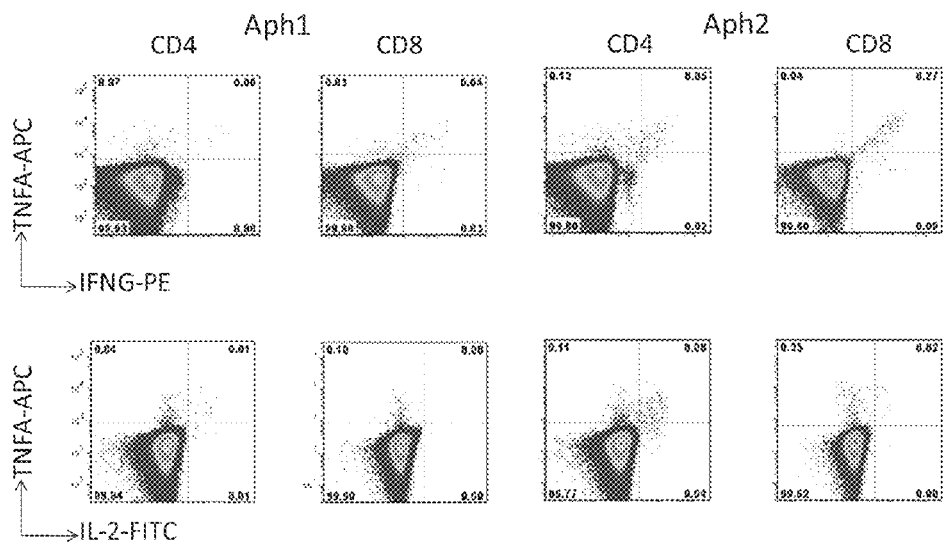
FIG. 8. D1-5: ICS after 6 hours LIPO5 long peptides mix stimulation f Aph1 and Aph2.
Figure 23:
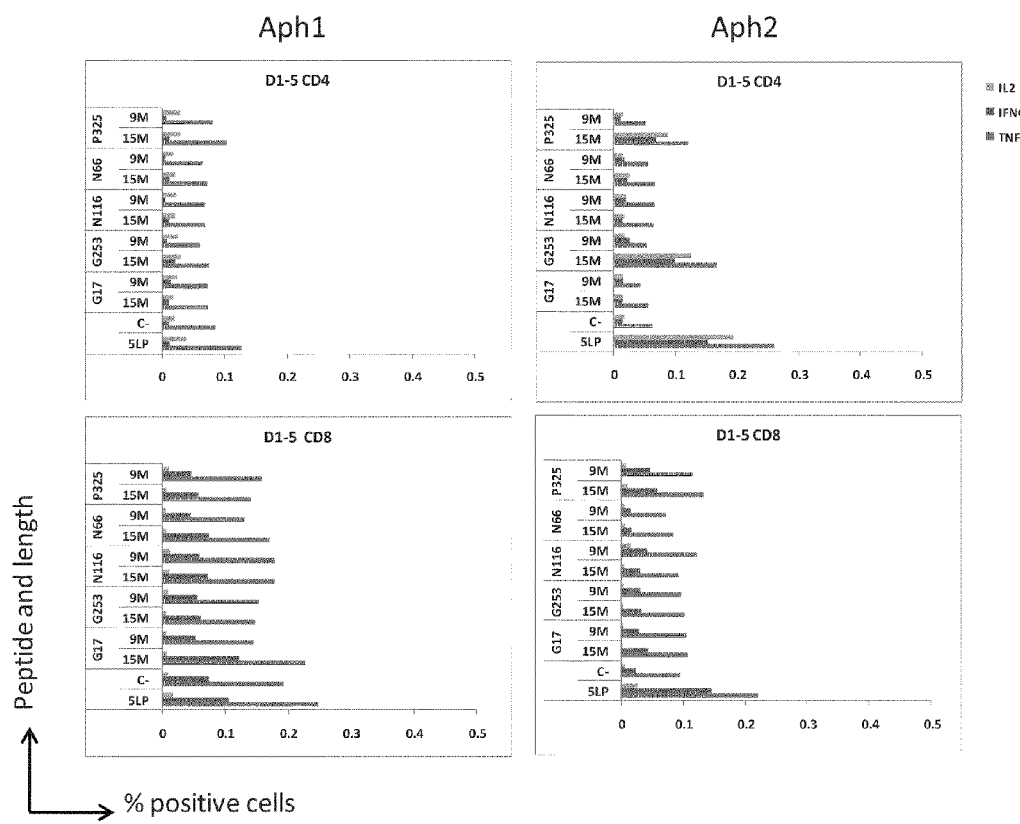
FIG. 23. D1-5: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

The inventors observed an increase in peptide specific CD8+ T cells from 0.07% IFNγ secreting cells to 0.36%. A decrease of double positive cells expressing TNFα and IFNγ from 0.04% to 0.27% after vaccination was observed (FIG. 8). The stimulation with pools of 15-mers and 9-mers derived from LIPO5 sequences showed small CD4 responses to Gag253 and Pol325 after vaccination, and CD8 responses to Pol325 were observed after vaccination (FIG. 23).

Cytokine secretion analysis: Luminex showed responses against Gag253 and Pol325 by secretion of IL-2, IL-13, IL-21, IFNΓ and IP10 (FIG. 30-41).

Gag253 stimulated 300 pg/ml IL-2, 60 pg/ml IL-13, 35 μg/ml IL-21, 1.6 μg/ml IFNγ and 12 μg/ml IP10.

Pol325 stimulated 80 pg/ml IL-2, 8 pg/ml IL-5, 20 pg/ml IL-13, 50 pg/ml IL-21, 1.5 μg/ml IFNγ and 18 μg/ml IP10.

Figure 52:
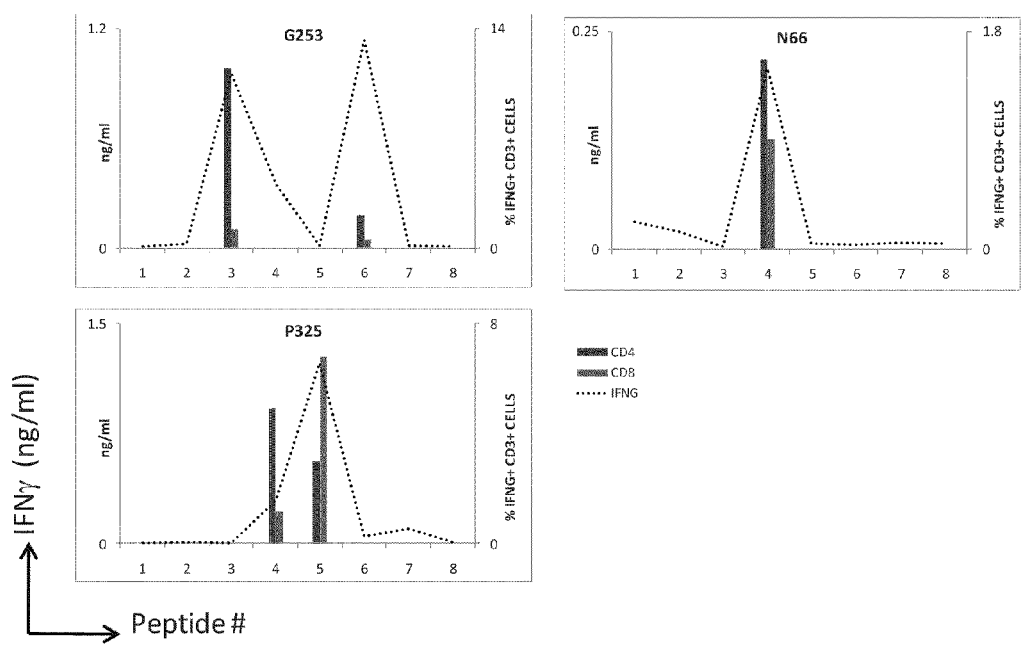
FIG. 52. D1-5: 7 days peptide stimulated cultures from Aph 2 were used for ICS after 6 hours 15-mer peptide stimulation.
Figure 53:
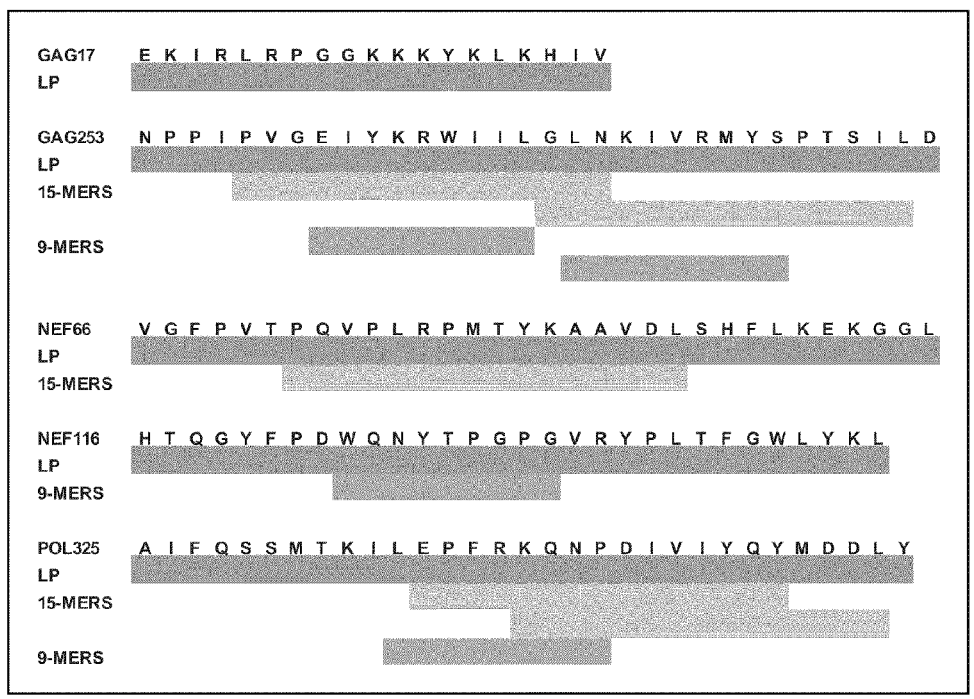
FIG. 53. Summary of the results obtained by Luminex analysis of patient D1-5 T cells stimulated with LIPO5 long peptides (19-32 aa), 15-mers and 9-mers, as listed, GAG17, GAG253, NEF 66, NEF116, POL325, SEQ ID NOS.: 1, 2, 3, 4, 5, respectively.
Figure 54:
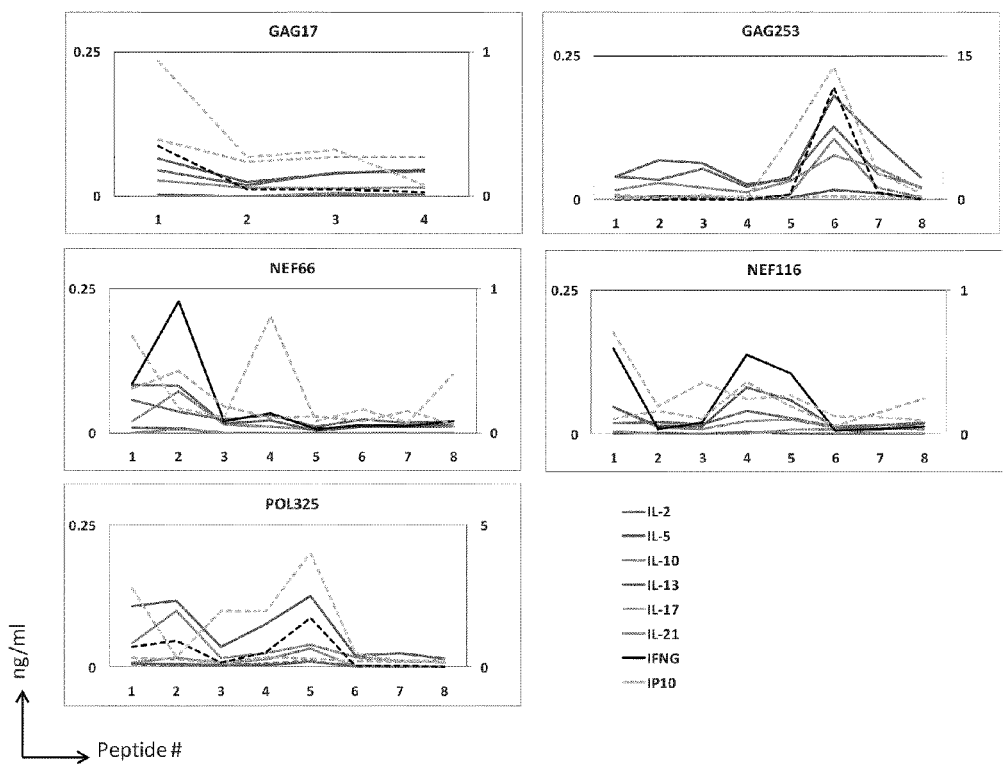
FIG. 54. DALIA vaccinated patient D1-6 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 55:
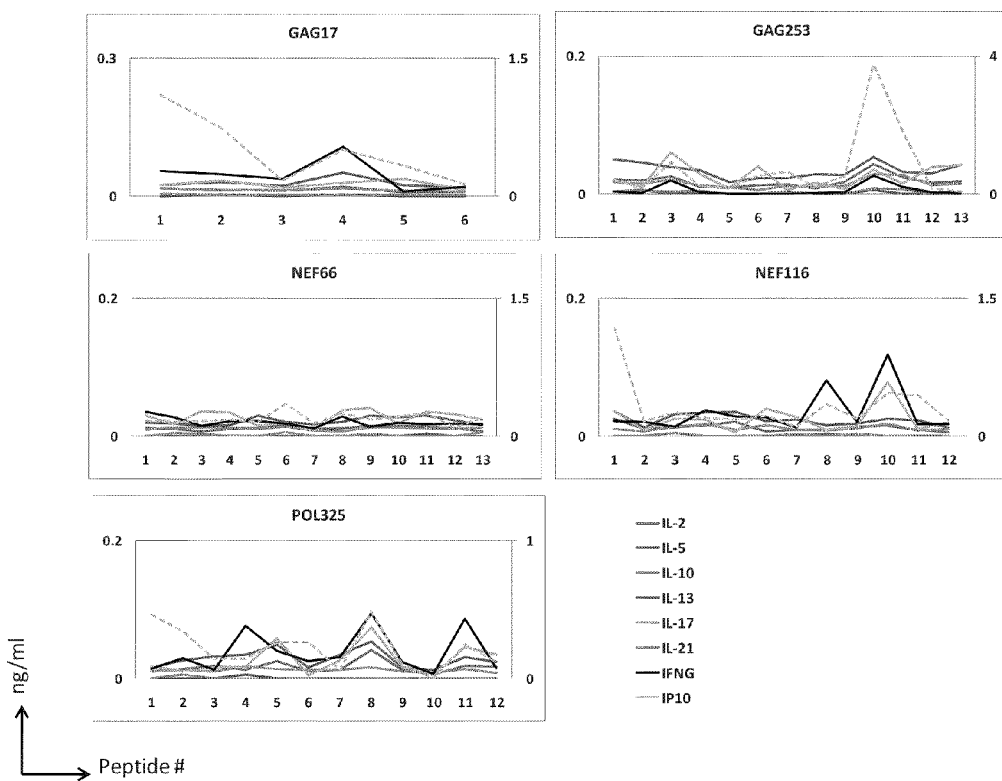
FIG. 55. DALIA vaccinated patient D1-6 PBMCs were stimulated with 9-mers of LIPO5 peptides for 48 hours. Luminex analysis of cytokine secretion post-vaccination samples. Dotted lines represent cytokines with high concentration in the supernatants (right side axes).

T cells recognize 15-mer peptides p3 and p6 in Gag 253, peptide p4 in Nef 66, and peptides p5 and p6 in Pol 325. They also recognize 9-mer peptides p5 and p10 in Gag 253, peptide p5 in Nef 116 and peptide p6 in Pol 325 (FIG. 50-53). Detailed ICS showed that Gag17 15-mer epitopes are mostly CD4+ T cell epitopes while Nef66 and Pol325 are both CD4+ and CD8+ T cell epitopes (FIG. 52).

Anti HIV-antibodies: The inventors observed no detectable antibodies against any of the LIPO5 peptides in serum from patient D1-5. However, antibodies recognizing Nef protein were detectable at the same level before and after vaccination (FIG. 74-76).

Polychromatic flow cytometry analysis: The longitudinal study showed no change in the numbers of CD4+ and CD8+ T cells. Vaccination does not seem to alter the CD4+/CD8+ ratio. However, after ATI, the CD8+ fraction increases, though the total number of CD3+, CD4+ and CD8+ T cells spike at 36 weeks.

Figure 86:
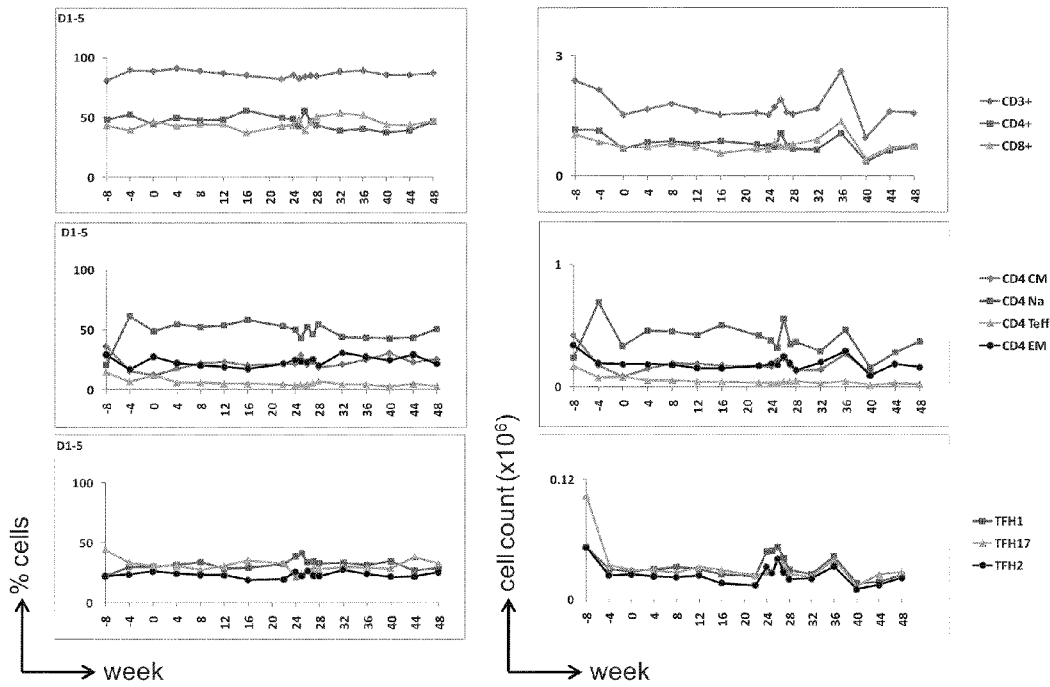
FIG. 86. Longitudinal study of CD4 T cell phenotype patient D1-5.
Figure 87:
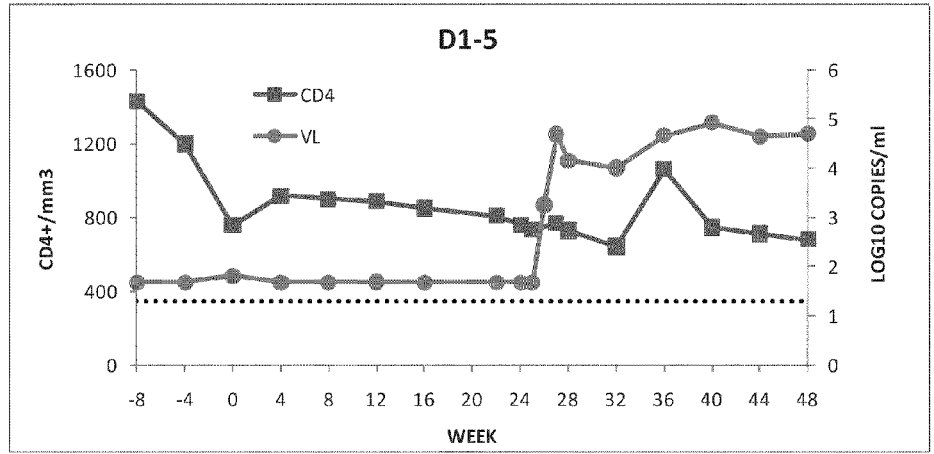
FIG. 87. Longitudinal study of CD4+ T cell count and viral load for patient D1-5.

CD4+ T cells: At study entry, CD4+ T cells are about 60% naïve (CCR7+ CD45RA+), 20% central memory (CCR7+ CD45RA−) and 20% effector memory (CCR7− CD45RA−). The vaccination does not appear to considerably alter the balance between the subsets. ATI results in a decrease of CD4+ T cells, which affects the naïve and central memory populations, which is linked to an increase in effector cell numbers. There is no significant change in the percentage or cell number of each subset of follicular helper cells (FIG. 86).

Figure 94:
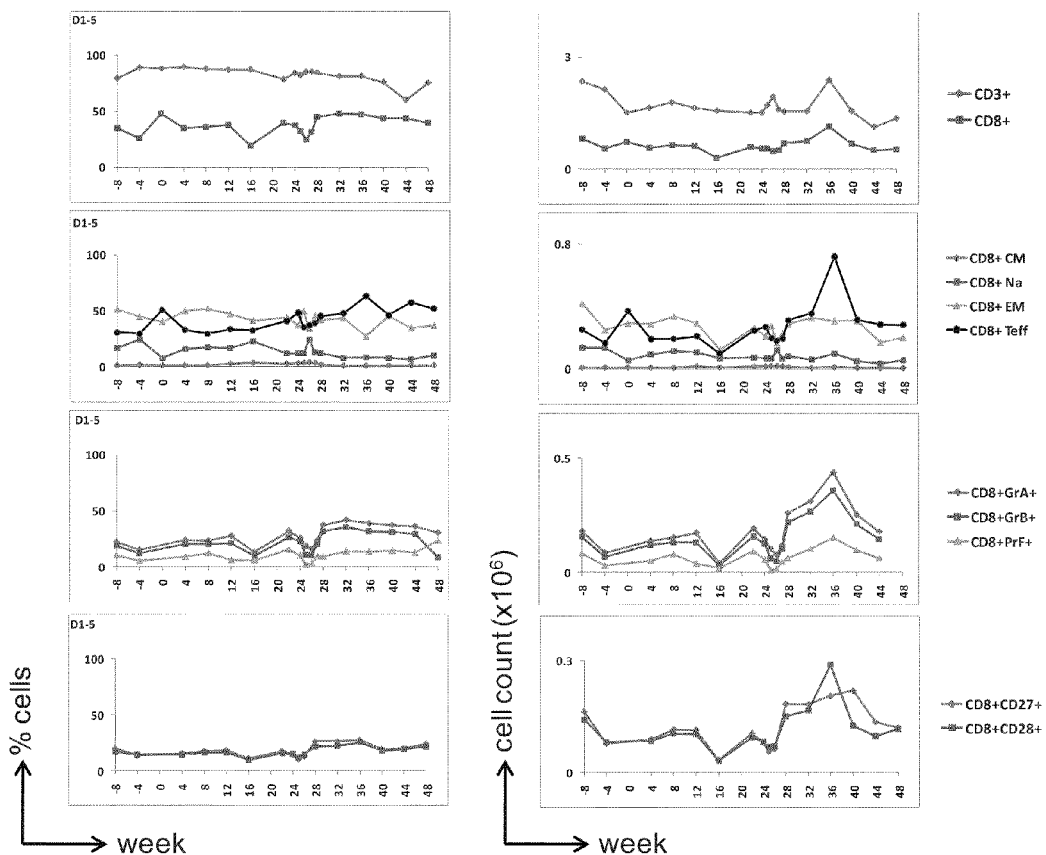
FIG. 94. Longitudinal study of CD8 T cell phenotype patient D1-5.

CD8+ T cells: At study entry, more than 50% of this patient's CD8+ T cells are effector memory cells (CCR7− CD45RA−), while effector (CCR7-CD45RA+) and naive (CCR7+ CD45RA+) cells represent about 30% and 20% of the CD8+ T cells, respectively. The vaccination procedure does not seem to affect significantly the number of each subset. ATI, on the other hand, has a significant impact on CD8+ T cell composition; the effector cell numbers increase with a peak at week 36. The increase of effector CD8+ T cells corresponds to an increase of intracellular cytotoxic molecules (Granzyme A, Granzyme B and perforin) (FIG. 94).

Figure 100:
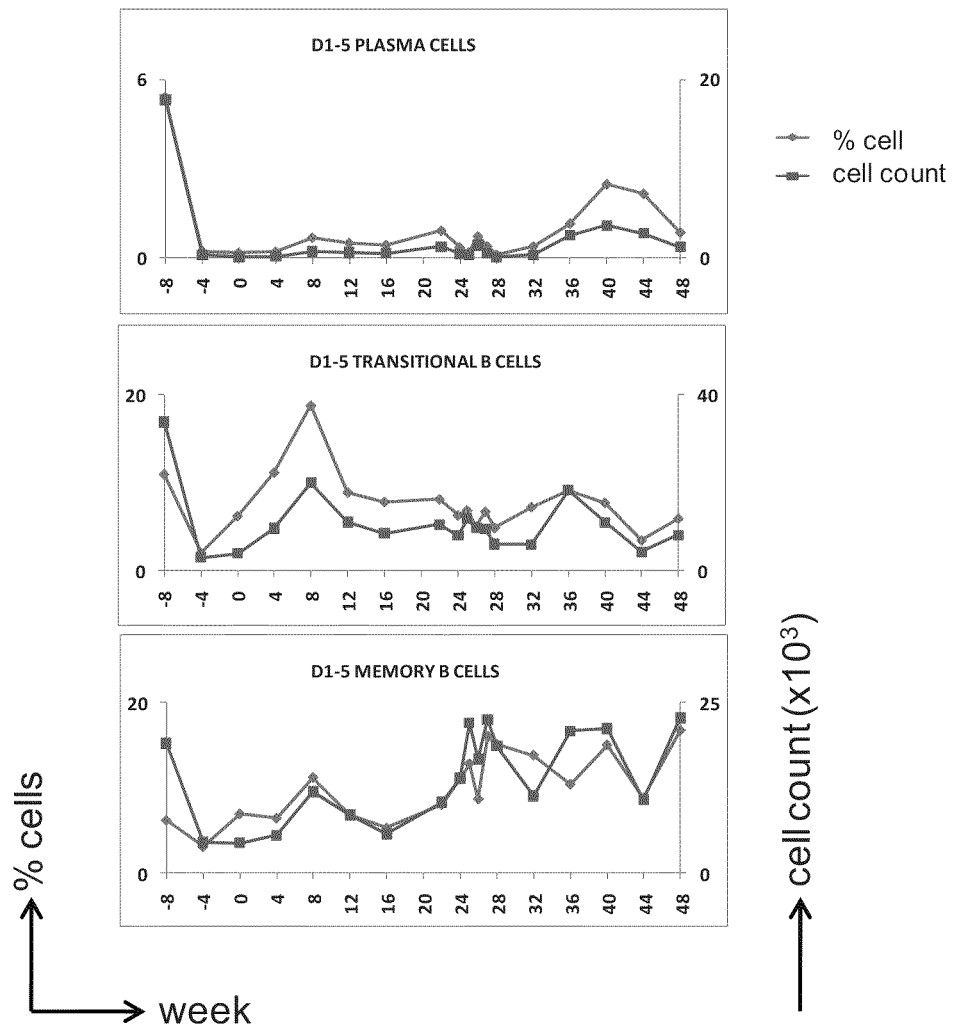
FIG. 100. Longitudinal study of B cell phenotype patient D1-5.

The study of the B cell subsets shows an increase of plasma cells after ATI (starting at week 32). The inventors also observed an increase of transitional cells (CD24+ CD38+) and memory B cells (CD19+CD20+CD27+IgD−−) after ATI (FIG. 100).

Figure 106:
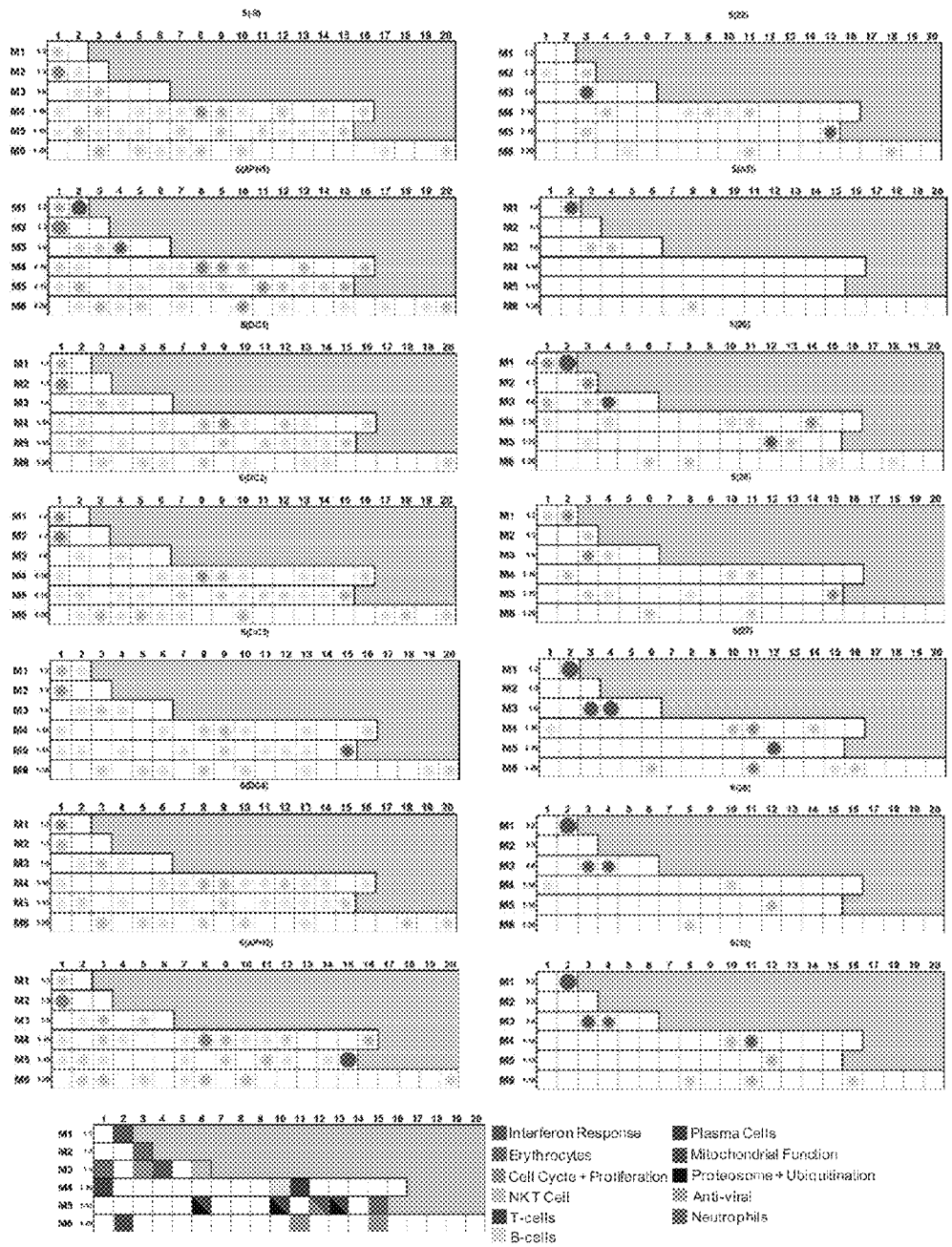
FIG. 106. D1-5 transcriptional module framework.
Figure 112:
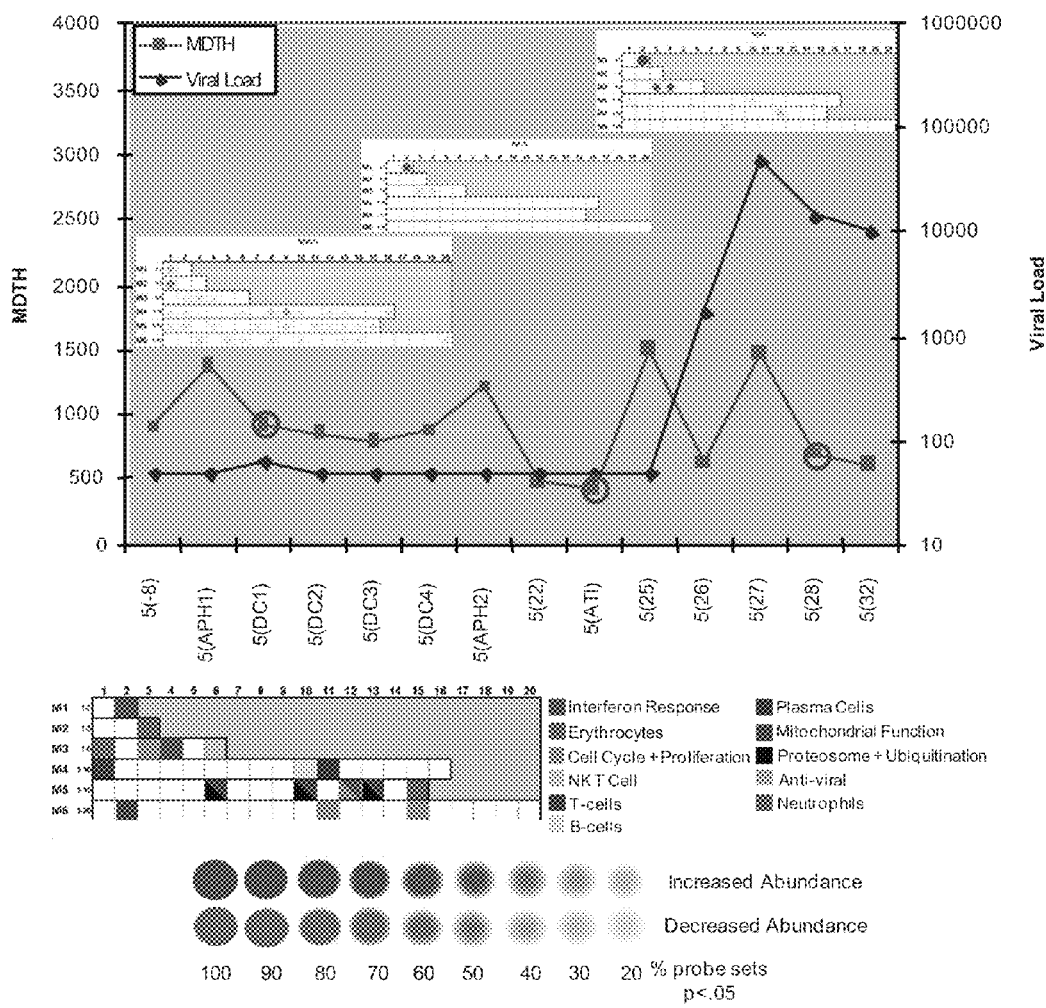
FIG. 112. D1-5 module activity summary.

Blood Transcriptome: D1-5 exhibited interferon activity at the time of apheresis 1 and transient neutrophil activity at DC3, APH2, and week 22. At week 22, the cell cycle module (M3.3) was active. Interferon module (M1.2) exhibited increased activity at ATI with the full interferon signature (M1.2, M3.4, M5.12) active one week later. Notably, this precedes the first measured increase in circulating virus by one week. This interferon response wanes at week 26 but resurges and is maintained from week 27 to 32. During this time, cell cycle module M3.3 exhibits increased activity (FIG. 106 and FIG. 112).

Figure 9:
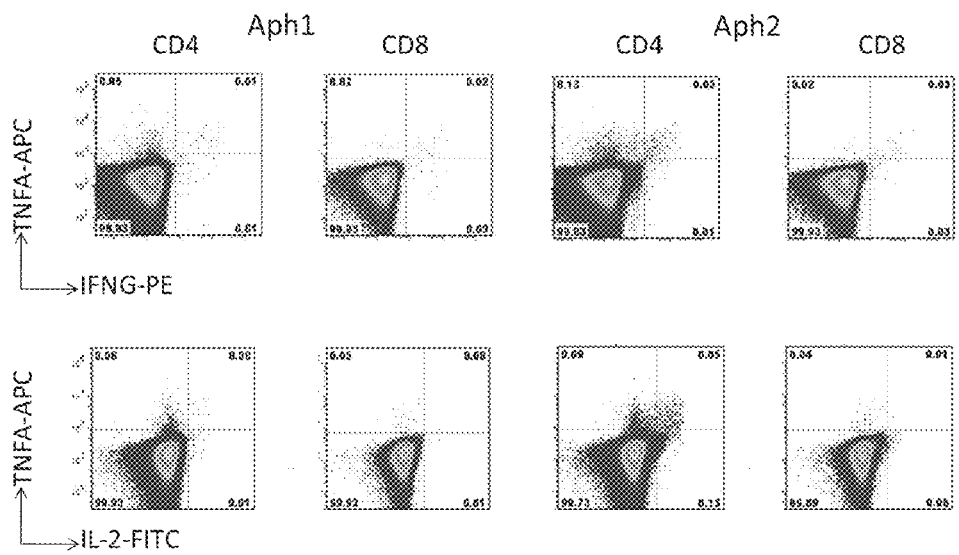
FIG. 9. D1-6: ICS after 6 hours LIPO5 long peptides mix stimulation f Aph1 and Aph2.
Figure 24:
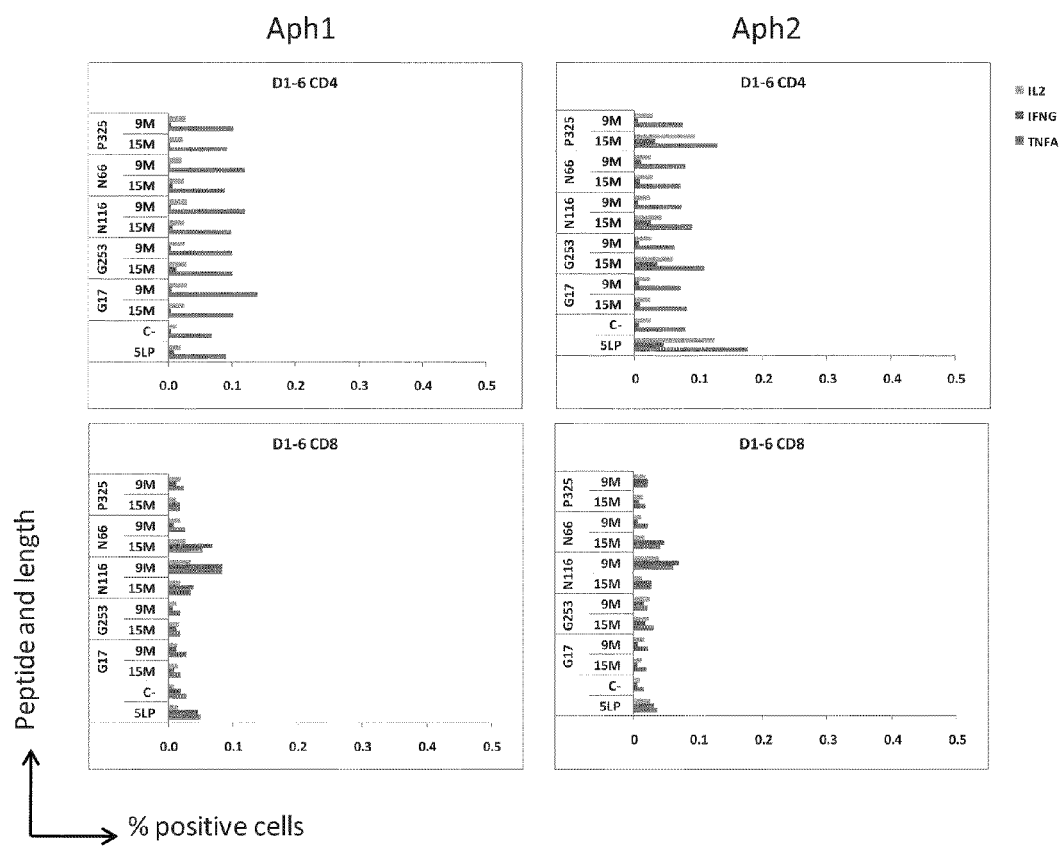
FIG. 24. D1-6: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

Patient D1-6:

ICS analysis: There is an increased peptide-specific CD4+ T cell response after vaccination: From 0.06% to 0.14% TNF+ cells, from 0.01% to 0.18% IL-2+ cells and 0.02% to 0.04% IFNγ+ cells. Among HIV-specific CD4+ T cells 0.05% express both IL-2 and TNFα and 0.03% are double positive for TNFα and IFNγ. The inventors observed no significant change in peptide-specific CD8+ T cells responses in this patient after vaccination (FIG. 9). The stimulation with pools of 15-mers and 9-mers derived from LIPO5 sequences showed small CD4 responses to Gag253, Nef66 and Pol325 after vaccination and CD8 responses to Nef66 and Nef116 observed after vaccination (FIG. 24).

Cytokine secretion analysis: Responses against Gag253 and Pol325 were detected by secretion of IL-2, IL-5, IL-10, IL-13, IL-21, IFNΓ and IP10 (FIG. 19-30).

Gag253 stimulated 170 pg/ml IL-2, 20 pg/ml IL-5, 80 pg/ml IL-10, 180 pg/ml IL-13, 100 pg/ml IL-21, 3 μg/ml IFNγ and 14 μg/ml IP10.

Pol325 stimulated 225 pg/ml IL-2, 30 pg/ml IL-5, 70 pg/ml IL-10, 140 pg/ml IL-13, 40 pg/ml IL-21, 2.2 μg/ml IFNγ and 7.5 μg/ml IP10.

The inventors observed 7.5 μg/ml IP10 secretion in response to Nef116.

Figure 56:
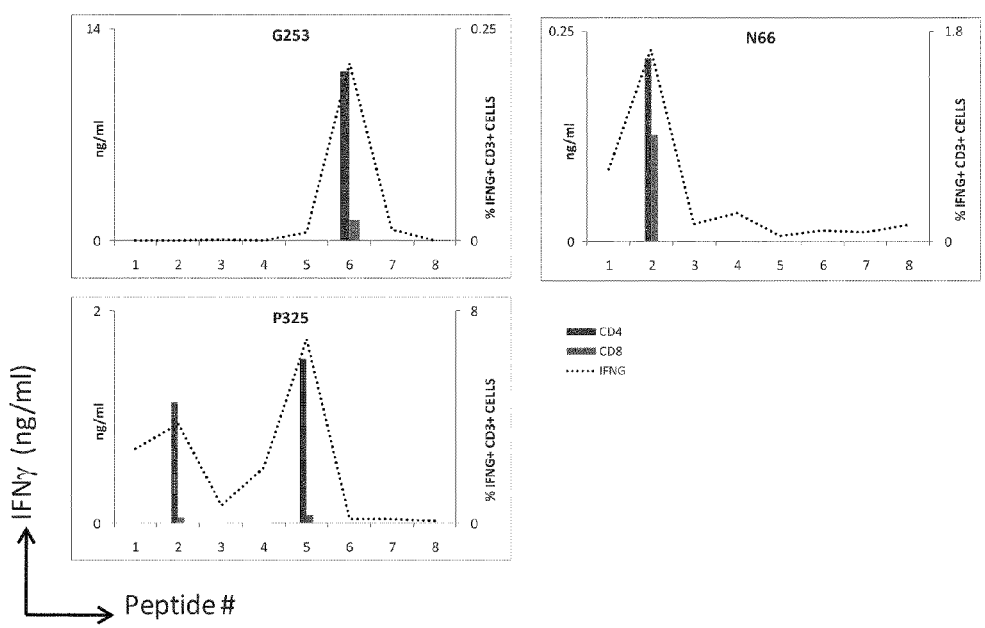
FIG. 56. D1-6: 7 days peptide stimulated cultures from Aph 2 were used for ICS after 6 hours 15-mer peptide stimulation.
Figure 57:
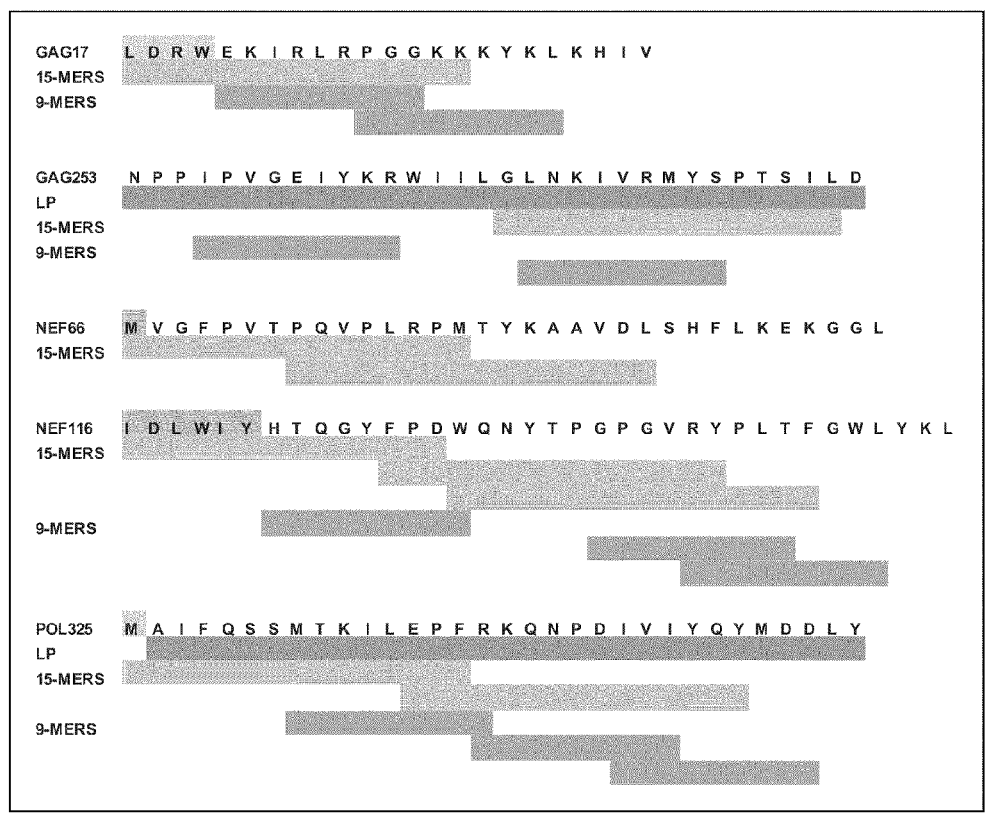
FIG. 57. Summary of the results obtained by Luminex analysis of patient D1-6 T cells stimulated with LIPO5 long peptides (19-32 aa), 15-mers and 9-mers (SEQ ID NOs. 9, 2, 10, 11, 12).
Figure 58:
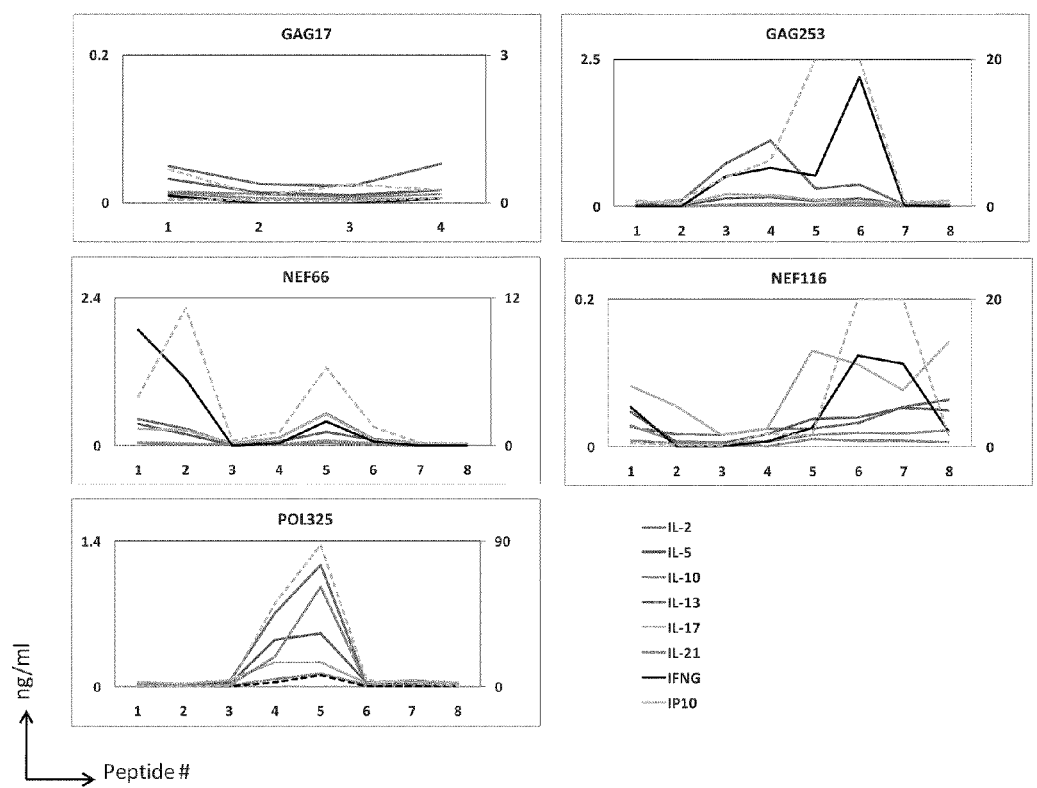
FIG. 58. DALIA vaccinated patient D1-7 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 59:
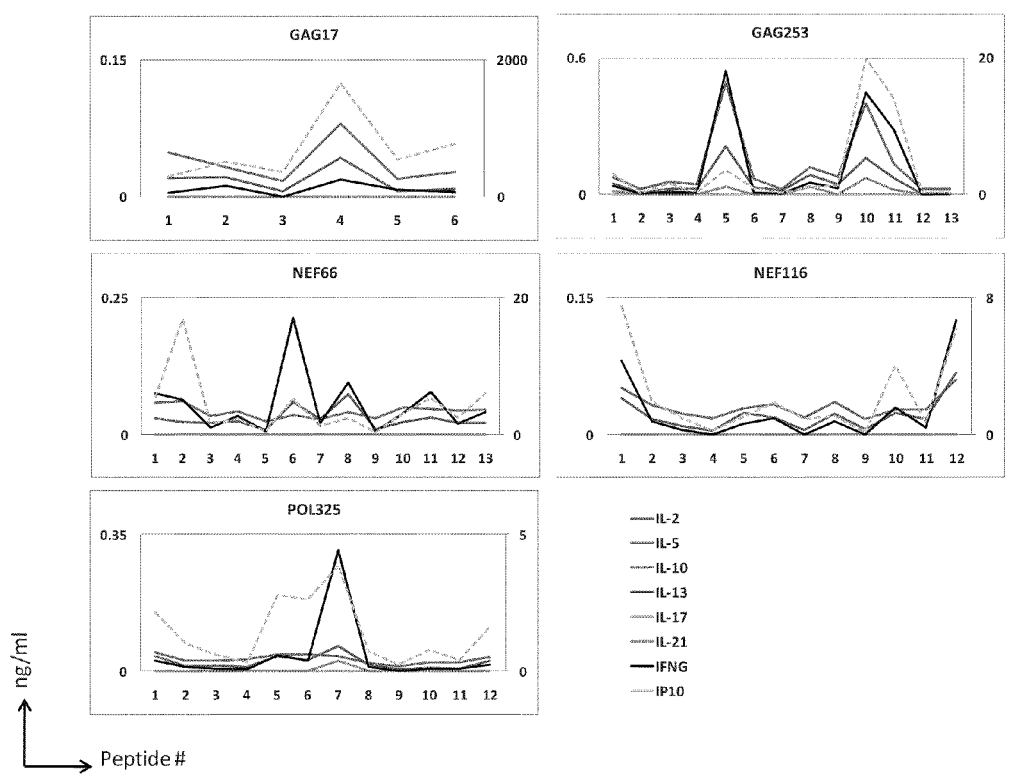
FIG. 59. DALIA vaccinated patient D1-7 PBMCs were stimulated with 9-mers of LIPO5 peptides for 48 hours. Luminex analysis of cytokine secretion post-vaccination samples. Dotted lines represent cytokines with high concentration in the supernatants (right side axes).

T cells recognize 15-mer peptide p1 in Gag 17; peptide p6 in Gag 253; peptides p2 and p4 in Nef 66; peptides p1, p4 and p5 in Nef 116; and peptides p2 and p5 in Pol 325. They also recognize 9-mer peptides p1 and p4 in Gag 17; peptides p3 and p10 in Gag 253; peptides p1, p8 and p10 in Nef 116; and peptides p4, p8 and p11 in Pol 325 (FIG. 54-57). Detailed ICS showed that Gag253 and Pol325 15-mer epitopes are mostly CD4+ T cell epitopes while Nef66 are both CD4+ and CD8+ cell epitopes (FIG. 56).

Anti HIV-antibodies: The inventors observed no detectable antibodies against any of the LIPO5 peptides in serum from patient D1-6. However, antibodies recognizing Nef and Gag p24 proteins were detectable at the same level before and after vaccination (FIG. 74-76).

Polychromatic flow cytometry analysis: The longitudinal study showed 60% CD4+ and 40% CD8+ T cells. Vaccination does not seem to alter the CD4+/CD8+ ratio. However, after ATI, the CD8+ fraction increases, while the total number of CD3+ and CD4+ populations decrease slightly.

Figure 88:
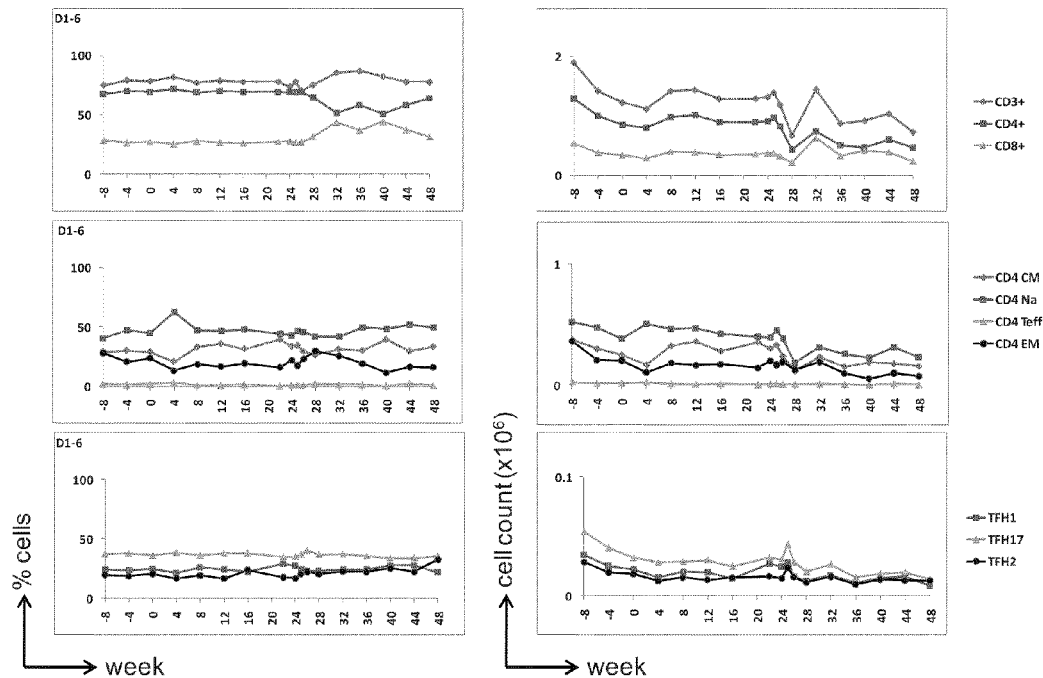
FIG. 88. Longitudinal study of CD4 T cell phenotype patient 1-6.
Figure 89:
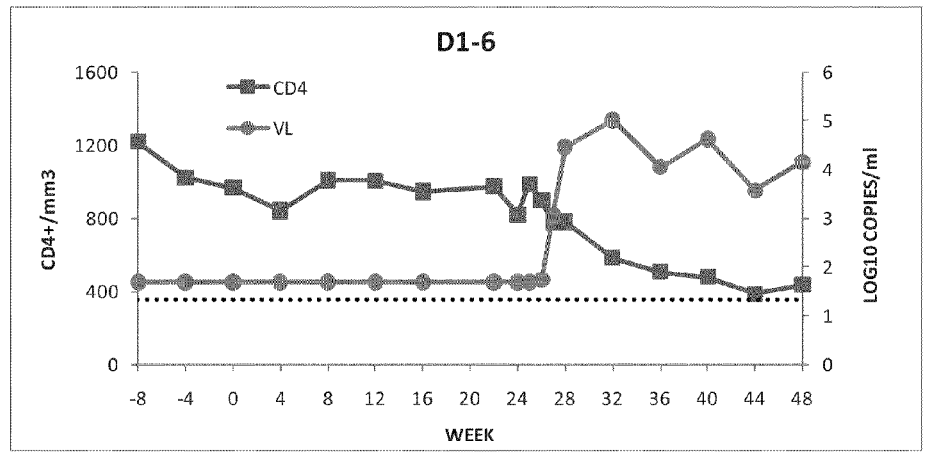
FIG. 89. Longitudinal study of CD4+ T cell count and viral load for patient D1-6.

CD4+ T cells: At study entry, CD4+ T cells are about 50% naïve (CCR7+ CD45RA+), 20% central memory (CCR7+ CD45RA−) and 20% effector memory (CCR7− CD45RA−). The vaccination does not appear to considerably alter the balance between the subsets. ATI results in a decrease of CD4+ T cells, which affects the naïve and central memory populations. There is no significant change in the percentage or cell number of each subset of follicular helper cells (FIG. 88).

Figure 95:
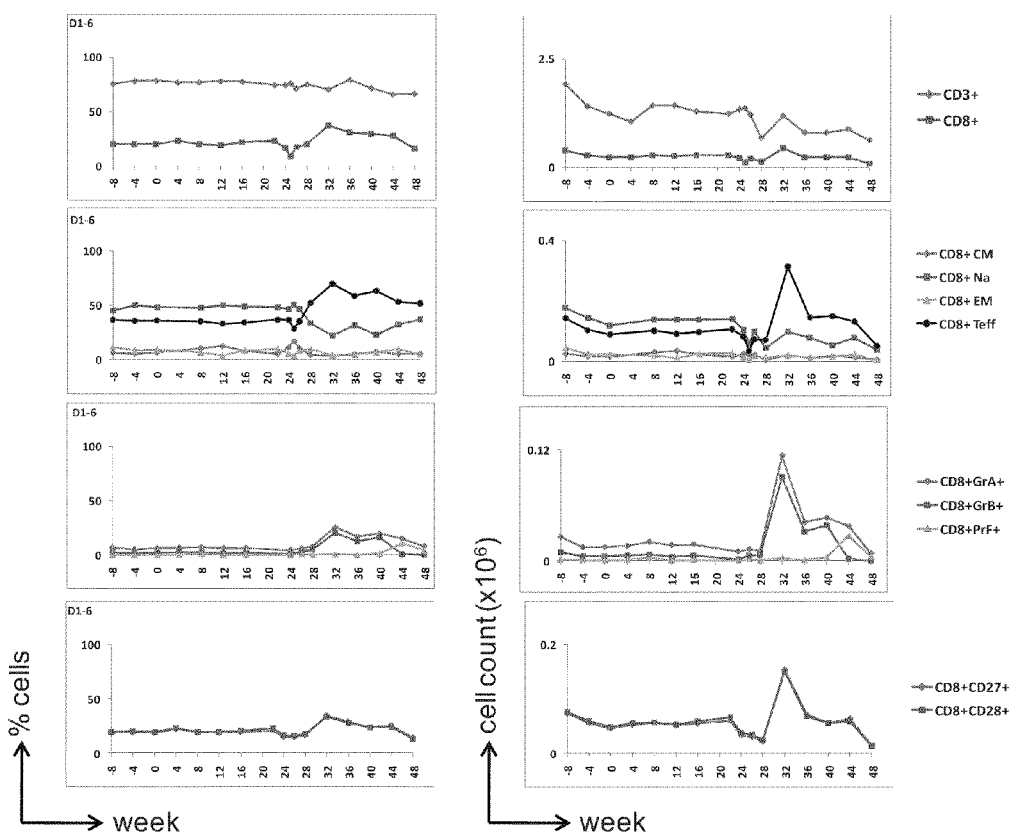
FIG. 95. Longitudinal study of CD8 T cell phenotype patient D1-6.

CD8+ T cells: At study entry, more of 50% of this patient's CD8+ T cells are naïve cells (CCR7+ CD45RA−), 40% effector cells, while effector memory (CCR7− CD45RA−) and central memory (CCR7+ CD45RA−) cells each represent about 5% of the CD8+ T cells. The vaccination procedure does not seem to affect significantly the number of each subset. ATI, on the other hand, has a significant impact on CD8+ T cell composition, the number of effector cells increase while the number of naïve cells decrease. The increase of effector CD8+ T cells corresponds to an increase of intracellular cytotoxic molecules (Granzyme A and Granzyme B) (FIG. 95).

Figure 101:
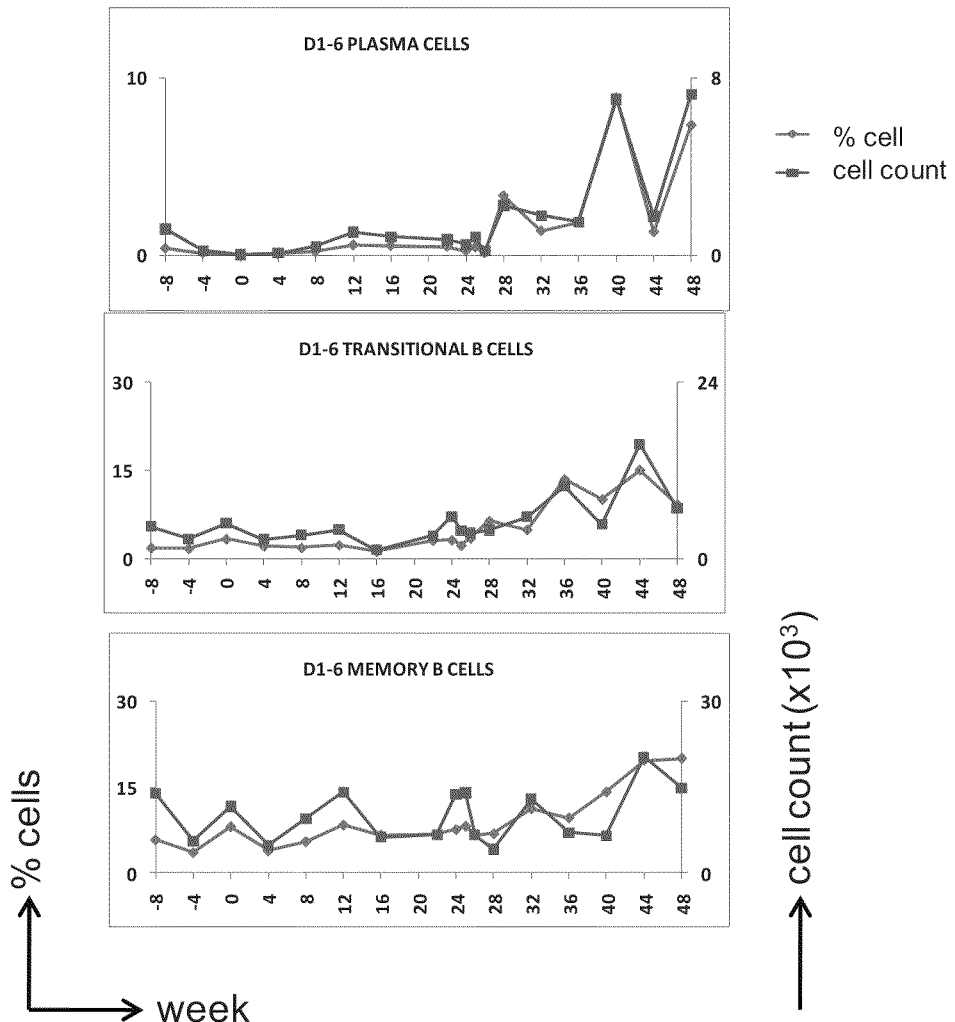
FIG. 101. Longitudinal study of B cell phenotype patient D1-6.

The study of the B cell subsets shows an increase of plasma cells after ATI (starting at week 32). The inventors also observed an increase of transitional cells (CD24+ CD38+) and memory cells (CD19+CD20+CD27+IgD−) after ATI (FIG. 101).

Figure 107:
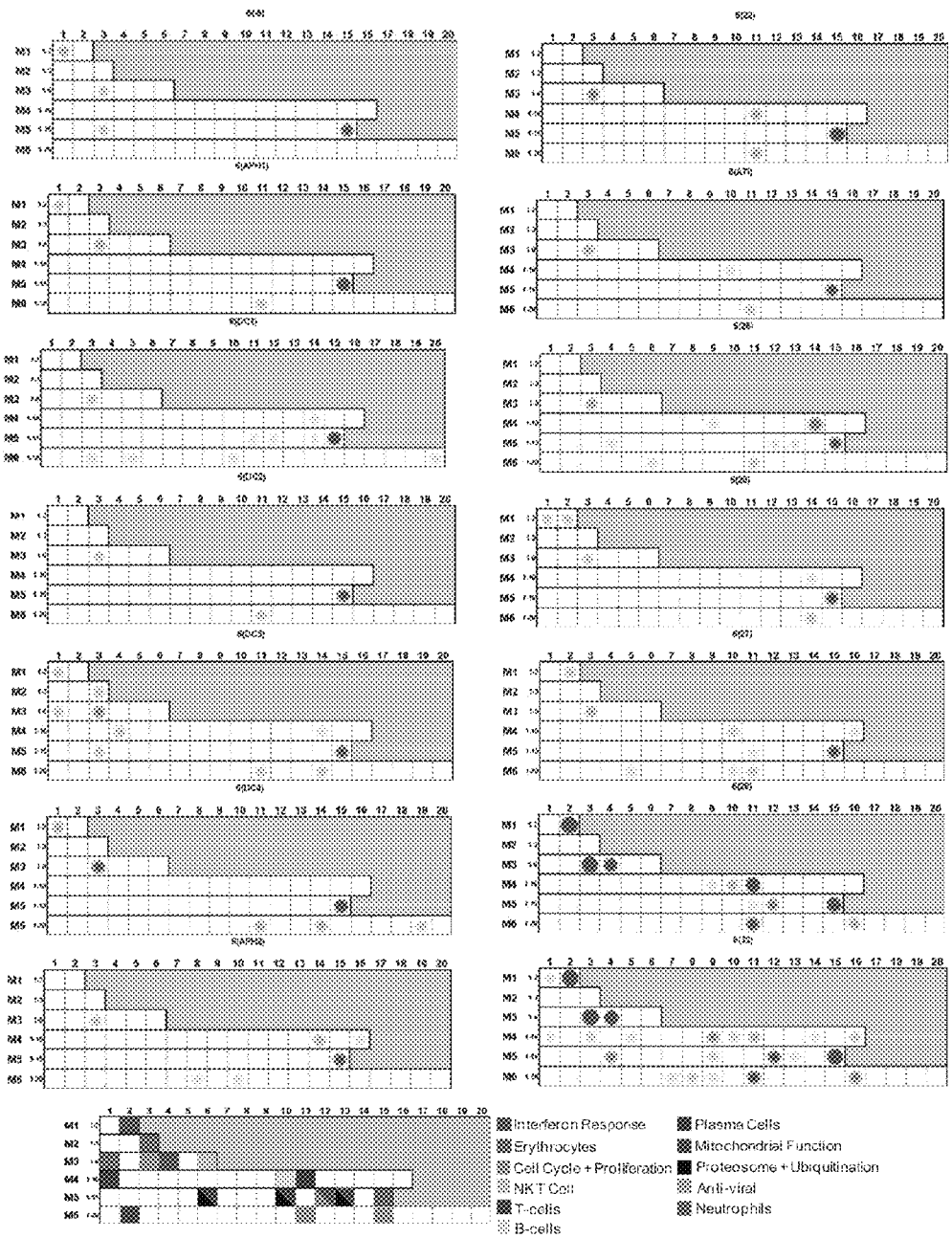
FIG. 107. D1-6 transcriptional module framework.
Figure 113:
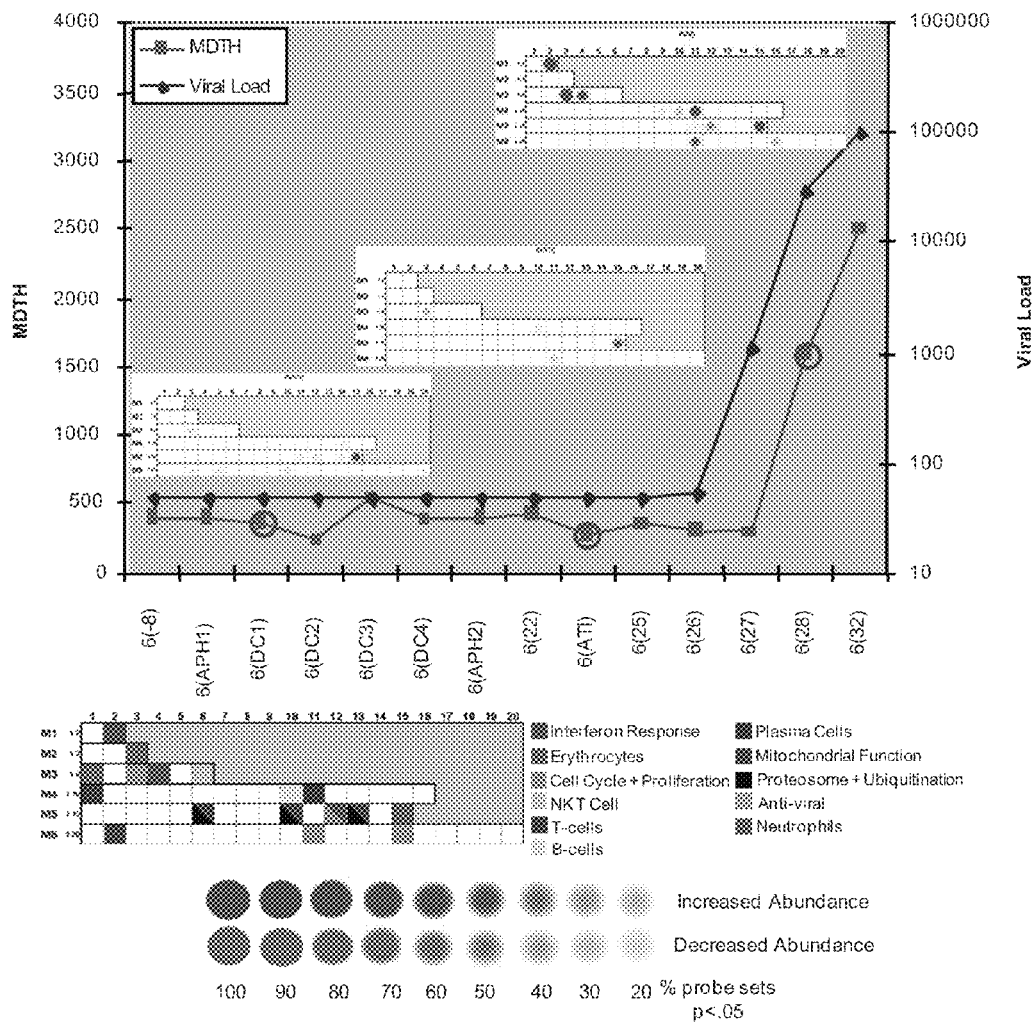
FIG. 113. D1-6 module activity summary.

Blood Transcriptome: D1-6 exhibited persistent neutrophil activity at all time points. Minimal perturbations in module activity were noted until 4 weeks post-ATI (week 28) when the complete interferon signature (M1.2, M3.4, M5.12) showed increased activity. This time point was also associated with increased cell cycle activity (M3.3, M6.11) and increased plasma cell activity (M4.11). This time point lagged behind the first measured increase in viral load by one week (FIG. 107 and FIG. 113).

Figure 10:
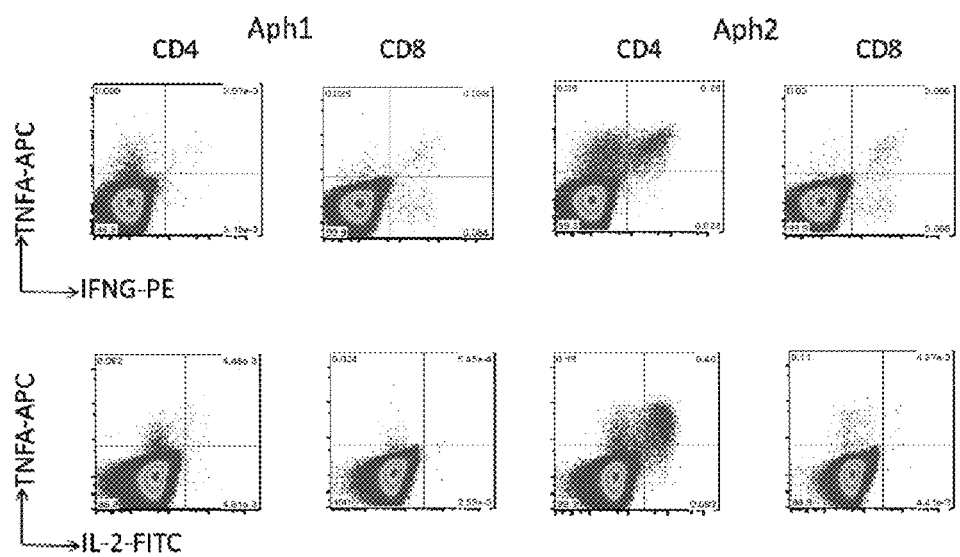
FIG. 10. D-7: ICS after 6 hours LIPO5 long peptides mix stimulation of Aph1 and Aph2.
Figure 25:
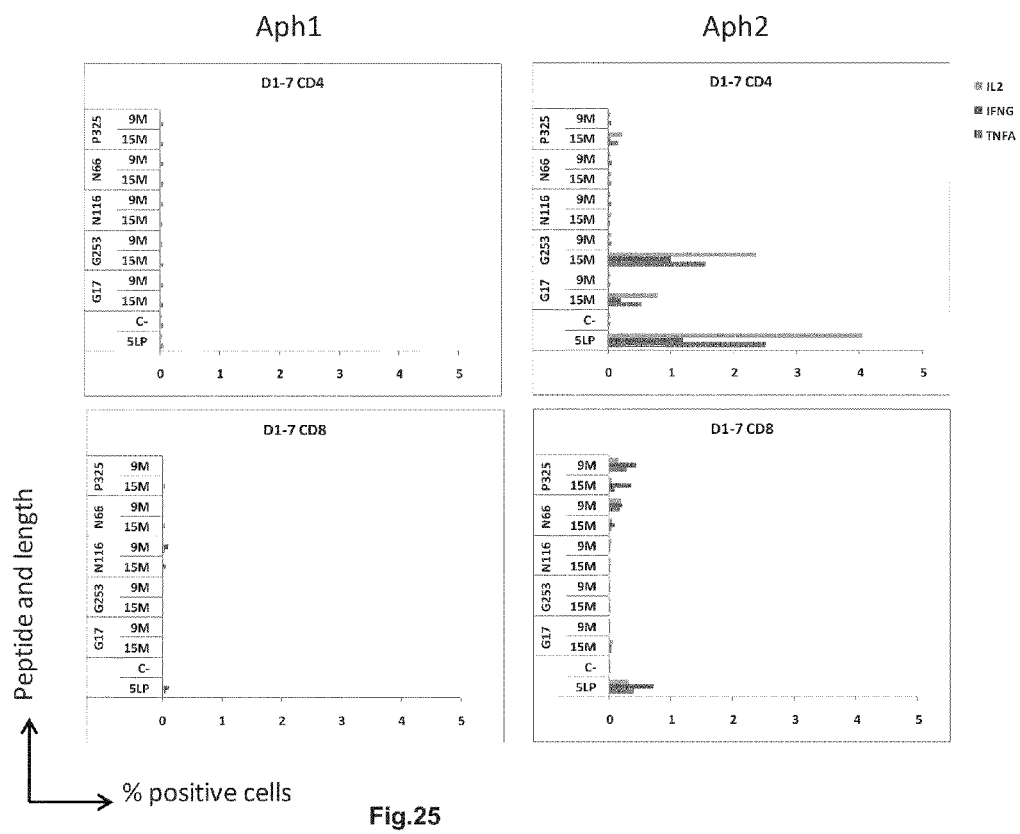
FIG. 25. D1-7: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

Patient D1-7:

ICS analysis: There is an increased peptide-specific CD4+ T cell response after vaccination: From 0.093% to 0.68% TNFα+ cells, from 0.009% to 0.563% IL-2+ cells and 0.007% to 0.52% IFNγ+ cells. Among HIV-specific CD4+ T cells, 0.48% express both IL-2 and TNFα and 0.29% are double positive for TNFα and IFNγ. The inventors observed an increased of peptide-specific CD8+ T cell response after vaccination: From 0.067% to 0.116% TNFα+ cells and 0.102% to 0.174% IFNγ+ cells. In the peptide-specific CD8+ T cell population, 0.086% are double positive for TNFα and IFNγ (FIG. 10). The stimulation with pools of 15-mers and 9-mers derived from LIPO5 sequences showed small CD4 responses to Gag17, Gag253 and Pol325 after vaccination, and CD8 responses to Nef116 and Pol325 were observed after vaccination (FIG. 25).

Cytokine secretion analysis: Responses against Gag253, Nef66, Nef116 and Pol325 were detected by secretion of IL-2, IL-10, IL-13, IL-17, IL-21, IFNΓ and IP10 (FIG. 30-41).

Gag253 stimulated 1300 pg/mL IL-2, 80 pg/mL IL-10, 500 pg/mL IL-13, 220 pg/mL IL-17, 500 pg/mL IL-21, 9 µg/ml IFNγ and ≥20 µg/mL IP10.

Nef66 stimulated 720 pg/mL IL-2, 80 pg/mL IL-10, 650 pg/mL IL-13, 350 pg/mL IL-17, 6.5 µg/l IFNγ and 18 µg/mL IP10.

Nef116 stimulated 110 pg/mL IL-2, 40 pg/mL IL-10, 130 pg/mL IL-13, 130 pg/mL IL-17, 590 pg/ml IFNγ and ≥20 µg/mL IP10

Pol325 stimulated 1360 pg/mL IL-2, 150 pg/mL IL-10, 600 pg/mL IL-13, 300 pg/mL IL-17, 1400 pg/mL IL-21, 6 µg/ml IFNγ and ≥20 µg/mL IP10.

Figure 60:
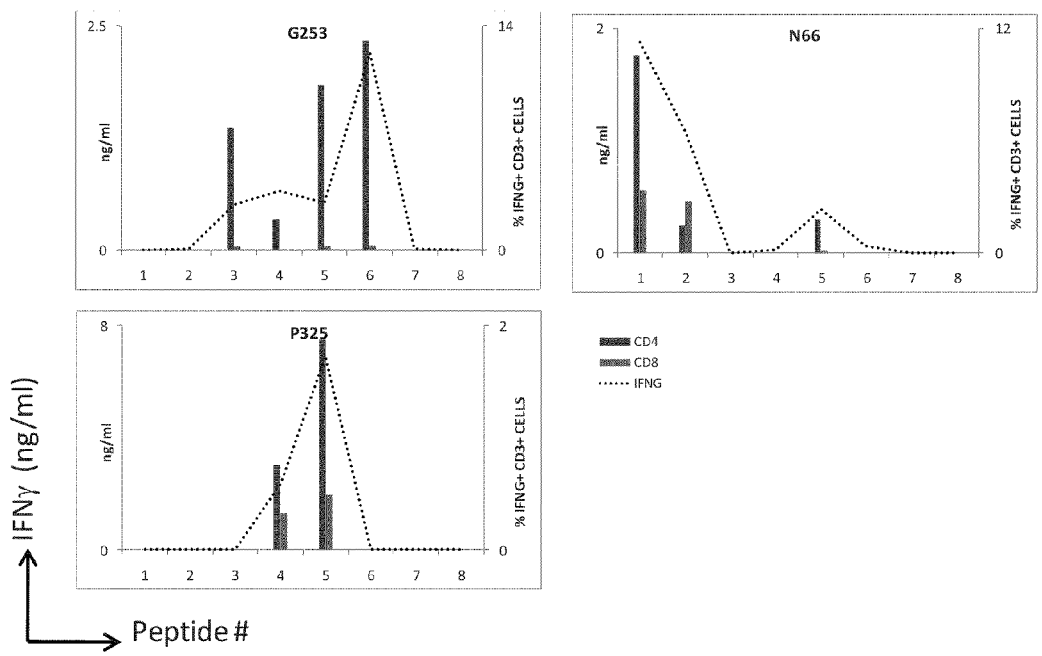
FIG. 60. D1-7: 7 days peptide stimulated cultures from Aph 2 were used for ICS after 6 hours 15-mer peptide stimulation.
Figure 61:
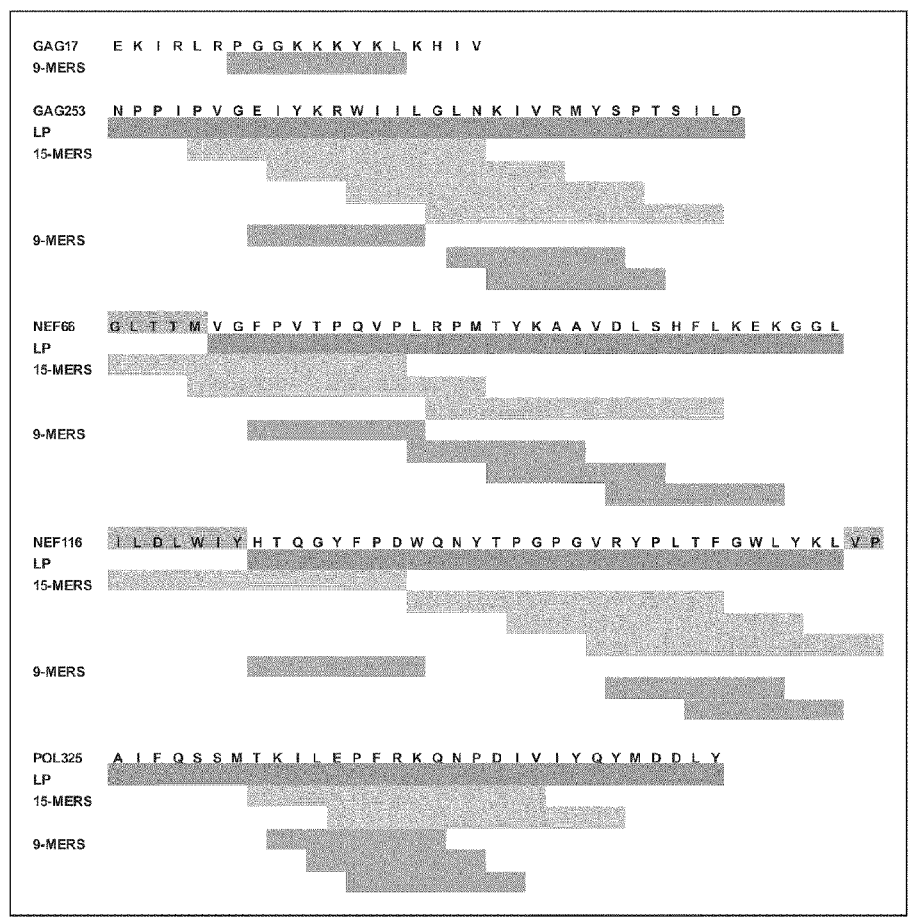
FIG. 61. Summary of the results obtained by Luminex analysis of patient D 1-7 T cells stimulated with LIPO5 long peptides (19-32 aa), 15-mers and 9-mers (SEQ ID NOs. 1, 2, 13, 14, 5).
Figure 62:
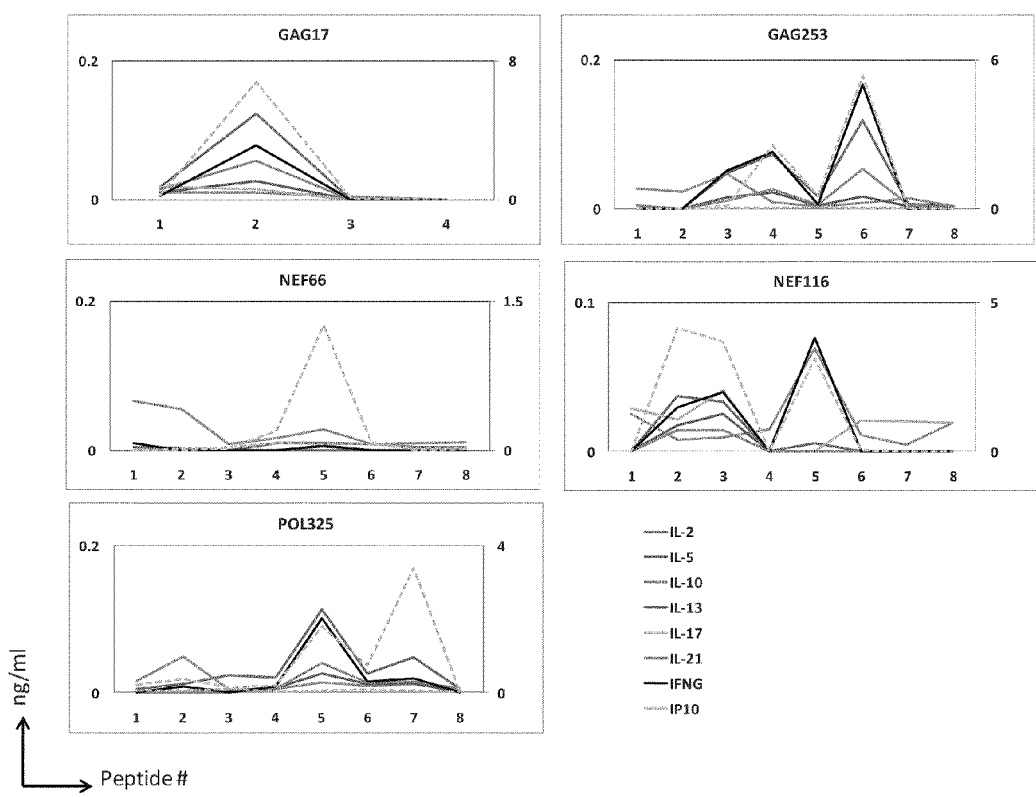
FIG. 62. DALIA vaccinated patient D1-8 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 63:
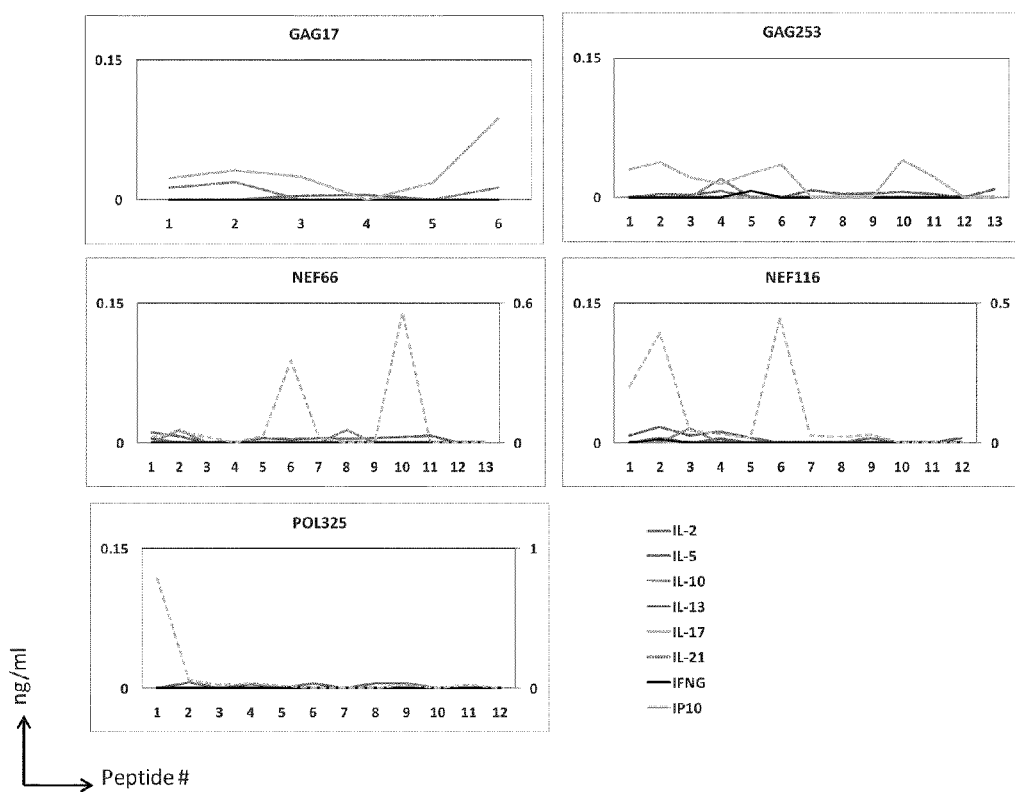
FIG. 63. DALIA vaccinated patient D1-8 PBMCs were stimulated with 9-mers of LIPO5 peptides for 48 hours. Luminex analysis of cytokine secretion post-vaccination samples. Dotted lines represent cytokines with high concentration in the supernatants (right side axes).

T cells recognize 15-mer peptides p3, p4, p5 and p6 in Gag 253; peptides p1, p2 and p5 in Nef 66; peptides p1, p5, p6 and p7 in Nef 116; and peptides p4 and p5 in Pol 325. They also recognize 9-mer peptide p4 in Gag 17; peptides p5, p10 and p11 in Gag 253; peptides p2, p6, p8 and p11 in Nef 66; peptides p1, p10 and p12 in Nef 116; and peptides p5, p6 and p7 in Pol 325 (FIG. 58-61). Detailed ICS showed that Gag253, Nef66 and Pol325 15-mer epitopes are mostly CD4+ T cell epitopes (FIG. 60).

Anti HIV-antibodies: The inventors observed no detectable antibodies against any of the LIPO5 peptides in serum from patient D1-7. Antibodies recognizing Nef and Gag p24 proteins were not detectable in samples before or after vaccination (FIG. 74-76).

Figure 11:
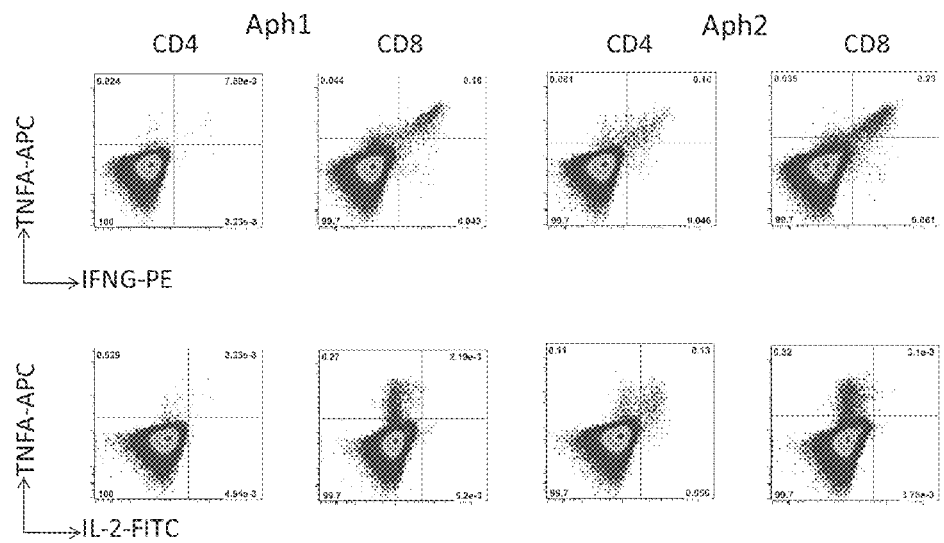
FIG. 11. D1-8: ICS after 6 hours LIPO5 long peptides mix stimulation of Aph1 and Aph2.
Figure 26:
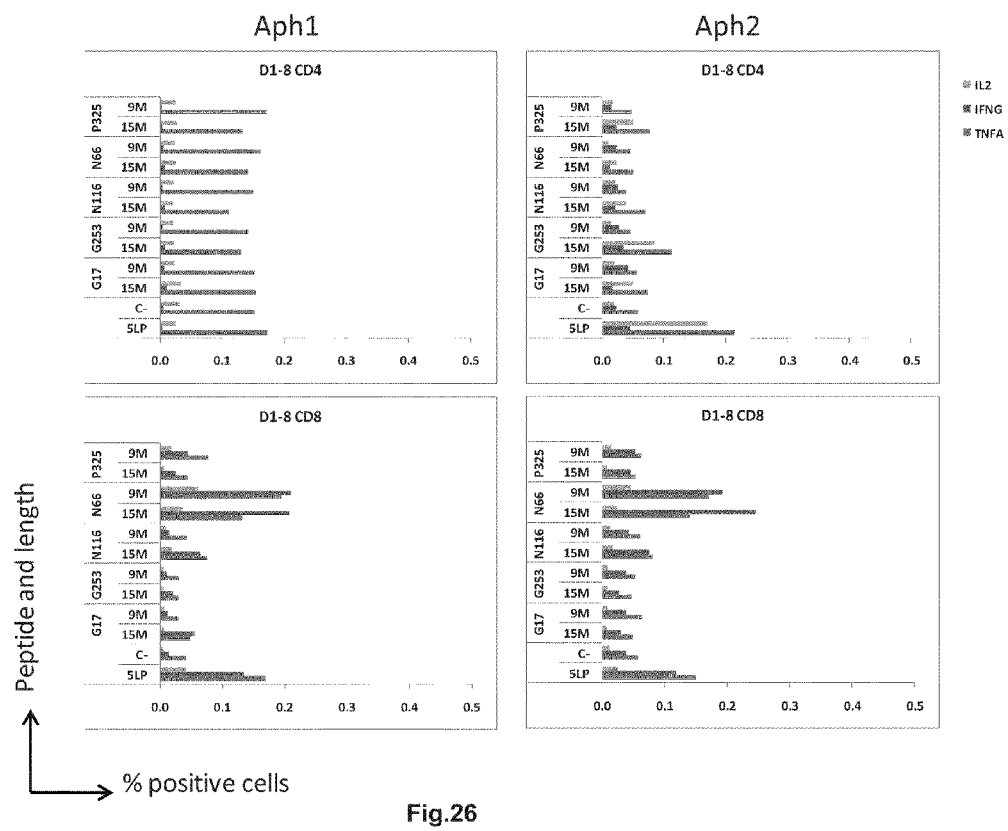
FIG. 26. D1-8: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

Patient D1-8:

ICS analysis: There is an increased peptide-specific CD4+ T cell response after vaccination: From 0.03% to 0.24% TNFα+ cells, from 0.01% to 0.20% IL-2+ cells and 0.01% to 0.20% IFNγ+ cells. Among HIV-specific CD4+ T cells, 0.13% express both IL-2 and TNF and 0.16% are double positive for TNFα and IFNγ. The inventors observed no significant change in peptide-specific CD8+ T cell responses in this patient after vaccination (FIG. 11). The stimulation with pools of 15-mers and 9-mers derived from LIPO5 sequences showed small CD4 responses to Gag253 and Pol325 after vaccination and CD8 responses to Nef116 observed after vaccination (FIG. 26).

Cytokine secretion analysis: Responses against Gag 17, Gag253, Nef66, Nef116 and Pol325 were detected by secretion of IL-2, IL-10, IL-13, IL-17, IL-21, IFNγ and IP10 (FIG. 30-41).

Gag17 stimulated 170 pg/mL IL-2, 130 pg/mL IL-21, 400 pg/mL IFNγ and 8.1 µg/mL IP10.

Gag253 stimulated 390 pg/mL IL-2, 60 pg/mL IL-10, 60 pg/mL IL-13, 220 pg/mL IL-21, 3 µg/ml IFNγ and 2.3 µg/mL IP10.

Nef66 stimulated 80 pg/mL IL-2, 50 pg/mL IL-10, 80 pg/mL IL-17 and 115 pg/mL IFNγ.

Nef116 stimulated 50 pg/mL IL-2, 140 pg/mL IFNγ and 15.8 µg/mL IP10. Pol325 stimulated 150 pg/mL IL-2, 75 pg/mL IL-10, 90 pg/mL IL-13, 65 pg/mL IL-17, 65 pg/mL IL-21 and 650 pg/mL IFNγ.

Figure 64:
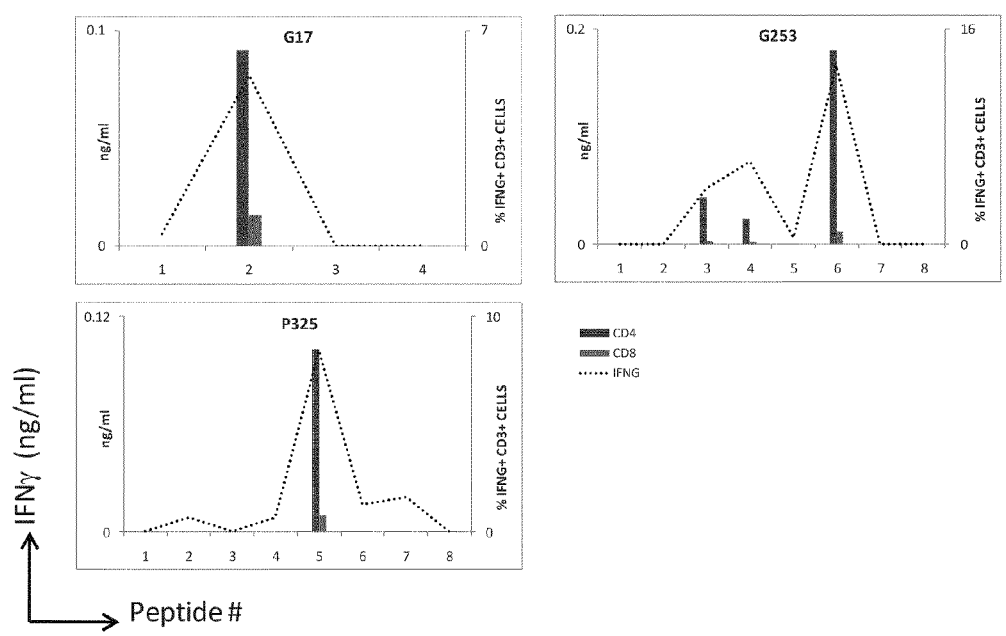
FIG. 64. D1-8: 7 days peptide stimulated cultures from Aph 2 were used for ICS after 6 hours 15-mer peptide stimulation.
Figure 65:
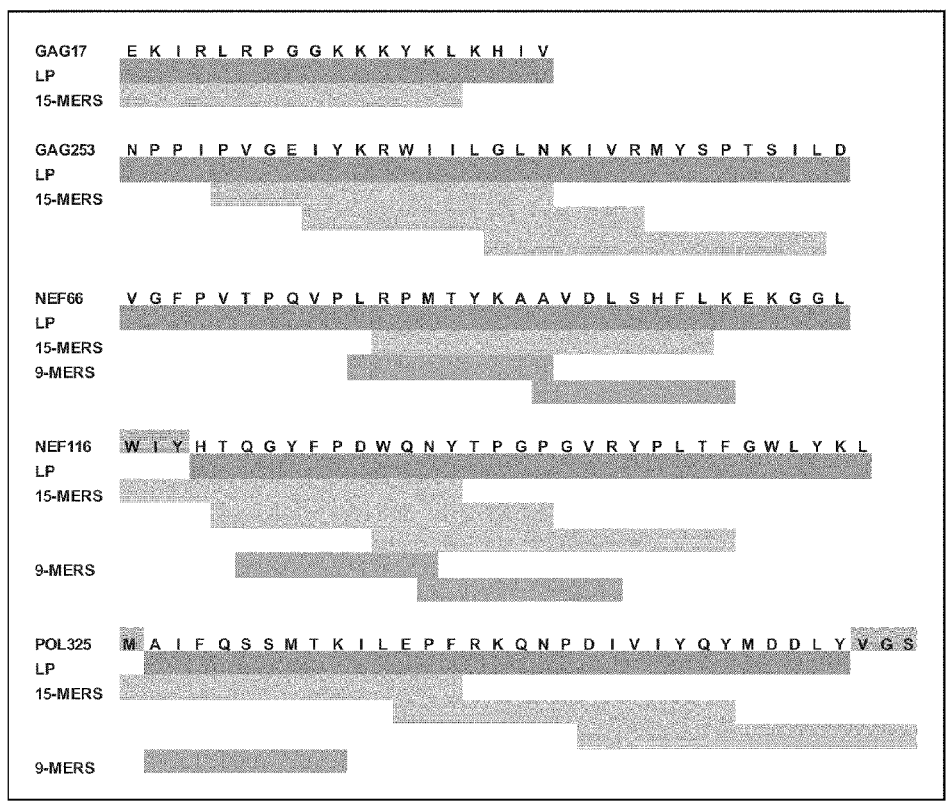
FIG. 65. Summary of the results obtained by Luminex analysis of patient D1-8 T cells stimulated with LIPO5 long peptides (19-32 aa), 15-mers and 9-mers (SEQ ID NOs. 1, 2, 3, 15, 16).
Figure 66:
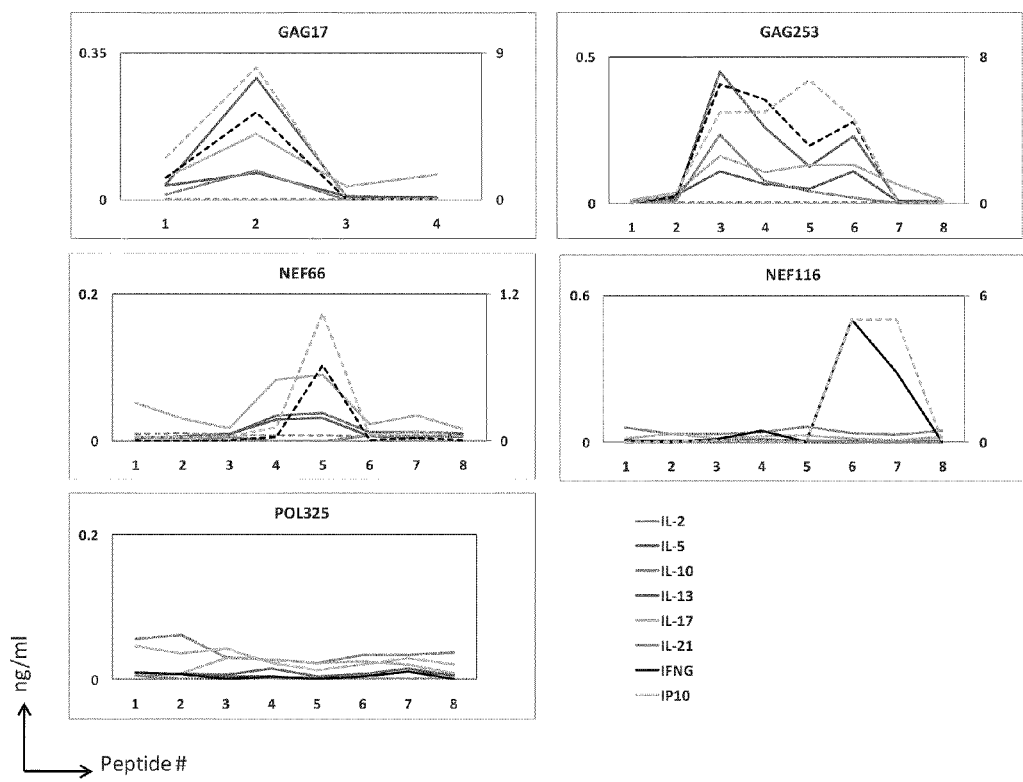
FIG. 66. DALIA vaccinated patient D1-9 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 67:
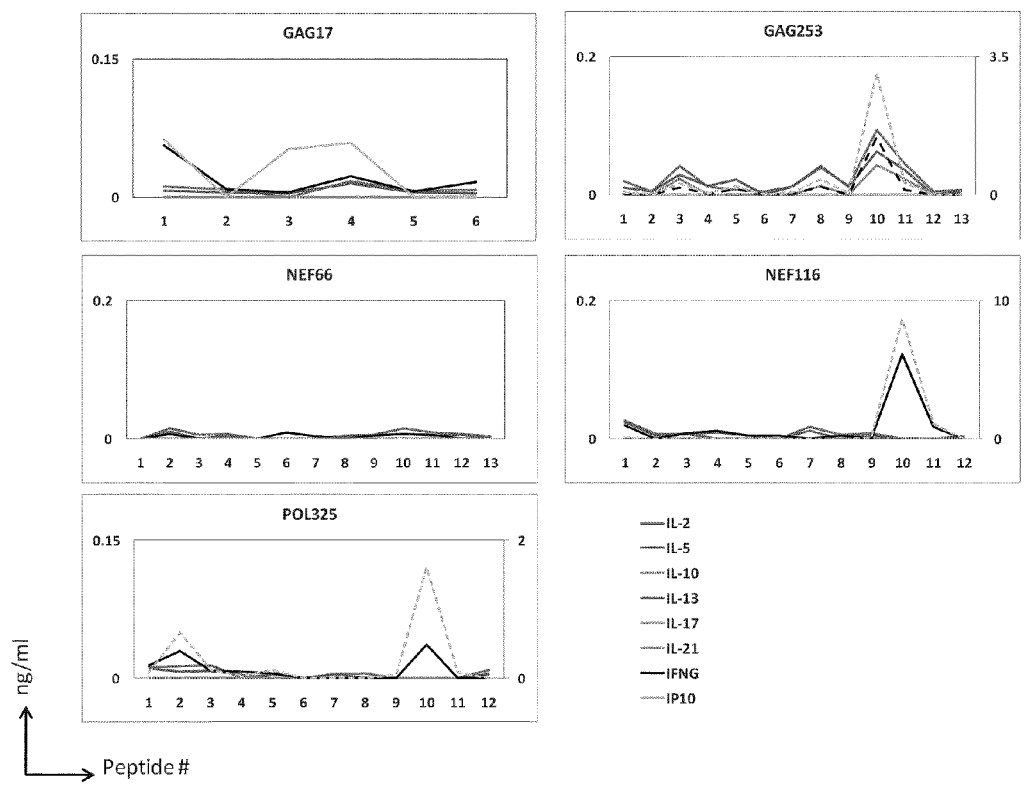
FIG. 67. DALIA vaccinated patient D1-9 PBMCs were stimulated with 9-mers of LIPO5 peptides for 48 hours. Luminex analysis of cytokine secretion post-vaccination samples. Dotted lines represent cytokines with high concentration in the supernatants (right side axes).

T cells recognize 15-mer peptide p2 in Gag 17; peptides p3, p4 and p6 in Gag 253; peptide p5 in Nef 66; peptides p2, p3 and p5 in Nef 116; and peptides p2, p5 and p7 in Pol 325. They also recognize 9-mer peptides p6 and p10 in Nef 66, peptides p2 and p6 in Nef 116 and peptide p1 in Pol 325 (FIG. 62-65). Detailed ICS showed that Gag17, Gag253 and Pol325 15-mer epitopes are mostly CD4+ T cell epitopes (FIG. 64).

Anti HIV-antibodies: The inventors observed no detectable antibodies against any of the LIPO5 peptides in serum from patient D1-8. However, antibodies recognizing Nef and Gag p24 proteins were detectable at the same level before and after vaccination (FIG. 74-76).

Figure 12:
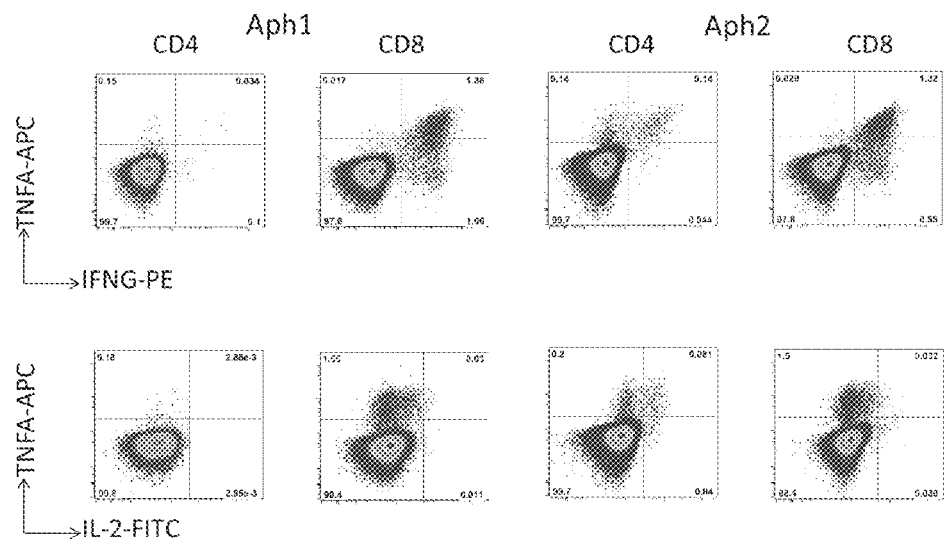
FIG. 12. D1-9: ICS after 6 hours LIPO5 long peptides mix stimulation of Aph1 and Aph2.
Figure 27:
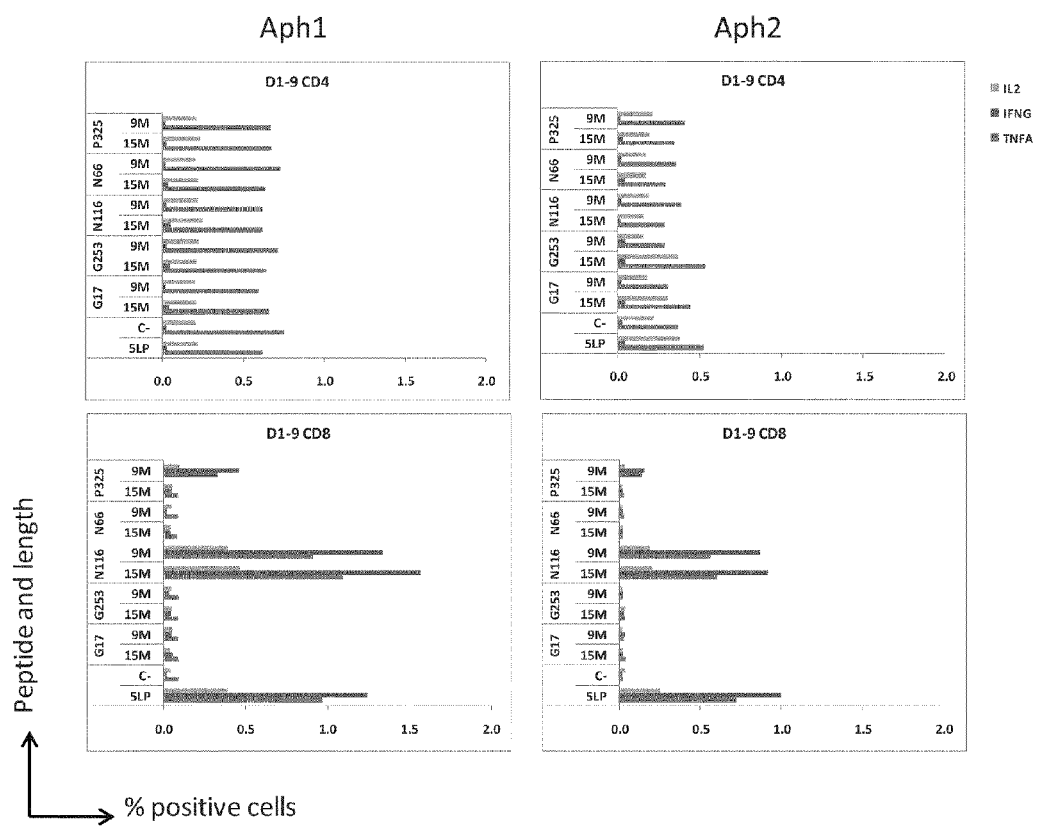
FIG. 27. D1-9: Summary of CD4+ and CD8+ T cell responses against LIPO5 derive 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

Patient D1-9:

ICS analysis: There is an increased peptide-specific CD4+ T cell response after vaccination: From 0.18% to 0.28% TNFα+ cells and 0.13% to 0.18% IFNγ+ cells. Among HIV-specific CD4+ T cells, 0.08% express both IL-2 and TNFα and 0.14% are double positive for TNFα and IFNγ. The inventors observed no significant change in peptide-specific CD8+ T cell responses in this patient after vaccination (FIG. 12). The stimulation with pools of 15-mers and 9-mers derived from LIPO5 sequences showed small CD4 responses to Gag253 observed after vaccination and CD8 responses to Nef116 and Pol325 before and after vaccination (FIG. 27).

Cytokine secretion analysis: Responses against Gag 17, Gag253, Nef66 and Nef116 were detected by secretion of IL-2, IL-13, IL-21, IFNγ and IP10 (FIG. 30-41).

Gag17 stimulated 400 pg/mL IL-2, 6.6 µg/ml IFNγ and ≥25 µg/ml IP10.

Gag253 stimulated 765 pg/mL IL-2, 200 pg/mL IL-13, 360 pg/mL IL-21, 5.3 µg/mL IFNγ and ≥25 µg/mL IP10.

Nef66 stimulated 400 pg/mL IFNγ and 1200 pg/mL IP10.

Nef116 stimulated 805 pg/mL IFNγ and ≥25 µg/mL IP10.

Figure 68:
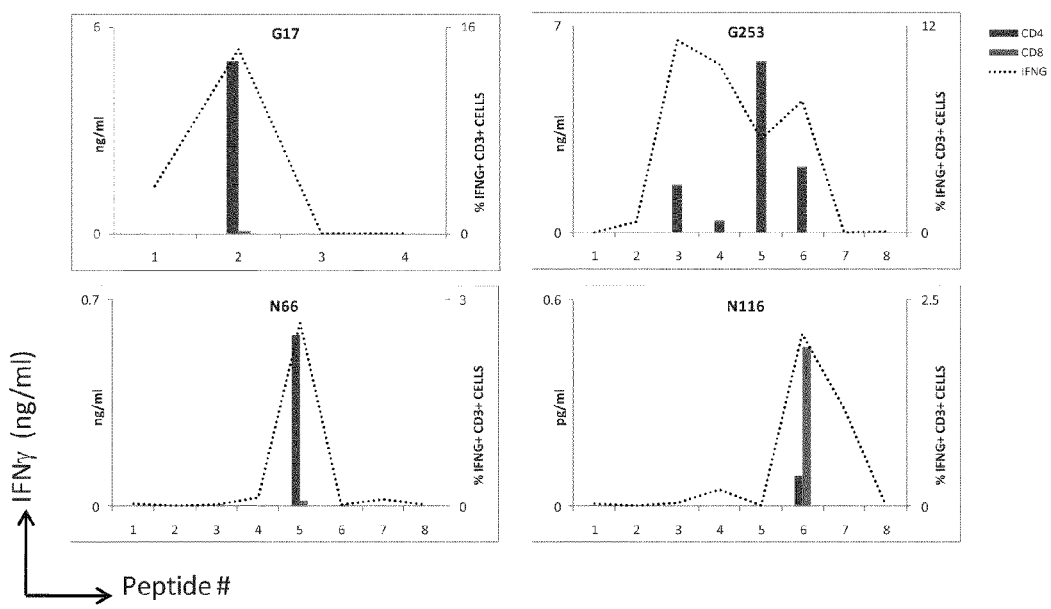
FIG. 68. D1-9: 7 days peptide stimulated cultures from Aph 2 were used for ICS after 6 hours 15-mer peptide stimulation.
Figure 69:
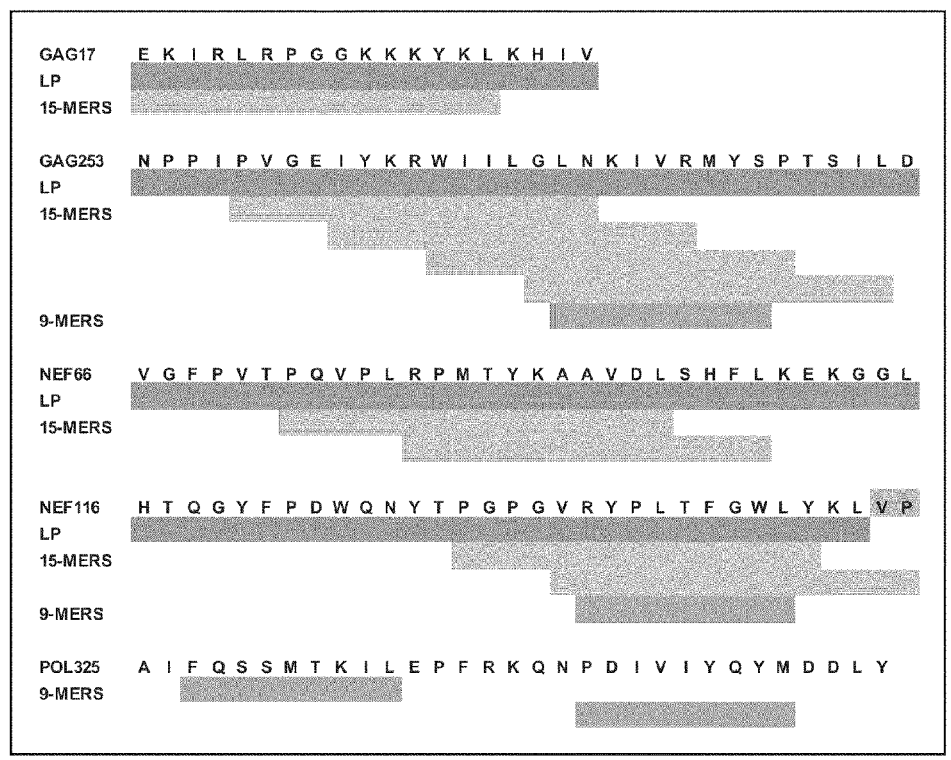
FIG. 69. Summary of the results obtained by Luminex analysis of patient D1-9 T cells stimulated with LIPO5 long peptides (19-32 aa), 15-mers and 9-mers (SEQ ID NOs. 1, 2, 3, 6, 5).
Figure 70:
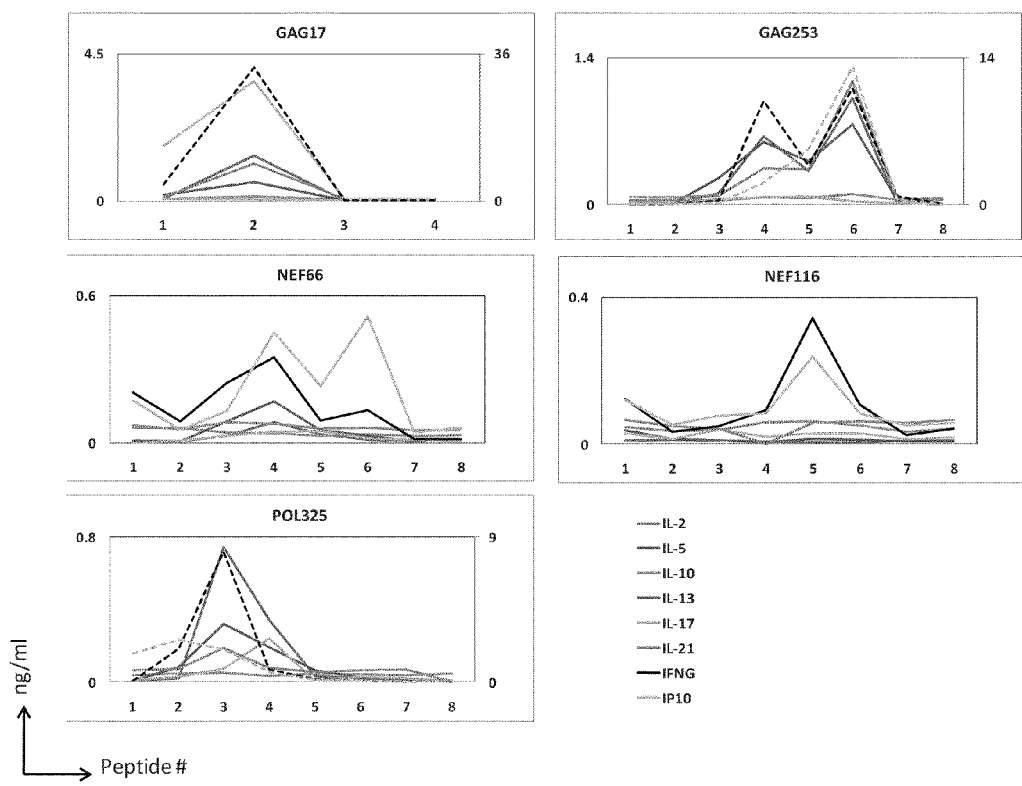
FIG. 70. DALIA vaccinated patient D1-11 PBMCs were stimulated with 15-mers of LIPO5 peptides for 48 hours. Luminex analysis of cytokine secretion post-vaccination samples. Dotted lines represent cytokines with high concentration in the supernatants (right side axes).
Figure 71:
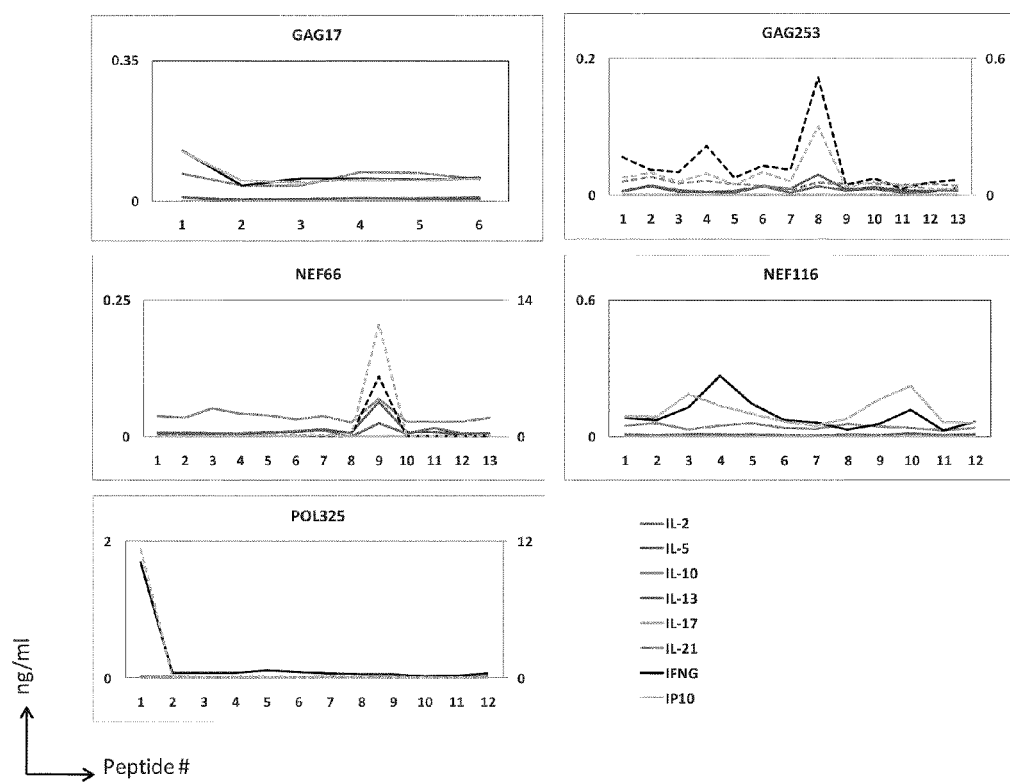
FIG. 71. DALIA vaccinated patients were stimulated with 9-mers of LIPO5 peptides for 48 hours. Luminex analysis of cytokine secretion post-vaccination samples. Dotted lines represent cytokines with high concentration in the supernatants (right side axes).

T cells recognize 15-mer peptide p2 in Gag 17; peptides p3, p4, p5 and p6 in Gag 253; peptides p4 and p5 in Nef 66; and peptides p6 and p7 in Nef 116. They also recognize 9-mer peptide p10 in Gag 253, peptide p10 in Nef 116 and peptides p2 and p10 in Pol 325 (FIG. 66-69). Detailed ICS showed that Gag17, Gag253 and Nef66 15-mer epitopes are mostly CD4+ T cell epitopes while Nef116 are mostly CD8+ T cell epitopes (FIG. 68).

Anti HIV-antibodies: The inventors observed no detectable antibodies against any of the LIPO5 peptides in serum from patient D1-9. However, antibodies recognizing Nef protein were detectable at the same level before and after vaccination (FIG. 74-76).

Figure 13:
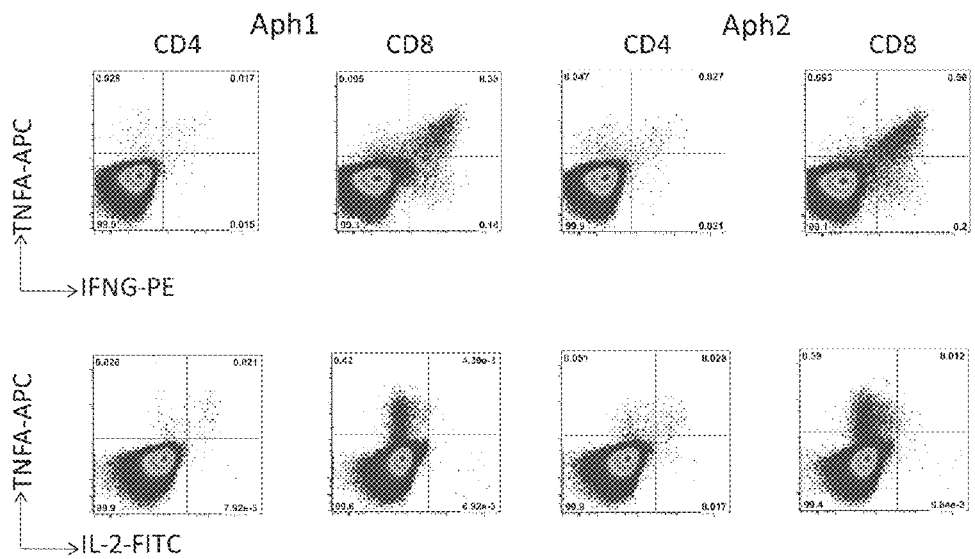
FIG. 13. D1-10: ICS after 6 hours LIPO5 long peptides mix stimulation of Aph1 and Aph2.
Figure 28:
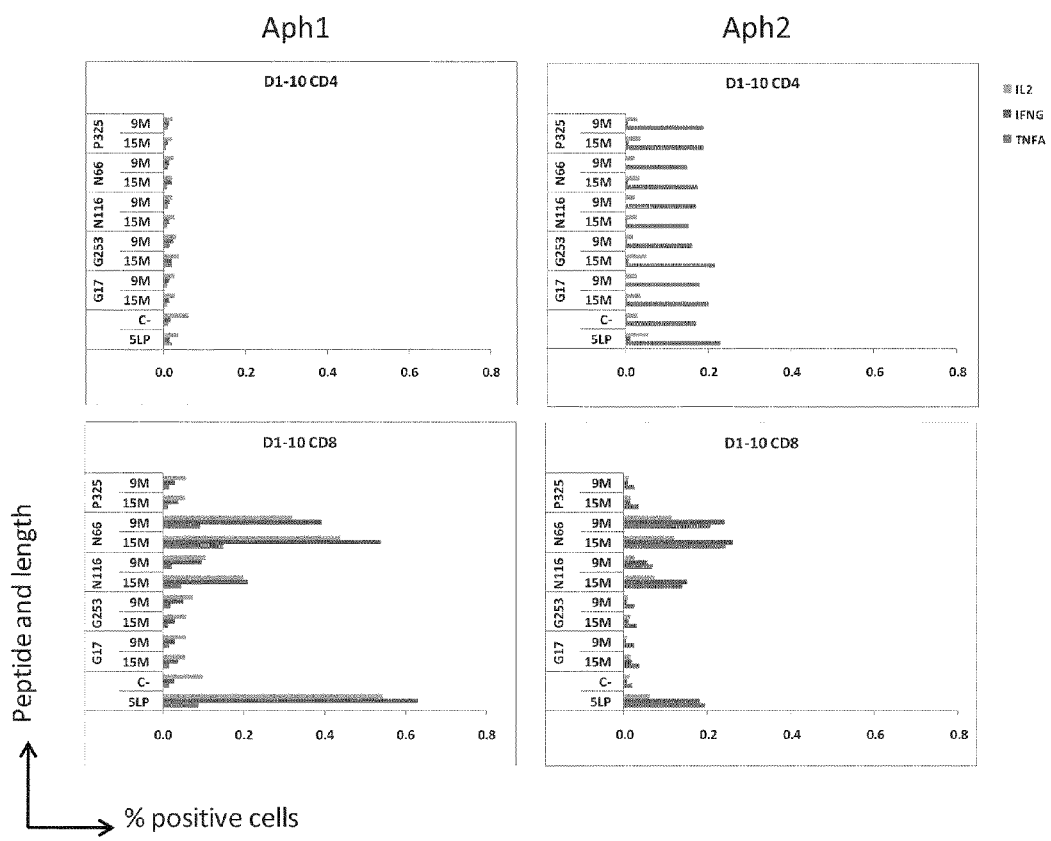
FIG. 28. D1-10: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.

Patient D1-10:

ICS analysis: There is an increased peptide-specific CD4+ T cell response after vaccination: From 0.045% to 0.07% TNFα+ cells, from 0.03% to 0.045% IL-2+ cells and 0.03% to 0.05% IFNγ+ cells. Among HIV-specific CD4+ T cells, 0.028% express both IL-2 and TNFα and 0.03% are double positive for TNFα and IFNγ. The inventors observed an increased peptide-specific CD8+ T cell response in this patient after vaccination from 0.5% to 0.7% TNFα+ cells, from 0.01% to 0.03% IL-2+ cells, and 0.55% to 0.8% IFNγ+ cells. In the CD8+ specific cell population, 0.012% express both IL-2 and TNFα and 0.56% are double positive for TNFα and IFNγ. (FIG. 13). The stimulation with pools of 15-mers and 9-mers derived from LIPO5 sequences showed CD8 responses to Nef66 and Nef116 before and after vaccination (FIG. 28).

Cytokine secretion analysis: Responses against Gag 17, Nef66, Nef116 and Pol325 were detected by secretion of IL-2, IL-10 and IP10 (FIG. 30-41).

Gag17 stimulated 290 pg/mL IL-10.

Nef66 stimulated 240 pg/mL IL-10 and 2.4 µg/mL IP10.

Nef116 stimulated 4.9 µg/mL IP10.

Pol325 stimulated 240 pg/mL IL-10.

Anti HIV-antibodies: The inventors observed no detectable antibodies against any of the LIPO5 peptides in serum from patient D1-10. However, antibodies recognizing Nef protein were detectable at the same level before and after vaccination (FIG. 74-76).

Figure 14:
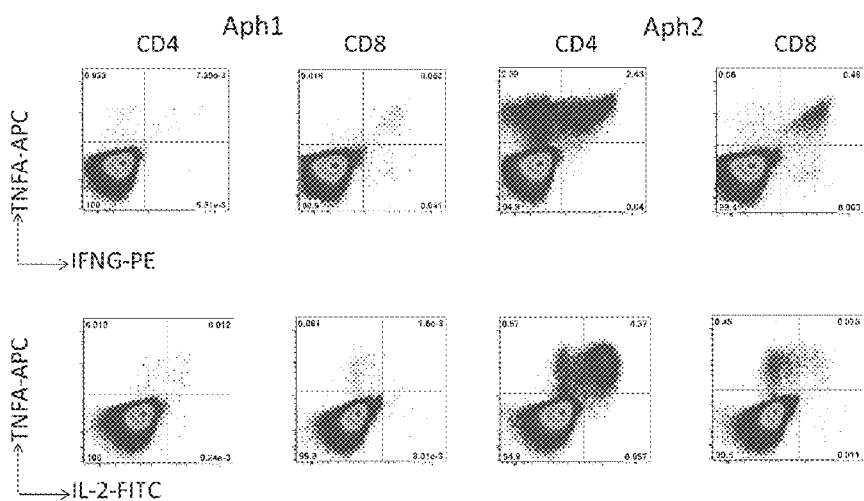
FIG. 14. D1-11: ICS after 6 hours LIPO5 long peptides mix stimulation of Ap1 and Aph2.
Figure 15:
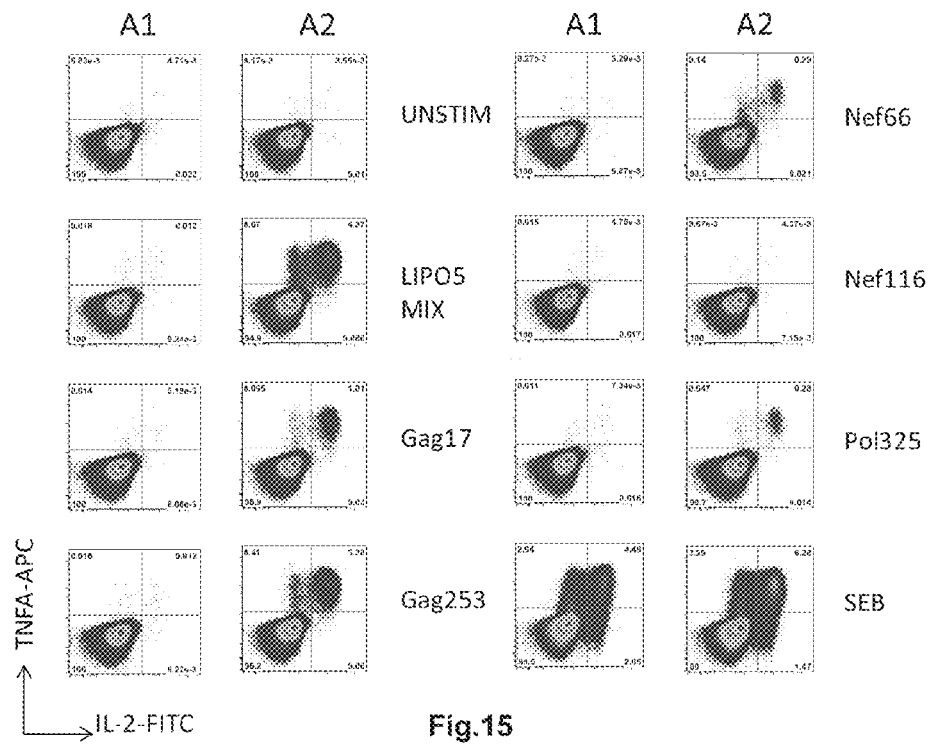
FIG. 15. D1-11: CD4+ T cell responses to LIPO5 long peptides. ICS after 6 hours stimulation of Aph1 and Aph2 with LIPO5 individual long peptides.
Figure 16:
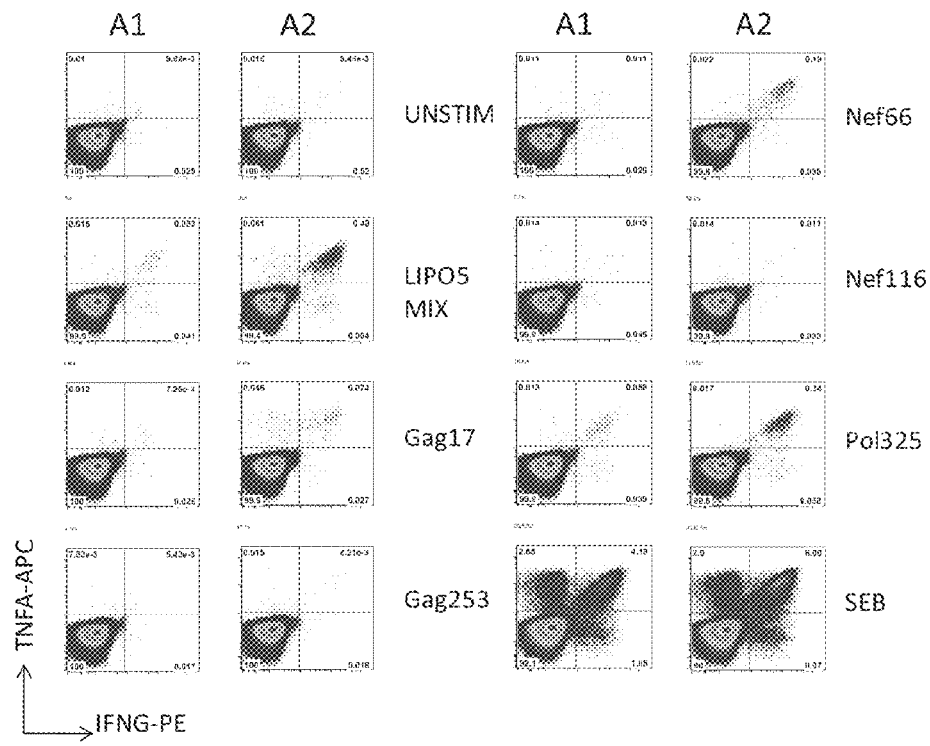
FIG. 16. D1-11: CD8+ T cell responses to LIPO5 long peptides. ICS after 6 hours stimulation of Aph1 and Aph2 with LIPO5 individual long peptides.
Figure 29:
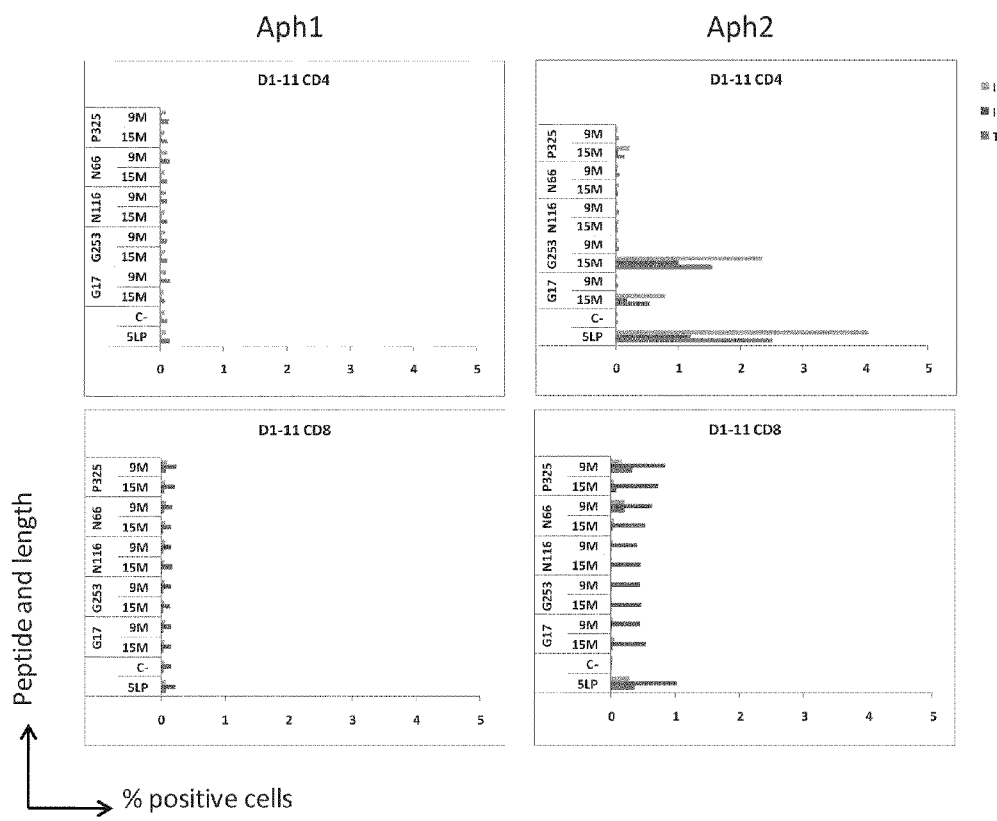
FIG. 29. D1-11: Summary of CD4+ and CD8+ T cell responses against LIPO5 derived 15-mers and 9-mers pools. ICS LIPO5 stimulation of samples pre (A1) and post-vaccination (A2) from DALIA patients were stimulated with 2 mM of each peptide and anti-CD28 and anti CD49d for 6 hours in presence of BFA followed by intracellular staining for IFNγ, TNFα and IL-2.
Figure 30:
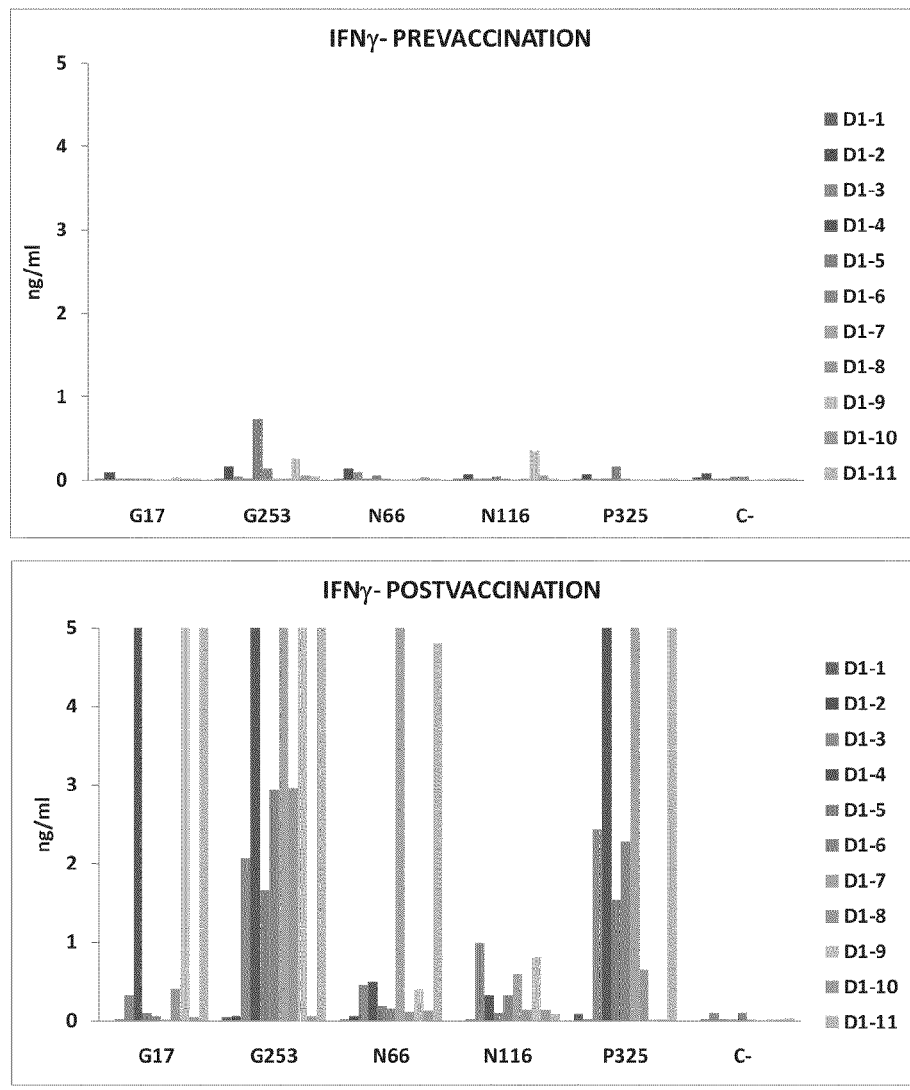
FIG. 30. DALIA vaccinated patients were stimulated with LIPO5 peptides for 48 hours. Luminex analysis for IFNγ secretion in pre (A1) and post-vaccination (A2) is shown. D1-1 to D1-11 secreted different levels of IFNγ in response to at least one peptide.
Figure 31:
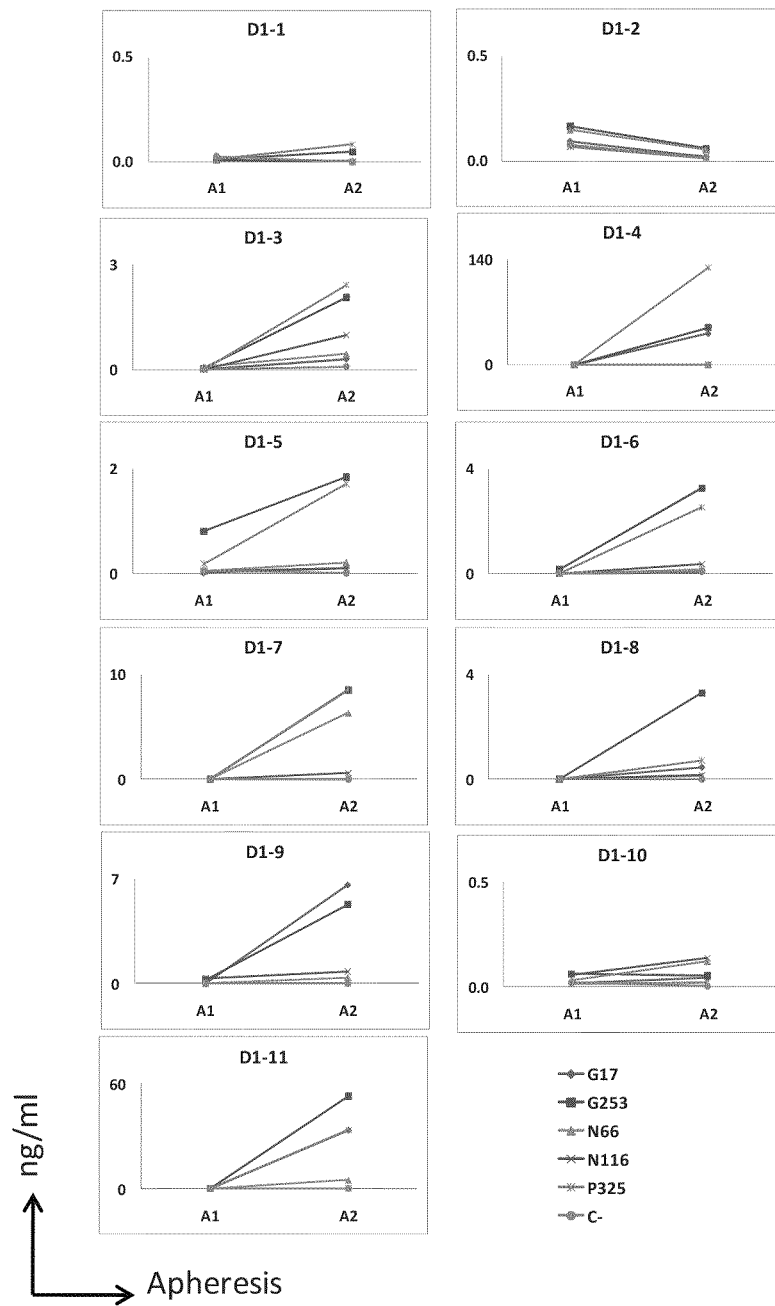
FIG. 31. DALIA vaccinated patients were stimulated with LIPO5 peptides for 48 hours. Luminex analysis for IFNγ secretion in pre (A1) and post-vaccination (A2) samples is shown. Individual responses against each of the LIPO5 long peptides.
Figure 32:
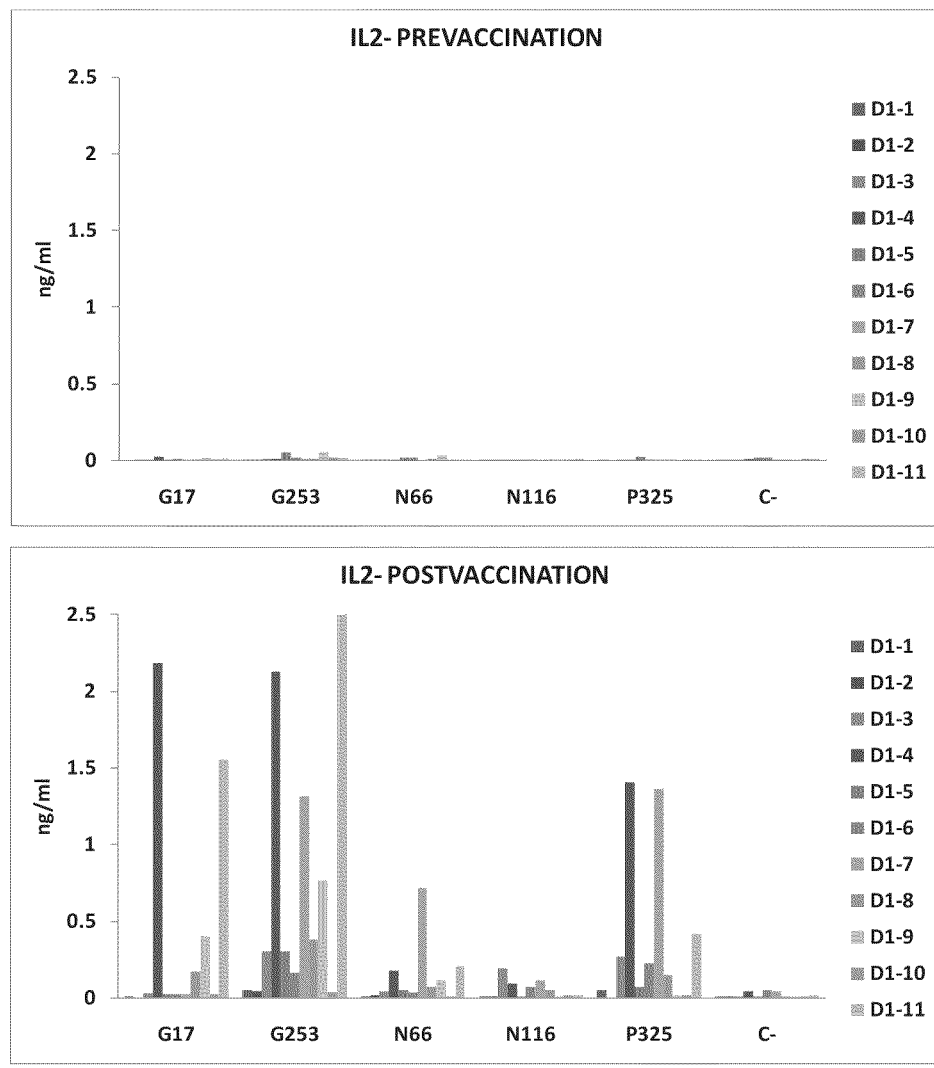
FIG. 32. DALIA vaccinated patients were stimulated with LIPO5 peptides for 48 hours. Luminex analysis for IL-2 secretion in pre (A1) and post-vaccination (A2). All the samples obtained after vaccination showed an increase of IL-2 secreted in response to at least one peptide compared with the pre-vaccination apheresis.
Figure 33:
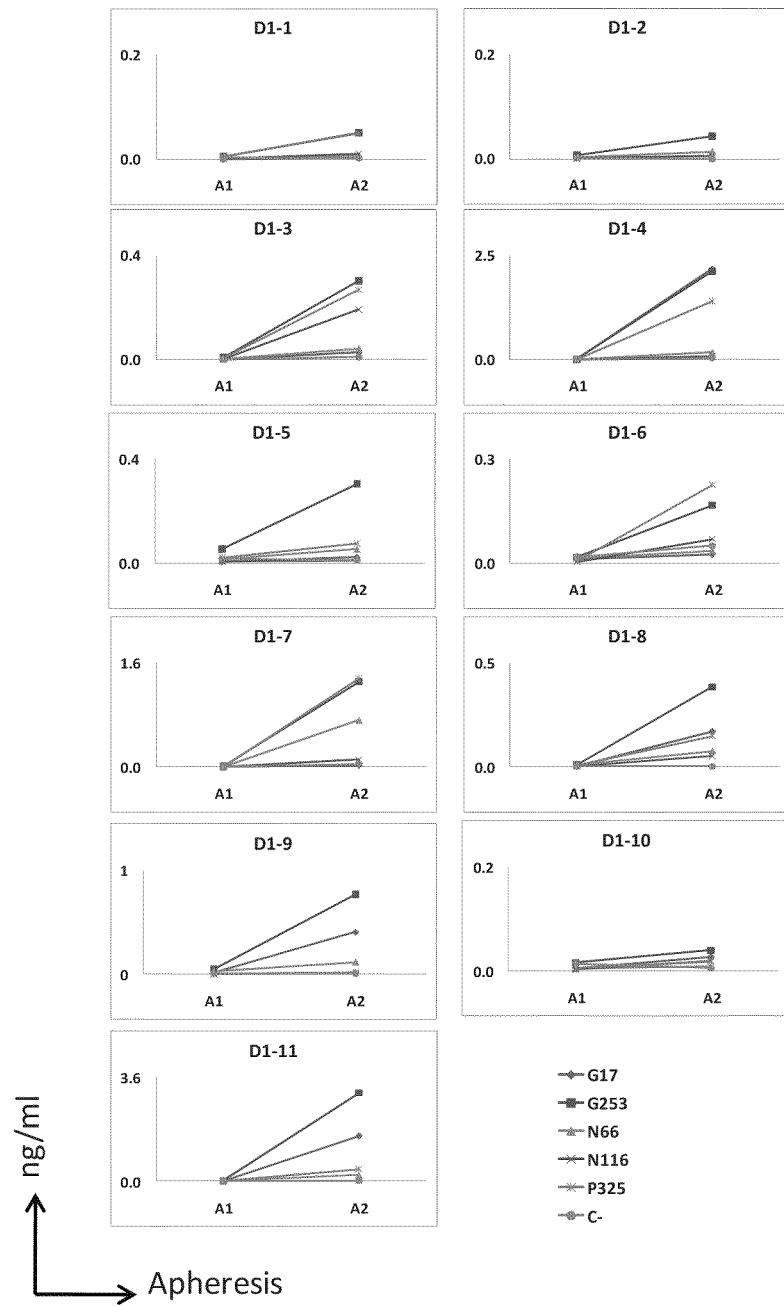
FIG. 33. DALIA vaccinated patients were stimulated with LIPO5 peptides for 48 hours. Luminex analysis for IL-2 secretion in pre (A1) and post-vaccination (A2) samples. Individual responses against each of the LIPO5 long peptides.
Figure 34:
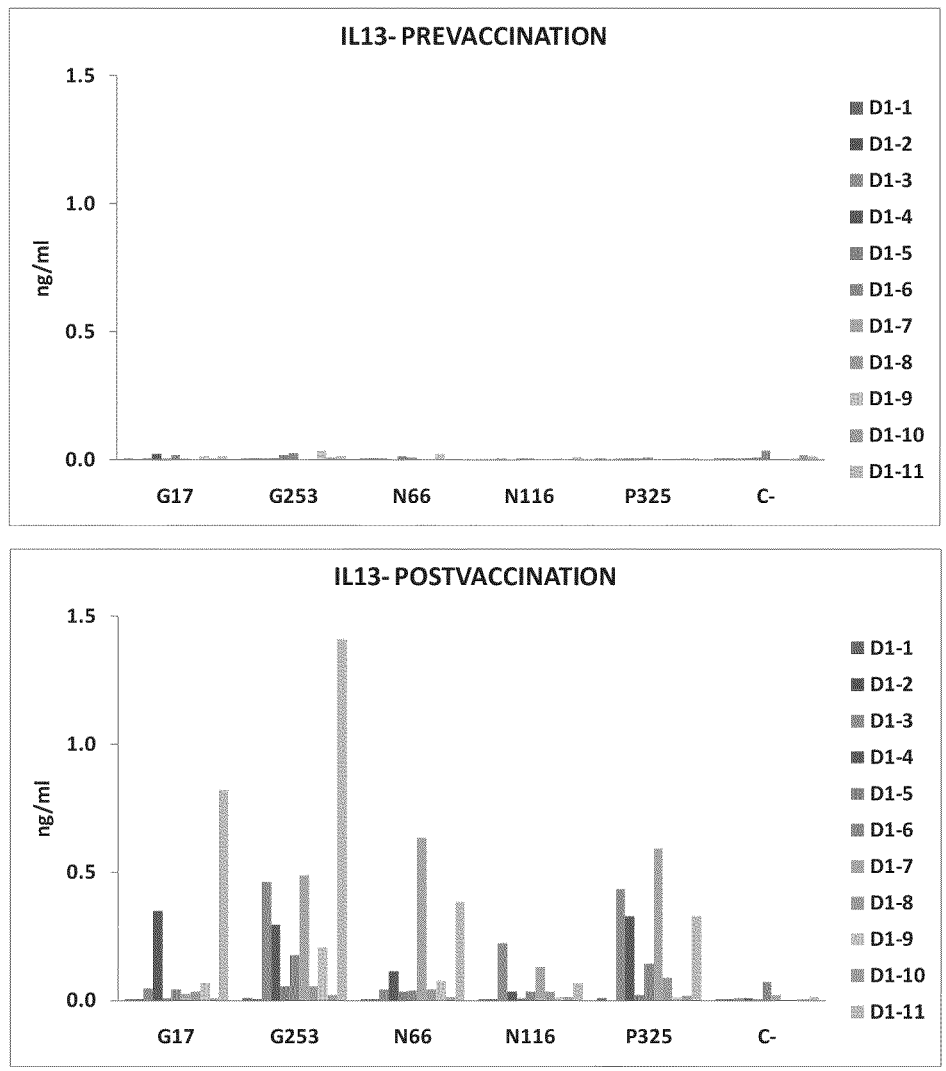
FIG. 34. DALIA vaccinated patients were stimulated with LIPO5 peptides for 48 hours. Luminex analysis for IL-13 secretion in pre (A1) and post-vaccination (A2) samples. Individual responses against each of the LIPO5 long peptides.
Figure 35:
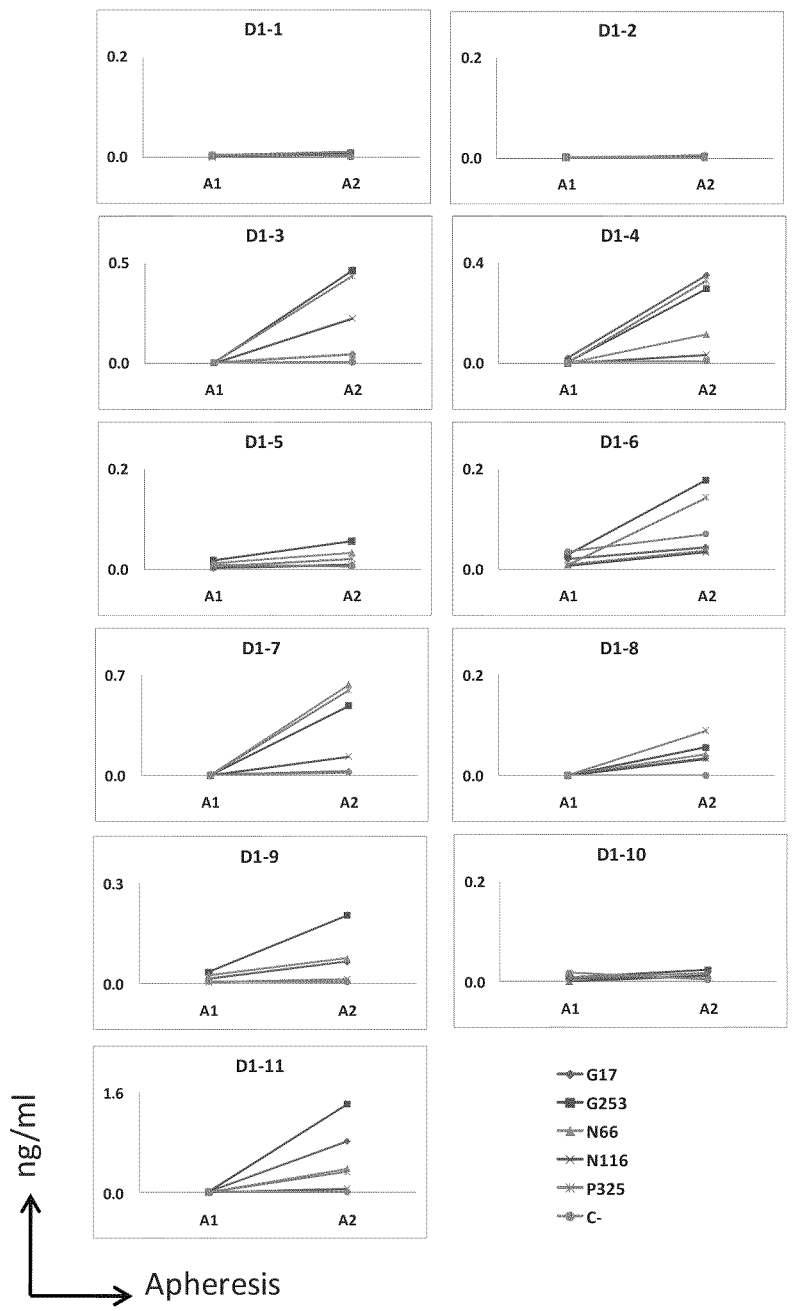
FIG. 35. DALIA vaccinated patients were stimulated with LIPO5 peptides for 48 hours. Luminex analysis for IL-13 secretion in pre (A1) and post-vaccination (A2) samples. Individual responses against each of the LIPO5 long peptides.
Figure 36:
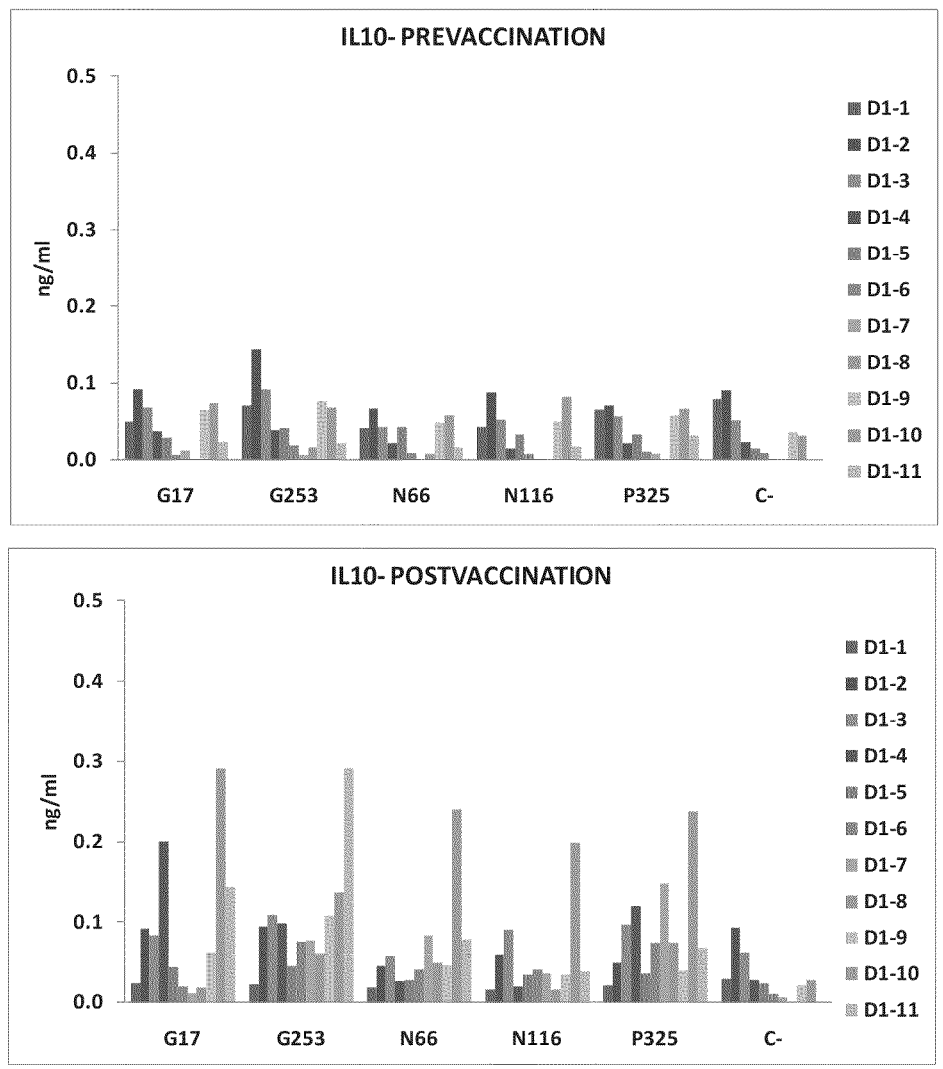
FIG. 36. DALIA vaccinated patients were stimulated with LIPO5 peptides for 8 hours. Luminex analysis for IL-10 secretion in pre (A1) and post-vaccination (A2) samples is shown. Individual responses against each of the LIPO5 long peptides.
Figure 37:
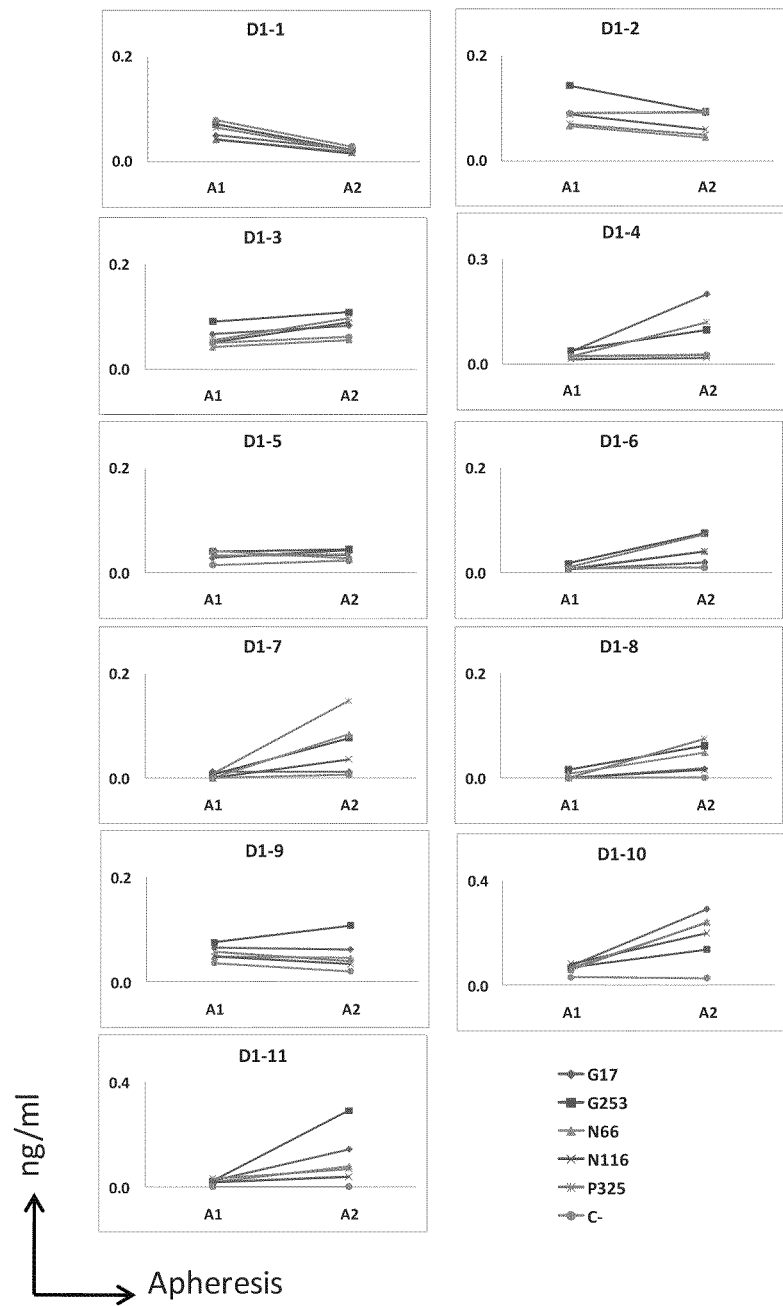
FIG. 37. DALIA vaccinated patients were stimulated with LIPO5 peptides for 48 hours. Luminex analysis for IL-10 secretion in pre (A1) and post-vaccination (A2) samples. Individual responses against each of the LIPO5 long peptides.
Figure 38:
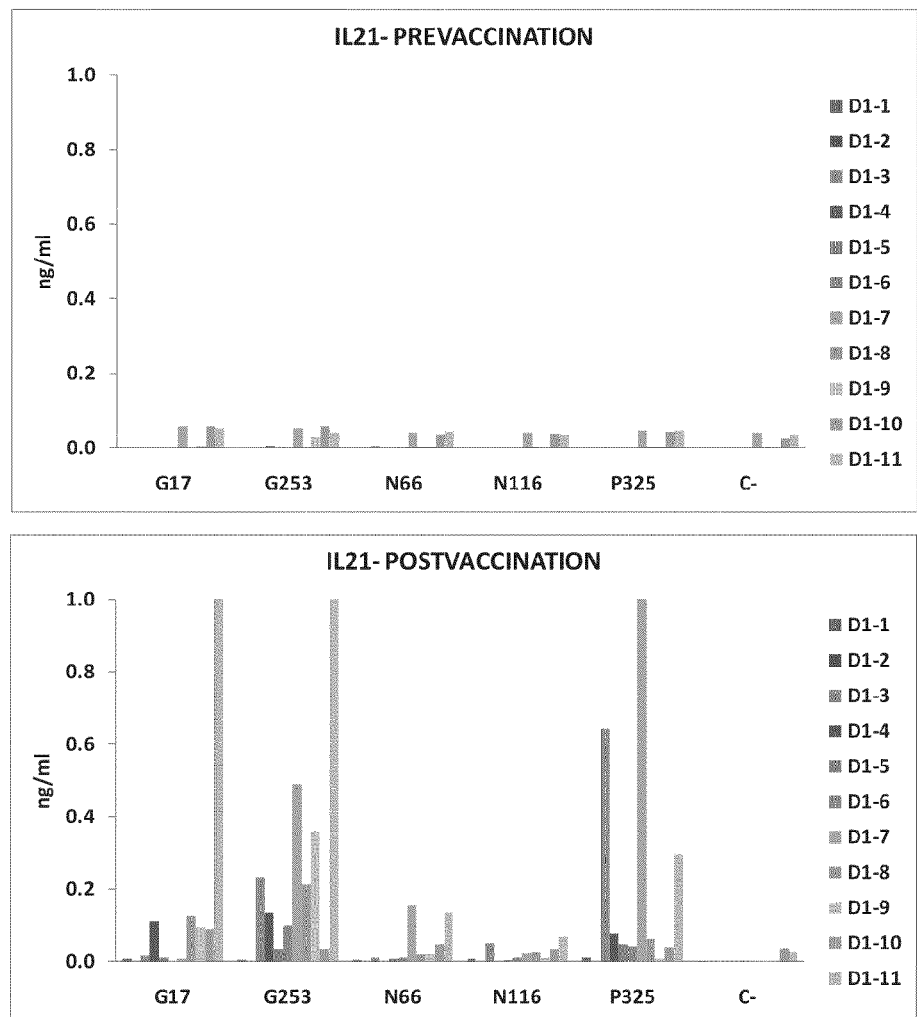
FIG. 38. DALIA vaccinated patients were stimulated with LIPO5 peptides for 48 hours. Luminex analysis for IL-21 secretion in pre (A1) and post-vaccination (A2) samples. Individual responses against each of the LIPO5 long peptides.
Figure 39:
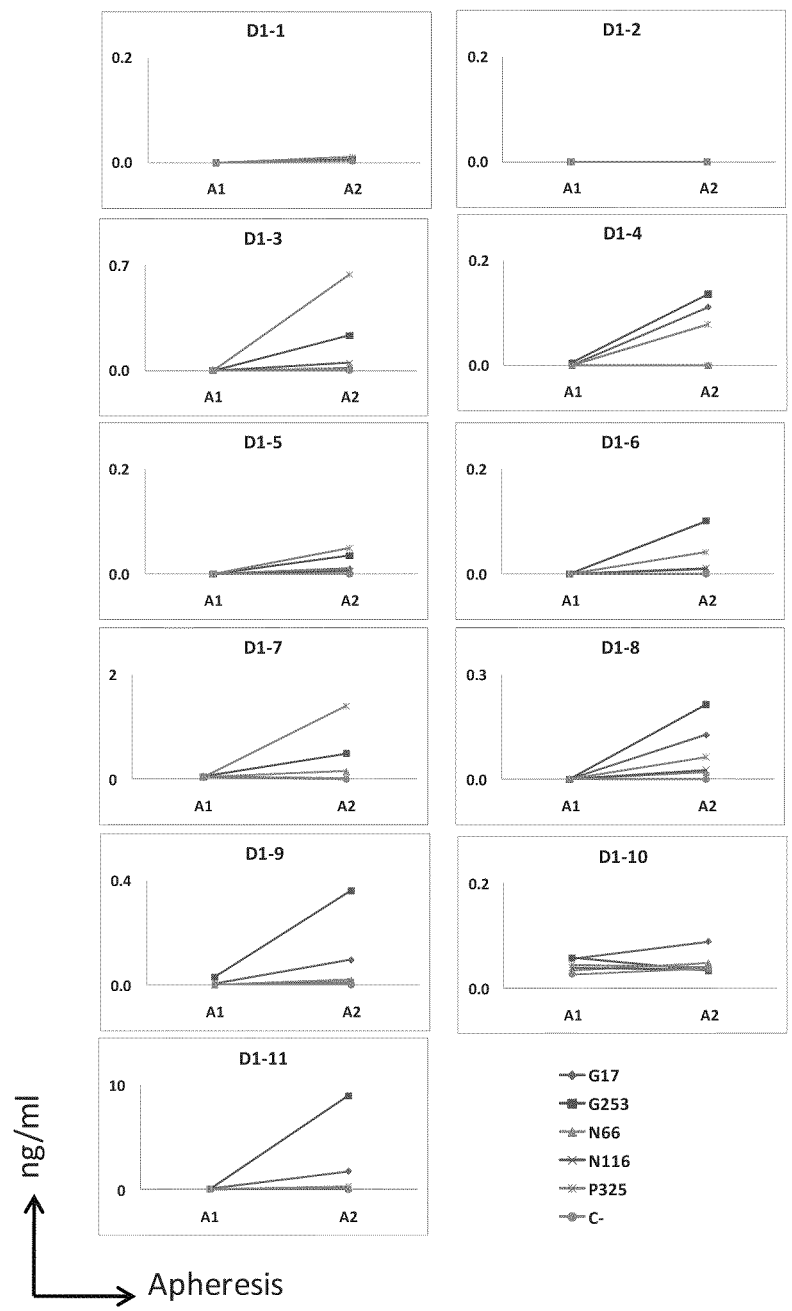
FIG. 39. DALIA vaccinated patients were stimulated with LIPO5 peptides for 48 hours. Luminex analysis for IL-21 secretion in pre (A1) and post-vaccination (A2) samples. Individual responses against each of the LIPO5 long peptides.
Figure 40:
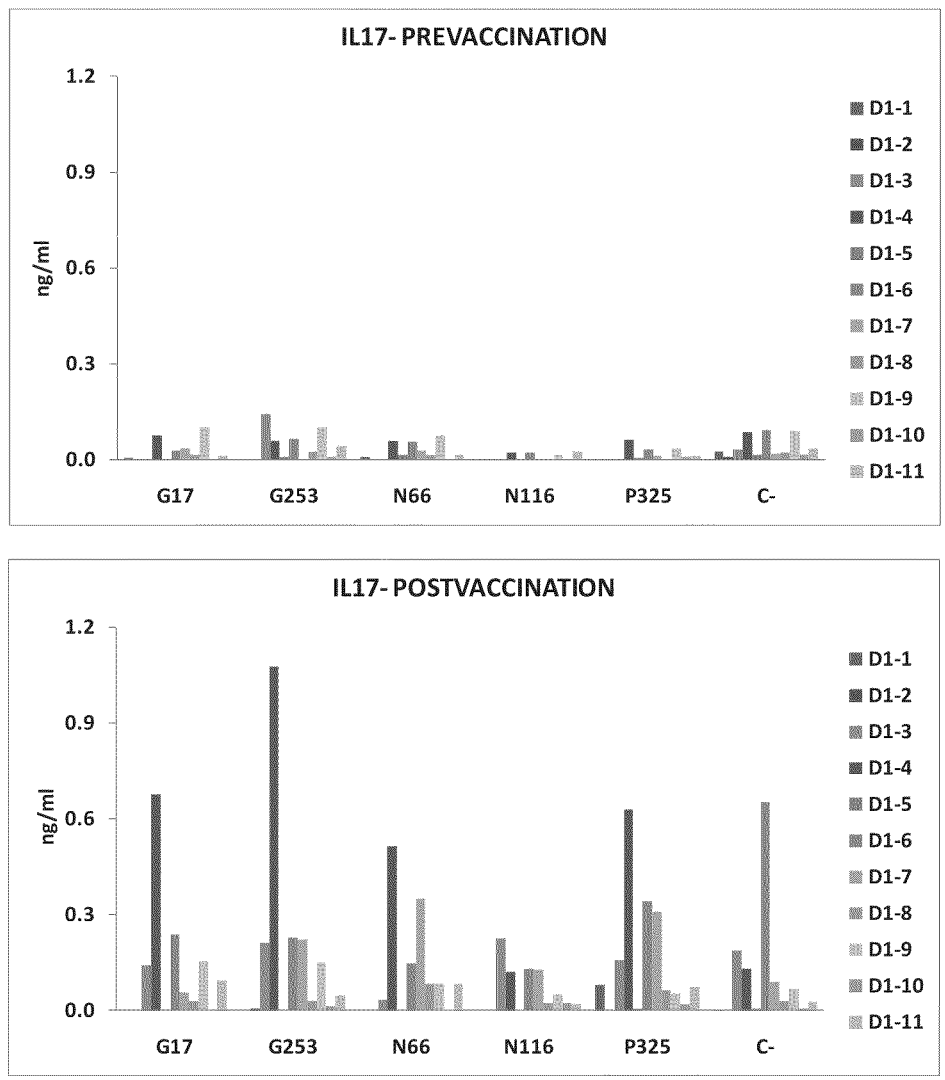
FIG. 40. DALIA vaccinated patients were stimulated with LIPO5 peptides for 48 hours. Luminex analysis for IL-17 secretion in pre (A1) and post-vaccination (A2) samples. Individual responses against each of the LIPO5 long peptides.
Figure 41:
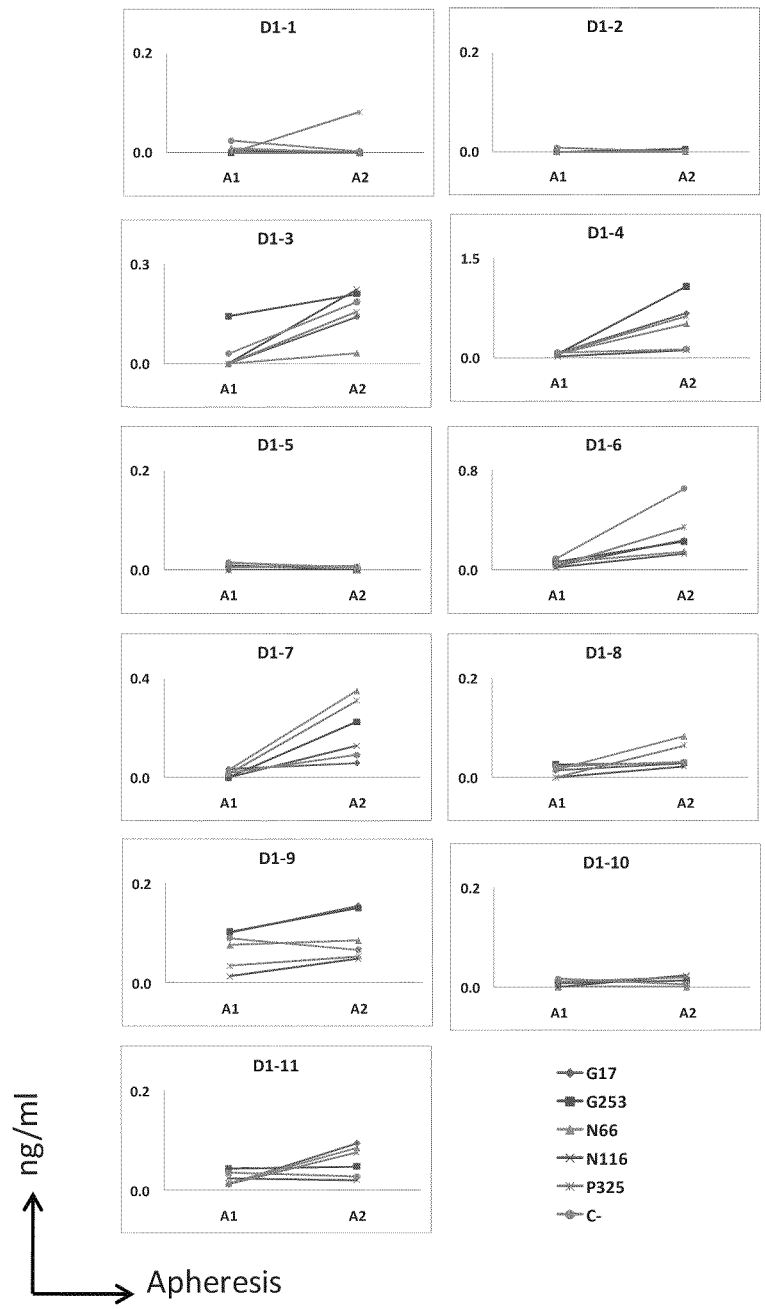
FIG. 41. DALIA vaccinated patients were stimulated with LIPO5 peptides for 48 hours. Luminex analysis for IL-17 secretion in pre (A1) and post-vaccination (A2) samples. Individual responses against each of the LIPO5 long peptide.
Figure 42:
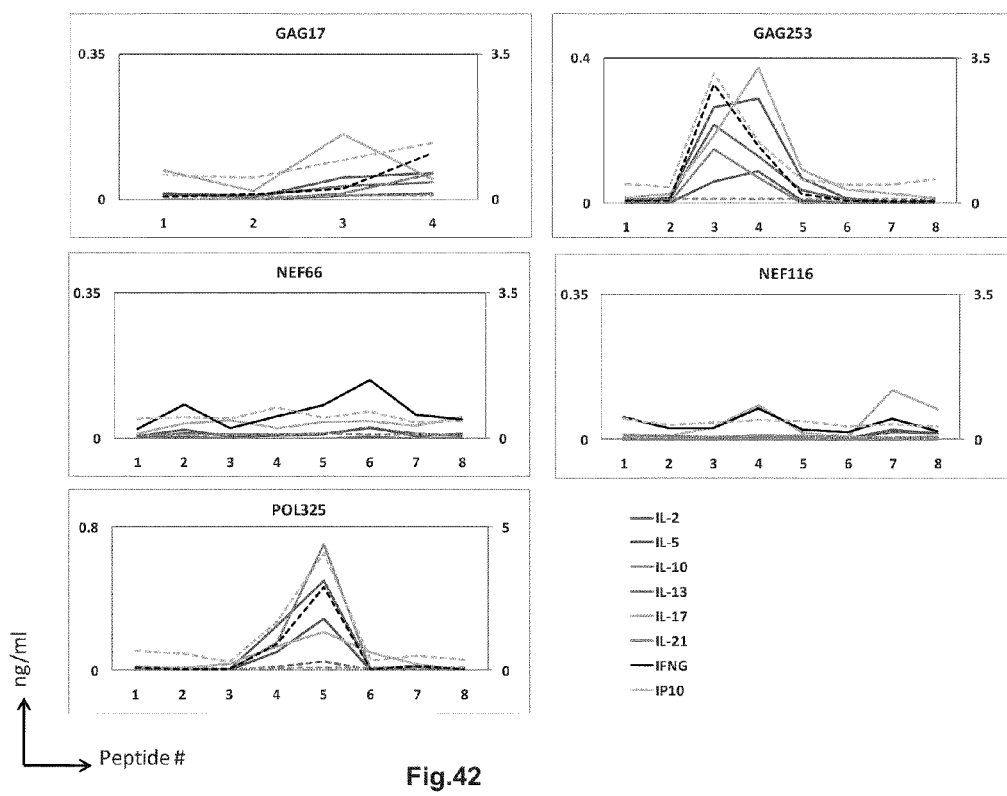
FIG. 42. DALIA vaccinated patient D1-3 PBMCs were stimulated with 15-mers of LIPO5 peptides for 48 hours. Luminex analysis of cytokine secretion in post-vaccination. Dotted lines represent cytokines with high concentration in the supernatants (right side axes).
Figure 43:
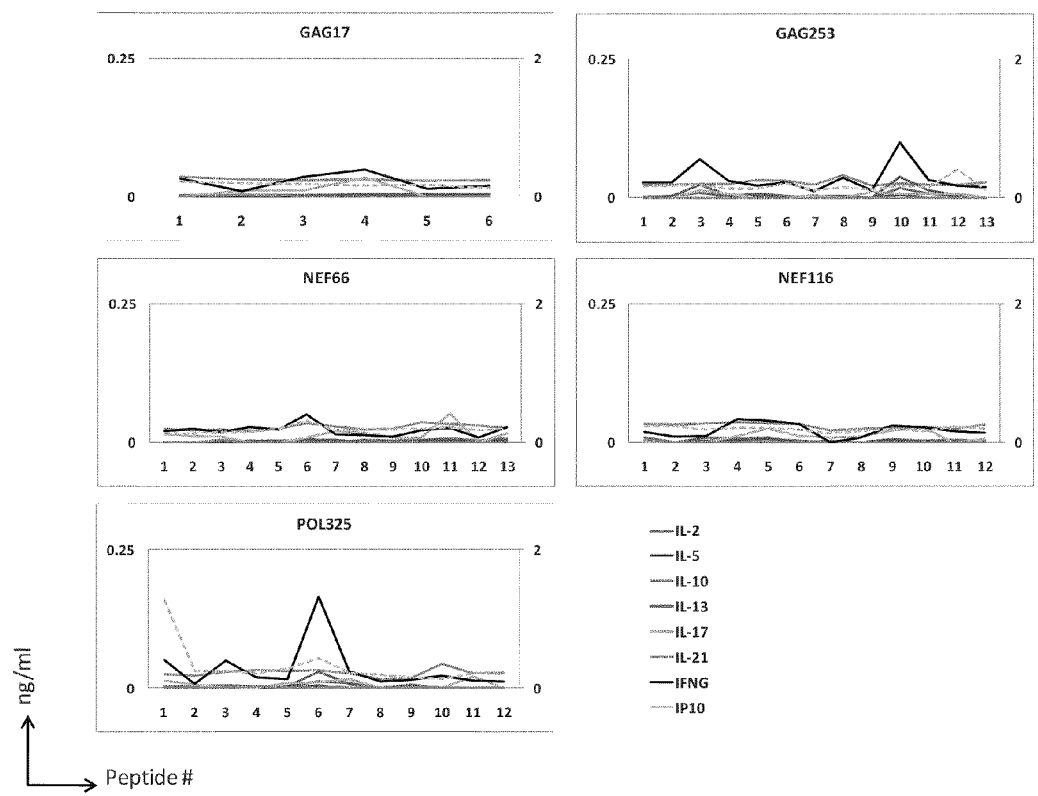
FIG. 43. DALIA vaccinated patient D1-3 PBMCs were stimulated with 9-mers of LIPO5 peptides for 48 hours. Luminex analysis of cytokine secretion post-vaccination samples. Dotted lines represent cytokines with high concentration in the supernatants (right side axes).

Patient D1-11:

ICS analysis: There is an increased peptide-specific CD4+ T cell response after vaccination: From 0.01% to 5% TNFα+ cells, from 0.02% to 4.5% IL-2+ cells and 0.03% to 2.5% IFNγ+ cells. Among HIV-specific CD4+ T cells, 4.5% express both IL-2 and TNFα and 2.5% are double positive for TNFα and IFNγ. The inventors observed a significant increase of peptide-specific CD8+ T cell responses in this patient after vaccination from 0.07% to 0.55% TNFα+ cells, from 0.01% to 0.09% IL-2+ cells and 0.09% to 0.55% IFNγ+ cells. In the CD8+ specific cell population, 0.08% express both IL-2 and TNFα and 0.5% are double positive for TNFα and IFNγ (FIG. 14-16). The stimulation with pools of 15-mers and 9-mers derived from LIPO5 sequences showed CD4 responses to Gag17, Gag253 and Pol325 and CD8 responses to Nef66 and Pol325 after vaccination (FIG. 29).

Cytokine secretion analysis: Responses against Gag 17, Gag253, Nef66 and Pol325 were detected by secretion of IL-2, IL-10, IL-13, IL-17, IL-21, IFNΓ and IP10 (FIG. 30-41).

Gag17 stimulated 1600 pg/mL IL-2, 150 pg/mL IL-10, 800 pg/mL IL-13, 1700 pg/mL IL-21, 33.3 µg/ml IFNγ and 5.3 µg/mL IP10.

Gag253 stimulated 3 µg/ml IL-2, 300 pg/mL IL-10, 1400 pg/mL IL-13, 9 µg/ml IL-21, 52.7 µg/ml IFNγ and 16.6 µg/mL IP10.

Nef66 stimulated 210 pg/mL IL-2, 380 pg/mL IL-13, 80 pg/mL IL-17, 4.8 µg/ml IFNγ and 1300 pg/mL IP10.

Pol325 stimulated 420 pg/mL IL-2, 330 pg/mL IL-13, 75 pg/mL IL-17, 300 pg/mL IL-21, 33.5 µg/ml IFNγ and 6.6 µg/mL IP10.

Figure 72:
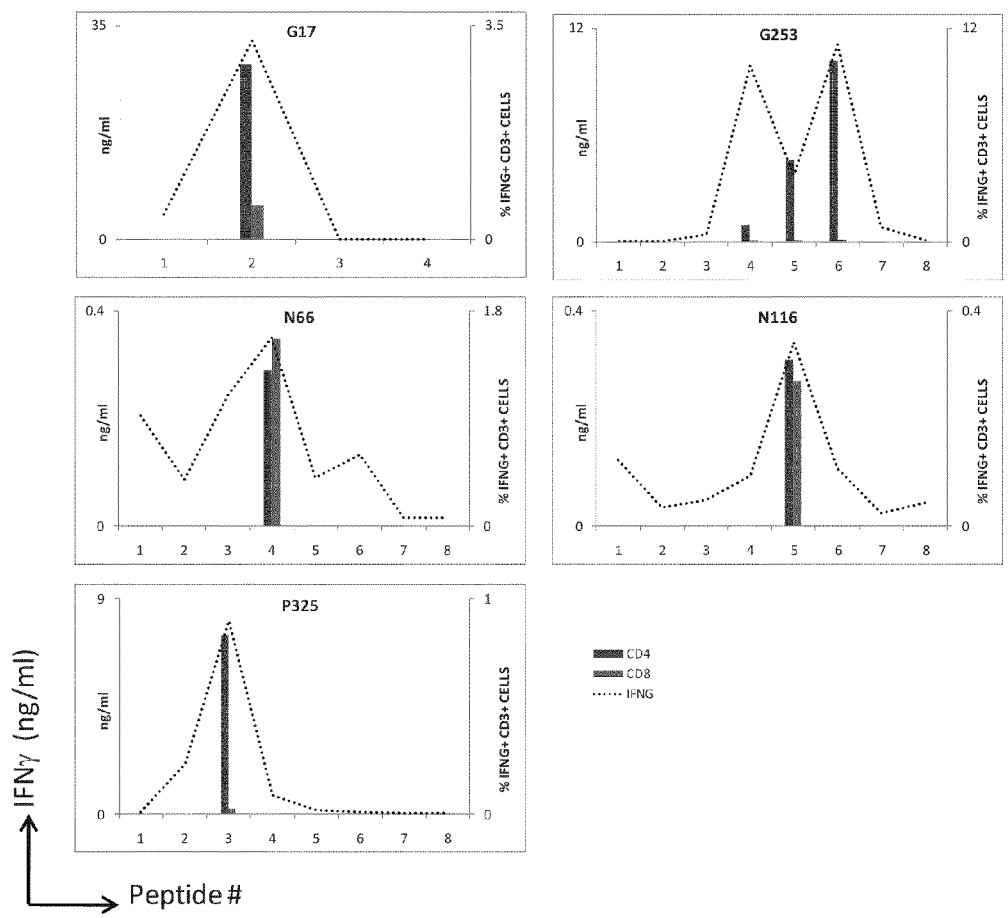
FIG. 72. D1-11: 7 days peptide stimulated cultures from Aph 2 were used for ICS after 6 hours 15-mer peptide stimulation.
Figure 73:
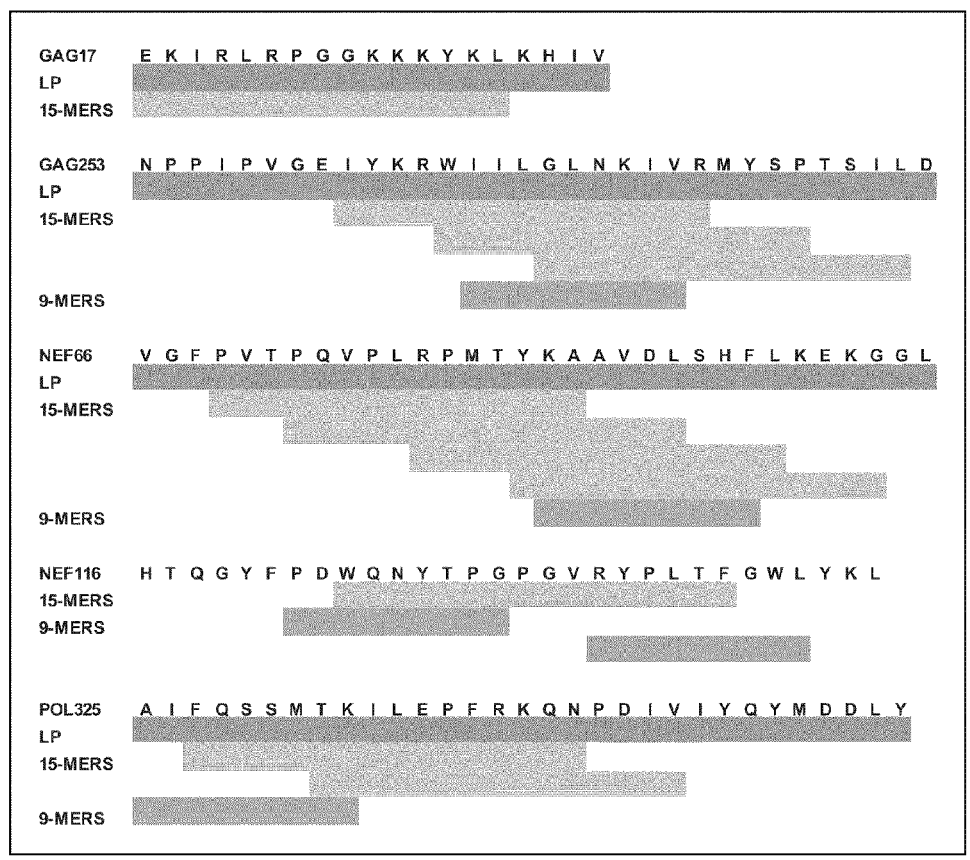
FIG. 73. Summary of the results obtained by Luminex analysis of patient D1-11 T cells stimulated with LIP05 long peptides (19-32 aa), 15-mers and 9-mers (SEQ ID NOs. 1, 2, 3, 4, 5).

T cells recognize 15-mer peptide p2 in Gag 17; peptides p4, p5 and p6 in Gag 253; peptides p3, p4, p5 and p6 in Nef 66; peptide p5 in Nef 116; and peptides p3 and p4 in Pol 325. They also recognize 9-mer peptide p8 in Gag 253, peptide p9 in Nef 66, peptides p4 and p10 in Nef 116, and peptide p1 in Pol 325 (FIG. 70-73). Detailed ICS showed that Gag17, Gag253 and Pol325 15-mer epitopes are mostly CD4+ T cell epitopes while Nef66 and Nef116 are mostly CD8+ T cell epitopes (FIG. 72).

Anti HIV-antibodies: The inventors observed no detectable antibodies against any of the LIPO5 peptides in serum from patient D1-11. However, antibodies recognizing Nef protein were detectable at the same level before and after vaccination (FIG. 74-76).

PATIENT D1-12: Due to break in the protocol, patient D1-12 was not included in the immunomonitoring.

PATIENT D1-13: The inventors were unable to collect apheresis #2 at week 16. The immune responses for this patient are not included herein.

Patient D1-14.

Figure 17:
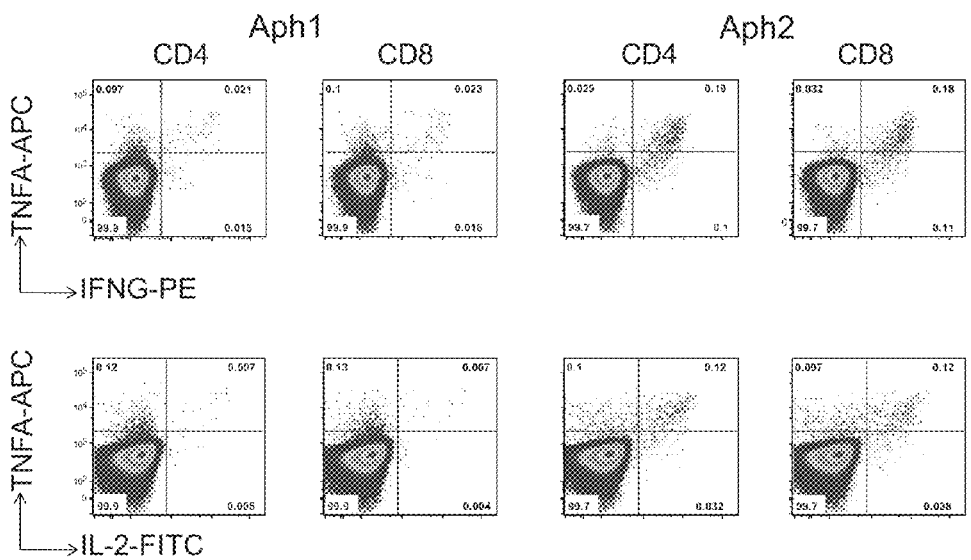
FIG. 17. D1-14: ICS after 6 hours LIPO5 long peptides mix stimulation of Ap1 and Aph2.

ICS analysis: There is an increased peptide-specific CD4+ T cell response after vaccination: From 0.12% to 0.22% TNFα+ cells, from 0.01% to 0.15% IL-2+ cells and 0.03% to 0.3% IFNγ+ cells. Among HIV-specific CD4+ T cells, 0.12% express both IL-2 and TNFα and 0.19% are double positive for TNFα and IFNγ. The inventors observed a significant increase of peptide-specific CD8+ T cell responses in this patient after vaccination from 0.12% to 0.21% TNFα+ cells, from 0.1% to 0.15% IL-2+ cells and 0.04% to 0.3% IFNγ+ cells. In the CD8+ specific cell population, 0.12% expresses both IL-2 and TNFα and 0.18% are double positive for TNFα and IFNγ (FIG. 17).

Patient D1-15.

Figure 18:
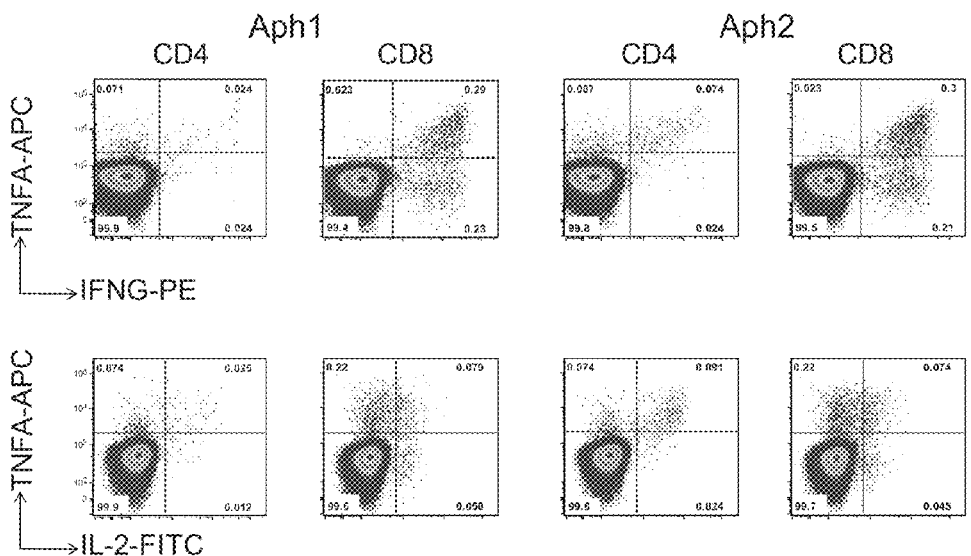
FIG. 18. D1-15: ICS after 6 hours LIPO5 long peptides mix stimulation of Ap1 and Aph2.

ICS analysis: There is an increased peptide-specific CD4+ T cell response after vaccination: From 0.01% to 0.16% TNFα+ cells, from 0.03% to 0.11% IL-2+ cells and 0.04% to 0.1% IFNγ+ cells. Among HIV-specific CD4+ T cells, 0.09% express both IL-2 and TNFα and 0.074% are double positive for TNFα and IFNγ. The inventors observed no change of peptide-specific CD8+ T cell responses in this patient after vaccination from 0.31% to 0.32% TNFα+ cells, from 0.14% to 0.11% IL-2+ cells and 0.52% to 0.51% IFN+ cells. In the CD8+ specific cell population, 0.076% express both IL-2 and TNF and 0.3% are double positive for TNFα and IFNγ (FIG. 18).

SUMMARY

The analysis ex-vivo of aphereses from vaccinated patients showed an increase of peptide-specific CD4+ T cells in ten out of thirteen patients analyzed. These cells secreted IFNγ, TNFα and IL-2 upon LIPO5 stimulation.

Luminex analysis of supernatants following 48 h restimulation identified: Gag253 responses in eight the patients, Pol325 responses in seven patients, Nef66 and Nef116 responses in five patients and Gag17 responses in five patients.

The inventors observed no detectable antibodies against any of the LIPO5 peptides in serum from any of the patients in the trial. However, antibodies recognizing Nef and Gag p24 proteins were detectable in 10 out of 11 patients, with no significant change in their level after vaccination.

Utilizing module-level blood transcriptional profiling, no conserved response to vaccination was observed in the first 6 patients. It was noted, however, that patients 1 and 2 had elevated molecular distance from the healthy baselines (MDTH) compared to patients 3-6 during the pre-ATI vaccination window. Post-ATI, all patients exhibited increase interferon, cell cycle, and plasma cell activity. The timing of these responses in relation to the first measured increase in circulating virus varied from patient to patient.

Figure 115:
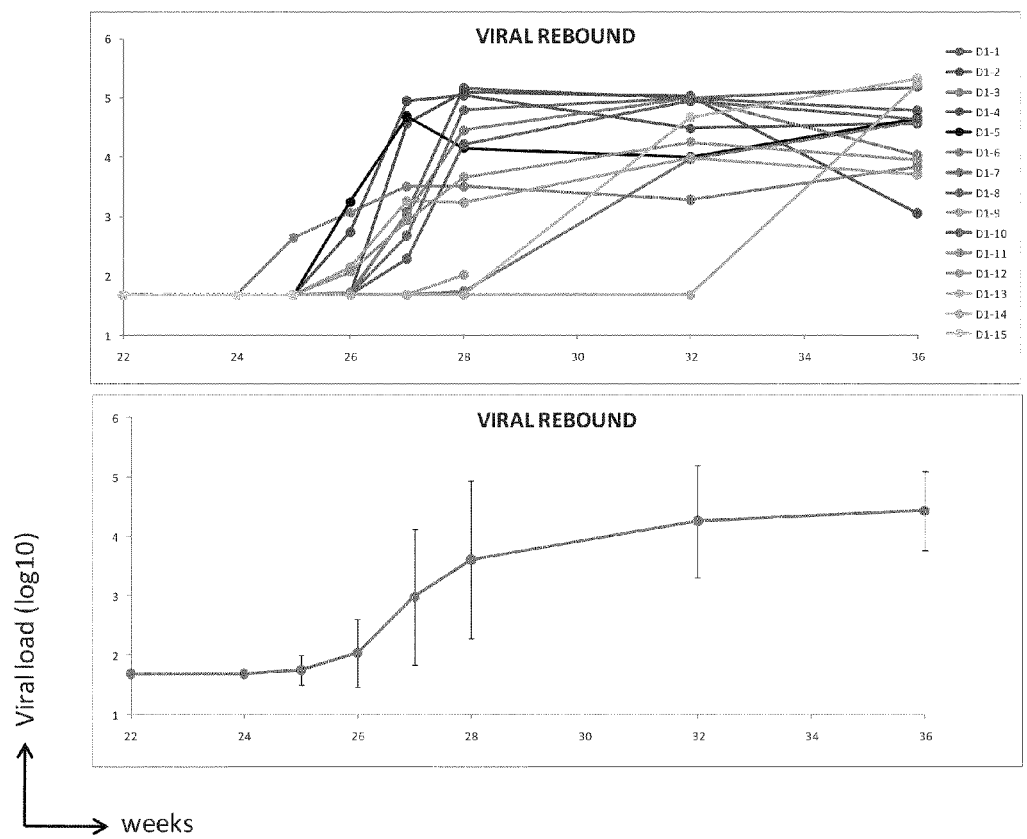
FIG. 115. D1-1 to D1-15 Viral load after ATI (week 24).

The viral rebound after ATI in each patient at this point of the trial is showed in FIG. 115.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,083,787: Yeast-Dendritic Cell Vaccines and Uses Thereof
U.S. Pat. No. 7,348,015: Antigen Modified Cancer Cell Vaccines for Cancer Therapy.
U.S. Patent Application No. 20090010948: Anti-Tumor Vaccines Delivered by Dendritic Cells Devoid of Interleukin-10.

What is claimed is:

1. A method of inducing a therapeutic immune response against a human immunodeficiency virus (HIV) infection in a patient comprising:
   injecting into the patient a composition comprising autologous dendritic cells (DCs) loaded with a lipopeptide mixture comprising five HIV antigenic peptides,
   wherein the five HIV antigen peptides are Gag p17(17-35) (SEQ ID NO: 1), Gag p24(253-284) (SEQ ID NO: 2), Nef(66-97) (SEQ ID NO: 3), Nef (116-145) (SEQ ID NO: 4), and Pol(325-355) (SEQ ID NO: 5) and wherein the therapeutic immune response includes an increase in CD4+ T cells that secrete IL-2.

2. The method of claim 1, further comprising the step of activating the lipopeptide loaded DCs with a lipopolysaccharide.

3. The method of claim 1, wherein the HIV antigenic peptides are linked to a lipid by a covalent bond between the C-terminal group of the peptide and a palmitolyl-lysylamide group of a lipid.

4. The method of claim 1, further comprising administering to the patient one or more anti-viral therapies selected from Highly Active AntiRetroviral Therapy (HAART), protease inhibitors, reverse transcriptase inhibitors or nucleotide analogs.

5. The method of claim 1, further comprising determining whether the patient has developed antibodies against the HIV antigenic peptides after injecting the composition.

6. The method of claim 1, further comprising formulating the composition as a pharmaceutically acceptable formulation.

7. The method of claim 1, further comprising generating the composition comprising the following steps:
   isolating monocytes comprising one or more DCs from the blood of the patient;
   loading the lipopeptide mixture; and isolating the loaded DCs.

8. The method of claim 2, further comprising:
   washing activated and loaded DCs;
   resuspending the activated and loaded DCs in a freezing solution in a suitable container; and
   freezing the solution in the suitable container.

9. The method of claim 7, wherein the monocytes are stimulated by cytokines comprising a granulocyte macrophage colony stimulating factor (GM-CSF) and an interferon alpha 2b (IFN-α).

10. A method of inducing a therapeutic immune response against a human immunodeficiency virus (HIV) infection in a patient comprising:
    loading dendritic cells (DCs) from the patient with a lipopeptide mixture comprising five antigenic HIV peptides;
    isolating the loaded DCs; and,
    injecting the loaded DCs into the patient,
    wherein the five antigenic peptides are Gag p17(17-35) (SEQ ID NO: 1), Gag p24(253-284) (SEQ ID NO: 2), Nef(66-97) (SEQ ID NO: 3), Nef (116-145) (SEQ ID NO: 4), and Pol(325-355) (SEQ ID NO: 5) and wherein the therapeutic immune response includes an increase in CD4+ T cells that secrete IL-2.

11. A method of inducing a therapeutic immune response against a human immunodeficiency virus (HIV) infection in a patient comprising:
    loading dendritic cells (DCs) from the patient with a lipopeptide mixture comprising five antigenic HIV peptides;
    activating the loaded dendritic cells with a lipopolysaccharide; and, injecting the loaded DCs into the patient,
    wherein the five antigenic peptides are Gag p17(17-35) (SEQ ID NO: 1), Gag p24(253-284) (SEQ ID NO: 2), Nef(66-97) (SEQ ID NO: 3), Nef (116-145) (SEQ ID NO: 4), and Pol(325-355) (SEQ ID NO: 5) and wherein the therapeutic immune response includes an increase in CD4+ T cells that secrete IL-2.

12. The method of claim 1, wherein the patient is determined to have been infected with HIV.

13. A method for increasing CD4+ T cells that secrete IL-2 in a patient comprising injecting into the patient a composition comprising autologous dendritic cells (DCs) loaded with a lipopeptide mixture comprising Gag p17(17-35) (SEQ ID NO: 1), Gag p24(253-284) (SEQ ID NO: 2), Nef(66-97) (SEQ ID NO: 3), Nef(116-145) (SEQ ID NO: 4), and Pol(325-355) (SEQ ID NO: 5), wherein CD4+ T cells that secrete IL-2 are increased in the patient.

* * * * *

SEQUENCE LISTING

```
<160> NUMBER OF SEQ ID NOS: 16

<210> SEQ ID NO 1
<211> LENGTH: 19
<212> TYPE: PRT
<213> ORGANISM: Human immunodeficiency virus

<400> SEQUENCE: 1

Glu Lys Ile Arg Leu Arg Pro Gly Gly Lys Lys Lys Tyr Lys Leu Lys
1               5                   10                  15

His Ile Val
```

-continued

```
<210> SEQ ID NO 2
<211> LENGTH: 32
<212> TYPE: PRT
<213> ORGANISM: Human immunodeficiency virus

<400> SEQUENCE: 2

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

<210> SEQ ID NO 3
<211> LENGTH: 32
<212> TYPE: PRT
<213> ORGANISM: Human immunodeficiency virus

<400> SEQUENCE: 3

Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30

<210> SEQ ID NO 4
<211> LENGTH: 30
<212> TYPE: PRT
<213> ORGANISM: Human immunodeficiency virus

<400> SEQUENCE: 4

His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu
            20                  25                  30

<210> SEQ ID NO 5
<211> LENGTH: 31
<212> TYPE: PRT
<213> ORGANISM: Human immunodeficiency virus

<400> SEQUENCE: 5

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
            20                  25                  30

<210> SEQ ID NO 6
<211> LENGTH: 32
<212> TYPE: PRT
<213> ORGANISM: Human immunodeficiency virus

<400> SEQUENCE: 6

His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu Val Pro
            20                  25                  30

<210> SEQ ID NO 7
<211> LENGTH: 34
<212> TYPE: PRT
<213> ORGANISM: Human immunodeficiency virus
```

```
<400> SEQUENCE: 7

Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30

Glu Gly

<210> SEQ ID NO 8
<211> LENGTH: 34
<212> TYPE: PRT
<213> ORGANISM: Human immunodeficiency virus

<400> SEQUENCE: 8

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr Val
            20                  25                  30

Gly Ser

<210> SEQ ID NO 9
<211> LENGTH: 23
<212> TYPE: PRT
<213> ORGANISM: Human immunodeficiency virus

<400> SEQUENCE: 9

Leu Asp Arg Trp Glu Lys Ile Arg Leu Arg Pro Gly Gly Lys Lys Lys
1               5                   10                  15

Tyr Lys Leu Lys His Ile Val
            20

<210> SEQ ID NO 10
<211> LENGTH: 33
<212> TYPE: PRT
<213> ORGANISM: Human immunodeficiency virus

<400> SEQUENCE: 10

Met Val Gly Phe Pro Val Thr Pro Gln Val Pro Leu Arg Pro Met Thr
1               5                   10                  15

Tyr Lys Ala Ala Val Asp Leu Ser His Phe Leu Lys Glu Lys Gly Gly
            20                  25                  30

Leu

<210> SEQ ID NO 11
<211> LENGTH: 36
<212> TYPE: PRT
<213> ORGANISM: Human immunodeficiency virus

<400> SEQUENCE: 11

Ile Asp Leu Trp Ile Tyr His Thr Gln Gly Tyr Phe Pro Asp Trp Gln
1               5                   10                  15

Asn Tyr Thr Pro Gly Pro Gly Val Arg Tyr Pro Leu Thr Phe Gly Trp
            20                  25                  30

Leu Tyr Lys Leu
        35

<210> SEQ ID NO 12
<211> LENGTH: 32
<212> TYPE: PRT
<213> ORGANISM: Human immunodeficiency virus
```

```
<400> SEQUENCE: 12

Met Ala Ile Phe Gln Ser Ser Met Thr Lys Ile Leu Glu Pro Phe Arg
1               5                   10                  15

Lys Gln Asn Pro Asp Ile Val Ile Tyr Gln Tyr Met Asp Asp Leu Tyr
                20                  25                  30

<210> SEQ ID NO 13
<211> LENGTH: 37
<212> TYPE: PRT
<213> ORGANISM: Human immunodeficiency virus

<400> SEQUENCE: 13

Gly Leu Thr Thr Met Val Gly Phe Pro Val Thr Pro Gln Val Pro Leu
1               5                   10                  15

Arg Pro Met Thr Tyr Lys Ala Ala Val Asp Leu Ser His Phe Leu Lys
                20                  25                  30

Glu Lys Gly Gly Leu
            35

<210> SEQ ID NO 14
<211> LENGTH: 38
<212> TYPE: PRT
<213> ORGANISM: Human immunodeficiency virus

<400> SEQUENCE: 14

Ile Asp Leu Trp Ile Tyr His Thr Gln Gly Tyr Phe Pro Asp Trp Gln
1               5                   10                  15

Asn Tyr Thr Pro Gly Pro Gly Val Arg Tyr Pro Leu Thr Phe Gly Trp
                20                  25                  30

Leu Tyr Lys Leu Val Pro
            35

<210> SEQ ID NO 15
<211> LENGTH: 33
<212> TYPE: PRT
<213> ORGANISM: Human immunodeficiency virus

<400> SEQUENCE: 15

Trp Ile Tyr His Thr Gln Gly Tyr Phe Pro Asp Trp Gln Asn Tyr Thr
1               5                   10                  15

Pro Gly Pro Gly Val Arg Tyr Pro Leu Thr Phe Gly Trp Leu Tyr Lys
                20                  25                  30

Leu

<210> SEQ ID NO 16
<211> LENGTH: 35
<212> TYPE: PRT
<213> ORGANISM: Human immunodeficiency virus

<400> SEQUENCE: 16

Met Ala Ile Phe Gln Ser Ser Met Thr Lys Ile Leu Glu Pro Phe Arg
1               5                   10                  15

Lys Gln Asn Pro Asp Ile Val Ile Tyr Gln Tyr Met Asp Asp Leu Tyr
                20                  25                  30

Val Gly Ser
        35
```